United States Patent
Nakanishi et al.

(10) Patent No.: US 10,689,705 B2
(45) Date of Patent: Jun. 23, 2020

(54) FGFR3 FUSION GENE AND PHARMACEUTICAL DRUG TARGETING SAME

(71) Applicant: Chugai Seiyaku Kabushiki Kaisha, Tokyo (JP)

(72) Inventors: Yoshito Nakanishi, Kanagawa (JP); Nukinori Akiyama, Kanagawa (JP); Yukari Nishito, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/380,399

(22) PCT Filed: Sep. 27, 2013

(86) PCT No.: PCT/JP2013/076200
§ 371 (c)(1),
(2) Date: Aug. 22, 2014

(87) PCT Pub. No.: WO2014/051022
PCT Pub. Date: Apr. 3, 2014

(65) Prior Publication Data
US 2015/0307945 A1    Oct. 29, 2015

(30) Foreign Application Priority Data

Sep. 27, 2012  (JP) .................................. 2012-214739
Jul. 18, 2013   (JP) .................................. 2013-149217

(51) Int. Cl.
| | |
|---|---|
| C07K 14/50   | (2006.01) |
| C12Q 1/6886  | (2018.01) |
| A61K 31/713  | (2006.01) |
| A61K 31/4184 | (2006.01) |
| A61K 31/4439 | (2006.01) |
| A61K 31/454  | (2006.01) |
| A61K 31/496  | (2006.01) |
| A61K 31/5377 | (2006.01) |
| C07K 14/71   | (2006.01) |
| G01N 33/50   | (2006.01) |
| G01N 33/574  | (2006.01) |
| A61K 45/06   | (2006.01) |
| A61K 31/506  | (2006.01) |
| A61K 31/517  | (2006.01) |
| A61K 31/519  | (2006.01) |
| A61K 39/395  | (2006.01) |
| A61K 39/00   | (2006.01) |

(52) U.S. Cl.
CPC ........ *C12Q 1/6886* (2013.01); *A61K 31/4184* (2013.01); *A61K 31/4439* (2013.01); *A61K 31/454* (2013.01); *A61K 31/496* (2013.01); *A61K 31/506* (2013.01); *A61K 31/517* (2013.01); *A61K 31/519* (2013.01); *A61K 31/5377* (2013.01); *A61K 31/713* (2013.01); *A61K 39/39558* (2013.01); *A61K 45/06* (2013.01); *C07K 14/50* (2013.01); *C07K 14/71* (2013.01); *G01N 33/5011* (2013.01); *G01N 33/57423* (2013.01); *A61K 2039/505* (2013.01); *C07K 2319/01* (2013.01); *C12Q 2600/156* (2013.01); *C12Q 2600/158* (2013.01); *G01N 2333/90* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,745,437 B2 * | 6/2010  | Ren ..................... | C07D 401/14 | 514/235.8 |
| 7,825,132 B2 * | 11/2010 | Cai ..................... | A61K 31/496 | 514/314 |
| 8,026,243 B2 * | 9/2011  | Albaugh .............. | C07D 239/42 | 514/256 |
| 8,158,360 B2 * | 4/2012  | Heise ................... | C12Q 1/6886 | 435/6.14 |
| 8,828,385 B2 * | 9/2014  | Yayon ................. | C07K 16/2863 | 424/133.1 |
| 8,829,199 B2 * | 9/2014  | Taka ................... | A61K 31/4184 | 544/114 |

(Continued)

FOREIGN PATENT DOCUMENTS

| | | |
|---|---|---|
| AU | 2013228389 | 9/2014 |
| CN | 102574836  | 7/2012 |

(Continued)

OTHER PUBLICATIONS

UniProtKB/Swiss-Prot Accession No. Q9UHR4 (version Q9UHR4.2), Sep. 5, 2012.*
NCBI Accession No. NP_061330 (version 2), Jun. 29, 2012.*
Habermann et al., EMBO Reports, 5(3):250-255, 2004.*
Aranguez et al., Anales De La Real Academia Nacional de Farmacia, 2011;77(1):4-11.
Kataoka et al., "Foretinib (GSK1363089), a multi-kinase inhibitor of MET and VEGFRs, inhibits growth of gastric cancer cell lines by blocking inter-receptor tyrosine kinase networks," *Invest New Drugs*, Aug. 2012;30(4):1352-60. doi: 10.1007/s10637-011-9699-0. Epub Jun. 8, 2011.

(Continued)

*Primary Examiner* — Marianne P Allen
(74) *Attorney, Agent, or Firm* — Fish & Richardson P.C.

(57) ABSTRACT

The FGFR-encoding gene was studied extensively with regard to its expression, hyperamplification, mutation, translocation, or such in various cancer cells. As a result, novel fusion polypeptides in which the FGFR3 polypeptide is fused with a different polypeptide were identified and isolated from several types of bladder cancer-derived cells and lung cancer cells. The use of a fusion polypeptide of the present invention as a biomarker in FGFR inhibitor-based cancer therapy enables one to avoid side effects in cancer therapy and control the therapeutic condition to produce the best therapeutic effect, thereby enabling individualized medicine.

32 Claims, 13 Drawing Sheets
Specification includes a Sequence Listing.

(56) References Cited

U.S. PATENT DOCUMENTS

| | | | |
|---|---|---|---|
| 9,102,692 B2* | 8/2015 | Taka | A61K 31/4184 |
| 9,499,623 B2* | 11/2016 | Ashkenazi | C07K 16/2863 |
| 2009/0175844 A1 | 7/2009 | Nakamura et al. | |
| 2010/0003258 A1 | 1/2010 | Weng et al. | |
| 2012/0208811 A1 | 8/2012 | Taka et al. | |
| 2014/0142084 A1* | 5/2014 | Kameda | C07D 403/12 |
| | | | 514/210.18 |

FOREIGN PATENT DOCUMENTS

| | | |
|---|---|---|
| CN | 104144915 | 11/2014 |
| EA | 012621 | 10/2009 |
| EP | 2 821 402 | 1/2015 |
| EP | 2 471 786 | 11/2015 |
| EP | 3 339 305 | 6/2018 |
| JP | 2005-500034 | 1/2005 |
| JP | 2012-180344 | 9/2012 |
| JP | 2012-521759 | 9/2012 |
| KR | 2012/0085736 | 8/2012 |
| TW | 2011/16521 | 5/2011 |
| WO | WO 2002/102972 | 12/2002 |
| WO | WO 2004/085676 | 10/2004 |
| WO | WO 2004/110487 | 12/2004 |
| WO | WO 2005/046589 | 5/2005 |
| WO | WO 2007/014123 | 2/2007 |
| WO | WO 2007/144893 | 12/2007 |
| WO | WO 2009/014565 | 1/2009 |
| WO | WO 2009/113436 | 9/2009 |
| WO | WO 2010/111367 | 9/2010 |
| WO | WO 2011/016528 | 2/2011 |
| WO | WO 2013/089882 | 6/2013 |
| WO | WO 2013/133351 | 9/2013 |
| WO | WO 2014/018673 | 1/2014 |
| WO | WO 2015/150900 | 10/2015 |
| WO | WO 2016/048833 | 3/2016 |

OTHER PUBLICATIONS

Prinos et al., "A common FGFR3 gene mutation in hypochondroplasia," Hum Mol Genet., Nov. 1995;4(11):2097-101.

Wuchner et al., "Human fibroblast growth factor receptor 3 gene (FGFR3): genomic sequence and primer set information for gene analysis," Hum Genet., Aug. 1997;100(2):215-9.

Cappellen et al., "Frequent activating mutations of FGFR3 in human bladder and cervix carcinomas," Nat Genet., Sep. 1999;23(1):18-20.

Eswarakumar et al., "Cellular signaling by fibroblast growth factor receptors," Cytokine Growth Factor Rev., Apr. 2005;16(2):139-49. Epub Feb. 1, 2005.

Fonseca et al., "Clinical and biologic implications of recurrent genomic aberrations in myeloma," Blood, Jun. 1, 2003;101(11):4569-75. Epub Feb. 6, 2003.

Gavine et al., "AZD4547: an orally bioavailable, potent, and selective inhibitor of the fibroblast growth factor receptor tyrosine kinase family," Cancer Res., Apr. 15, 2012;72(8):2045-56. Epub Feb. 27, 2012.

Guagnano et al., "Discovery of 3-(2,6-dichloro-3,5-dimethoxyphenyl)-1- {6-[4-(4-ethyl-piperazin-1-yl)-phenylamino]-pyrimidin-4-yl}-1-methyl-urea (NVP-BGJ398), a potent and selective inhibitor of the fibroblast growth factor receptor family of receptor tyrosine kinase," J Med Chem., Oct. 27, 2011;54(20):7066-83. Epub Sep. 21, 2011.

Millard et al., "Characterisation of IRTKS, a novel IRSp53/MIM family actin regulator with distinct filament bundling properties," J Cell Sci., May 1, 2007;120(Pt 9):1663-72. Epub Apr. 12, 2007.

Singh et al., "Transforming fusions of FGFR and TACC genes in human glioblastoma," Science, Sep. 7, 2012;337(6099):1231-5. Epub Jul. 26, 2012.

Williams et al., "Oncogenic FGFR3 gene fusions in bladder cancer," Hum Mol Genet., Feb. 15, 2013;22(4):795-803. Epub Nov. 21, 2012.

Wu et al., "Identification of targetable FGFR gene fusions in diverse cancers," Cancer Discov., Jun. 2013;3(6):636-47. Epub Apr. 4, 2013.

Nakanishi et al., "Mechanism of Oncogenic Signal Activation by the Novel Fusion Kinase FGFR3-BAIAP2L1," Mol Cancer Ther., Mar. 2015;14(3):704-12. doi: 10.1158/1535-7163.MCT-14/0927-T. Epub Jan. 14, 2015.

Phospho-FGF Receptor (Try653/654) Antibody. #3471 Cell Signaling Technology, Inc. (2012), retrieved online at: http://media.cellsignal.com/pdf/3471.pdf.

Trudel et al., "The inhibitory anti-FGFR3 antibody, PRO-001, is cytotoxic to t(4;14) multiple myeloma cells," Blood, May 15, 2006;107(10):4039-46. Epub Feb. 7, 2006.

Zhu et al., "Fibroblast growth factor receptor 3 inhibition by short hairpin RNAs leads to apoptosis in multiple myeloma," Mol Cancer Ther., May 2005;4(5):787-98.

Kyriazis et al., "Morphological, Biological, and Biochemical Characteristics of Human Bladder Transitional Cell Carcinomas Grown in Tissue Culture and in Nude Mice," Cancer Res., Sep. 1984, 44(9):3997-4005.

Lamont et al., "Small molecule FGF receptor inhibitors block FGFR-dependent urothelial carcinoma growth in vitro and in vivo," Br J Cancer, Jan. 4, 2011, 104(1):75-82.

Coviello et al., "A genome-wide association meta-analysis of circulating sex hormone-binding globulin reveals multiple Loci implicated in sex steroid hormone regulation," PLoS Genet, Jul. 2012, 8(7):e1002805. doi: 10.1371/journal.pgen.1002805. Epub Jul. 19, 2012.

Sharma et al., "Targeting Gene Fusion Events in Bladder Carcinoma," J Mol Genet Med, 2018, vol. 12(3):361.

GenBank Accession No. EAW82562.1, Dec. 18, 2006.

GenBank Accession No. EAW82565.1, Dec. 18, 2006.

GenBank Accession No. EAW76706.1, Dec. 18, 2006.

Declaration of Dr. Yoshito Nakanishi, signed May 8, 2019 (submitted in opposition proceedings for corresponding EP Patent No. 2 902 489 on May 10, 2019), 2 pages.

Prescribing information for Erdafitinib, Apr. 2019 (submitted in opposition proceedings for corresponding EP Patent No. 2 902 489 on May 10, 2019), 21 pages.

Sequence Alignment (submitted in opposition proceedings for corresponding EP Patent No. 2 902 489 on May 10, 2019), 1 page.

Tomlinson et al., "FGFR3 protein expression and its relationship to mutation status and prognostic variables in bladder cancer," J Pathol, Sep. 2007, 213(1):91-8.

Turner et al., "Fibroblast growth factor signalling: from development to cancer," Nat Rev Cancer, Feb. 2010, 10(2):116-29.

\* cited by examiner

A 1.

A 2.

B 1.

B 2.

MONOLAYER CULTURE
WILD-TYPE FGFR3

FGFR3-BAIAP2L1

SPHEROID CULTURE

PARENT CELL

WILD-TYPE FGFR3- EXPRESSING CELL

FGFR3- BAIAP2L1- EXPRESSING CELL (MEAN RADIUS)

FGFR3 FUSION GENE AND PHARMACEUTICAL DRUG TARGETING SAME

CROSS-REFERENCE TO RELATED APPLICATIONS

This application is the National Stage of International Application Serial No. PCT/JP2013/076200, filed on Sep. 27, 2013, which claims the benefit of Japanese Application Serial No. 2012-214739, filed on Sep. 27, 2012, and Japanese Application Serial No. 2013-149217, filed on Jul. 18, 2013.

TECHNICAL FIELD

The present invention relates to novel fusion polypeptides expressed in abnormal cells such as cancer cells; polynucleotides encoding the polypeptides; vectors comprising the polynucleotides; cells comprising the vectors; antibodies and fragments thereof which specifically bind to the polypeptides; oligonucleotide primers that hybridize to the polynucleotides; oligonucleotides that cleave the polynucleotides; pharmaceutical compositions comprising the antibodies or oligonucleotides; methods and kits for detecting the polynucleotides or fusion polypeptides; methods for testing cancer susceptibility, whether a subject is affected with cancer, or whether cancer has progressed based on the presence or absence of the polynucleotides or fusion polypeptides; methods for selecting cancer patients to which an FGFR inhibitor is applicable; pharmaceutical compositions for treating cancer wherein compounds having FGFR inhibitory activity or pharmaceutically acceptable salts thereof are used for administration to patients expressing the fusion polypeptides or carrying the polynucleotides; methods for treating or preventing cancer which comprise the step of administering an effective amount of compounds having FGFR inhibitory activity or pharmaceutically acceptable salts thereof to patients expressing the fusion polypeptides or carrying the polynucleotides; use of compounds having FGFR inhibitory activity or pharmaceutically acceptable salts thereof in the production of pharmaceutical compositions for cancer treatment for administration to patients expressing the fusion polypeptides or carrying the polynucleotides; compounds having FGFR inhibitory activity or pharmaceutically acceptable salts thereof for use in treating or preventing patients expressing the fusion polypeptides or carrying the polynucleotides; as well as methods for identifying FGFR inhibitors, and such.

BACKGROUND ART

Cancer can develop in any organ or tissue, and is highly refractory and lethal. It goes with saying that cancer is a very troublesome disease. Recent statistical data showed that one out of every two persons is diagnosed with cancer during life, and one out of four men and one out of six women die of cancer. Thus, cancer remains an extremely severe disease.

To date, a number of anticancer agents have been developed and prescribed to many cancer patients, and certain therapeutic outcome has been achieved. However, anticancer agents are well known to cause serious side effects as well. Meanwhile, it has long been known that there are individual differences in the response to anticancer agents, i.e., therapeutic effects and side effects, although the cause remains undissolved.

Recent advances in science and technology, in particular, rapid progress of pharmacogenomics (PGx), has enabled us to understand various diseases including cancer (such as cancer, diabetes, and hypertension) at the molecular level. It has been revealed that among patients showing similar symptoms, there are cases where genetic polymorphism (including gene mutation) is involved in the various individual differences observed, for example, differences in the absorption, distribution, metabolism, and excretion of administered pharmaceutical agents, as well as differences in the response at sites of action, differences in pathological conditions, and differences in disease susceptibility.

This suggests that for patients who are already affected with cancer, therapeutic effects can be enhanced and side effects can be reduced, for example, by analyzing the patients' genomic information in advance before administration of anticancer agents, and selecting an agent to be administered and determining the mode of prescription based on the presence or absence of specific genetic polymorphisms.

Likewise, for healthy persons also, genomic information of an individual can be analyzed using pharmacogenomics to predict the person's susceptibility to a disease (likelihood of being affected with a disease) as well as the person's responsiveness to pharmaceutical agents, based on the presence or absence of specific genetic polymorphisms.

This novel type of therapeutic method, which uses specific genetic polymorphisms thus identified or mutant polypeptides resulting from such polymorphisms as a biomarker, is referred to as order-made medicine, tailor-made medicine, personalized medicine, or custom-made medicine, and has been adopted for the clinical development of pharmaceutical products and clinical practice in various countries.

Similarly, agents that target the specific genetic polymorphisms identified as described above or mutant polypeptides resulting from such polymorphisms are referred to as molecularly targeted drugs, and their development is setting off actively.

Fibroblast growth factor receptors (FGFRs) are kinases belonging to the receptor tyrosine kinase family. FGFR1, FGFR2, FGFR3, and FGFR4 constitute the FGFR family. The ligand is fibroblast growth factor (FGF), and 22 types of structurally similar proteins form the family.

Signals transmitted via FGFR are conveyed to the MAPK pathway or PI3K/AKT pathway. It has been reported that in cancer, signal transduction is involved in cell growth, angiogenesis, cell migration, invasion, metastasis, etc.; and FGFR is activated as a result of overexpression, gene hyperamplification, mutation, or translocation (Non-patent Document 1). For example, it is known that for FGFR3, genetic translocation is observed in multiple myeloma (Non-patent Document 2); gene mutation is observed in bladder cancer (Non-patent Document 3); and overexpression is observed in ovarian cancer, non-small cell lung carcinoma, and hepatocellular carcinoma.

The findings described above suggest a connection between FGFR and cancer. Thus, attempts have been made to develop compounds with FGFR inhibitory activity as anticancer agents (Non-patent Documents 4 and 5).

While it has been reported very recently that genetic translocation that suggests the presence of a fusion polypeptide of FGFR3 and transforming acidic coiled-coil protein 3 (TACC3) or a fusion polypeptide of FGFR1 and TACC1 was found in very few cases of brain tumor glioblastoma multiforme (GBM) (three of 97 samples, 3.1%)

(Non-patent Document 6), the connection between fusion polypeptides of FGFR with other proteins and other types of cancer remains unclear.

PRIOR ART DOCUMENTS

Non-Patent Documents

[Non-patent Document 1] Cytokine & Growth Factor Reviews, 2005, 16: 139-149
[Non-patent Document 2] Blood, 2003, 101: 4569-4575
[Non-patent Document 3] Nature Genetics, 1999 September, 23(1): 18-20
[Non-patent Document 4] Cancer Research, 2012, 72: 2045-2056
[Non-patent Document 5] J. Med. Chem., 2011, 54: 7066-7083
[Non-patent Document 6] Science, Vol. 337, Issue 6099, 7 Sep. 2012: 1231-1235

SUMMARY OF THE INVENTION

Problems to be Solved by the Invention

In view of the above circumstances, the present invention aims to identify and provide cancer cell-specific molecules that can be used as a biomarker to enable personalized medicine for FGFR inhibitor-based cancer therapy, and cancer cell-specific molecules that are useful in development of molecularly targeted drugs targeting FGFR, as well as to provide various materials and methods to be used in personalized medicine and development of molecularly targeted drugs that utilize such molecules as a biomarker or molecular target.

Means for Solving the Problems

As mentioned above, a connection between FGFR and cancer has been suggested; however, connections between fusion proteins of FGFR with other proteins and various types of cancer remain unrevealed.

To achieve the above-described objective, the present inventors conducted dedicated studies on expression, hyper-amplification, mutation, translocation, and such of FGFR-encoding genes in various cancer cells. As a result, the present inventors discovered in multiple bladder cancer cells and lung cancer cells, novel fusion polypeptide genes between an FGFR3 polypeptide gene and other polypeptide genes, in particular, fusion polypeptide genes between an FGFR3 polypeptide gene and a BAIAP2L1 polypeptide gene, and fusion polypeptide genes between an FGFR3 polypeptide gene and a TACC3 polypeptide gene. The present inventors have thereby completed the present invention.

Specifically, the present invention relates to:
novel fusion polypeptides expressed in abnormal cells such as cancer cells,
polynucleotides encoding the polypeptides,
vectors comprising the polynucleotides,
cells comprising the vectors,
antibodies and fragments thereof that specifically bind to the polypeptides,
oligonucleotide primers that hybridize to the polynucleotides,
oligonucleotides that cleave the polynucleotides,
pharmaceutical compositions comprising the antibodies or oligonucleotides,
methods and kits for detecting the fusion polypeptides or polynucleotides,
methods for testing cancer susceptibility, whether a subject is affected with cancer, or whether cancer has progressed based on the presence or absence of the fusion polypeptides or polynucleotides,
methods for selecting cancer patients to which an FGFR inhibitor is applicable,
pharmaceutical compositions for cancer treatment which are characterized by their use of being administered to patients expressing the fusion polypeptides or carrying the polynucleotides, methods for identifying FGFR inhibitors, and such, as described below:

[1] a fusion polypeptide comprising an FGFR3 polypeptide and a BAIAP2L1 polypeptide or TACC3 polypeptide: wherein the FGFR3 polypeptide is the whole or a part of a wild-type polypeptide consisting of the amino acid sequence of SEQ ID NO: 6 or 7, or the whole or a part of a mutant polypeptide with one or more amino acid substitutions, deletions, or insertions in the wild-type polypeptide; the BAIAP2L1 polypeptide is the whole or a part of a wild-type polypeptide consisting of the amino acid sequence of SEQ ID NO: 8, or the whole or a part of a mutant polypeptide with one or more amino acid substitutions, deletions, or insertions in the wild-type polypeptide; and the TACC3 polypeptide is the whole or a part of a wild-type polypeptide consisting of the amino acid sequence of SEQ ID NO: 9, or the whole or a part of a mutant polypeptide with one or more amino acid substitutions, deletions, or insertions in the wild type polypeptide;
[2] the fusion polypeptide of [1] described above, wherein the FGFR3 polypeptide is a wild-type polypeptide consisting of the amino acid sequence of SEQ ID NO: 6 or 7;
[3] the fusion polypeptide of [1] or [2] described above, wherein the fusion polypeptide comprises an FGFR3 polypeptide and a BAIAP2L1 polypeptide;
[4] the fusion polypeptide of [3] described above, wherein the fusion polypeptide consists of the amino acid sequence of SEQ ID NO: 32 or 38;
[5] the fusion polypeptide of [1] or [2] described above, wherein the fusion polypeptide comprises an FGFR3 polypeptide and a TACC3 polypeptide;
[6] the fusion polypeptide of [5] described above, wherein the fusion polypeptide consists of the amino acid sequence of SEQ ID NO: 28, 30, 34, or 36;
[7] the fusion polypeptide of any of [1] to [5] described above, wherein the fusion polypeptide is derived from bladder cancer or lung cancer;
[8] a polynucleotide encoding the fusion polypeptide of any of [1] to [7] described above;
[9] the polynucleotide of [8] described above, which comprises the nucleotide sequence of SEQ ID NO: 14, 15, or 16;
[10] the polynucleotide of [9] described above, which comprises the nucleotide sequence of SEQ ID NO: 27, 29, 31, 33, 35, or 37;
[11] a vector comprising the polynucleotide of any of [8] to [10] described above;
[12] a recombinant cell comprising the vector of [11] described above;
[13] an antibody or antigen-binding fragment thereof which specifically binds to the fusion polypeptide of any of [1] to [7] described above;
[14] a pair of oligonucleotide primers consisting of sense and antisense primers each hybridizing to a polynucleotide encoding the fusion polypeptide of any of [1] to [7] described above for detecting or amplifying the polynucleotide;

[15] an oligonucleotide that binds to an mRNA polynucleotide encoding the fusion polypeptide of any of [1] to [7] described above and has an activity to inhibit translation of the mRNA polynucleotide into protein;
[16] the oligonucleotide of [15] described above, which is an siRNA that cleaves the mRNA polypeptide;
[17] a pharmaceutical composition comprising the antibody or antigen-binding fragment thereof of [13] described above;
[18] a pharmaceutical composition comprising the oligonucleotide of [15] or [16] described above;
[19] a method for detecting a fusion polypeptide that comprises an FGFR3 polypeptide and a BAIAP2L1 polypeptide or TACC3 polypeptide, which comprises the step of detecting the fusion polypeptide in a sample isolated from a subject by using an antibody or antigen-binding fragment thereof that binds to the fusion polypeptide of any of [1] to [7] described above;
[20] a method for detecting a polynucleotide encoding a fusion polypeptide that comprises an FGFR3 polypeptide and a BAIAP2L1 polypeptide or TACC3 polypeptide, which comprises the step of detecting a polynucleotide encoding the fusion polypeptide in a sample isolated from a subject by using a pair of oligonucleotide primers consisting of sense and antisense primers each hybridizing to a polynucleotide encoding the fusion polypeptide of any of [1] to [7] described above for detecting or amplifying the polynucleotide;
[21] a kit for detecting a polynucleotide encoding a fusion polypeptide that comprises an FGFR3 polypeptide and a BAIAP2L1 polypeptide or TACC3 polypeptide, which comprises a pair of oligonucleotide primers consisting of sense and antisense primers each hybridizing to a polynucleotide encoding the fusion polypeptide of any of [1] to [7] described above for detecting or amplifying the polynucleotide;
[22] a kit for detecting a fusion polypeptide that comprises an FGFR3 polypeptide and a BAIAP2L1 polypeptide or TACC3 polypeptide, which comprises an antibody or antigen-binding fragment thereof that binds to the fusion polypeptide of any of [1] to [7] described above;
[23] a method for testing cancer susceptibility of a subject, whether a subject is affected with cancer, or whether cancer has progressed in a subject by determining the presence or absence of the fusion polypeptide of any of [1] to [7] described above in a sample isolated from the subject, wherein the method is based on the criterion that a subject is more likely to develop cancer, is affected with cancer, or has progressed cancer when the fusion polypeptide is detected;
[24] a method for testing cancer susceptibility of a subject, whether a subject is affected with cancer, or whether cancer has progressed in a subject by determining the presence or absence of a polynucleotide encoding the fusion polypeptide of any of [1] to [7] described above in a sample isolated from the subject, wherein the method is based on the criterion that a subject is more likely to develop cancer, is affected with cancer, or has progressed cancer when the polynucleotide encoding the fusion polypeptide is detected;
[25] the method of [23] or [24] described above, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;
[26] a method for selecting a patient to which an anticancer agent comprising a compound having FGFR inhibitory activity or a pharmaceutically acceptable salt thereof is applicable, which comprises the steps of:
  (a) determining the presence or absence of the fusion polypeptide of any of [1] to [7] described above in a sample isolated from a subject; and
  (b) selecting a patient confirmed to have the fusion polypeptide as a patient to which the anticancer agent is applicable;
[27] a method for selecting a patient to which an anticancer agent comprising a compound having FGFR inhibitory activity or a pharmaceutically acceptable salt thereof is applicable, which comprises the steps of:
  (a) determining the presence or absence of a polynucleotide encoding the fusion polypeptide of any of [1] to [7] described above in a sample isolated from a subject; and
  (b) selecting a patient confirmed to have a polynucleotide encoding the fusion polypeptide as a patient to which the anticancer agent is applicable;
[28] the method of [26] or [27] described above, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;
[29] the method of any of [26] to [28] described above, wherein the compound having FGFR inhibitory activity or a pharmaceutically acceptable salt thereof is any one of the compounds or a pharmaceutically acceptable salt thereof represented by:

[Compound 1]

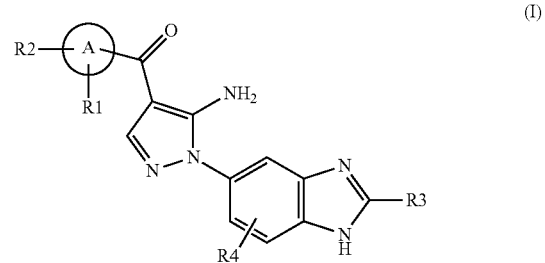

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P> halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R$_{16}$, —CN, —NO$_2$, and 3- to 10-membered heterocyclyl;

<Group Q> halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, and 3- to 10-membered heterocyclyl which is optionally substituted by $C_{1-4}$ alkyl.

[Compound 2]

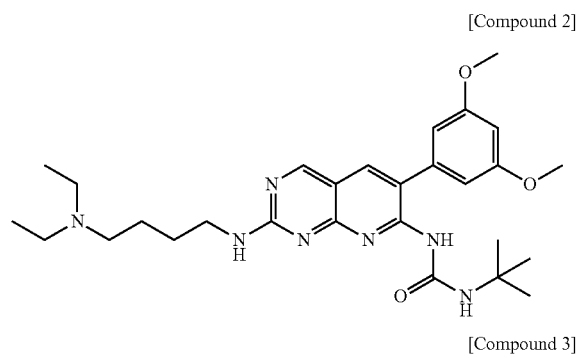

[Compound 3]

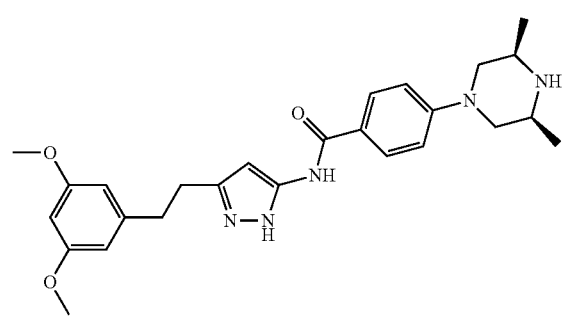

[Compound 4]

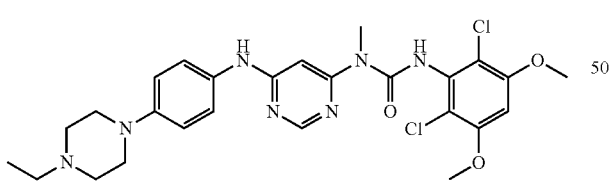

[Compound 5]

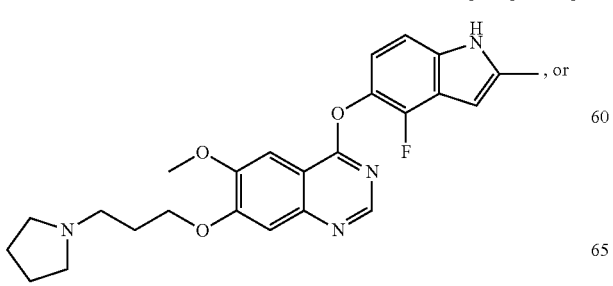, or

[Compound 6]

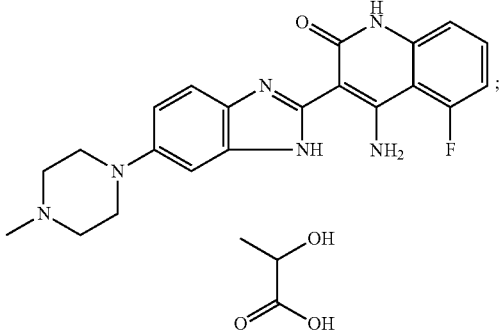

[30] the method of [29] described above, wherein the compound having FGFR inhibitory activity or a pharmaceutically acceptable salt thereof is a compound of formula (I), wherein A is indole, and $R_3$ and $R_4$ are both hydrogen, or a pharmaceutically acceptable salt thereof;

[31] a pharmaceutical composition for cancer treatment, which comprises a compound having FGFR inhibitory activity or a pharmaceutically acceptable salt thereof and is used in such a manner that the compound or a pharmaceutically acceptable salt thereof is administered to a patient who expresses the fusion polypeptide of any of [1] to [7] described above or has a polynucleotide that encodes the fusion polypeptide;

[32] the pharmaceutical composition of [31] described above for cancer treatment, wherein the patient is selected by the method of any of [26] to [30] described above;

[33] the pharmaceutical composition of [31] or [32] described above for cancer treatment, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;

[34] the pharmaceutical composition of [31] or [32] described above for cancer treatment, wherein the cancer is bladder cancer;

[35] the pharmaceutical composition of [34] described above for cancer treatment, wherein the bladder cancer is classified as stage 3 or later according to TNM classification;

[36] the pharmaceutical composition of any of [31] to [35] for cancer treatment, wherein the compound having FGFR inhibitory activity or a pharmaceutically acceptable salt thereof is any one of the compounds or a pharmaceutically acceptable salt thereof represented by:

[Compound 1]

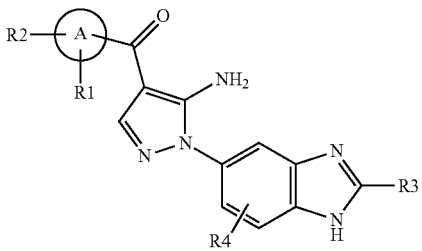

(I)

wherein $R_1$, $R_2$, $R_3$, and $R_4$ each independently represents the group listed below:

R₁ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —OR₅, —NR₆R₇, —(CR₈R₉)ₙZ₁, —C(O)NR₁₂R₁₃, —SR₁₄, —SOR₁₅, —SO₂R₁₆, —NR₁₇SO₂R₁₈, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —COR₁₉, —COOR₂₀, —OC(O)R₂₁, —NR₂₂C(O)R₂₃, —NR₂₄C(S)R₂₅, —C(S)NR₂₆R₂₇, —SO₂NR₂₈R₂₉, —OSO₂R₃₀, —SO₃R₃₁, or —Si(R₃₂)₃;

R₂ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —OR₅, —NR₆R₇, —(CR₈R₉)ₙZ₁, —C(O)NR₁₂R₁₃, —SR₁₄, —SOR₁₅, —SO₂R₁₆, —NR₁₇SO₂R₁₈, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —COR₁₉, —COOR₂₀, —OC(O)R₂₁, —NR₂₂C(O)R₂₃, —NR₂₄C(S)R₂₅, —C(S)NR₂₆R₂₇, —SO₂NR₂₈R₂₉, —OSO₂R₃₀, —SO₃R₃₁, or —Si(R₃₂)₃; or R₁ and R₂, together with an atom linked thereto, form 3- to 10-membered heterocyclyl or 5- to 10-membered heteroaryl, wherein the heterocyclyl or heteroaryl is optionally substituted by halogen;

R₃ represents hydrogen, $C_{1-5}$ alkyl, $C_{6-10}$ aryl $C_{1-6}$ alkyl, or $C_{1-4}$ haloalkyl;

R₄ represents hydrogen, halogen, $C_{1-3}$ alkyl, $C_{1-4}$ haloalkyl, hydroxy, cyano, nitro, $C_{1-4}$ alkoxy, —(CH₂)ₙZ₁, —NR₆R₇, —OR₅, —C(O)NR₁₂R₁₃, —SR₁₄, —SOR₁₅, —SO₂R₁₆, NR₁₇SO₂R₁₈, COOH, —COR₁₉, —COOR₂₀, —OC(O)R₂₁, —NR₂₂C(O)R₂₃, —NR₂₄C(S)R₂₅, —C(S)NR₂₆R₂₇, —SO₂NR₂₈R₂₉, —OSO₂R₃₀, —SO₃R₃₁, or —Si(R₃₂)₃;

A represents a 5- to 10-membered heteroaryl ring or $C_{6-10}$ aryl ring;

R₅ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

R₆ and R₇, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively R₆ and R₇, together with a nitrogen atom linked thereto, form 3- to 10-membered heterocyclyl or 5- to 10-membered heteroaryl;

n represents 1 to 3;

R₈ and R₉, which can be the same or different, each represents hydrogen, $C_{1-4}$ alkyl, or halogen; or alternatively R₈ and R₉, together with a carbon atom linked thereto, form a cycloaliphatic ring;

Z₁ represents hydrogen, NR₁₀R₁₁, —OH, or 3- to 10-membered heterocyclyl or 5- to 10-membered heteroaryl which is optionally substituted by one or more groups independently selected from group Q;

R₁₀ and R₁₁, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively R₁₀ and R₁₁, together with a nitrogen atom linked thereto, form 3- to 10-membered heterocyclyl or 5- to 10-membered heteroaryl;

R₁₂ and R₁₃, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively R₁₂ and R₁₃, together with a nitrogen atom linked thereto, form 3- to 10-membered heterocyclyl or 5- to 10-membered heteroaryl which is optionally substituted by one or more groups independently selected from group Q;

R₁₄ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R₁₅ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R₁₆ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R₁₇ represents hydrogen or $C_{1-4}$ alkyl;

R₁₈ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

R₁₉ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

R₂₀ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

R₂₁ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

R₂₂ represents hydrogen, $C_{1-4}$ alkyl, or $C_{1-4}$ haloalkyl;

R₂₃ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

R₂₄ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P>
halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<Group Q>
halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl which is optionally substituted by $C_{1-4}$ alkyl.

[Compound 2]

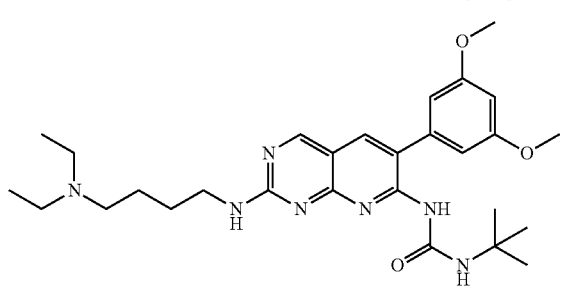

[Compound 3]

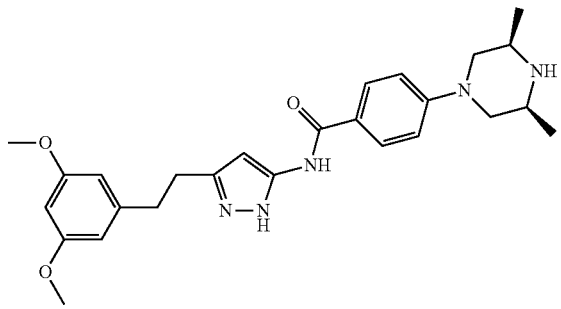

[Compound 4]

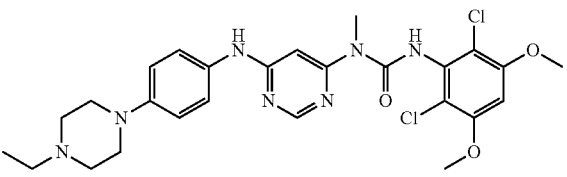

[Compound 5]

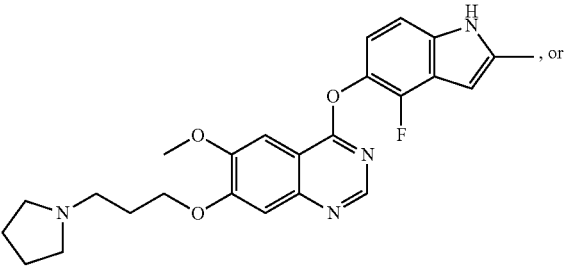

, or

[Compound 6]

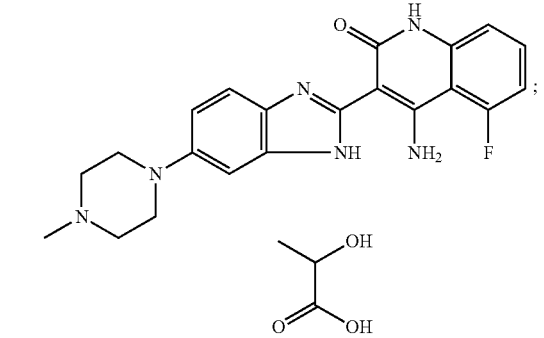

;

[37] the pharmaceutical composition of [36] described above for cancer treatment, wherein the compound having FGFR inhibitory activity or a pharmaceutically acceptable salt thereof is a compound of formula (I), wherein A is indole, and $R_3$ and $R_4$ are both hydrogen, or a pharmaceutically acceptable salt thereof;

[38] a method for treating or preventing cancer, comprising the step of administering an effective amount of a compound having FGFR inhibitory activity or a pharmaceutically acceptable salt thereof to a cancer patient expressing the fusion polypeptide of any of [1] to [7] described above or carrying a polynucleotide encoding the fusion polypeptide;

[39] the method of [38] described above, wherein the patient is selected by the method of any of [26] to [30] described above;

[40] the method of [38] or [39] described above, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;

[41] the method of [38] or [39] described above, wherein the cancer is bladder cancer;

[42] the method of [41] described above, wherein the bladder cancer is classified as stage 3 or later according to TNM classification;

[43] the method of any of [38] to [42] described above, wherein the compound having FGFR inhibitory activity or a pharmaceutically acceptable salt thereof is any one of the compounds or a pharmaceutically acceptable salt thereof represented by:

[Compound 1]

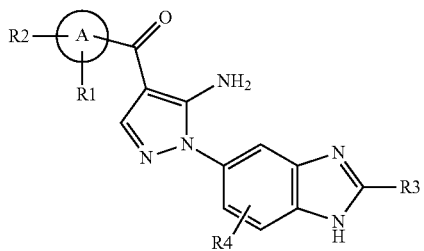

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P>
halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<Group Q>
halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl which is optionally substituted by $C_{1-4}$ alkyl.

[Compound 2]

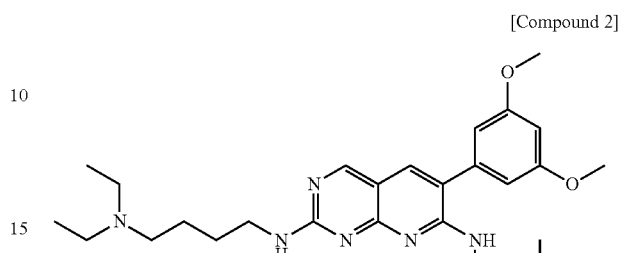

[Compound 3]

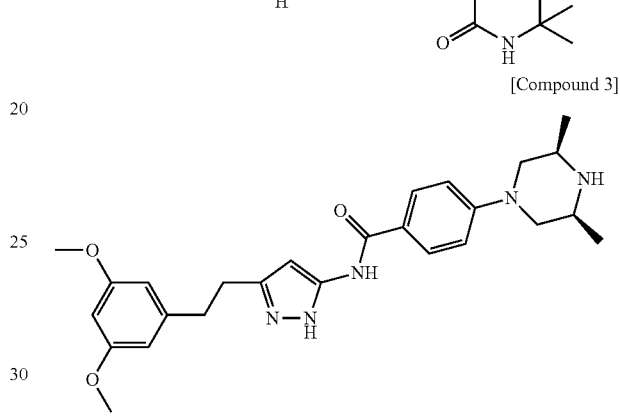

[Compound 4]

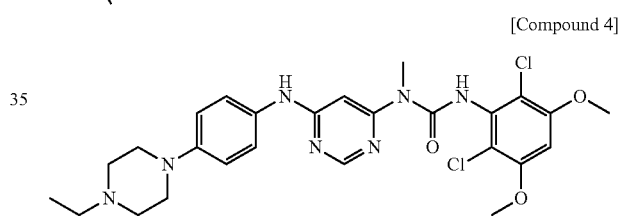

[Compound 5]

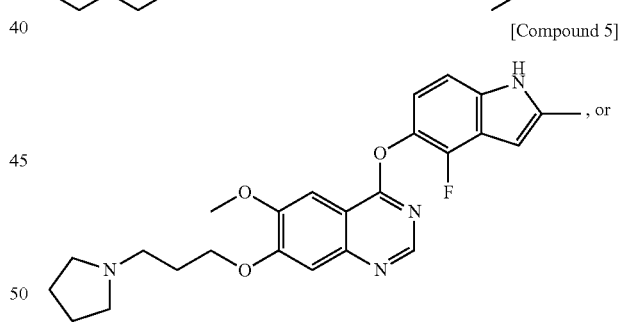

[Compound 6]

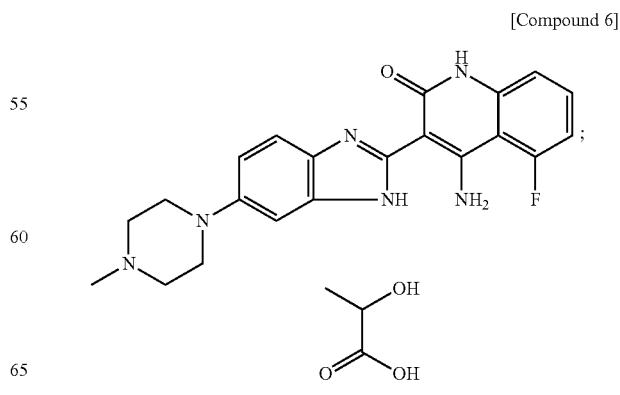

[44] the method of [43] described above, wherein the compound having FGFR inhibitory activity or a pharmaceutically acceptable salt thereof is a compound of formula (I), wherein A is indole, and $R_3$ and $R_4$ are both hydrogen, or a pharmaceutically acceptable salt thereof;

[45] use of a compound having FGFR inhibitory activity or a pharmaceutically acceptable salt thereof in the manufacture of a pharmaceutical composition for cancer treatment to be administered to a patient expressing the fusion polypeptide of any of [1] to [7] described above or carrying a polynucleotide encoding the fusion polypeptide;

[46] the use of [45] described above, wherein the patient is selected by the method of any of [26] to [30] described above;

[47] the use of [45] or [46] described above, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;

[48] the use of [45] or [46] described above, wherein the cancer is bladder cancer;

[49] the use of [48] described above, wherein the bladder cancer is classified as stage 3 or later according to TNM classification;

[50] the use of any of [45] to [49] described above, wherein the compound having FGFR inhibitory activity or a pharmaceutically acceptable salt thereof is any one of the compounds or a pharmaceutically acceptable salt thereof represented by:

[Compound 1]

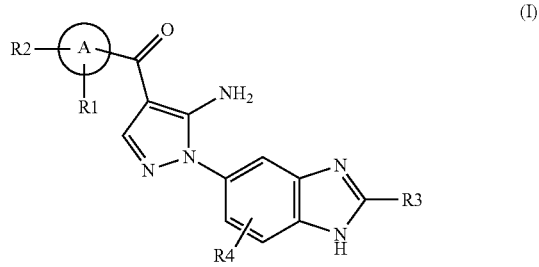

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring; $Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P> halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R$_{16}$, —CN, —NO$_2$, and 3- to 10-membered heterocyclyl;

<Group Q> halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, and 3- to 10-membered heterocyclyl which is optionally substituted by $C_{1-4}$ alkyl.

[Compound 2]

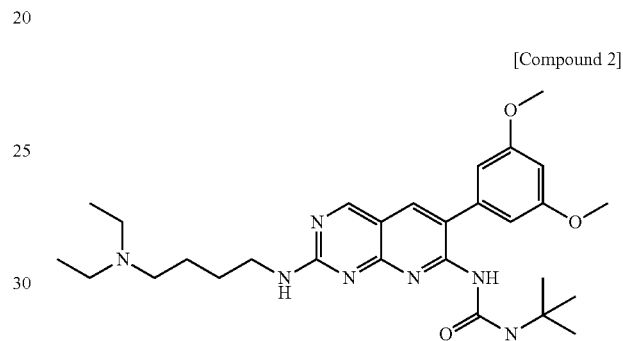

[Compound 3]

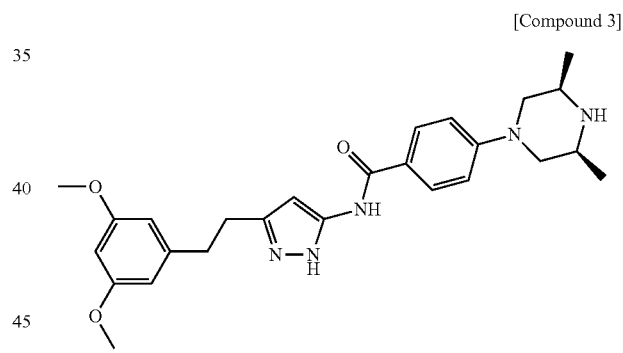

[Compound 4]

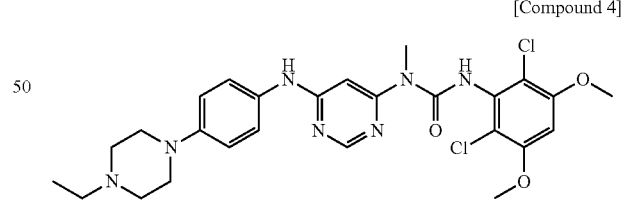

[Compound 5]

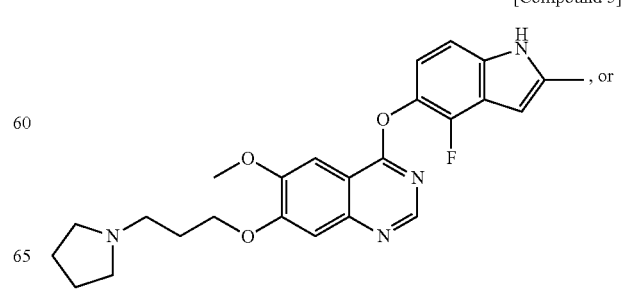

, or

[Compound 6]

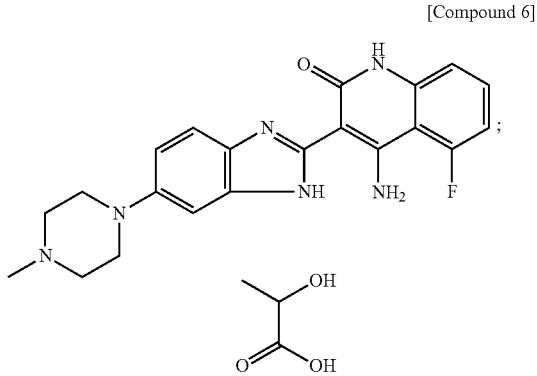

[51] the use of [50] described above, wherein the compound having FGFR inhibitory activity or a pharmaceutically acceptable salt thereof is a compound of formula (I), wherein A is indole, and $R_3$ and $R_4$ are both hydrogen, or a pharmaceutically acceptable salt thereof;

[52] a compound having FGFR inhibitory activity or a pharmaceutically acceptable salt thereof for therapeutic or prophylactic use in a cancer patient expressing the fusion polypeptide of any of [1] to [7] described above or carrying a polynucleotide encoding the fusion polypeptide;

[53] the compound or a pharmaceutically acceptable salt thereof of [52] described above, wherein the patient is selected by the method of any of [26] to [30] described above;

[54] the compound or a pharmaceutically acceptable salt thereof of [52] or [53] described above, wherein the cancer is bladder cancer, brain tumor, head and neck squamous cell carcinoma, lung cancer, lung adenocarcinoma, lung squamous cell carcinoma, skin melanoma, esophageal cancer, gastric cancer, or liver cancer;

[55] the compound or a pharmaceutically acceptable salt thereof of [52] or [53] described above, wherein the cancer is bladder cancer;

[56] the compound or a pharmaceutically acceptable salt thereof of [55] described above, wherein the bladder cancer is classified as stage 3 or later according to TNM classification;

[57] the compound or a pharmaceutically acceptable salt thereof of any of [52] to [56] described above, wherein the compound having FGFR inhibitory activity or a pharmaceutically acceptable salt thereof is any one of the compounds or a pharmaceutically acceptable salt thereof represented by:

[Compound 1]

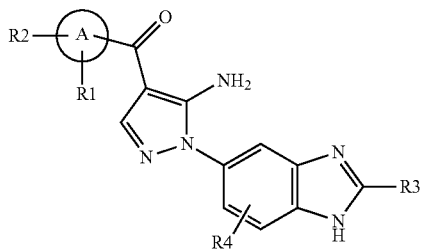

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring; $Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P>
halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R$_{16}$, —CN, —NO$_2$, and 3- to 10-membered heterocyclyl;

<Group Q>
halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —SO$_2$R$_{16}$, —CN, —NO$_2$, $C_{3-7}$ cycloalkyl, —COR$_{19}$, and 3- to 10-membered heterocyclyl which is optionally substituted by $C_{1-4}$ alkyl.

[Compound 2]

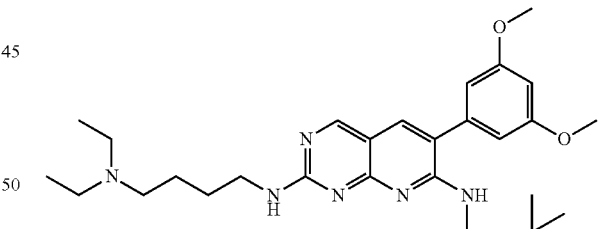

[Compound 3]

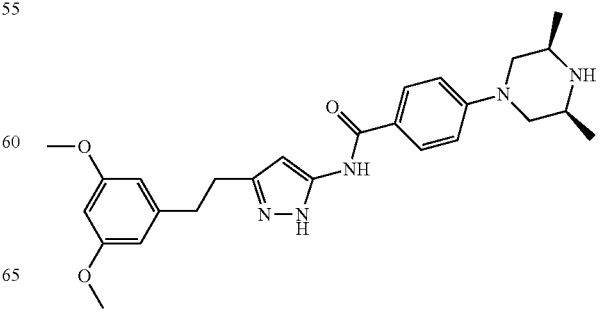

-continued

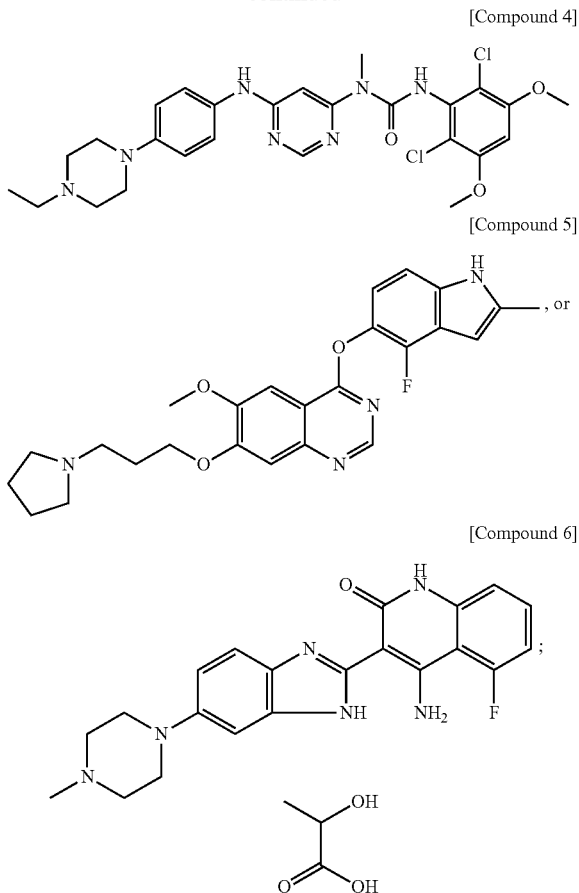

[Compound 4]

[Compound 5]

[Compound 6]

[58] the compound a pharmaceutically acceptable salt thereof of [57] described above, wherein the compound having FGFR inhibitory activity or a pharmaceutically acceptable salt thereof is a compound of formula (I), wherein A is indole, and $R_3$ and $R_4$ are both hydrogen, or a pharmaceutically acceptable salt thereof;
[59] a method for identifying a compound having FGFR inhibitory activity, which comprises the steps of:
  (a) culturing a cell that expresses the fusion polypeptide of any of [1] to [7] described above in the presence or absence of a test compound and determining the level of cell proliferation;
  (b) comparing the proliferation level of the cultured cell between in the presence and absence of the test compound; and
  (c) judging that the test compound has FGFR inhibitory activity when the proliferation level of the cell cultured in the presence of the test compound is lower than that of the cell cultured in the absence of the test compound;
[60] a method for identifying a compound having FGFR inhibitory activity, which comprises the steps of:
  (a) administering a test compound to a non-human mammal transplanted with a cell that expresses the fusion polypeptide of any of [1] to [7] described above and determining the proliferation level of the cell;
  (b) comparing the cell proliferation level determined in step (a) with that determined using a non-human mammal transplanted with the cell but not administered with the test compound; and
  (c) judging that the test compound has FGFR inhibitory activity when the cell proliferation level determined in step (a) is lower than that determined using a non-human mammal transplanted with the cell but not administered with the test compound;
[61] the method of [59] or [60] described above, wherein the cell is a cancer cell; and
[62] the method of [61] described above, wherein the cancer cell is a bladder cancer cell, brain tumor cell, head and neck squamous cell carcinoma cell, lung cancer cell, lung adenocarcinoma cell, lung squamous cell carcinoma cell skin melanoma cell, esophageal cancer cell, gastric cancer cell, or liver cancer cell.

Effects of the Invention

Fusion polypeptides of the present invention comprising an FGFR3 polypeptide and another polypeptide are expressed specifically in various types of cancer cells including bladder cancer cells. The proliferation of cells expressing such fusion polypeptides is significantly inhibited by compounds having FGFR inhibitory activity. Thus, use of a fusion polypeptide of the present invention as a biomarker for FGFR inhibitor-based cancer therapy enables one to assess the applicability and mode of use of an FGFR inhibitor for individual patients, and enables one to avoid side effects and control the mode of treatment to produce the best therapeutic effect in the FGFR inhibitor-based therapy. This enables personalized medicine.

In addition, the use of fusion polypeptides of the present invention as a target in developing cancer therapeutic agents targeting FGFR, i.e., molecularly targeted drugs, makes it possible to provide FGFR inhibitors with high levels of specificity and antitumor activity against target cancer cells as well as cancer therapeutic agents comprising the inhibitors.

FGFR inhibitors obtained as described above have high specificity towards target cancer cells, and it becomes possible to provide cancer therapeutic agents with great antitumor activity and few side effects.

Furthermore, fusion polypeptides of the present invention have a close correlation to various types of cancers, and thus the likelihood of developing cancer (cancer susceptibility) of a subject, whether a subject is affected with cancer, or whether cancer has progressed in a subject can be tested by determining whether samples from the subject, which is not limited to cancer patients but also includes healthy persons, contain the fusion polypeptide of the present invention or a polynucleotide encoding the fusion polypeptide.

In addition, fusion polypeptides of the present invention have a close correlation to various types of cancers. Thus, by identifying a test compound that suppresses proliferation of cells (such as cancer cells) which express the fusion polypeptides of the present invention, it becomes possible to provide FGFR inhibitors with high FGFR specificity, and this can be done by comparing the level of cell proliferation between in the presence and absence of the test compound.

using cDNAs derived from bladder cancer samples collected from bladder cancer patients (20 patients) and cDNAs synthesized from RT4 RNA.

Figure 3:
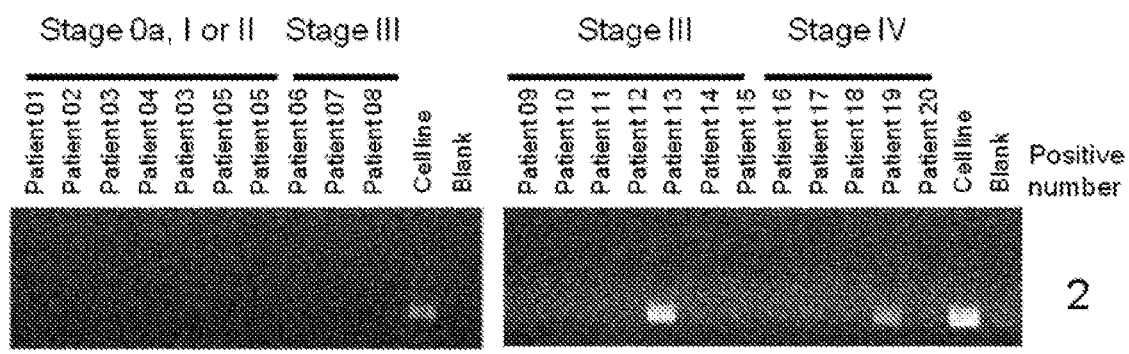

FIG. 3 is a photograph showing results on amplification of a polynucleotide encoding the FGFR3-BAIAP2L1 polypeptide, as tested by polymerase chain reaction (PCR) using cDNAs derived from bladder cancer samples collected from bladder cancer patients (20 patients) and cDNAs synthesized from SW780 RNA.

Figure 4:
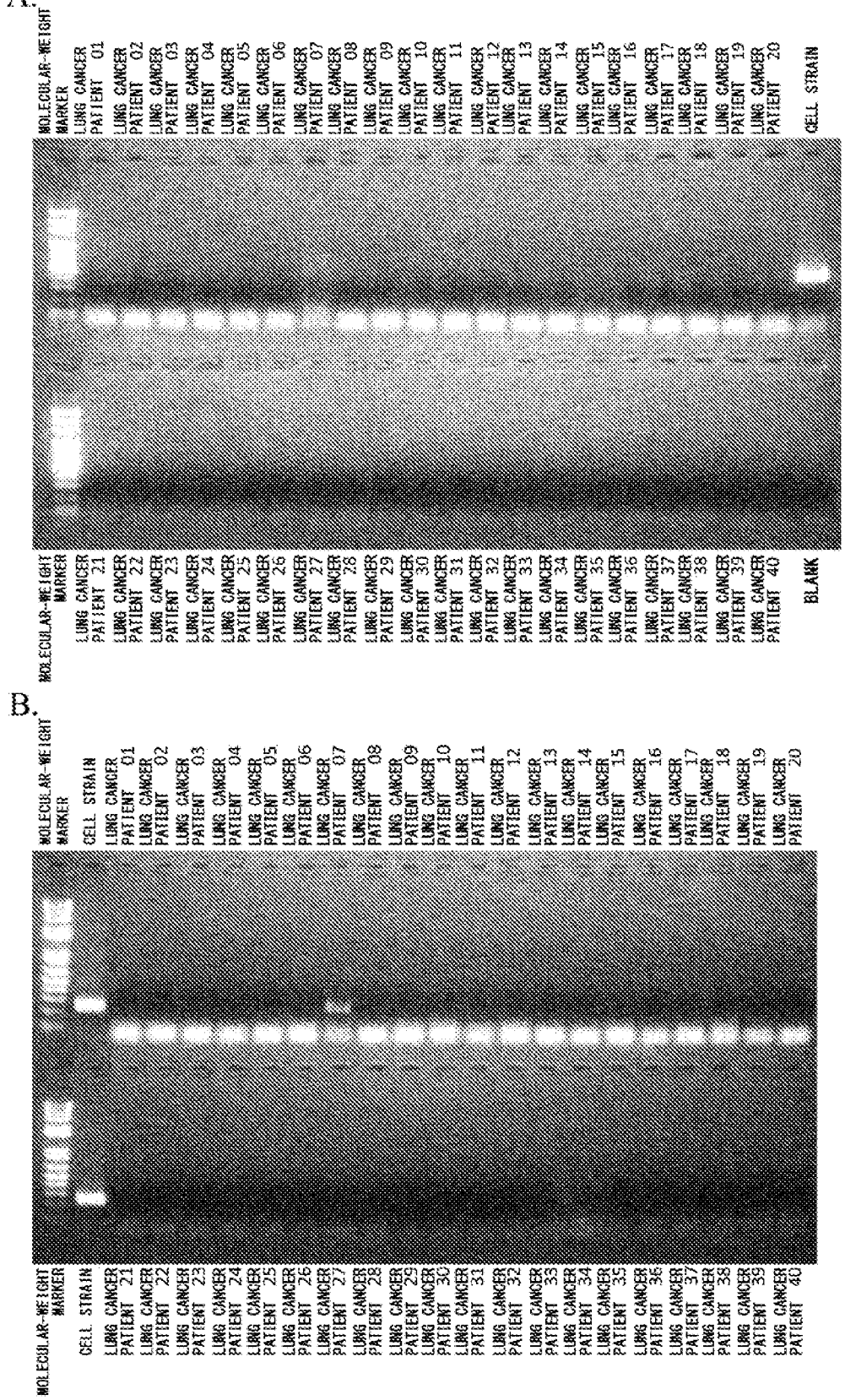

FIG. 4 is a photograph showing results on amplification of a polynucleotide encoding the FGFR3-BAIAP2L1 polypeptide, as tested by polymerase chain reaction (PCR) using cDNAs derived from lung cancer samples collected from lung cancer patients (40 patients) and cDNA synthesized from SW780 RNA.

View A shows a result of the test using a pair of oligonucleotide primers (SEQ ID NOs: 3 and 4). The leftmost lanes on the top and bottom gels show the results for molecular-weight markers.

View B shows a result of the test using a pair of oligonucleotide primers (SEQ ID NOs: 17 and 18).

The leftmost lanes on the top and bottom gels show the results for molecular-weight markers.

Figure 5:
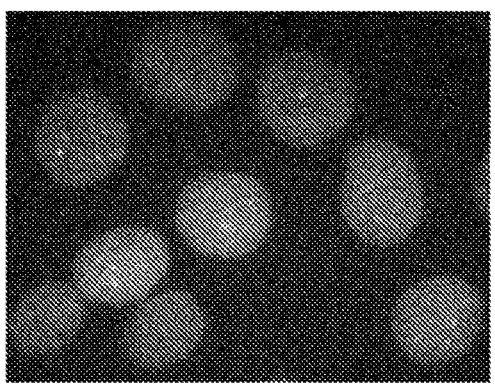
Figure 5:
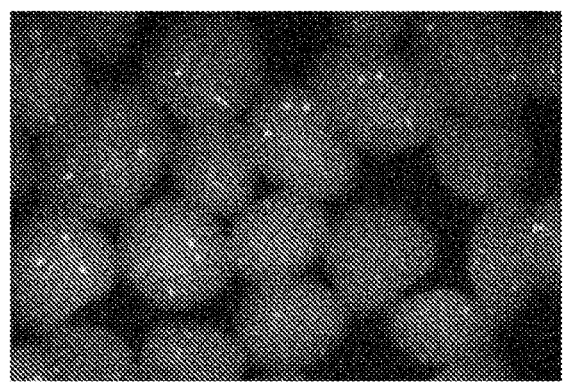
Figure 5:
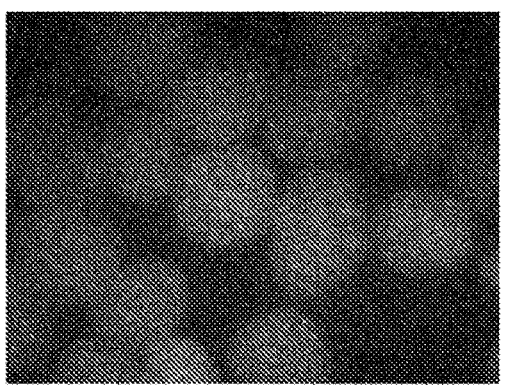
Figure 5:
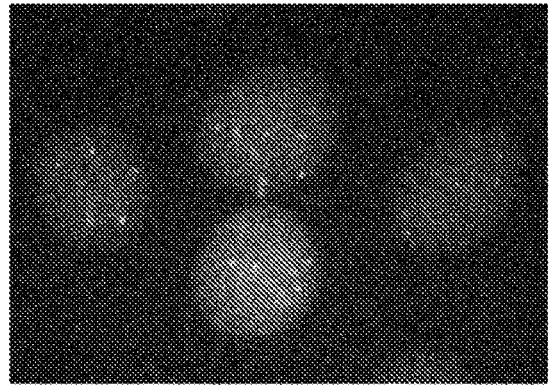

FIG. 5 is a photograph showing results of detecting a polynucleotide encoding a FGFR3-BAIAP2L1 polypeptide in various types of bladder cancer cell lines tested by FISH analysis.

View A1 shows a test result of the RT112/84 cell line using a split-signal probe.

View A2 shows a test result of the SW780 cell line using a split-signal probe.

View B1 shows a test result of the RT112/84 cell line using a fusion-signal probe.

View B2 shows a test result of the SW780 cell line using a fusion-signal probe.

Figure 6:
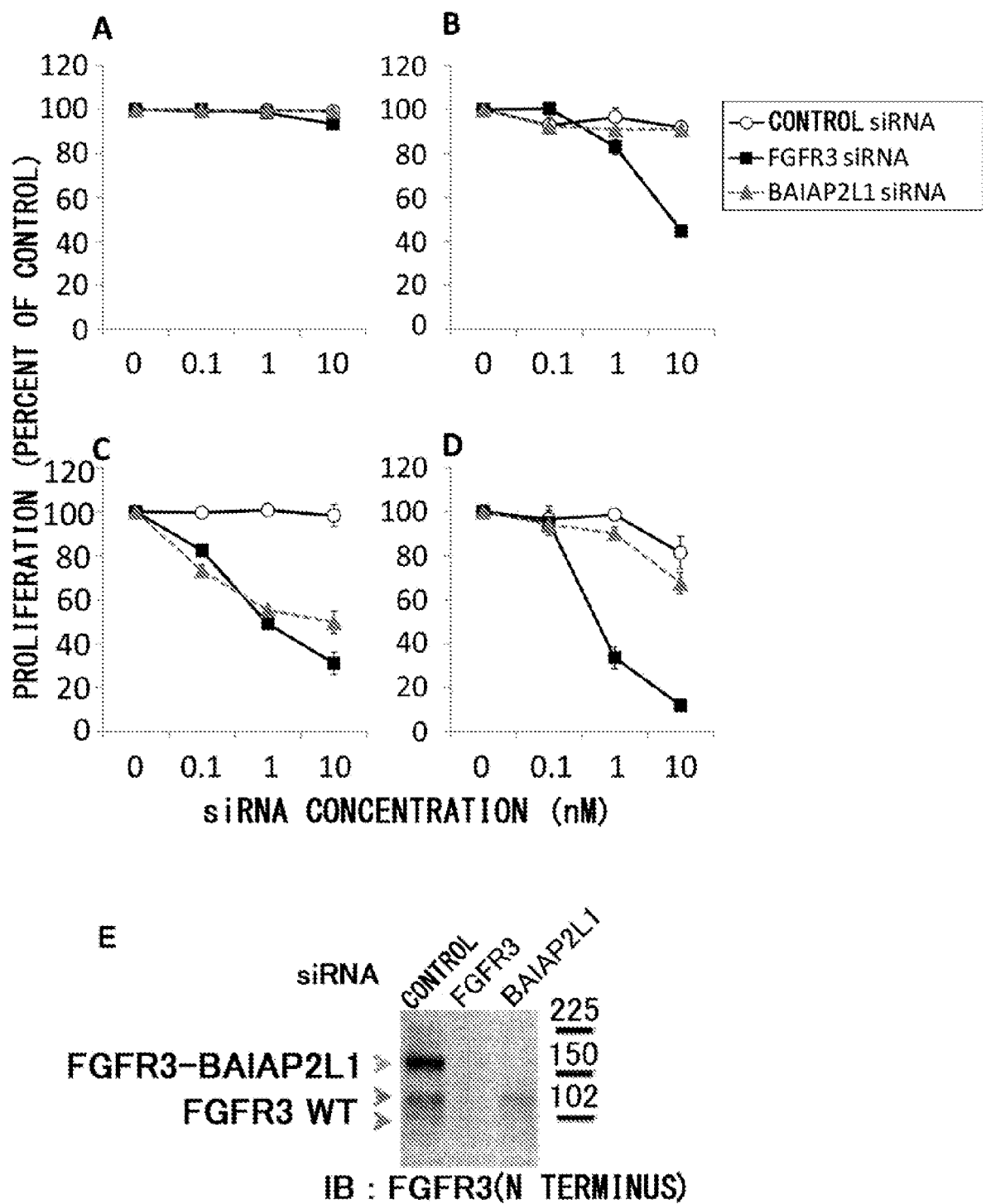

FIG. 6 shows results of testing the presence or absence of FGFR3 dependency in the proliferation of various bladder cancer cell lines using siRNA against FGFR3 or BAIAP2L1.

View A shows a result of the test using the BFTC-905 cell line.

View B shows a result of the test using the UM-UC-14 cell line.

View C shows a result of the test using the RT4 cell line.

View D shows a result of the test using the SW780 cell line.

Figure 7:
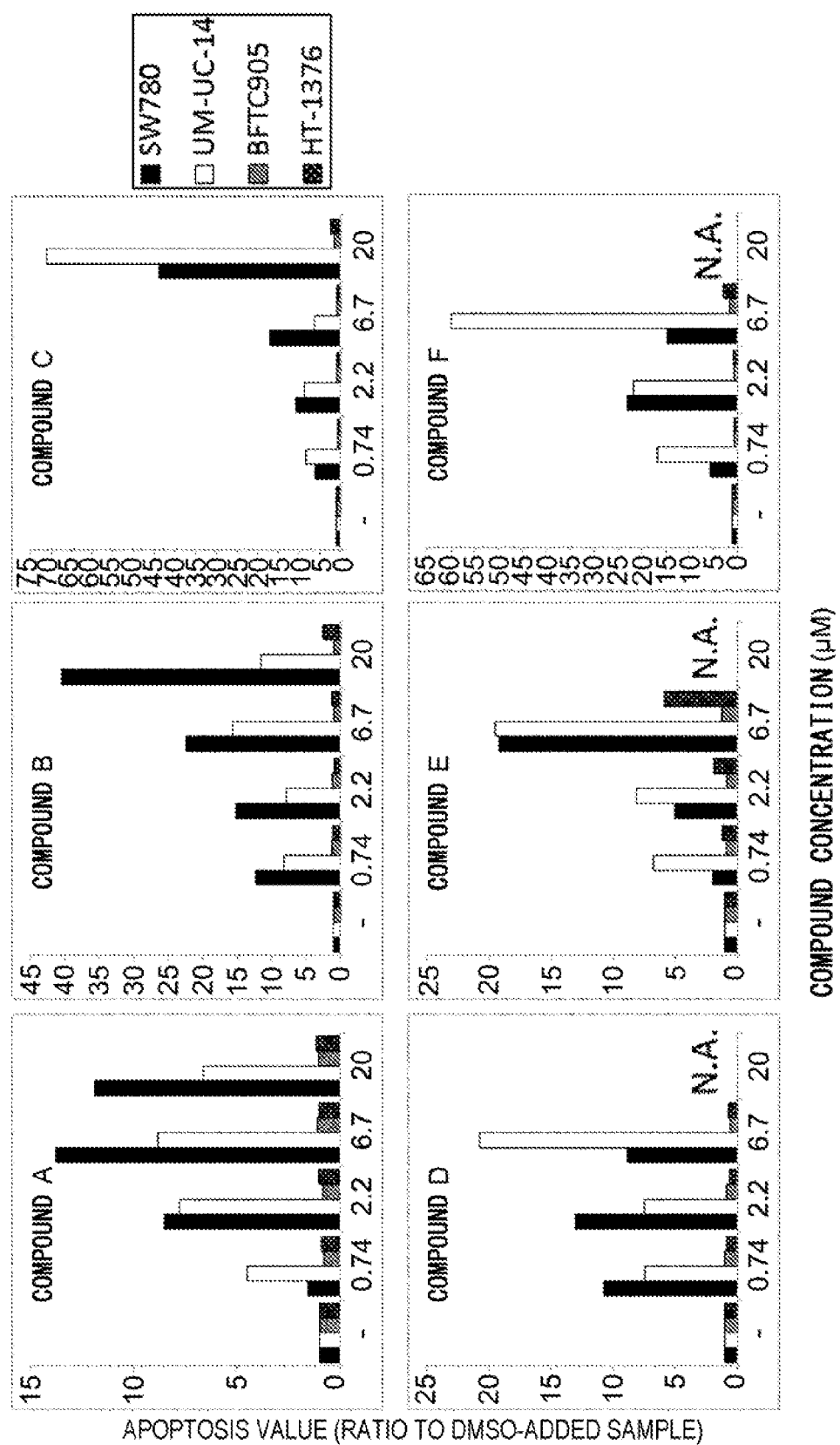

FIG. 7 shows results of testing the effect of FGFR inhibitors in inducing apoptosis in various cancer cells expressing the FGFR3-BAIAP2L1 fusion polypeptide.

Figure 8:
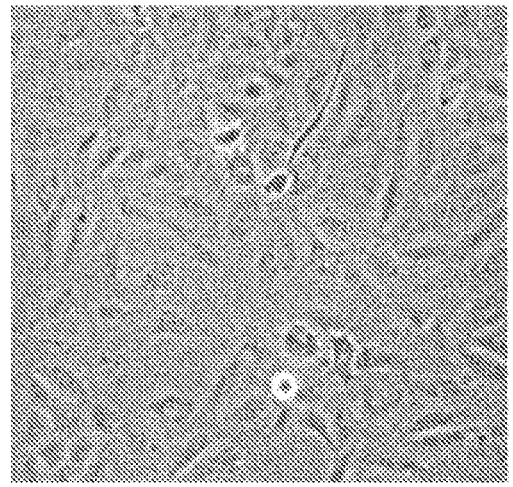
Figure 8:
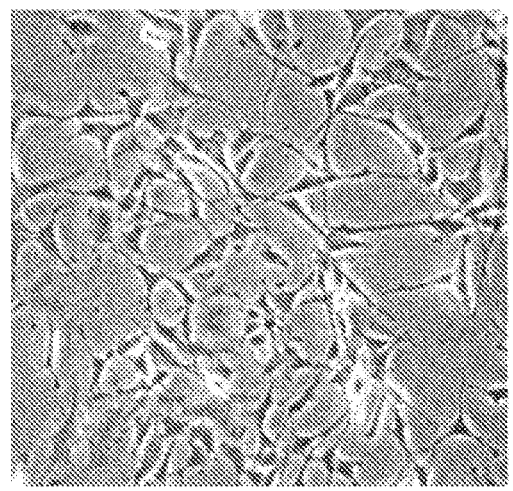

FIG. 8 shows results of examining the ability of the FGFR3-BAIAP2L1 fusion polypeptide to transform normal cells by testing the cells in monolayer culture.

The upper figure shows a result of wild-type FGFR3-expressing cells in monolayer culture.

The lower figure shows a result of FGFR3-BAIAP2L1 fusion polypeptide-expressing cells in monolayer culture.

Figure 9:
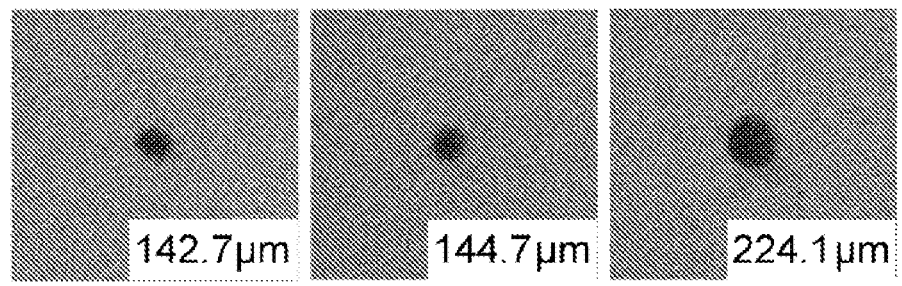
Figure 9:
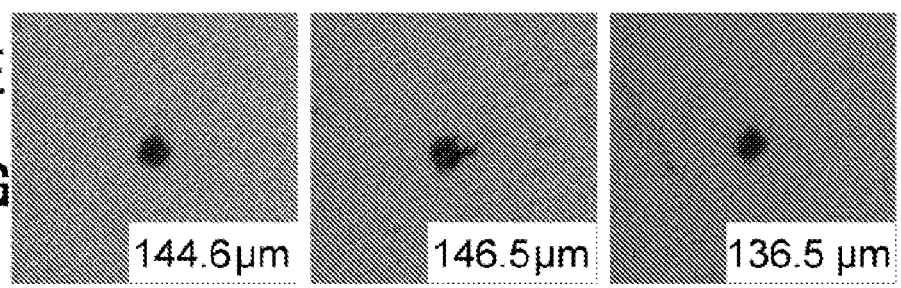
Figure 9:
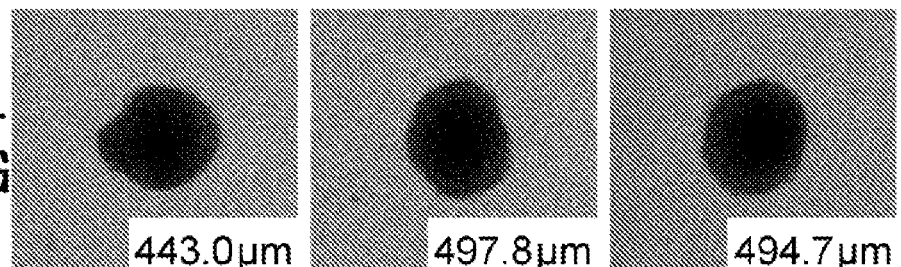

FIG. 9 shows results of examining the transforming ability and tumorigenic ability of the FGFR3-BAIAP2L1 fusion polypeptide in normal cells by testing the cells in spheroid culture.

The upper row photographs show results of culturing the untreated parent cells.

The middle row photographs show results of culturing the wild-type FGFR3-expressing cells.

The lower row photographs show results of culturing the FGFR3-BAIAP2L1 fusion polypeptide-expressing cells.

Figure 10:
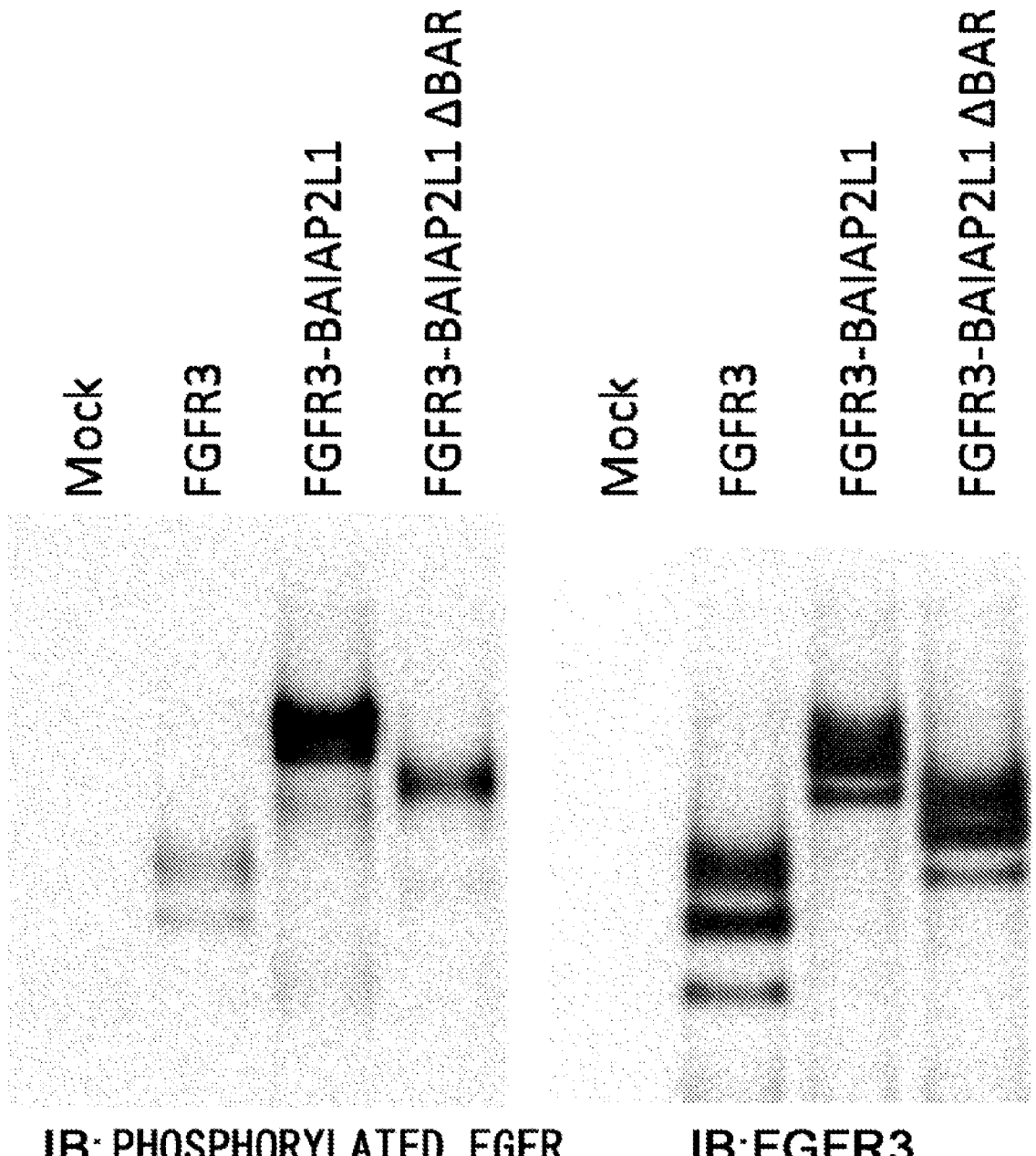

FIG. 10 presents photographs showing results of examining the ability of the FGFR3-BAIAP2L1 fusion polypeptide to transform normal cells and the contribution of BAIAP2L1 to the transforming ability, by performing tests using the autophosphorylation ability of FGFR3 as an indicator.

Figure 11:
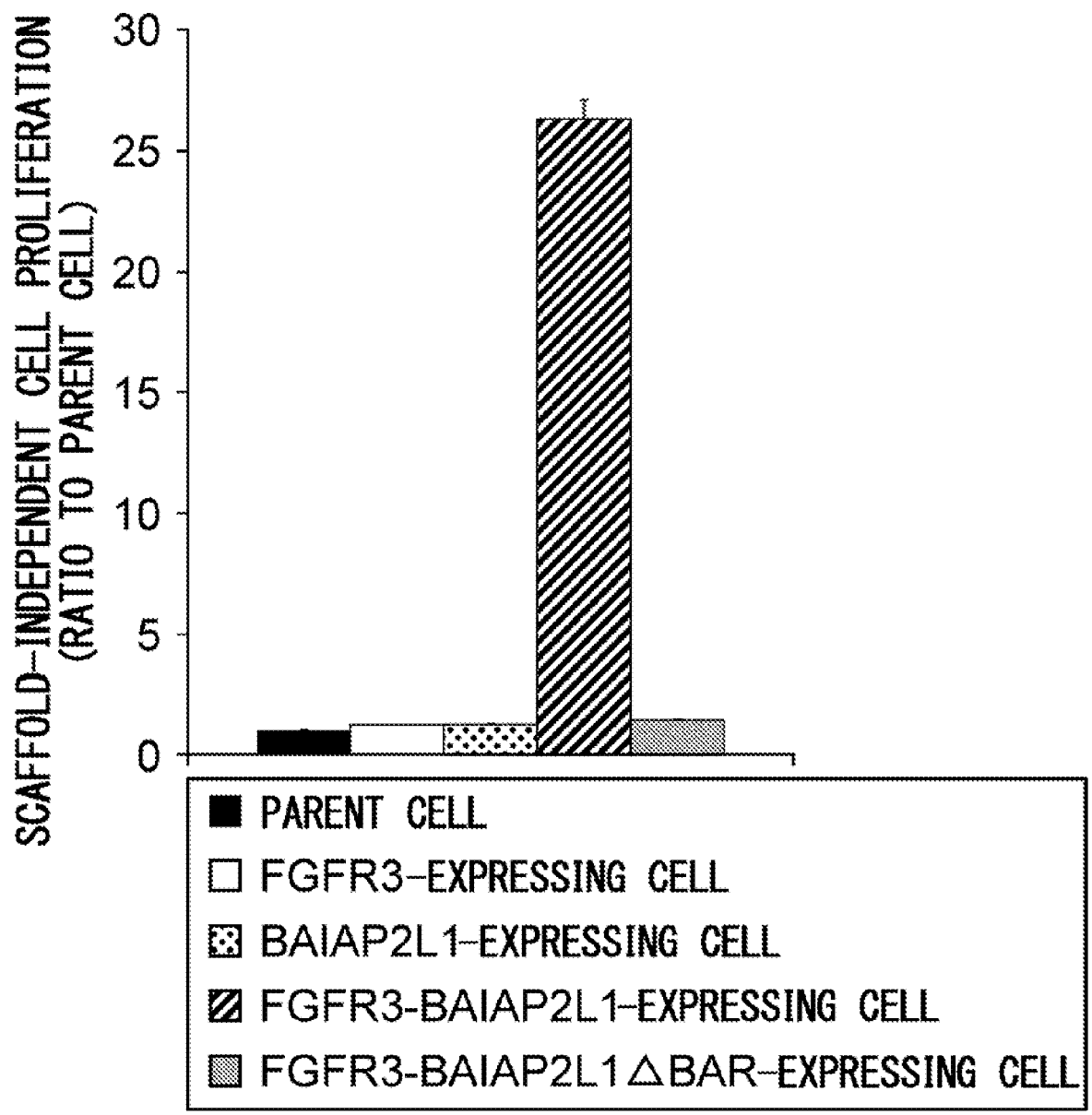

FIG. 11 shows a result of examining the ability of the FGFR3-BAIAP2L1 fusion polypeptide to transform normal cells and the contribution of BAIAP2L1 to the transforming ability, by performing tests using scaffold-independent cell proliferation as an indicator.

Figure 12:
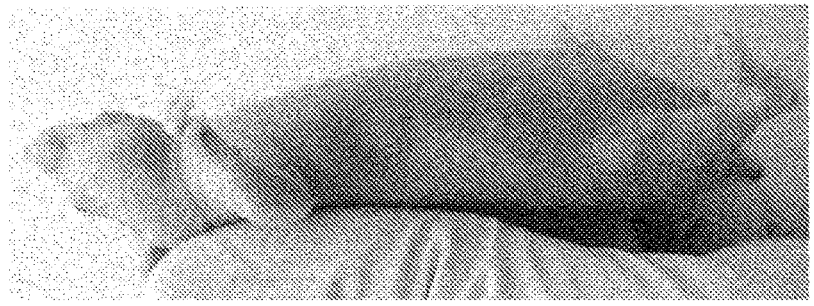
Figure 12:
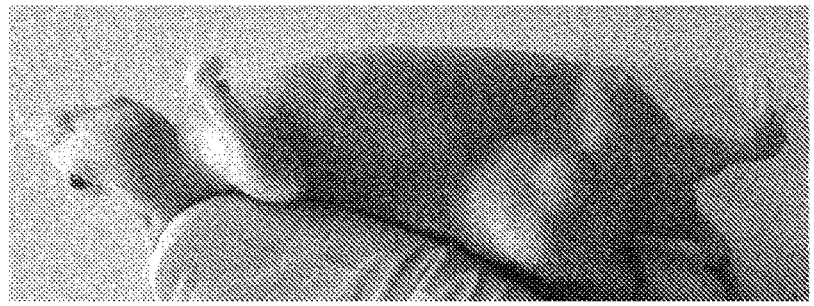
Figure 12:
Figure 12:
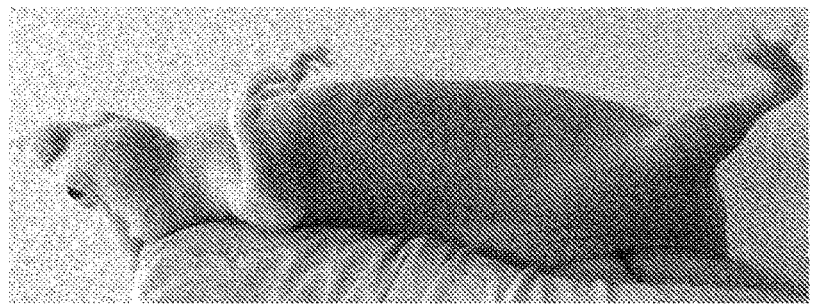

FIG. 12 shows results of examining the in vivo tumorigenic ability of the FGFR3-BAIAP2L1 fusion polypeptide by performing tests using nude mice.

In order from the left, the states 15 days after inoculating subcutaneously to the inguinal region of nude mice, wild-type FGFR3-expressing cells, wild-type BAIAP2L1-expressing cells, FGFR3-BAIAP2L1 fusion polypeptide-expressing cells, and cells expressing a fusion polypeptide of FGFR3 and a BAR-domain-deficient BAIAP2L1, respectively, are shown.

Figure 13:
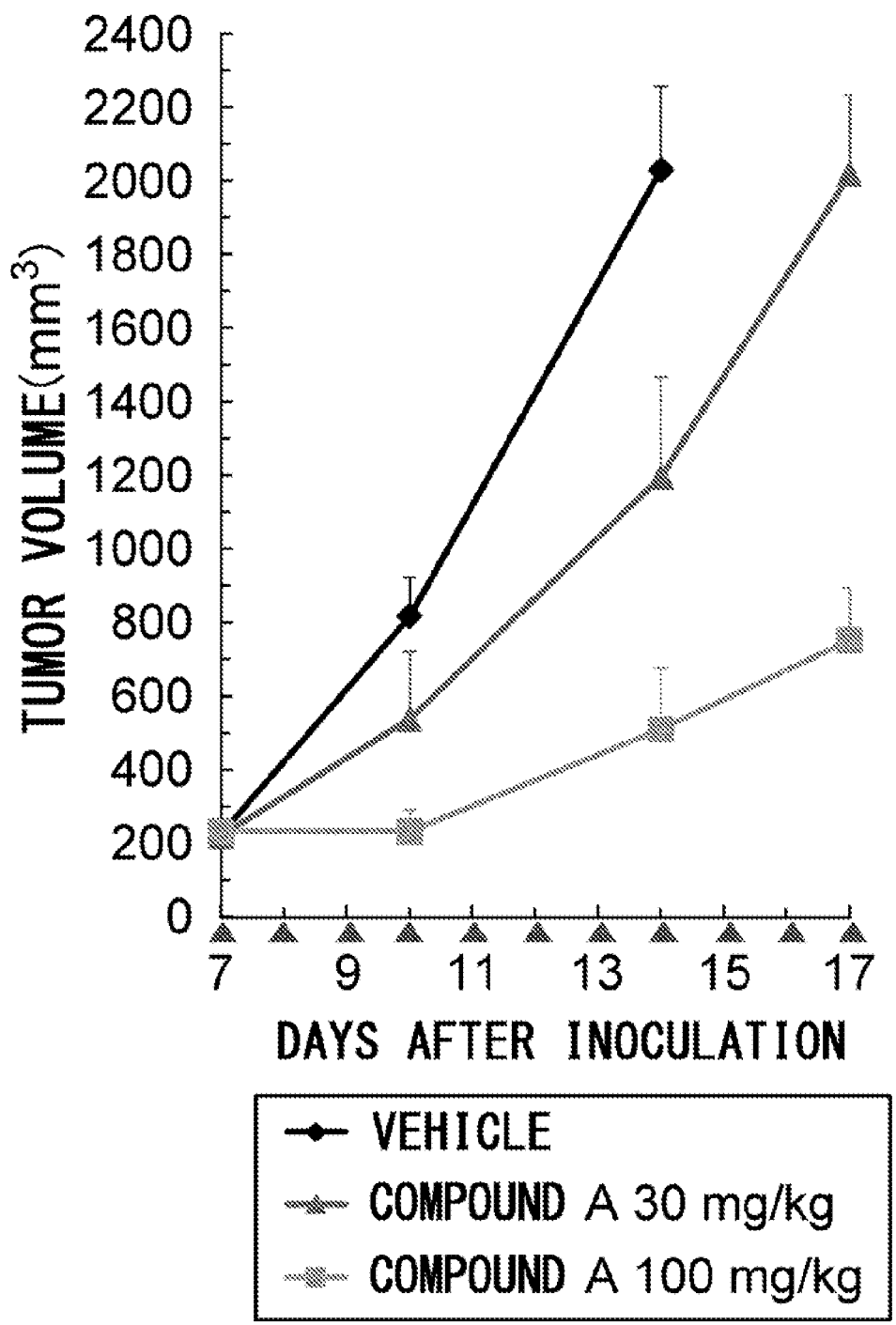

FIG. 13 shows a result of examining the tumor-growth-inhibiting effect of the FGFR inhibitor on the in vivo tumor formation by a FGFR3-BAIAP2L1 fusion polypeptide by using nude mice for tests.

MODE FOR CARRYING OUT THE INVENTION

The present invention is as illustrated in [1] to [62] described above, and provides novel fusion polypeptides expressed in abnormal cells such as cancer cells; polynucleotides encoding the polypeptides; vectors comprising the polynucleotides; cells comprising the vectors; antibodies and fragments thereof which specifically bind to the polypeptides; oligonucleotide primers that hybridize to the polynucleotides; oligonucleotides that cleave the polynucleotides; pharmaceutical compositions comprising the antibodies or oligonucleotides; methods and kits for detecting the polynucleotides or fusion polypeptides; methods for testing cancer susceptibility, whether a subject is affected with cancer, or whether cancer has progressed based on the presence or absence of the polynucleotides or fusion polypeptides; methods for selecting cancer patients to which an FGFR inhibitor is applicable; pharmaceutical compositions for cancer treatment which are characterized by their use of being administered to patients expressing the fusion polypeptides or carrying the polynucleotides; methods for treating or preventing cancer which comprise the step of administering an effective amount of compounds having FGFR inhibitory activity or pharmaceutically acceptable salts thereof to patients expressing the fusion polypeptides or carrying the polynucleotides; use of compounds having FGFR inhibitory activity or pharmaceutically acceptable salts thereof in the production of pharmaceutical compositions for cancer treatment for administration to patients expressing the fusion polypeptides or carrying the polynucleotides; and compounds having FGFR inhibitory activity or pharmaceutically acceptable salts thereof for use in treatment or prevention for patients expressing the fusion polypeptides or carrying the polynucleotides.

In the present invention, "FGFR" refers to any FGFR belonging to the FGFR family comprising FGFR1, FGFR2, FGFR3, and FGFR4, which are fibroblast growth factor receptors (FGFRs) belonging to the receptor tyrosine kinase family (Cytokine & Growth Factor Reviews, 2005, 16: 139-149). FGFRs of the present invention may be of any origin, and are preferably FGFRs derived from mammals (humans, mice, rats, guinea pigs, rabbits, sheep, monkeys, goats, donkeys, bovines, horses, pigs, etc.), more preferably human FGFRs, and still more preferably human FGFR3 comprising the amino acid sequence of SEQ ID NO: 6 or 7 (cDNA sequences, SEQ ID NOs: 10 and 11, respectively/GenBank Accession Nos. NM_001163213.1 and NM_000142.4, respectively). The human FGFR3 gene locus is 4p16.3.

In the present invention, "human FGFR3" refers to a wild-type human FGFR3 polypeptide comprising the amino acid sequence of SEQ ID NO: 6 or 7, or a mutant polypeptide with a substitution, deletion, or insertion of one or more amino acids (preferably one to ten amino acids, and more preferably one to five amino acids) in the wild-type polypeptide.

The mutant polypeptide also includes polypeptides having 70% or higher homology, preferably 80% or higher homology, more preferably 90% or higher homology, and still more preferably 95% or higher homology to the amino acid sequence of the wild-type polypeptide.

In the present invention, "BAIAP2L1" refers to brain-specific angiogenesis inhibitor 1-associated protein 2-like protein 1 (BAIAP2L1; also referred to as "insulin receptor tyrosine kinase substrate" (IRTKS)) (Journal of Cell Science, 2007, 120: 1663-1672). BAIAP2L1 of the present invention may be of any origin, and is preferably a mammalian BAIAP2L1, more preferably a human BAIAP2L1, and still more preferably a human BAIAP2L1 comprising the amino acid sequence of SEQ ID NO: 8 (cDNA sequence, SEQ ID NO: 12/GenBank Accession No. NM_018842.4). The human BAIAP2L1 gene locus is 7q22.1, and it is located on a chromosome different from the one that carries the FGFR3 gene.

In the present invention, "human BAIAP2L1" refers to a wild-type human BAIAP2L1 polypeptide comprising the amino acid sequence of SEQ ID NO: 8, or a mutant polypeptide with a substitution, deletion, or insertion of one or more amino acids (preferably one to ten amino acids, and more preferably one to five amino acids) in the wild-type polypeptide.

The mutant polypeptide also includes polypeptides having 70% or higher homology, preferably 80% or higher homology, more preferably 90% or higher homology, and still more preferably 95% or higher homology to the amino acid sequence of the wild-type polypeptide.

In the present invention, "TACC3" refers to transforming acidic coiled-coil protein 3 (TACC3) (Genomics. 1999 Jun. 1; 58(2): 165-70). TACC3 of the present invention may be of any origin, and is preferably a mammalian TACC3, more preferably a human TACC3, and still more preferably a human TACC3 comprising the amino acid sequence of SEQ ID NO: 9 (cDNA sequence, SEQ ID NO: 13/GenBank Accession No. NM_006342.2). The human TACC3 gene locus is 4p16.3, and it is located upstream of the FGFR3 gene on the same chromosome.

In the present invention, "human TACC3" refers to a wild-type human TACC3 polypeptide comprising the amino acid sequence of SEQ ID NO: 9, or a mutant polypeptide with a substitution, deletion, or insertion of one or more amino acids (preferably one to ten amino acids, and more preferably one to five amino acids) in the wild-type polypeptide.

The mutant polypeptide also includes polypeptides having 70% or higher homology, preferably 80% or higher homology, more preferably 90% or higher homology, and still more preferably 95% or higher homology to the amino acid sequence of the wild-type polypeptide.

Amino acid sequence (or nucleotide sequence) identity can be determined using the BLAST algorithm by Karlin and Altschul (Proc. Natl. Acad. Sci. USA (1993) 90, 5873-7). Programs such as BLASTN and BLASTX were developed based on this algorithm (Altschul et al., J. Mol. Biol. (1990) 215, 403-10). To analyze nucleotide sequences according to BLASTN based on BLAST, the parameters are set to, for example, score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (one can refer to the information on the website of the National Center for Biotechnology Information (NCBI), Basic Local Alignment Search Tool (BLAST)).

In the present invention, "fusion polypeptide" refers to a polypeptide in which the whole or a part of the wild-type or mutant FGFR3 polypeptide described above is fused to the whole or a part of the wild-type or mutant TACC3 polypeptide described above, or a polypeptide in which the whole or a part of the wild-type or mutant FGFR3 polypeptide described above is fused to the whole or a part of the wild-type or mutant BAIA2P2L1 described above.

Furthermore, the fusion polypeptides of the present invention include fusion polypeptides in which the fusion site formed between the whole or a part of each of the two types of polypeptides comprises an amino acid sequence encoded by a portion of the intron sequence in the genomic DNA (including exons and introns) encoding the wild-type FGFR3 polypeptide or a mutant FGFR3 polypeptide.

Examples of such fusion polypeptides include polypeptides comprising the amino acid sequences of SEQ ID NOs: 30 and 36. The amino acid sequence of positions 761 to 793 and the amino acid sequence of positions 759 to 791 are encoded by portions of the intron sequence of the FGFR3 gene, respectively (the nucleotide sequence of positions 2,281 to 2,379 in SEQ ID NO: 29, and the nucleotide sequence of positions 2,275 to 2,373 in SEQ ID NO: 35, respectively).

Herein, "a part of a polypeptide" refers to a polypeptide consisting of an arbitrary partial sequence from the full-length amino acid sequence of a wild-type or mutant polypeptide.

Examples of specific embodiments include a fusion polypeptide of FGFR3 and TACC3 comprising the amino acid sequence of SEQ ID NO: 28, a fusion polypeptide of FGFR3 and TACC3 comprising the amino acid sequence of SEQ ID NO: 30, a fusion polypeptide of FGFR3 and BAIAP2L1 comprising the amino acid sequence of SEQ ID NO: 32, a fusion polypeptide of FGFR3 and TACC3 comprising the amino acid sequence of SEQ ID NO: 34, a fusion polypeptide of FGFR3 and TACC3 comprising the amino acid sequence of SEQ ID NO: 36, and a fusion polypeptide of FGFR3 and BAIAP2L1 comprising the amino acid sequence of SEQ ID NO: 38.

As described above, the fusion polypeptides comprising the amino acid sequences of SEQ ID NOs: 30 and 36 comprise in their fusion site an amino acid sequence encoded by a portion of the FGFR3 gene intron sequence.

Polynucleotides of the present invention include polynucleotides encoding a fusion polypeptide of the present invention described above, which include any polynucleotides that can encode a fusion polypeptide of the present invention. The polynucleotides include genomic DNAs and cDNAs. Genomic DNAs include exons and introns. Furthermore, the cDNAs may include nucleic acid sequences derived from a portion of an intron sequence that encodes amino acid sequence.

The polynucleotides also include degenerate polynucleotides constituted with any codons as long as the codons encode the same amino acids.

The polynucleotides of the present invention also include polynucleotides encoding fusion polypeptides derived from mammals. In a preferred embodiment, the polynucleotides of the present invention include polynucleotides encoding fusion polypeptides derived from humans.

In a specific embodiment, the polynucleotides of the present invention are polynucleotides encoding a fusion polypeptide in which the whole or a part of the wild-type FGFR3 polypeptide (SEQ ID NO: 6 or 7) or mutant FGFR3 polypeptide is fused to the whole or a part of the wild-type TACC3 polypeptide (SEQ ID NO: 9) or mutant TACC3 polypeptide described above or a fusion polypeptide in which the whole or a part of the wild-type or mutant FGFR3 polypeptide is fused to the whole or a part of the wild-type BAIA2P2L1 polypeptide (SEQ ID NO: 8) or mutant BAIA2P2L1 polypeptide described above.

Examples of more specific embodiments include a polynucleotide comprising a nucleotide sequence corresponding to the junction site of two polypeptides in the fusion polypeptide of SEQ ID NOs: 14, 15, or 16.

Examples of even more specific embodiments include a polynucleotide comprising the nucleic acid sequence of SEQ ID NO: 27 which encodes the fusion polypeptide of FGFR3 and TACC3 comprising the amino acid sequence of SEQ ID NO: 28, a polynucleotide comprising the nucleic acid sequence of SEQ ID NO: 29 which encodes the fusion polypeptide of FGFR3 and TACC3 comprising the amino acid sequence of SEQ ID NO: 30, a polynucleotide comprising the nucleic acid sequence of SEQ ID NO: 31 which encodes the fusion polypeptide of FGFR3 and BAIAP2L1 comprising the amino acid sequence of SEQ ID NO: 32, a polynucleotide comprising the nucleic acid sequence of SEQ ID NO: 33 which encodes the fusion polypeptide of FGFR3 and TACC3 comprising the amino acid sequence of SEQ ID NO: 34, a polynucleotide comprising the nucleic acid sequence of SEQ ID NO: 35 which encodes the fusion polypeptide of FGFR3 and TACC3 comprising the amino acid sequence of SEQ ID NO: 36, and a polynucleotide comprising the nucleic acid sequence of SEQ ID NO: 37 which encodes the fusion polypeptide of FGFR3 and BAIAP2L1 comprising the amino acid sequence of SEQ ID NO: 38.

As described above, the nucleotide sequence at positions 2,281 to 2,379 of SEQ ID NO: 29 is a nucleic acid sequence derived from an FGFR3 gene intron, and encodes the amino acid sequence of positions 761 to 793 in the polypeptide comprising the amino acid sequence of SEQ ID NO: 30.

Similarly, the nucleotide sequence at positions 2,275 to 2,373 of SEQ ID NO: 35 is a nucleic acid sequence derived from an FGFR3 gene intron, and encodes the amino acid sequence of positions 759 to 791 in the polypeptide comprising the amino acid sequence of SEQ ID NO: 36.

The polynucleotides of the present invention may be obtained by any methods. The polynucleotides of the present invention include, for example, all complementary DNAs (cDNAs) prepared from mRNAs, DNAs prepared from genomic DNA, DNAs obtained by chemical synthesis, DNAs obtained by PCR amplification using RNA or DNA as template, and DNAs constructed by appropriately combining these methods.

Polynucleotides encoding fusion polypeptides of the present invention can be obtained using routine methods by cloning cDNA from mRNA encoding a fusion polypeptide of the present invention or isolating genomic DNA and subjecting it to splicing treatment, or by chemical synthesis.

For example, in a method that clones cDNA from mRNA encoding a fusion polypeptide of the present invention, first, mRNA encoding a fusion polypeptide of the present invention is prepared from arbitrary tissues or cells expressing and producing the fusion polypeptide of the present invention according to routine methods. This may be achieved, for example, by preparing total RNA using a method such as the guanidine-thiocyanate method, hot phenol method, or AGPC method, and treating the total RNA with affinity chromatography using oligo(dT) cellulose, poly U-Sepharose, or the like.

Then, cDNA strand synthesis is carried out using the prepared mRNA as template by a known method that uses, for example, reverse transcriptase (Mol. Cell. Biol., Vol. 2, p. 161, 1982; Mol. Cell. Biol., Vol. 3, p. 280, 1983; Gene, Vol. 25, p. 263, 1983). The cDNA is converted to double-stranded cDNA, and inserted into a plasmid vector, phage vector, cosmid vector, or such. To prepare a cDNA library, the resulting vector is transformed into *E. coli*, or transfected into *E. coli* after in vitro packaging.

The present invention also relates to vectors (recombinant vectors) carrying the above-described polynucleotide encoding a fusion polypeptide of the present invention.

The vectors of the present invention are not particularly limited as long as they can replicate and maintain or self-propagate in various prokaryotic and/or eukaryotic cells as a host. The vectors of the present invention include plasmid vectors and phage vectors.

Cloning vectors include, for example, pUC19, λgt10, and λgt11. When isolating host cells capable of expressing a fusion polypeptide of the present invention, preferably the vector is one that has a promoter which enables expression of the polynucleotide of the present invention.

Recombinant vectors of the present invention can be prepared using routine methods simply by ligating a polynucleotide encoding a fusion polypeptide of the present invention to a recombinant vector available in the art (plasmid DNA and bacteriophage DNA).

Recombinant vectors for use in the present invention include, for example, *E. coli*-derived plasmids (pBR322, pBR325, pUC12, pUC13, pUC19, etc.), yeast-derived plasmids (pSH19, pSH15, etc.), and *Bacillus subtilis*-derived plasmids (pUB110, pTP5, pC194, etc.).

Examples of phages are bacteriophages such as k phage, and animal or insect viruses (pVL1393, Invitrogen) such as retrovirus, vaccinia virus, nuclear polyhedrosis virus, and lentivirus.

Expression vectors are useful for the purpose of producing a fusion polypeptide of the present invention by expressing a polynucleotide encoding the fusion polypeptide of the present invention. Expression vectors are not particular limited as long as they have the function of producing fusion polypeptides of the present invention by expressing polynucleotides encoding the polypeptides in various prokaryotic and/or eukaryotic cells as a host.

Such expression vectors include, for example, pMAL C2, pEF-BOS (Nucleic Acid Research, Vol. 18, 1990, p. 5322) and pME18S (Jikken Igaku Bessatsu (Experimental Medicine: SUPPLEMENT), "Idenshi Kougaku Handbook (Handbook of Genetic Engineering)" (1992)).

Alternatively, fusion polypeptides of the present invention may be produced as fusion proteins with other proteins. For example, when preparing as a fusion protein with glutathione S-transferase (GST), cDNA encoding a fusion polypeptide of the present invention can be subcloned into, for example, plasmid pGEX4T1 (Pharmacia). *E. coli* DH5α is transformed with the resulting plasmid, and the transformants are cultured to prepare the fusion protein.

Alternatively, fusion polypeptides of the present invention may be produced as fusions with influenza hemagglutinin (HA), immunoglobulin constant region, β-galactosidase, maltose-binding protein (MBP), or such. Furthermore, fusion polypeptides of the present invention may be produced as fusions with known peptides, for example, FLAG (Hopp, T. P. et al., BioTechnology (1988) 6, 1204-1210), 6×His consisting of 6 histidine (His) residues, 10×His, influenza hemagglutinin (HA), fragments of human c-myc, fragments of VSV-GP, fragments of p18HIV, T7-tag, HSV-tag, E-tag, fragments of SV40T antigen, lck tag, fragments of α-tubulin, B-tag, fragments of Protein C, Stag, StrepTag, and HaloTag.

When using bacteria, in particular *E coli.*, as a host cell, vectors of the present invention preferably contain at least a promoter-operator region, a start codon, a polynucleotide encoding a fusion polypeptide of the present invention, a stop codon, a terminator region, and a replicon.

When yeast, animal cells, or insect cells are used as a host, expression vectors preferably contain a promoter, a start codon, a polynucleotide encoding a fusion polypeptide of the present invention, and a stop codon.

The vectors may also contain DNA encoding a signal peptide, an enhancer sequence, 5' and 3' untranslated regions of the gene encoding a protein of the present invention, splice junctions, polyadenylation sites, a selection marker region, a replicon, and such.

Furthermore, if necessary, the vectors may contain marker genes (genes for gene amplification, drug resistance genes, etc.) that enable selection of transformed hosts or hosts with gene amplification.

Marker genes include, for example, the dihydrofolate reductase (DHFR) gene, thymidine kinase gene, neomycin resistance gene, glutamate synthase gene, adenosine deaminase gene, ornithine decarboxylase gene, hygromycin-B-phosphotransferase gene, and aspartate transcarbamylase gene.

A promoter-operator region for expressing the fusion polypeptide of the present invention in bacteria comprises a promoter, an operator, and a Shine-Dalgarno (SD) sequence (for example, AAGG).

For example, when the host is the genus *Escherichia*, it comprises, for example, the Trp promoter, lac promoter, recA promoter, kPL promoter, lpp promoter, tac promoter, or such.

Examples of a promoter for expressing the fusion polypeptide of the present invention in yeast are the PH05 promoter, PGK promoter, GAP promoter, ADH promoter, and such.

When the host is *Bacillus*, examples are the SL01 promoter, SP02 promoter, penP promoter, and such.

When the host is a eukaryotic cell such as a mammalian cell, examples are an SV40-derived promoter, retrovirus promoter, heat shock promoter, and such; and SV40 and retrovirus are preferred. Nevertheless, the promoter is not limited to the above examples. In addition, use of an enhancer is effective for expression.

A preferable initiation codon is, for example, a methionine codon (ATG). A commonly used termination codon (for example, TAG, TAA, TGA) is exemplified as a termination codon. Commonly used natural or synthetic terminators are used as a terminator region.

A replicon refers to a DNA capable of replicating the whole DNA sequence in host cells, and includes a natural plasmid, an artificially modified plasmid (DNA fragment prepared from a natural plasmid), a synthetic plasmid, and such. Examples of preferable plasmids for *E. coli* are pBR322 or its artificial derivatives (DNA fragment obtained by treating pBR322 with appropriate restriction enzymes), for yeast are yeast 2 pt plasmid or yeast chromosomal DNA, and pRSVneo ATCC 37198, and for mammalian cells are plasmid pSV2dhfr ATCC 37145, plasmid pdBPV-MMTneo ATCC 37224, plasmid pSV2neo ATCC 37149, and such.

An enhancer sequence, polyadenylation site, and splicing junction that are usually used in the art, such as those derived from SV40 can also be used.

The expression vector of the present invention can be prepared by continuously and circularly linking at least the above-mentioned promoter, initiation codon, polynucleotide encoding the fusion polypeptide of the present invention, termination codon, and terminator region, to an appropriate replicon. If desired, appropriate DNA fragments (for example, linkers, restriction sites, and such), can be used by a common method such as restriction enzyme digestion or ligation using T4 DNA ligase.

The present invention also relates to recombinant cells transformed with the above-mentioned vectors of the present invention, and recombinant cells of the present invention can be prepared by introducing the expression vector mentioned above into host cells.

Host cells used in the present invention are not particularly limited as long as they are compatible with an expression vector mentioned above and can be transformed. Examples thereof include various cells such as wild-type cells or artificially established recombinant cells commonly used in the technical field of the present invention (for example, bacteria (the genera *Escherichia* and *Bacillus*), yeast (the genus *Saccharomyces*, the genus *Pichia*, and such), animal cells, or insect cells).

*E. coli* or animal cells are preferred. Specific examples are *E. coli* (DH5c, TB1, HB101, and such), mouse-derived cells (COP, L, C127, Sp2/0, NS-1, NIH3T3, and such), rat-derived cells (PC12, PC12h), hamster-derived cells (BHK, CHO, and such), monkey-derived cells (COS1, COS3, COS7, CV1, Velo, and such), and human-derived cells (Hela, diploid fibroblast-derived cells, myeloma cells, and HepG2, and such).

An expression vector can be introduced (transformed (transfected)) into host cells according to routine methods. [when the host is *E. coli, Bacillus subtilis*, or such]: Proc. Natl. Acad. Sci. USA, Vol. 69, p. 2110 (1972); Mol. Gen. Genet., Vol. 168, p. 111 (1979); J. Mol. Biol., Vol. 56, p. 209 (1971);
[when the host is *Saccharomyces cerevisiae*]: Proc. Natl. Acad. Sci. USA, Vol. 75, p. 1927 (1978); J. Bacteriol., Vol. 153, p. 163 (1983);
[when the host is an animal cell]: Virology, Vol. 52, p. 456 (1973);
[when the host is an insect cell]: Mol. Cell. Biol., Vol. 3, pp. 2156-2165 (1983).

Fusion polypeptides of the present invention can be produced by culturing transformed recombinant cells (hereinafter, the term also refers to inclusion bodies) comprising an expression vector prepared as described above in nutritive media according to routine methods.

Fusion polypeptides of the present invention can be produced by culturing the above-described recombinant cells, in particular animal cells, and allowing them to secrete into culture supernatants.

The resulting culture is filtered or centrifuged to obtain a culture filtrate (supernatant). Fusion polypeptides of the present invention are purified and isolated from the culture filtrate by routine methods commonly used to purify and isolate natural or synthetic proteins. Examples of an isolation and purification method are methods that utilize solubility such as the salting out and solvent precipitation methods; methods that utilize difference in molecular weight such as dialysis, ultrafiltration, gel filtration, and sodium dodecyl sulfate-polyacrylamide gel electrophoresis; methods that utilize charge such as ion exchange chromatography and hydroxylapatite chromatography; method that utilize specific affinity such as affinity column chromatography; methods that utilize difference in hydrophobicity such as reverse phase high performance liquid chromatography; and methods that utilize difference in the isoelectric point such as isoelectric focusing.

Meanwhile, when a fusion polypeptide of the present invention is in the periplasm or cytoplasm of cultured recombinant cells (such as E. coli), the cells are collected by routine methods such as filtration and centrifugation of the culture, and then suspended in an appropriate buffer. After the cell wall and/or cell membrane of the cells are disrupted using methods such as sonication, lysozyme, and cryolysis, a membrane fraction containing the protein of the present invention is obtained using methods such as centrifugation and filtration. The membrane fraction is solubilized with a detergent such as Triton-X100 to obtain the crude solution. Then, the protein of the present invention can be isolated and purified from the crude solution using routine methods such as those exemplified above.

The present invention also relates to arbitrary oligonucleotides that hybridize to polynucleotides (cDNAs and genomic DNAs) encoding the above-described fusion polypeptides of the present invention.

Oligonucleotides of the present invention have nucleotide sequences that are complementary to arbitrary partial nucleotide sequences of the cDNAs and genomic DNAs, and which are useful as a pair of oligonucleotide primers consisting of sense and antisense primers in polymerase chain reaction (PCR). The whole nucleotide sequence of a polynucleotide encoding a fusion polypeptide of the present invention or an arbitrary portion of the nucleotide sequence can be amplified by PCR using the pair of oligonucleotide primers.

Oligonucleotide primers of the present invention include oligonucleotides of any length that are complementary to the nucleotide sequence of a polynucleotide of the present invention. The oligonucleotide primers of the present invention preferably include those having a sequence of at least 12 consecutive nucleotides, more preferably 12 to 50 nucleotides, and still more preferably 12 to 20 nucleotides.

Oligonucleotides of the present invention are also useful as a probe when handling DNA or RNA hybridization. When used as a probe, the DNAs include a partial nucleotide sequence of 20 or more consecutive nucleotides, preferably a partial nucleotide sequence of 50 or more consecutive nucleotides, more preferably a partial nucleotide sequence of 100 or more consecutive nucleotides, even more preferably a partial nucleotide sequence of 200 or more consecutive nucleotides, and still more preferably a partial nucleotide sequence of 300 or more consecutive nucleotides, which hybridize to a polynucleotide of the present invention.

The present invention also relates to oligonucleotides that bind to mRNA polynucleotides encoding fusion polypeptides of the present invention and have an activity of inhibiting translation of the mRNAs into proteins. It is particularly preferable that the oligonucleotides include siRNAs that cleave the mRNAs by binding to the mRNA polynucleotides encoding fusion polypeptides of the present invention.

The oligonucleotides refer to those which bind to mRNAs encoding fusion polypeptides of the present invention and thereby inhibit their expression and include, for example, antisense oligonucleotides, ribozymes, and short interfering RNAs (siRNA). They bind to the mRNAs and then inhibit their translation into proteins.

An antisense oligonucleotide refers to an oligonucleotide that specifically hybridizes to genomic DNA and/or mRNA, and inhibits their protein expression by inhibiting the transcription and/or translation.

The binding to a target polynucleotide (mRNA, etc.) may be a result of common base pair complementarity. Alternatively, when an antisense oligonucleotide binds to, for example, a DNA duplex, the binding may be a result of specific interaction at the major grooves in double helix. Target sites for an antisense oligonucleotide include the 5' end of an mRNA, for example, 5' untranslated sequences up to or including the AUG start codon, and 3' untranslated sequences of an mRNA, as well as coding region sequences.

When using as an antisense oligonucleotide of the present invention, antisense oligonucleotides include partial nucleotide sequences of 5 to 100 consecutive nucleotides, preferably partial nucleotide sequences of 5 to 70 consecutive nucleotides, more preferably partial nucleotide sequences of 5 to 50 consecutive nucleotides, and still more preferably partial nucleotide sequences of 5 to 30 consecutive nucleotides.

Furthermore, antisense oligonucleotides of the present invention can be partially modified by chemical modification to prolong their half-life in blood (to stabilize them) or increase their intracellular membrane permeability when administered to patients, or to enhance their resistance to degradation or absorption in the digestive organs in oral administration. Such chemical modification includes, for example, chemical modification of a phosphate bond, ribose, nucleobase, sugar moiety in oligonucleotides, and 3' and/or 5' ends of oligonucleotides.

The modification of phosphate bonds includes, for example, conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds and methyl phosphonothioate bonds, and combinations thereof. The modification of ribose includes, for example, conversion to 2'-fluororibose or 2'-O-methylribose. The modification of nucleotide base includes, for example, conversion to 5-propynyluracil or 2-aminoadenine.

Ribozyme refers to oligonucleotides having a catalytic activity of cleaving mRNA. In general, ribozymes have endonuclease, ligase, or polymerase activity. Ribozymes include various types of trans-acting ribozymes, for example, hammerhead ribozymes and hairpin ribozymes.

siRNA refers to double-stranded oligonucleotides capable of carrying out RNA interference (for example, Bass, 2001, Nature, 411, 428-429; Elbashir et al., 2001, Nature, 411, 494-498).

siRNA cleaves mRNA in a sequence-specific manner, and as a result inhibits translation of the mRNA into protein. siRNA includes double-stranded RNAs that are 20 to 25 base pairs long and comprise a sequence complementary to the target polynucleotide sequence. siRNAs of the present invention also include oligonucleotides comprising chemically modified nucleotides and non-nucleotides.

The present invention also relates to antibodies which bind to the above-described fusion polypeptide of the present invention, and antigen-binding fragments thereof.

Antibodies of the present invention are not limited by their origin, form, function, etc. Antibodies of the present invention may be any antibodies, monoclonal or polyclonal antibodies. However, preferred antibodies of the present invention are monoclonal antibodies. Antibodies of the present invention may be those derived from any animal, such as human antibodies, mouse antibodies, and rat antibodies. Antibodies of the present invention may also be recombinant antibodies such as chimeric antibodies and humanized antibodies. Preferred antibodies of the present invention include chimeric antibodies, human antibodies, and humanized antibodies.

The humanized antibodies of the present invention can be prepared by methods known to those skilled in the art. The variable region of an antibody is typically composed of three complementarity-determining regions (CDRs) sandwiched by four frames (FRs). The CDRs practically determine the binding specificity of an antibody. The amino acid sequences of CDRs are highly diverse. On the other hand, amino acid sequences that constitute FRs often exhibit high homology among antibodies having different binding specificities. Therefore, it is said that in general the binding specificity of an antibody can be transplanted to a different antibody by grafting the CDRs.

Humanized antibodies are also referred to as reshaped human antibodies, and they are prepared by transferring the CDRs of an antibody derived from a non-human mammal such as a mouse, to the complementarity determining regions of a human antibody. General genetic recombination techniques for their preparation are also known (see European Patent Application Publication No. 125023 and WO 96/02576).

Specifically, for example, when the CDRs are derived from a mouse antibody, a DNA sequence is designed such that the CDRs of the mouse antibody are linked with the framework regions (FRs) of a human antibody, and it is synthesized by PCR using, as primers, several oligonucleotides that have portions overlapping the ends of both CDRs and FRs (see the method described in WO 98/13388). The resulting DNA is then ligated to a DNA encoding a human antibody constant region, inserted into an expression vector, and introduced into a host to produce the antibody (see European Patent Application Publication No. EP 239400 and International Patent Application Publication No. WO 96/02576).

Human antibody framework regions to be linked with CDRs are selected so that the complementarity determining regions form a favorable antigen-binding site. If needed, amino acids of the framework region in an antibody variable region may be substituted, deleted, added, and/or inserted so that the complementarity determining regions of the reshaped human antibody form a proper antigen-binding site. For example, mutations can be introduced into the amino acid sequence of the FR by applying the PCR method used to graft mouse CDRs to human FRs. Specifically, mutations can be introduced into a portion of the nucleotide sequences of primers that anneal to the FRs. The mutations are introduced into FRs synthesized using such primers. Mutant FR sequences having desired properties can be selected by assessing and determining the antigen-binding activity of amino acid-substituted mutant antibodies by the method described above and (Sato, K. et al., Cancer Res. (1993) 53, 851-856).

In general, constant regions from human antibodies are used for those of humanized antibodies.

There are no particular limitations to the human antibody constant regions to be used in the present invention; and for example, when using a heavy-chain constant region, it may be a human IgG1 constant region, human IgG2 constant region, human IgG3 constant region, human IgG4 constant region, or human IgM, IgA, IgE, or IgD constant region. Alternatively, when using a light-chain constant region, it may be a human κ chain constant region or human λ chain constant region. Furthermore, constant regions derived from a human antibody may have a naturally-occurring sequence or may be a constant region having a sequence with modification (substitution, deletion, addition, and/or insertion) of one or more amino acids in the naturally-occurring sequence.

Moreover, after a humanized antibody is prepared, amino acids in the variable region (for example, CDR and FR) and constant region of the humanized antibody may be deleted, added, inserted, and/or substituted with other amino acids. The humanized antibodies of the present invention also include such humanized antibodies with amino acid substitutions and such.

The origin of the CDRs of a humanized antibody is not particularly limited, and may be any animal. For example, it is possible to use sequences of mouse antibodies, rat antibodies, rabbit antibodies, camel antibodies, and such. CDR sequences of mouse antibodies are preferred.

When administered to humans for therapeutic purposes, humanized antibodies are useful because their immunogenicity in the human body is reduced.

Chimeric antibodies comprise, for example, heavy and light chain constant regions of a human antibody, and heavy and light chain variable regions of an antibody of a non-human mammal, such as mouse. Chimeric antibodies can be prepared using known methods. For example, antibodies can be produced by cloning an antibody gene from hybridomas, inserting it into an appropriate vector, and introducing the construct into hosts (see, for example, Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, cDNAs of the antibody variable regions (V regions) are synthesized from the hybridoma mRNAs using reverse transcriptase. Once DNAs encoding the V regions of an antibody of interest are obtained, they are linked with DNAs encoding the constant regions (C regions) of a desired human antibody. The resulting constructs are inserted into expression vectors. Alternatively, DNAs encoding the antibody V regions may be inserted into an expression vector comprising DNAs encoding the C regions of a human antibody. The DNAs are inserted into an expression vector so that they are expressed under the regulation of expression regulatory regions, for example, enhancers and promoters. In the next step, host cells can be transformed with the expression vector to allow expression of chimeric antibodies.

Human antibodies can be obtained using methods known to those skilled in the art. For example, desired human antibodies with antigen-binding activity can be obtained by sensitizing human lymphocytes with an antigen of interest or cells expressing an antigen of interest in vitro; and fusing the sensitized lymphocytes with human myeloma cells such as U266 (see Japanese Patent Application Kokoku Publication No. (JP-B) H01-59878 (examined, approved Japanese patent application published for opposition)). Alternatively, the desired human antibody can also be obtained by immunizing a transgenic animal having an entire repertoire of human antibody genes with a desired antigen (see International Patent Application Publication Nos. WO 93/12227, WO 92/03918, WO 94/02602, WO 94/25585, WO 96/34096, and WO 96/33735).

Alternatively, B cells expressing antibodies that have antigen-binding activity are isolated from a pool of human lymphocytes by flow cytometry, cell array, or such. The antibody genes from selected B cells can be analyzed, and DNA sequences of the human antibodies that bind to the antigen can be determined (Jin, A. et al., Nature Medicine (2009) 15, 1088-92; Scheid, J. F. et al., Nature (2009) 458, 636-640; Wrammert, J. et al., Nature (2008) 453, 667-672; Tiller, T. et al., Journal of Immunological Methods (2008) 329, 112-124). When DNA sequences of the antigen-binding antibodies are revealed, human antibodies can be prepared by constructing appropriate expression vectors carrying the sequences. Such methods are known, and WO 92/01047, WO 92/20791, WO 93/06213, WO 93/11236, WO 93/19172, WO 95/01438, and WO 95/15388 can be used as references.

Furthermore, techniques for obtaining human antibodies by panning with a human antibody phage library are known. For example, the variable region of a human antibody is expressed as a single chain antibody (scFv) on the phage surface using a phage display method, and phages that bind to the antigen can be selected. By analyzing the genes of selected phages, DNA sequences encoding the variable regions of human antibodies that bind to the antigen can be determined. If the DNA sequences of scFvs that bind to the antigen are identified, appropriate expression vectors comprising these sequences can be constructed to obtain human antibodies. Such methods are well known. Reference can be made to WO 92/01047, WO 92/20791, WO 93/06213, WO 93/11236, WO 93/19172, WO 95/01438, WO 95/15388, and such.

The antibodies of the present invention include not only divalent antibodies as represented by IgG, but also monovalent antibodies, multivalent antibodies as represented by IgM. In addition, the antibodies of the present invention also include bispecific antibodies capable of binding to different antigens.

Antibodies of the present invention include not only whole antibody molecules but also any antigen-binding fragments such as low-molecular-weight antibodies.

Antibodies of the present invention also include modified antibodies that are linked to cytotoxic substances. Antibodies of the present invention also include those with altered sugar chains.

Low-molecular-weight antibodies (minibodies) included in antigen-binding fragments of the present invention are antibodies comprising an antibody fragment that lacks part of a whole antibody (for example, whole IgG, etc.). The minibodies are not particularly limited, as long as they have the activity to bind to a fusion polypeptide of the present invention.

Minibodies of the present invention are not particularly limited, as long as they comprise a portion of a whole antibody. It is however preferable that the minibodies comprise an antigen-binding domain. In general, the antigen-binding domain is antibody CDR, and is preferably six CDRs of an antibody. Thus, the preferred antigen-binding domains include, for example, six CDRs of an antibody and antibody variable regions (heavy chain and/or light chain variable regions).

The minibodies of the present invention preferably have a smaller molecular weight than whole antibodies. However, the minibodies may form multimers, for example, dimers, trimers, or tetramers, and thus their molecular weights can be greater than those of whole antibodies.

Other specific examples of the antigen-binding molecule fragments include, for example, Fab, Fab', F(ab')2, and Fv. Meanwhile, specific examples of low-molecular-weight antibodies include, for example, Fab, Fab', F(ab')2, Fv, scFv (single chain Fv), diabodies, and sc(Fv)2 (single chain (Fv)2). Multimers (for example, dimers, trimers, tetramers, and polymers) of these antibodies are also included in the low-molecular-weight antibodies of the present invention.

Antigen-binding fragments can be obtained, for example, by treating antibodies with enzymes to produce antibody fragments. Enzymes known to generate antibody fragments include, for example, papain, pepsin, and plasmin. Alternatively, a gene encoding such an antibody fragment can be constructed, introduced into an expression vector, and expressed in appropriate host cells (see, for example, Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; Bird, R. E. et al., TIBTECH (1991) 9, 132-137).

Digestive enzymes cleave at a specific site in an antibody fragment, yielding antibody fragments of specific structures shown below. Genetic engineering techniques can be applied to such enzymatically-obtained antibody fragments to delete an arbitrary portion of the antibody.

Antibody fragments obtained by using the above-described digestive enzymes are as follows:
Papain digestion: F(ab)2 or Fab
Pepsin digestion: F(ab')2 or Fab'
Plasmin digestion: Facb The minibodies of the present invention include antibody fragments lacking an arbitrary region, as long as they have the activity to bind to a fusion polypeptide of the present invention.

"Diabody" refers to a bivalent antibody fragment constructed by gene fusion (Holliger P et al., Proc. Natl. Acad. Sci. USA 90: 6444-6448 (1993); EP 404,097; WO 93/11161, etc.). Diabodies are dimers composed of two polypeptide chains. In each of the polypeptide chains forming a dimer, a VL and a VH are usually linked by a linker in the same chain. In general, the linker in a diabody is short enough such that the VL and VH cannot bind to each other. Specifically, the number of amino acid residues constituting the linker is, for example, about five residues. Thus, the VL and VH encoded on the same polypeptide cannot form a single-chain variable region fragment, and will form a dimer with another single-chain variable region fragment. As a result, the diabody has two antigen binding sites.

scFv antibodies are single-chain polypeptides produced by linking a heavy chain variable region ([VH]) to a light chain variable region ([VL]) via a linker or such (Huston, J. S. et al., Proc. Natl. Acad. Sci. U.S.A. (1988) 85, 5879-5883; Plickthun "The Pharmacology of Monoclonal Antibodies" Vol. 113, eds., Resenburg and Moore, Springer Verlag, New York, pp. 269-315, (1994)). The H-chain V region and L-chain V region of scFv may be derived from any antibody described herein. The peptide linker for linking the V regions is not particularly limited.

For example, an arbitrary single-chain peptide containing about three to 25 residues can be used as a linker. Specifically, it is possible to use the peptide linkers or such described below.

The V regions of both chains can be linked, for example, by PCR as described above. To link the V regions by PCR, first, a DNA from the DNAs below that encodes a complete or desired partial amino acid sequence is used as a template:

DNA sequence encoding an H chain or H-chain V region of an antibody, and

DNA sequence encoding an L chain or L-chain V region of an antibody.

DNAs encoding the H-chain and L-chain V regions are amplified by PCR using a pair of primers having sequences corresponding to sequences at both ends of the DNA to be amplified. Then, a DNA encoding the peptide linker portion is prepared. The peptide linker-encoding DNA can also be synthesized by PCR. Here, nucleotide sequences that can be ligated to the amplification products of V regions synthesized separately are added to the 5' end of the primers to be used. Then, PCR is carried out using each DNA of the [H chain V region DNA]-[peptide linker DNA]-[L chain V region DNA], and assembly PCR primers.

The assembly PCR primers are composed of a combination of a primer that anneals to the 5' end of the [H chain V region DNA] and a primer that anneals to the 3' end of the [L chain V region DNA]. In other words, the assembly PCR primers are a set of primers that can be used to amplify DNA encoding the full-length sequence of an scFv to be synthesized. Meanwhile, nucleotide sequences that can be ligated to the V-region DNAs have been added to the [peptide linker DNA]. Thus, these DNAs are linked together, and then the whole scFv is ultimately generated as an amplification product by the assembly PCR primers. Once the scFv-encoding DNAs are generated, expression vectors carrying these DNAs and recombinant cells transformed with these expression vectors can be obtained by conventional methods. Furthermore, the scFv can be obtained by culturing the resulting recombinant cells to express the scFv-encoding DNAs.

The order of the heavy chain and light chain variable regions to be linked together is not particularly limited, and they may be arranged in any order. Examples of the arrangement are listed below.

[VH] linker [VL]
[VL] linker [VH]

sc(Fv)2 is a single-chain low-molecular-weight antibody produced by linking two VHs and two VLs using linkers and such (Hudson et al., J Immunol. Methods 1999; 231: 177-189). For example, sc(Fv)2 can be produced by linking scFvs via a linker.

Antibodies in which two VHs and two VLs are arranged in the order of VH, VL, VH, and VL ([VH] linker [VL] linker [VH] linker [VL]) from the N terminus of the single-chain polypeptide are preferred. However, the order of the two VHs and two VLs is not limited to the above arrangement, and they may be arranged in any order. Examples of the arrangement are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

The amino acid sequence of the heavy chain variable region or light chain variable region in a low-molecular-weight antibody may contain a substitution, deletion, addition, and/or insertion. Furthermore, the heavy chain variable region and light chain variable region may also lack some portions or be added with other polypeptides, as long as they have antigen binding ability when linked together. Alternatively, the variable regions may be chimerized or humanized.

In the present invention, linkers which bind the variable regions of the antibody include arbitrary peptide linkers that can be introduced using genetic engineering, or synthetic linkers such as those disclosed in Protein Engineering, 9(3), 299-305, 1996.

The preferred linkers in the present invention are peptide linkers. The length of the peptide linkers is not particularly limited, and those skilled in the art can appropriately select the length depending on the purpose. A typical length is one to 100 amino acids, preferably 3 to 50 amino acids, more preferably 5 to 30 amino acids, and particularly preferably 12 to 18 amino acids (for example, 15 amino acids).

Amino acid sequences of such peptide linkers include, for example:

```
Ser;

Gly·Ser;

Gly·Gly·Ser;

Ser·Gly·Gly;
                                          (SEQ ID NO: 19)
Gly·Gly·Gly·Ser;
                                          (SEQ ID NO: 20)
Ser·Gly·Gly·Gly;
                                          (SEQ ID NO: 21)
Gly·Gly·Gly·Gly·Ser;
                                          (SEQ ID NO: 22)
Ser·Gly·Gly·Gly·Gly;
                                          (SEQ ID NO: 23)
Gly·Gly·Gly·Gly·Gly·Ser;
                                          (SEQ ID NO: 24)
Ser·Gly·Gly·Gly·Gly·Gly;
                                          (SEQ ID NO: 25)
Gly·Gly·Gly·Gly·Gly·Gly·Ser;
                                          (SEQ ID NO: 26)
Ser·Gly·Gly·Gly·Gly·Gly·Gly;

(Gly·Gly·Gly·Gly·Ser (SEQ ID NO: 21))n;
and (Ser·Gly·Gly·Gly·Gly (SEQ ID NO: 22))n,
``` where n is an integer of 1 or larger.

The amino acid sequence of a peptide linker can be appropriately selected by those skilled in the art according to the purpose. For example, the above-mentioned "n", which determines the length of the peptide linker, is usually 1 to 5, preferably 1 to 3, and more preferably 1 or 2.

Synthetic linkers (chemical crosslinking agents) include crosslinking agents that are routinely used to crosslink peptides, for example, N-hydroxy succinimide (NHS), disuccinimidyl suberate (DSS), bis(sulfosuccinimidyl) suberate (BS3), dithiobis(succinimidyl propionate) (DSP), dithiobis (sulfosuccinimidyl propionate) (DTSSP), ethylene glycol bis(succinimidyl succinate) (EGS), ethylene glycol bis(sulfosuccinimidyl succinate) (sulfo-EGS), disuccinimidyl tartrate (DST), disulfosuccinimidyl tartrate (sulfo-DST), bis[2-(succinimidoxycarbonyloxy)ethyl]sulfone (BSOCOES), and bis[2-(sulfosuccinimidoxycarbonyloxy)ethyl]sulfone (sulfo-BSOCOES). These crosslinking agents are commercially available.

When four antibody variable regions are linked, three linkers are usually required. Such multiple linkers may be the same or different.

The antibodies of the present invention include antibodies in which one or more amino acid residues have been added to the amino acid sequence of an antibody of the present invention. Further, fusion proteins which result from a fusion between one of the above antibodies and a second peptide or protein is included in the present invention. The fusion proteins can be prepared by ligating a polynucleotide encoding an antibody of the present invention with a polynucleotide encoding a second peptide or polypeptide in frame, inserting this into an expression vector, and expressing the fusion construct in a host. Some techniques known to those skilled in the art are available for this purpose. The partner peptide or polypeptide to be fused with an antibody of the present invention may be a known peptide, for example, FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, Protein C fragment, Stag, StrepTag, HaloTag. Other partner polypeptides to be fused with the antibodies of the present invention include, for example, GST (glutathione-S-transferase), HA (influenza hemagglutinin), immunoglobulin constant region, β-galactosidase, and MBP (maltose-binding protein). A polynucleotide encoding one of these commercially available peptides or polypeptides can be fused with a polynucleotide encoding an antibody of the present invention. The fusion polypeptide can be prepared by expressing the fusion construct.

Furthermore, the antibodies of the present invention may be conjugated antibodies which are linked to any of various molecules including polymeric substances such as polyethylene glycol (PEG) and hyaluronic acid, radioactive substances, fluorescent substances, luminescent substances, enzymes, and toxins. Such conjugated antibodies can be obtained by chemically modifying the obtained antibodies. Methods for modifying antibodies have been established in this field (for example, U.S. Pat. Nos. 5,057,313 and 5,156,840). The "antibodies" of the present invention also include such conjugated antibodies.

Furthermore, the antibodies used in the present invention may be bispecific antibodies. The bispecific antibody refers to an antibody that has variable regions recognizing different epitopes in the same antibody molecule. In the present invention, the bispecific antibodies may recognize different epitopes on the fusion polypeptide molecule of the present invention, or recognize the fusion polypeptide of the present invention with one antigen-binding site and a different substance with the other antigen-binding site.

Methods for producing bispecific antibodies are known. Bispecific antibodies can be prepared, for example, by linking two antibodies that recognize different antigens. Antibodies to be linked together may be half molecules each of which contains an H chain and an L chain, or quarter molecules that consist of only one H chain. Alternatively, hybridomas producing different monoclonal antibodies can be fused to produce a bispecific antibody-producing fused cell. Furthermore, bispecific antibodies can be produced by genetic engineering techniques.

The antibodies of the present invention may differ in amino acid sequence, molecular weight, isoelectric point, presence/absence of sugar chains, and conformation depending on the cell or host producing the antibody or the purification method as described below. However, a resulting antibody is included in the present invention, as long as it is functionally equivalent to an antibody of the present invention. For example, when an antibody of the present invention is expressed in prokaryotic cells, for example E. coli, a methionine residue is added to the N terminus of the original antibody amino acid sequence. Such antibodies are included in the present invention.

Antibodies of the present invention may be antibodies with altered sugar chains. Methods for modifying antibody sugar chains are known to those skilled in the art, and include, for example, methods for improving ADCC by modifying antibody glycosylation, methods for adjusting ADCC by the presence or absence of fucose in antibody sugar chains, methods for preparing antibodies having sugar chains that do not contain α-1,6 core fucose by producing antibodies in YB2/0 cells, and methods for adding sugar chains having bisecting GlcNAc (WO 99/54342; WO 00/61739; WO 02/31140; WO 02/79255, etc.).

Antibodies of the present invention can be produced by known methods using as an immunogen a fusion polypeptide of the present invention (derived from mammals such as humans and mice) or a fragment thereof. Specifically, non-human mammals are immunized by a known immunization method, using as a sensitizing antigen a desired antigen or cells expressing a desired antigen. Immune cells prepared from the immunized animals are fused with known parental cells by a general cell fusion method. The resulting monoclonal antibody-producing cells (hybridomas) are sorted by general screening methods, and monoclonal antibodies are prepared by culturing the cells.

Non-human mammals to be immunized include, for example, animals such as mice, rats, rabbits, sheep, monkeys, goats, donkeys, cows, horses, and pigs. The antigen can be prepared using a polynucleotide encoding the fusion polypeptide of the present invention according to known methods, for example, by methods using baculovirus (for example, WO 98/46777) or such.

Hybridomas can be prepared, for example, according to the method of Milstein et al. (Kohler, G. and Milstein, C., Methods Enzymol. (1981) 73: 3-46) or such. When the immunogenicity of an antigen is low, immunization may be performed after linking the antigen with a macromolecule having immunogenicity, such as albumin.

In an embodiment, antibodies that bind to the fusion polypeptides of the present invention include monoclonal antibodies that bind to the fusion polypeptides of the present invention. Immunogens for preparing monoclonal antibodies having binding activity to a fusion polypeptide of the present invention are not particularly limited, as long as antibodies having binding activity to the fusion polypeptide of the present invention can be prepared. It is possible to use as an immunogen, for example, a wild-type fusion polypeptide or a fragment peptide thereof, or a polypeptide obtained by adding an artificial mutation into a wild-type fusion polypeptide.

Meanwhile, the activity of an antibody to bind to a fusion polypeptide of the present invention can be assayed by methods known to those skilled in the art.

Meanwhile, monoclonal antibodies can also be obtained by DNA immunization. DNA immunization is a method in which a vector DNA constructed such that an antigen protein-encoding gene can be expressed in an animal to be immunized is administered to the animal, and the immunogen is expressed within the body of the animal to provide immunostimulation. As compared to common immunization methods based on the administration of protein antigens, DNA immunization is expected to be advantageous in that:

it enables immunostimulation while retaining the structure of a membrane protein; and the immunogen does not need to be purified.

In order to obtain monoclonal antibodies by DNA immunization, first, a polynucleotide encoding a fusion polypeptide of the present invention is administered to an animal to be immunized. The polynucleotide encoding a fusion polypeptide of the present invention can be synthesized according to an above-described method by known techniques such as PCR. The resulting DNA (polynucleotide) is inserted into an appropriate expression vector and then administered to an animal to be immunized. The expression vector includes any vectors described above (for example, commercially available expression vectors such as pcDNA3.1). Vectors can be administered to a living body by commonly used methods. For example, DNA immunization can be performed, for example, by using a gene gun to inject gold particles immobilized with an expression vector into cells. A preferred method for obtaining monoclonal antibodies is to perform booster immunization with cells expressing the fusion polypeptide of the present invention after DNA immunization.

Once the mammal is immunized as described above and the serum level of a desired antibody is confirmed to be increased, immune cells are collected from the mammal and subjected to cell fusion. Preferred immune cells are spleen cells in particular.

Mammalian myeloma cells are used for fusion with the above immune cells. It is preferred that myeloma cells have appropriate selection markers for screening. The selection marker refers to a phenotype that allows (or does not allow) survival under particular culture conditions. Known selection markers include hypoxanthine-guanine-phosphoribosyltransferase deficiency (hereinafter abbreviated as "HGPRT deficiency") and thymidine kinase deficiency (hereinafter abbreviated as "TK deficiency"). HGPRT- or TK-deficient cells exhibit hypoxanthine-aminopterin-thymidine sensitivity (hereinafter abbreviated as "HAT sensitivity"). In HAT selection medium, HAT-sensitive cells cannot synthesize DNA and thus will die. However, when fused with normal cells, they can continue to synthesize DNA via the salvage pathway of the normal cells and thus can grow even in HAT selection medium.

HGPRT- or TK-deficient cells can be selected using a medium containing 6-thioguanine, 8-azaguanine (hereinafter abbreviated as "8AG"), or 5'-bromodeoxyuridine. While normal cells are killed due to incorporation of these pyrimidine analogs into DNA, cells lacking these enzymes can survive in the selection medium because they cannot incorporate these pyrimidine analogs. Another selection marker called G418 resistance confers resistance to 2-deoxystreptamine antibiotics (gentamicin analogs) due to the neomycin resistance gene. Various myeloma cells suitable for cell fusion are known.

Cell fusion between immune cells and myeloma cells can be essentially carried out according to known methods, for example, the method by Kohler and Milstein et al. (Kohler. G. and Milstein, C., Methods Enzymol. (1981) 73, 3-46).

More specifically, cell fusion can be carried out, for example, in a common culture medium in the presence of a cell fusion-promoting agent. The fusion-promoting agent includes, for example, polyethylene glycol (PEG) and Sendai virus (HVJ). If required, an auxiliary agent such as dimethyl sulfoxide may also be added to improve fusion efficiency.

The immune cells and myeloma cells may be used at an arbitrarily determined ratio. For example, the ratio of immune cells to myeloma cells is preferably from 1 to 10. Culture media to be used for cell fusion include, for example, media that are suitable for the cell growth of myeloma cell line, such as RPMI1640 and MEM, and other common culture media used for this type of cell culture. In addition, the culture media may also be supplemented with serum supplement such as fetal calf serum (FCS).

Predetermined amounts of immune cells and myeloma cells are mixed well in the culture medium, and then mixed with a PEG solution pre-heated to about 37° C. to produce fused cells (hybridomas). In the cell fusion method, for example, PEG with mean molecular weight of about 1,000-6,000 can be added to the cells typically at a concentration of 30% to 60% (w/v). Then, successive addition of the appropriate culture medium listed above and removal of supernatant by centrifugation are repeated to eliminate the cell fusion agent and such, which are unfavorable to the growth of hybridomas.

The resulting hybridomas can be screened using a selection medium according to the selection marker possessed by myeloma cells used in the cell fusion. For example, HGPRT- or TK-deficient cells can be screened by culturing them in a HAT medium (a medium containing hypoxanthine, aminopterin, and thymidine). Specifically, when HAT-sensitive myeloma cells are used in cell fusion, cells successfully fused with normal cells can be selectively grown in the HAT medium. The cell culture using the above HAT medium is continued for a sufficient period of time to allow all cells except the desired hybridomas (non-fused cells) to die. Specifically, in general, the desired hybridomas can be selected by culturing the cells for several days to several weeks. Then, screening and single cloning of hybridomas that produce an antibody of interest can be carried out by performing ordinary limiting dilution methods.

Screening and single cloning of an antibody of interest can be suitably carried out by known screening methods based on antigen-antibody reaction. For example, an antigen is bound to a carrier such as beads made of polystyrene or such and commercially available 96-well microtiter plates, and then reacted with the culture supernatant of hybridoma. Next, the carrier is washed and then reacted with an enzyme-labeled secondary antibody or such. When the culture supernatant contains an antibody of interest reactive to the sensitizing antigen, the secondary antibody binds to the carrier via this antibody. Finally, the secondary antibody bound to the carrier is detected to determine whether the culture supernatant contains the antibody of interest. Hybridomas producing a desired antibody capable of binding to the antigen can be cloned by the limiting dilution method or such.

In addition to the above-described method for preparing hybridomas through immunization of a nonhuman animal with an antigen, antibodies of interest can also be obtained by sensitizing human lymphocytes with an antigen. Specifically, first, human lymphocytes are sensitized with the fusion polypeptide of the present invention in vitro. Then, the sensitized lymphocytes are fused with an appropriate fusion partner. For example, human-derived myeloma cells with the ability to divide permanently can be used as the fusion partner (see JP-B (Kokoku) H01-59878). Antibodies obtained by this method are human antibodies having an activity of binding to the fusion polypeptide of the present invention.

The nucleotide sequence encoding an antibody that binds to the fusion polypeptide of the present invention obtained by the above-described method or such, and its amino acid sequence can be obtained by methods known to those skilled in the art.

Based on the obtained sequence of the antibody that binds to the fusion polypeptide of the present invention, the antibody that binds to the fusion polypeptide of the present invention can be prepared by genetic recombination techniques known to those skilled in the art. Specifically, a polynucleotide encoding an antibody can be constructed based on the sequence of the antibody that recognizes the fusion polypeptides of the present invention, inserted into an expression vector, and then expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

The vectors include M13 vectors, pUC vectors, pBR322, pBluescript, and pCR-Script. Alternatively, when aiming to subclone and excise cDNA, the vectors include, for example, pGEM-T, pDIRECT, and pT7, in addition to the vectors described above. Expression vectors are particularly useful when using vectors for producing the antibodies of the present invention. For example, when aiming for expression in E. coli such as JM109, DH5α, HB101, and XL1-Blue, the expression vectors not only have the above-described characteristics that allow vector amplification in E. coli, but must also carry a promoter that allows efficient expression in E. coli, for example, lacZ promoter (Ward et al., Nature (1989) 341, 544-546; FASEB J. (1992) 6, 2422-2427), araB promoter (Better et al., Science (1988) 240, 1041-1043), T7 promoter or such. Such vectors include pGEX-5X-1 (Pharmacia), "QIAexpress system" (Qiagen), pEGFP, or pET (in this case, the host is preferably BL21 that expresses T7 RNA polymerase) in addition to the vectors described above.

The vectors may contain signal sequences for antibody secretion. As a signal sequence for antibody secretion, a pelB signal sequence (Lei, S. P. et al J. Bacteriol. (1987) 169, 4379) may be used when a protein is secreted into the E. coli periplasm. The vector can be introduced into host cells by calcium chloride or electroporation methods, for example.

In addition to vectors for E. coli, the vectors for producing the antibodies of the present invention include mammalian expression vectors (for example, pcDNA3 (Invitrogen), pEF-BOS (Nucleic Acids. Res. 1990, 18(17), p5322), pEF, and pCDM8), insect cell-derived expression vectors (for example, the "Bac-to-BAC baculovirus expression system" (Gibco-BRL) and pBacPAK8), plant-derived expression vectors (for example, pMH1 and pMH2), animal virus-derived expression vectors (for example, pHSV, pMV, and pAdexLcw), retroviral expression vectors (for example, pZIPneo), yeast expression vectors (for example, "Pichia Expression Kit" (Invitrogen), pNV11, and SP-Q01), and Bacillus subtilis expression vectors (for example, pPL608 and pKTH50), for example.

When aiming for expression in animal cells such as CHO, COS, and NIH3T3 cells, the vectors must have a promoter essential for expression in cells, for example, SV40 promoter (Mulligan et al., Nature (1979) 277, 108), MMLV-LTR promoter, EF α promoter (Mizushima et al., Nucleic Acids Res. (1990) 18, 5322), and CMV promoter, and more preferably they have a gene for selecting transformed cells (for example, a drug resistance gene that allows evaluation using an agent (neomycin, G418, or such)). Vectors with such characteristics include pMAM, pDR2, pBK-RSV, pBK-CMV, pOPRSV, and pOP 13, for example.

In addition, the following method can be used for stable gene expression and gene amplification in cells: CHO cells deficient in a nucleic acid synthesis pathway are introduced with a vector (for example, pSV2-dhfr ("Molecular Cloning $2^{nd}$ edition", Cold Spring Harbor Laboratory Press, 1989)) that carries a DHFR gene which compensates for the deficiency, and the vector is amplified using methotrexate (MTX). Alternatively, the following method can be used for transient gene expression: COS cells with a gene expressing SV40 T antigen on their chromosome are transformed with a vector (pcD and such) with an SV40 replication origin. Replication origins derived from polyoma virus, adenovirus, bovine papilloma virus (BPV), and such can also be used. To amplify gene copy number in host cells, the expression vectors may further carry selection markers such as aminoglycoside transferase (APH) gene, thymidine kinase (TK) gene, E. coli xanthine-guanine phosphoribosyltransferase (Ecogpt) gene, and dihydrofolate reductase (dhfr) gene.

The antibodies of the present invention obtained by the methods described above can be isolated from inside host cells or from outside the cells (the medium, or such), and purified to homogeneity. The antibodies can be isolated and purified by methods routinely used for isolating and purifying antibodies, and the type of method is not limited. For example, the antibodies can be isolated and purified by appropriately selecting and combining column chromatography, filtration, ultrafiltration, salting out, solvent precipitation, solvent extraction, distillation, immunoprecipitation, SDS-polyacrylamide gel electrophoresis, isoelectrofocusing, dialysis, recrystallization, and such.

The chromatographies include, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). The chromatographic methods described above can be conducted using liquid chromatography, for example, HPLC and FPLC. Columns that can be used for affinity chromatography include protein A columns and protein G columns. Columns using protein A include, for example, Hyper D, POROS, and Sepharose FF (GE Amersham Biosciences). The present invention includes antibodies that are highly purified using these purification methods.

The binding activity to the fusion polypeptide of the present invention of the obtained antibodies can be determined by methods known to those skilled in the art. Methods for determining the antigen-binding activity of an antibody include, for example, ELISA (enzyme-linked immunosorbent assay), EIA (enzyme immunoassay), RIA (radioimmunoassay), and fluorescent antibody method. For example, when enzyme immunoassay is used, antibody-containing samples, such as purified antibodies and culture supernatants of antibody-producing cells, are added to antigen-coated plates. A secondary antibody labeled with an enzyme, such as alkaline phosphatase, is added and the plates are incubated. After washing, an enzyme substrate, such as p-nitrophenyl phosphate, is added, and the absorbance is measured to evaluate the antigen-binding activity.

In the present invention, "cancer" generally refers to malignant neoplasm which may be metastatic or non-metastatic. For instance, non-limiting examples of cancer that develops from epithelial tissues such as gastrointestinal tract and skin include brain tumor, skin cancer, head and neck cancer, esophageal cancer, lung cancer, gastric cancer, duodenal cancer, breast cancer, prostate cancer, cervical cancer, cancer of uterine body, pancreatic cancer, liver cancer, colorectal cancer, colon cancer, bladder cancer, and ovarian cancer. Meanwhile, non-limiting examples of sarcoma that develops from non-epithelial tissues (stroma) such as muscles include osteosarcoma, chondrosarcoma, rhabdomyosarcoma, leiomyosarcoma, liposarcoma, and angiosarcoma.

Furthermore, non-limiting examples of hematological cancer derived from hematopoietic organs include malignant lymphoma including Hodgkin's lymphoma and non-Hodgkin's lymphoma, leukemia including acute myelocytic leukemia, chronic myelocytic leukemia, acute lymphatic leukemia, and chronic lymphatic leukemia, and multiple myeloma.

In the present invention, cancer includes any newly developed pathological tissue tumor (neoplasm). In the present invention, neoplasm leads to tumor formation which is characterized by partial neovascularization. Neoplasm can be benign, for example, angioma, glioma, and teratoma, or malignant, for example, cancer, sarcoma, glial tumor, astrocytoma, neuroblastoma, and retinoblastoma.

In the present invention, preferred examples of cancer include bladder cancer, brain tumor, head and neck squamous cell carcinoma, lung cancer, lung adenocarcinoma, lung squamous cell carcinoma, skin melanoma, esophageal cancer, gastric cancer, and liver cancer.

In the present invention, "cancer tissue" refers to a tissue containing at least one cancer cell. For example, as cancer tissues contain cancer cells and blood vessels, cancer tissue refers to all cell types that contribute to the formation of tumor mass containing cancer cells and endothelial cells. Herein, tumor mass refers to foci of tumor tissue. The term "tumor" is generally used to refer to benign or malignant neoplasm.

The present invention relates to pharmaceutical compositions comprising an above-described antibody or antigen-binding fragment thereof, or oligonucleotides of the present invention.

In the present invention, the pharmaceutical composition generally refers to a pharmaceutical agent for treating, preventing, or examining/diagnosing diseases.

The pharmaceutical compositions of the present invention can be formulated by methods known to those skilled in the art. For example, they can be used parenterally, in an injectable form of sterile solutions or suspensions including water or other pharmaceutically acceptable liquid. For example, such compositions may be formulated by mixing in a unit dose form required by the generally approved pharmaceutical manufacturing practice, by appropriately combining with pharmacologically acceptable carriers or media, specifically sterile water, physiological saline, vegetable oil, emulsifier, suspension, surfactant, stabilizer, flavoring agent, excipient, vehicle, preservative, binder, or such. The amount of active ingredient in such formulations is adjusted so that an appropriate amount can be obtained within a specified range.

Sterile compositions for injection can be formulated according to general formulation practice using vehicles such as distilled water for injection. Aqueous solutions for injection include, for example, physiological saline, and isotonic solutions containing glucose or other adjuvants (e.g., D-sorbitol, D-mannnose, D-mannitol, and sodium chloride). These can be used in combination with appropriate solubilizers, for example, alcohol (ethanol, etc.), poly-alcohol (propylene glycol, polyethylene glycol, etc.), and non-ionic detergents (Polysorbate 80™, HCO-50, etc.).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, compositions are administered in an injectable form, or in a form for transnasal administration, transpulmonary administration, or transdermal administration. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule may be, for example, 0.0001 mg to 1,000 mg/kg for each administration. Alternatively, the dose may be, for example, 0.001 to 100,000 mg per patient. However, the present invention is not limited by the numeric values described above. The dosage and administration method vary according to the patient's weight, age, symptoms, and such. Those skilled in the art can set an appropriate dosage and administration method in consideration of the factors described above.

Amino acids in the amino acid sequences described herein may be modified after translation (for example, modification of N-terminal glutamine into pyroglutamic acid by pyroglutamylation is well known to those skilled in the art). As a matter of course, such posttranslationally modified amino acids are also included in the amino acid sequences of the present invention.

The present invention also relates to methods for detecting an above-described fusion polypeptide of the present invention or a polynucleotide encoding the fusion polypeptide in samples from subjects (including cancer patients and healthy persons).

The presence or absence of a fusion polypeptide of the present invention in a sample from a subject can be tested and determined, for example, using antigen-antibody reaction which is performed by contacting an above-described antibody or antigen-binding fragment thereof that binds to a fusion polypeptide of the present invention with a sample (tumor tissue, normal tissue, and various body fluid specimens containing cancer or normal cells (blood, serum, urine, saliva, ascites, pleural effusion, etc.)) collected from a subject (cancer patient, person who may be affected with cancer, person with the risk of getting cancer, or healthy person; however, it is not limited to human).

The antigen (i.e., a fusion polypeptide of the present invention) in an antigen-antibody reaction can be detected, for example, by using conventional immunoassay.

In the present invention, immunoassay refers to a method for detecting a fusion polypeptide of the present invention in a sample (tumor tissue, normal tissue, and various body fluid specimens containing cancer or normal cells (blood, serum, urine, saliva, ascites, pleural effusion, etc.)) based on the reaction mechanism between an antigen (i.e., a fusion polypeptide of the present invention) and an antibody that binds to the antigen or antigen-binding fragment thereof. Any immunoassay is included in the present invention as long as it is a method that can detect the fusion polypeptides of the present invention.

For immunoassay in the present invention, for example, the principles of various methods such as those described in "Kouso Men-eki Sokutei Hou (Enzyme immunoassay)" (3rd Ed., eds., Eiji Ishikawa et al., Igakushoin, 1987) can be applied. Specifically, these various methods can be carried out using one or more antibodies that bind to an antigen of interest to capture (trap) the antigen to be detected in a sample.

Applicable principles preferably include, for example, single antibody solid phase methods, double antibody liquid phase methods, double antibody solid phase methods, sandwich methods, and one-pot methods such as described in JP-B (Kokoku) H02-39747. Meanwhile, assays based on antigen-antibody reaction also include enzyme multiplied immunoassay technique (EMIT), enzyme channeling immunoassay, enzyme modulator mediated enzyme immunoassay (EMMIA), enzyme inhibitor immunoassay, immunoenzymometric assay, enzyme enhanced immunoassay, and proximal linkage immunoassay.

In the present invention, it is possible to select and use any appropriate immunoassay principle such as those described above depending on the objective of the test.

The immunoassays of the present invention also include sandwich methods using a biotin- or enzyme-labeled antibody, and multi-well microtiter plates having a number of wells including 96-well microplate, as well as one-pot methods using beads and antibodies labeled with biotin or enzyme such as peroxidase.

As described above, antibodies that bind to a fusion polypeptide of the present invention or antigen-binding fragments thereof, which are used in immunoassays of the present invention, may be labeled with a labeling substance that can provide a detectable signal by itself or upon reaction with other substances.

Such labeling substances include, for example, enzymes, fluorescent substances, chemiluminescent substances, biotin, avidin, and radioisotopes. More specifically, the substances include enzymes such as peroxidase (e.g., horseradish peroxidase), alkaline phosphatase, 3-D-galactosidase, glucose oxidase, glucose-6-phosphate dehydrogenase, alcohol dehydrogenase, malate dehydrogenase, penicillinase, catalase, apoglucoseoxidase, urease, luciferase, and acetylcholinesterase; fluorescent substances such as fluorescein isothiocyanate, phycobiliprotein, rare earth metal chelates, dansyl chloride, and tetramethylrhodamine isothiocyanate; radioisotopes such as $^{3}$H, $^{14}$C, $^{125}$I, and $^{131}$I; biotin; avidin; and chemiluminescent substances.

Such radioisotopes and fluorescent substances can provide a detectable signal by themselves.

Meanwhile, enzymes, chemiluminescent substances, biotin, and avidin cannot provide any detectable signal by themselves, but provide a detectable signal when reacting with one or more different substances.

For example, when an enzyme is used, at least a substrate is necessary. Various substrates are used according to the type of enzymatic activity assay method (colorimetric assay, fluorescent assay, bioluminescence assay, chemiluminescent assay, etc.). For example, hydrogen peroxide is used as a substrate for peroxidase. Meanwhile, biotin is generally reacted with at least avidin or enzyme-modified avidin, but substrates are not limited thereto. If needed, it is also possible to use various chromogenic substances according to the substrates.

The presence or absence of a polynucleotide encoding a fusion polypeptide of the present invention in a sample from a subject can be tested and determined, for example, according to routine methods using various oligonucleotides (a pair of oligonucleotide primers, oligonucleotide probes, etc.) of the present invention described above, and mRNA, cDNA prepared using mRNA as a template, genomic DNA, or such in a sample (tumor tissue, normal tissue, and various body fluid specimens containing cancer or normal cells (blood, serum, urine, saliva, ascites, pleural effusion, etc.)) collected from a subject (cancer patient, person who may be affected with cancer, person with the risk of getting cancer, or healthy person; however, it is not limited to human) by using various gene analysis methods. Such gene analysis methods include, for example, Northern blotting, polymerase chain reaction (PCR), Southern blotting, ligase chain reaction (LCR), strand displacement amplification (SDA), nucleic acid sequence-based amplification (NASBA), isothermal and chimeric primer-initiated amplification of nucleic acids (ICAN), loop-mediated isothermal amplification (LAMP), TMA method (Gen-Probe's TMA system), microarray, and next-generation sequencing method.

In these assays, oligonucleotides of the present invention are hybridized to a polynucleotide encoding a fusion polypeptide of the present invention derived from a sample. Desired stringent conditions for such hybridization include, for example, the conditions of 6 M urea, 0.4% SDS, 0.5× SSC, and 37° C.; and hybridization conditions of equivalent stringency. Depending on the objective, it is possible to use more stringent conditions, for example, 6 M urea, 0.4% SDS, and 0.1×SSC, and 42° C.

The present invention also relates to kits for detecting an above-described fusion polypeptide of the present invention or a polynucleotide encoding the fusion polypeptide in samples from subjects described above (including cancer patients and healthy persons).

Specifically, detection kits of the present invention may contain an above-described antibody or antigen-binding fragment thereof that binds to a fusion polypeptide of the present invention (including antibodies or antigen-binding fragments thereof labeled with above-described various labeling substances). Depending on the objective of each immunoassay described above, the kits may also contain various detection reagents (enzymes, substrates, etc.) and instruction manuals.

Specifically, detection kits of the present invention may contain various oligonucleotides of the present invention described above (a pair of oligonucleotide primers, oligonucleotide probes, etc.) that hybridize to mRNA derived from a polynucleotide encoding an above-described fusion polypeptide of the present invention, cDNA prepared using the mRNA as template, or genomic DNA. According to the objective of each gene analysis, the kits may also contain various reagents (enzymes, other oligonucleotides, nucleic acid, reaction buffer, etc.) and instruction manuals.

The present invention also relates to methods for testing cancer susceptibility of a subject, whether a subject is affected with cancer, or whether cancer has progressed in a subject based on the presence or absence of a fusion polypeptide of the present invention or a polynucleotide encoding the fusion polypeptide in a sample isolated from the subject.

Specifically, the methods of the present invention include methods for testing cancer susceptibility of a subject, whether a subject is affected with cancer, or whether cancer has progressed in a subject by testing/determining the presence or absence of a fusion polypeptide of the present invention in a sample (tumor tissue, normal tissue, and various body fluid specimens containing cancer or normal cells (blood, serum, urine, saliva, etc.)) collected from the subject (cancer patient, person who may be affected with cancer, person with the risk of getting cancer, or healthy person; however, it is not limited to human) using the above-described methods and kits for detecting the fusion polypeptide of the present invention, wherein the method is based on the criterion that a subject is more likely to develop cancer, is affected with cancer, or has progressed cancer when the fusion polypeptide is detected.

In addition, the methods of the present invention include methods of testing cancer susceptibility of a subject, whether a subject is affected with cancer, or whether cancer has progressed in a subject by testing/determining the presence or absence of a polynucleotide encoding a fusion polypeptide of the present invention in a sample (tumor tissue, normal tissue, and various body fluid specimens containing cancer or normal cells (blood, serum, urine, saliva, etc.)) collected from the subject (cancer patient, person who may be affected with cancer, person with the risk of getting cancer, or healthy person; however, it is not limited to human) using the above-described methods and kits for detecting the polynucleotide encoding the fusion polypeptide of the present invention, wherein the method is based on the criterion that a subject is more likely to develop cancer, is affected with cancer, or has progressed cancer when the polynucleotide encoding the fusion polypeptide is detected.

The present invention also relates to methods for selecting a patient to which an anticancer agent (as described below) comprising a compound having FGFR inhibitory activity is applicable, based on the presence or absence of a fusion polypeptide of the present invention or a polynucleotide encoding a fusion polypeptide in a sample isolated from a subject.

Specifically, the methods of the present invention include methods that test/determine the presence or absence of a fusion polypeptide of the present invention in a sample (tumor tissue, normal tissue, and various body fluid specimens containing cancer or normal cells (blood, serum, urine, saliva, etc.)) collected from the subject (cancer patient or person who may be affected with cancer; however, it is not limited to human) using the above-described methods and kits for detecting the fusion polypeptide of the present invention, and select a subject as a patient to which an anticancer agent (as described below) comprising a compound having FGFR inhibitory activity is applicable when the fusion polypeptide of the present invention is detected.

The methods of the present invention further include methods that test/determine the presence or absence of a polynucleotide encoding a fusion polypeptide of the present invention in a sample (tumor tissue, normal tissue, and various body fluid specimens containing cancer or normal cells (blood, serum, urine, saliva, etc.)) collected from a subject (cancer patient or person who may be affected with cancer; however, it is not limited to human) using the above-described methods and kits for detecting the polynucleotide encoding the fusion polypeptide of the present invention, and select a subject as a patient to which an anticancer agent (as described below) comprising a compound having FGFR inhibitory activity is applicable when a polynucleotide encoding the fusion polypeptide of the present invention is detected.

In the present invention, "FGFR inhibitor" and "compound having FGFR inhibitory activity" are used interchangeably, and refer to a compound having the activity of inhibiting the activity of the above-mentioned FGFR, specifically, one or more arbitrary FGFRs belonging to the FGFR family comprising FGFR1, FGFR2, FGFR3, and FGFR4, which are fibroblast growth factor receptors (FGFRs) belonging to the receptor tyrosine kinase family. Preferably, they refer to a compound having the activity of inhibiting human FGFR activity, and more preferably a compound having the activity of inhibiting the activity of human FGFR3 comprising the amino acid sequence of SEQ ID NO: 6 or 7 (cDNA sequences, SEQ ID NOs: 10 and 11, respectively/GenBank Accession Nos. NM_001163213.1 and NM_000142.4, respectively).

Any FGFR inhibitors are included in the FGFR inhibitors of the present invention as long as the compounds have the activity of inhibiting FGFR activity.

Specifically, the FGFR inhibitors of the present invention include any compounds, antibodies, nucleic acid pharmaceuticals (siRNA, antisense nucleic acids, ribozymes, and such) having an action mechanism of:

(1) inhibiting the FGFR kinase activity;
(2) inhibiting dimerization between FGFR, TACC3, and BAIAP2L1;
(3) inhibiting FGFR-mediated signaling (MAPK pathway and PI3K/AKT pathway) (for example, MEK inhibitors, RAF inhibitors, ERK inhibitors, PI3K inhibitors, mTOR inhibitors, AKT inhibitors, PDK inhibitors, S6K inhibitors, etc.); or
(4) inhibiting FGFR expression (for example, siRNA, HSP90 inhibitors, etc.).

Antibodies having the activity of inhibiting FGFR activity, which are included as FGFR inhibitors of the present invention, comprise antibodies identified by the following code names: RG7444, FP-1039, AV370, and PRO-001.

Low-molecular-weight compounds having the activity of inhibiting FGFR activity, which are included as FGFR inhibitors of the present invention, include, for example:

(1) compounds disclosed in the following Patent Document and Non-patent Documents: Cancer Research, 2012, 72: 2045-2056; J. Med. Chem., 2011, 54: 7066-7083; International Publication WO 2011/016528;
(2) compounds identified by the following generic names or code names: AZD-4547 (compound C in Table 2-1 described below), BGJ-398 (compound D in Table 2-2 described below), LY-2874455, cediranib (AZD2171; compound E in Table 2-2 described below), PD173074 (compound B in Table 2-1 described below), regorafenib, ponatinib, orantinib, nintedanib, masitinib, lenvatinib, dovitinib (TKI258; compound F in Table 2-2 described below), brivanib, volasertib, golvatinib, ENMD-2076, E-3810, XL-999, XL-228, ARQ087, Tivozanib, motesanib, and regorafenib; and
(3) compounds exemplified below; however, FGFR inhibitors are not limited thereto:

[Compound 1]

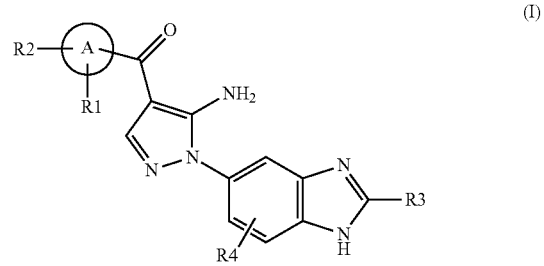

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{17}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<Group P> halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<Group Q> halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl which is optionally substituted by $C_{1-4}$ alkyl.

[Compound 2]

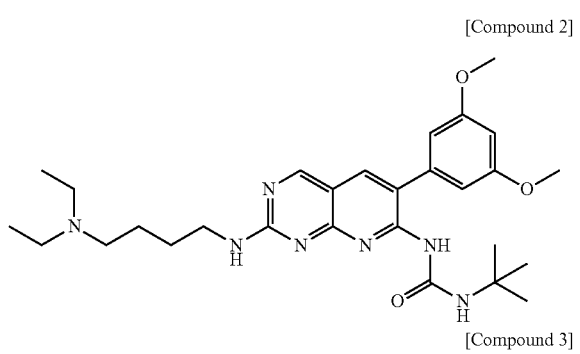

[Compound 3]

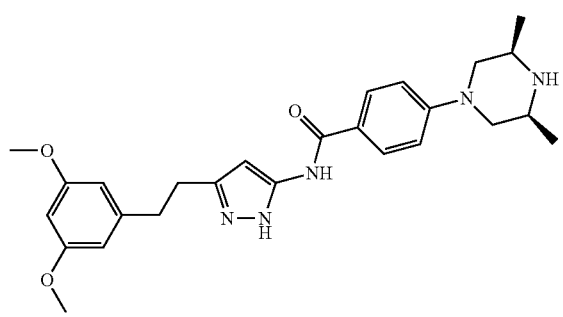

[Compound 4]

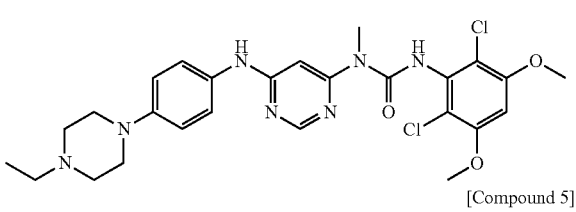

[Compound 5]

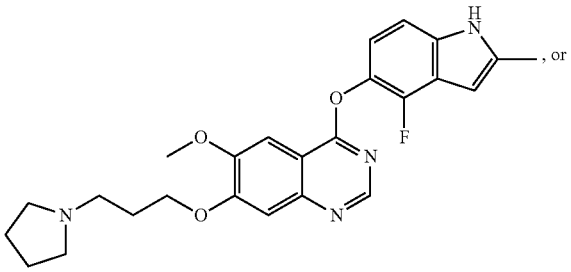

, or

[Compound 6]

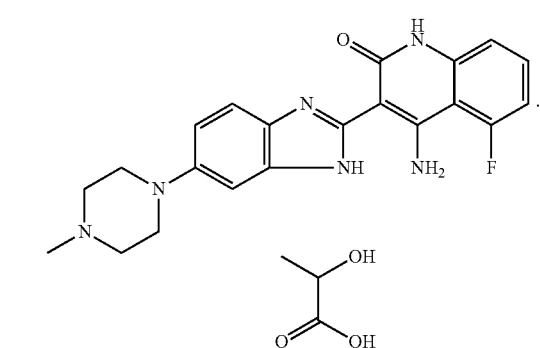

Herein, the "alkyl" refers to a monovalent group derived from an aliphatic hydrocarbon by removing an arbitrary hydrogen atom. It contains no heteroatom or unsaturated carbon-carbon bond in the backbone, and has a subset of hydrocarbyl or hydrocarbon group structures which contain hydrogen and carbon atoms. The alkyl group includes linear and branched structures. Preferred alkyl groups include alkyl groups with one to six carbon atoms ($C_{1-6}$; hereinafter, "$C_{p-q}$" means that the number of carbon atoms is p to q), $C_{1-5}$ alkyl groups, $C_{1-4}$ alkyl groups, and $C_{1-3}$ alkyl groups.

Specifically, the alkyl includes, for example, methyl group, ethyl group, n-propyl group, isopropyl group, n-butyl group, isobutyl group, s-butyl group, t-butyl group, pentyl group, isopentyl group, 2,3-dimethylpropyl group, 3,3-dimethylbutyl group, and hexyl group.

Herein, "alkenyl" refers to a monovalent hydrocarbon group having at least one double bond (two adjacent SP2 carbon atoms), and includes those of linear and branched forms. Depending on the configuration of the double bond and substituents (if any), the geometry of the double bond can be of entgegen (E) or zusammen (Z), or cis or trans configuration. Preferred alkenyl groups include $C_{2-6}$ alkenyl groups.

Specifically, the alkenyl includes, for example, vinyl group, allyl group, 1-propenyl group, 2-propenyl group, 1-butenyl group, 2-butenyl group (including cis and trans), 3-butenyl group, pentenyl group, and hexenyl group.

Herein, "alkynyl" refers to a monovalent hydrocarbon group having at least one triple bond (two adjacent SP carbon atoms), and includes those of linear and branched forms. Preferred alkynyl groups include $C_{2-6}$ alkynyl groups.

Specifically, the alkynyl includes, for example, ethynyl group, 1-propynyl group, propargyl group, 3-butynyl group, pentynyl group, and hexynyl group.

The alkenyl and alkynyl may each have one, two or more double bonds or triple bonds.

Herein, "cycloalkyl" refers to a saturated or partially saturated cyclic monovalent aliphatic hydrocarbon group, and includes monocyclic groups, bicyclo rings, and spiro rings.

Preferred cycloalkyl includes $C_{3-7}$ cycloalkyl groups. Specifically, the cycloalkyl group includes, for example, cyclopropyl group, cyclobutyl group, cyclopentyl group, cyclohexyl group, and cycloheptyl group.

Herein, "cycloalkylalkyl" refers to a group in which an arbitrary hydrogen atom of an "alkyl" defined above is substituted with a "cycloalkyl" defined above. Preferred cycloalkylalkyl groups include $C_{3-7}$ cycloalkyl$C_{1-3}$ alkyl, and specifically include, for example, cyclopropylmethyl group and cyclopropylethyl group.

Herein, "hetero atom" refers to a nitrogen atom (N), oxygen atom (O), or sulfur atom (S).

Herein, "halogen" refers to a fluorine atom, chlorine atom, bromine atom, or iodine atom.

Herein, "haloalkyl" refers to a group in which preferably one to nine, more preferably one to five identical or different "halogen atoms" defined above are linked to an "alkyl" defined above.

Specifically, the haloalkyl includes, for example, chloromethyl group, dichloromethyl group, trichloromethyl group, fluoromethyl group, difluoromethyl group, perfluoroalkyl group (such as trifluoromethyl group and —$CF_2CF_3$), and 2,2,2-trifluoroethyl group.

Herein, "alkoxy" refers to an oxy group linked with an "alkyl" defined above. Preferred alkoxy includes $C_{1-4}$ alkoxy groups and $C_{1-3}$ alkoxy groups. Specifically, alkoxy includes, for example, methoxy group, ethoxy group, 1-propoxy group, 2-propoxy group, n-butoxy group, i-butoxy group, sec-butoxy group, and tert-butoxy group.

Herein, "haloalkoxy" refers to a group in which preferably one to nine, more preferably one to five identical or different halogen atoms defined above are linked to an "alkoxy" defined above.

Specifically, the haloalkoxy includes, for example, chloromethoxy group, trichloromethoxy group, and trifluoromethoxy group.

Herein, "aryl" refers to a monovalent aromatic hydrocarbon ring. The aryl preferably includes $C_{6-10}$ aryl. Specifically, the aryl includes, for example, phenyl group and naphthyl groups (for example, 1-naphthyl group and 2-naphthyl group).

Herein, "alicyclic ring" refers to a monovalent non-aromatic hydrocarbon ring. The alicyclic ring may have unsaturated bonds within its ring, and may be a multicyclic group having two or more rings. The carbon atoms constituting the ring may be oxidized to form a carbonyl.

The number of atoms constituting an alicyclic ring preferably ranges from three to ten (3- to 10-membered aliphatic ring). The alicyclic ring includes, for example, cycloalkyl rings, cycloalkenyl rings, and cycloalkynyl rings.

Herein, "heteroaryl" refers to a monovalent aromatic heterocyclic group in which the ring-constituting atoms include preferably one to five hetero atoms. The heteroaryl may be partially saturated, and may be a monocyclic or condensed ring (for example, a bicyclic heteroaryl condensed with a benzene ring or monocyclic heteroaryl ring). The number of ring-constituting atoms preferably ranges from five to ten (5- to 10-membered heteroaryl).

Specifically, the heteroaryl includes, for example, furyl group, thienyl group, pyrrolyl group, imidazolyl group, pyrazolyl group, thiazolyl group, isothiazolyl group, oxazolyl group, isooxazolyl group, oxadiazolyl group, thiadiazolyl group, triazolyl group, tetrazolyl group, pyridyl group, pyrimidyl group, pyridazinyl group, pyrazinyl group, triazinyl group, benzofuranyl group, benzothienyl group, benzothiadiazolyl group, benzothiazolyl group, benzoxazolyl group, benzoxadiazolyl group, benzoimidazolyl group, indolyl group, isoindolyl group, azaindolyl group, indazolyl group, quinolyl group, isoquinolyl group, cinnolinyl group, quinazolinyl group, quinoxalinyl group, benzodioxolyl group, indolidinyl group, and imidazopyridyl group.

Herein, "heterocyclyl" refers to a non-aromatic monovalent heterocyclic group in which the ring-constituting atoms include preferably one to five hetero atoms. The heterocyclyl may contain double or triple bonds in its ring. The carbon atoms may be oxidized to form carbonyl. The ring may be a monocyclic or condensed ring. The number of the ring-constituting atoms preferably ranges from three to ten (3- to 10-membered heterocyclyl).

Specifically, the heterocyclyl includes, for example, oxetanyl group, dihydrofuryl group, tetrahydrofuryl group, dihydropyranyl group, tetrahydropyranyl group, tetrahydropyridyl group, morpholinyl group, thiomorpholinyl group, pyrrolidinyl group, piperidinyl group, piperazinyl group, pyrazolidinyl group, imidazolinyl group, imidazolidinyl group, oxazolidinyl group, isooxazolidinyl group, thiazolidinyl group, isothiazolidinyl group, thiadiazolidinyl group, azetidinyl group, oxazolidone group, benzodioxanyl group, benzoxazolyl group, dioxolanyl group, and dioxanyl group.

Herein, "arylalkyl" refers to a group in which an arbitrary hydrogen atom in an "alkyl" defined above is substituted with an "aryl" defined above. The arylalkyl preferably includes $C_{6-10}$ aryl $C_{1-4}$ alkyl and $C_{6-10}$ aryl $C_{1-3}$ alkyl. Specifically, the arylalkyl includes, for example, benzyl group, phenethyl group, and naphthylmethyl group.

Herein, "heteroarylalkyl" refers to a group in which an arbitrary hydrogen atom in an alkyl defined above is substituted with a "heteroaryl" defined above. The heteroarylalkyl preferably includes 5- to 10-membered heteroaryl $C_{1-3}$ alkyl. Specifically, the heteroarylalkyl includes, for example, pyrrolylmethyl group, imidazolylmethyl group, thienylmethyl group, pyridylmethyl group, pyrimidylmethyl group, quinolylmethyl group, and pyridylethyl group.

Herein, "heterocyclylalkyl" refers to a group in which an arbitrary hydrogen atom in an "alkyl" defined above is substituted with a "heterocyclyl" defined above. The heterocyclylalkyl preferably includes 3- to 10-membered heterocyclyl $C_{1-3}$ alkyl. Specifically, the heterocyclylalkyl includes, for example, morpholinylmethyl group, morpholinylethyl group, thiomorpholinylmethyl group, pyrrolidinylmethyl group, piperidinylmethyl group, piperazinylmethyl group, piperazinylethyl group, and oxetanylmethyl group.

Herein, "monohydroxyalkyl" refers to a group in which an arbitrary hydrogen atom in an "alkyl" defined above is substituted with a hydroxyl group. The monohydroxyalkyl preferably includes $C_{1-6}$ monohydroxyalkyl and $C_{2-6}$ monohydroxyalkyl. Specifically, the monohydroxyalkyl includes, for example, hydroxymethyl group, 1-hydroxyethyl group, and 2-hydroxyethyl group.

Herein, "dihydroxyalkyl" refers to a group in which two arbitrary hydrogen atoms in an "alkyl" defined above are substituted with two hydroxyl groups. The dihydroxyalkyl preferably includes $C_{1-6}$ dihydroxyalkyl and $C_{2-6}$ dihydroxyalkyl. Specifically, the dihydroxyalkyl includes, for example, 1,2-dihydroxyethyl group, 1,2-dihydroxypropyl group, and 1,3-dihydroxypropyl group.

Herein, "trihydroxyalkyl" refers to a group in which three arbitrary hydrogen atoms in an "alkyl" defined above are substituted with three hydroxyl groups. The trihydroxyalkyl preferably includes $C_{1-6}$ trihydroxyalkyl and $C_{2-6}$ trihydroxyalkyl.

Herein, "alkoxyalkyl" refers to a group in which an arbitrary hydrogen atom in an "alkyl" defined above is substituted with an "alkoxy" defined above. The alkoxyalkyl preferably includes $C_{1-3}$ alkoxy $C_{1-4}$ alkyl and $C_{1-3}$ alkoxy $C_{2-4}$ alkyl. Specifically, the alkoxyalkyl includes, for example, methoxyethyl.

Herein, "alkoxyalkoxyalkyl" refers to a group in which an arbitrary hydrogen atom in the terminal alkyl of an "alkoxyalkyl" defined above is substituted with an "alkoxy" defined above. The alkoxyalkoxyalkyl preferably includes $C_{1-3}$ alkoxy $C_{1-4}$ alkoxy $C_{1-4}$ alkyl and $C_{1-3}$ alkoxy $C_{2-4}$ alkoxy $C_{2-4}$ alkyl.

Herein, "aminoalkyl" refers to a group in which an arbitrary hydrogen atom in an "alkyl" defined above is substituted with an amino group. The aminoalkyl group preferably includes $C_{1-4}$ aminoalkyl and $C_{2-4}$ aminoalkyl.

Herein, "alkylamino" refers to an amino group linked with an "alkyl" defined above. The alkylamino preferably includes $C_{1-4}$ alkylamino.

Herein, "dialkylamino" refers to an amino group linked with two "alkyls" defined above. The two alkyl groups may be same or different. The dialkylamino preferably includes di($C_{1-4}$ alkyl)amino.

Herein, "alkylaminoalkyl" refers to a group in which an arbitrary hydrogen atom in an "alkyl" defined above is substituted with an "alkylamino" defined above. The alkylaminoalkyl preferably includes $C_{1-4}$ alkylamino $C_{1-4}$ alkyl and $C_{1-4}$ alkylamino $C_{2-4}$ alkyl.

Herein, "dialkylaminoalkyl" refers to a group in which an arbitrary hydrogen atom in an "alkyl" defined above is substituted with a "dialkylamino" defined above. The dialkylaminoalkyl preferably includes di($C_{1-4}$ alkyl)amino $C_{1-4}$ alkyl and di($C_{1-4}$ alkyl)amino $C_{2-4}$ alkyl.

Herein, "heterocyclylamino" refers to an amino group linked with a "heterocyclyl" defined above. The heterocyclylamino preferably includes 3- to 10-membered heterocyclylamino.

Herein, "cyanoalkyl" refers to a group in which an arbitrary hydrogen atom in an "alkyl" defined above is substituted with a cyano group. The cyanoalkyl preferably includes cyano($C_{1-3}$ alkyl).

Herein, "alkylsulfonyl" refers to a sulfonyl group linked with an "alkyl" defined above (i.e. alkyl-$SO_2$—). The alkylsulfonyl preferably includes $C_{1-3}$ alkylsulfonyl. Specifically, the alkylsulfonyl includes methylsulfonyl, ethylsulfonyl, n-propylsulfonyl, and i-propylsulfonyl.

Herein, "alkylsulfonylalkyl" refers to a group in which an arbitrary hydrogen atom in an "alkyl" defined above is substituted with an "alkylsulfonyl" defined above. The alkylsulfonylalkyl preferably includes $C_{1-3}$ alkylsulfonyl $C_{1-4}$ alkyl and $C_{1-3}$ alkylsulfonyl $C_{2-4}$ alkyl.

Preferably, the compounds represented by formula (I) shown above are as follows:

$R_1$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_1$ shown above more preferably represents hydrogen, hydroxy, halogen, cyano, $C_{1-4}$ haloalkyl, $C_{1-6}$ alkyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SO_2R_{16}$, —$NR_{17}SO_2R_{18}$, COOH, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q. Specifically, the above 5- to 10-membered heteroaryl is particularly preferably an imidazolyl group, thienyl group, pyridyl group, pyridazinyl group, or pyrazolyl group. The above 3- to 10-membered heterocyclyl is particularly preferably a morpholinyl group, tetrahydropyridyl group, or piperidinyl group.

$R_2$ shown above preferably represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted with one or more groups independently selected from group P, 5- to 10-membered heteroaryl or 3- to 10-membered heterocyclyl each of which is optionally substituted with one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$.

$R_2$ shown above more preferably represents hydrogen, halogen, $C_{1-4}$ haloalkyl, $C_{1-6}$ alkyl, —$OR_5$, $C_{6-10}$ aryl which is optionally substituted with one or more groups independently selected from group P, or 5- to 10-membered heteroaryl which is optionally substituted with one or more groups independently selected from group Q. Specifically, this 5- to 10-membered heteroaryl is particularly preferably a pyridyl group.

$R_1$ and $R_2$ shown above can preferably be taken together with the atoms to which they are attached to form 3- to 10-membered heterocyclyl or 5- to 10-membered heteroaryl. The heterocyclyl or heteroaryl may have a halogen atom as a substituent. Specifically, the 3- to 10-membered heterocyclyl formed together with the atoms to which $R_1$ and $R_2$ are attached, is particularly preferably a dioxolanyl group or dioxanyl group.

$R_3$ shown above preferably represents hydrogen, $C_{1-5}$ alkyl, $C_{6-10}$ aryl $C_{1-6}$ alkyl, or $C_{1-4}$ haloalkyl, more preferably hydrogen, $C_{1-4}$ alkyl, $C_{6-10}$ aryl $C_{1-4}$ alkyl, or $C_{1-3}$perfluoroalkyl, and particularly preferably $C_1$ alkyl.

$R_4$ shown above preferably represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$—$SO_3R_{31}$, or —$Si(R_{32})_3$.

$R_4$ shown above more preferably represents hydrogen, halogen, $C_{1-3}$ alkyl, $C_{1-3}$ perfluoroalkyl, cyano, methanesulfonyl, hydroxyl, alkoxy, or amino, and particularly preferably hydrogen or halogen.

Ring A mentioned above is preferably a 5- to 10-membered heteroaryl ring or $C_{6-10}$ aryl ring, more preferably benzene, indole, azaindole, benzofuran, benzothiophene, benzothiazole, quinoline, or pyrrole, and particularly preferably indole or pyrrole.

$R_5$ shown above preferably represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ amino alkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, or 5- to 10-membered heteroaryl $C_{1-3}$ alkyl, each of which is optionally substituted with one or more groups independently selected from group Q, $C_{1-6}$ monohydroxyalkyl, $C_{1-6}$ dihydroxyalkyl, or $C_{1-6}$ trihydroxyalkyl.

$R_5$ shown above more preferably represents $C_{1-5}$ alkyl, $C_{3-7}$ cycloalkyl $C_{1-3}$ alkyl, $C_{1-4}$ haloalkyl, $C_{1-3}$ alkoxy $C_{1-4}$ alkyl, $C_{6-10}$ aryl, $C_{6-10}$ aryl $C_{1-3}$ alkyl, or 3- to 10-membered heterocyclyl $C_{1-3}$ alkyl or 3- to 10-membered heterocyclyl each of which is optionally substituted with one or more groups independently selected from group Q. Specifically, the above 3- to 10-membered heterocyclylalkyl is particularly preferably a piperazinylethyl group, oxetanylmethyl group, or morpholinylethyl group. The above 3- to 10-membered heterocyclyl is particularly preferably an oxetanyl group or tetrahydropyranyl group.

$R_6$ and $R_7$ shown above may be the same or different, and each preferably represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{2-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxyalkyl, $C_{1-6}$ dihydroxyalkyl, $C_{1-6}$ trihydroxyalkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano ($C_{1-3}$ alkyl).

$R_6$ and $R_7$ shown above more preferably each independently represent hydrogen, $C_{1-3}$ alkoxy $C_{1-4}$ alkyl, 3- to 10-membered heterocyclyl $C_{1-3}$ alkyl, 5- to 10-membered heteroaryl $C_{1-3}$ alkyl, or $C_{1-6}$ dihydroxyalkyl. Specifically, the 3- to 10-membered heterocyclylalkyl is particularly preferably a morpholinylethyl group, and the 5- to 10-membered heteroarylalkyl is particularly preferably a pyridylethyl group.

Alternatively, $R_6$ and $R_7$ shown above can preferably be taken together with the nitrogen atoms to which they are attached to form 3- to 10-membered heterocyclyl or 5- to 10-membered heteroaryl.

"n" shown above represents an integer from 1 to 3. Preferably, n is 1.

$R_8$ and $R_9$ shown above preferably may be the same or different, and each represents hydrogen, $C_{1-4}$ alkyl, or halogen, and more preferably hydrogen.

Alternatively, $R_8$ and $R_9$ shown above can preferably be taken together with the carbon atoms to which they are attached to form an alicyclic ring.

$Z_1$ shown above preferably represents hydrogen, $NR_{10}R_{11}$, —OH, or 3- to 10-membered heterocyclyl or 5- to 10-membered heteroaryl each of which is optionally substituted with one or more groups independently selected from group Q, more preferably $NR_{10}R_{11}$ or —OH, or 3- to 10-membered heterocyclyl which is optionally substituted with one or more groups independently selected from group Q. Specifically, the above 3- to 10-membered heterocyclyl is particularly preferably a pyrrolidinyl group, piperazinyl group, piperidinyl group, or morpholinyl group.

$R_{10}$ and $R_{11}$ shown above preferably may be the same or different, and each preferably represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl, more preferably $C_{1-4}$ alkyl, $C_{2-6}$ alkynyl, or $C_{1-3}$ alkoxy $C_{2-4}$ alkyl.

Alternatively, $R_{10}$ and $R_{11}$ shown above can preferably be taken together with the nitrogen atoms to which they are attached to form 3- to 10-membered heterocyclyl or 5- to 10-membered heteroaryl.

$R_{12}$ and $R_{13}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring, more preferably hydrogen, $C_{1-4}$ alkyl, or $C_{1-4}$ haloalkyl.

Alternatively, $R_{12}$ and $R_{13}$ shown above preferably can be taken together with the nitrogen atoms to which they are attached to form 3- to 10-membered heterocyclyl or 5- to 10-membered heteroaryl each of which is optionally substituted with one or more groups independently selected from group Q, and particularly preferably 3- to 10-membered heterocyclylalkyl. Specifically, piperazinyl group, morpholinyl group, pyrrolidinyl group, and piperidinyl group are more preferred.

$R_{14}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl or $C_{1-4}$ haloalkyl.

$R_{15}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q.

$R_{16}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{17}$ shown above preferably represents hydrogen or $C_{1-4}$ alkyl, and more preferably hydrogen.

$R_{18}$ shown above preferably represents $C_{1-4}$ alkyl, $C_{2-6}$ alkenyl, $C_{2-6}$ alkynyl, $C_{1-4}$ haloalkyl, $C_{6-10}$ aryl which is optionally substituted with one or more groups independently selected from group P, or 5- to 10-membered heteroaryl or 3- to 10-membered heterocyclyl each of which is optionally substituted with one or more groups independently selected from group Q, and more preferably represents $C_{1-4}$ alkyl.

$R_{19}$ shown above preferably represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl each of which is optionally substituted with one or more groups independently selected from group Q, and more preferably represents hydrogen, or 5- to 10-membered heteroaryl or 3- to 10-membered heterocyclyl each of which is optionally substituted with one or more groups independently selected from group Q. Specifically, this 3- to 10-membered heterocyclyl is more preferably a piperazinyl group, morpholinyl group, pyrrolidinyl group, or piperidinyl group.

$R_{20}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{21}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{22}$ shown above preferably represents hydrogen, $C_{1-4}$ alkyl, or $C_4$ haloalkyl.

$R_{23}$ shown above preferably represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{24}$ shown above preferably represents hydrogen, $C_{1-4}$ alkyl, or $C_{1-4}$ haloalkyl.

$R_{25}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{26}$ and $R_{27}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{26}$ and $R_{27}$ shown above can preferably be taken together with the nitrogen atoms to which they are attached to form 3- to 10-membered heterocyclyl or 5- to 10-membered heteroaryl.

$R_{28}$ and $R_{29}$ shown above preferably may be the same or different, and each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered alicyclic ring.

Alternatively, $R_{28}$ and $R_{29}$ shown above preferably can be taken together with the nitrogen atoms to which they are attached to form 3- to 10-membered heterocyclyl or 5- to 10-membered heteroaryl.

$R_{30}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{31}$ shown above preferably represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl.

$R_{32}$ shown above preferably represents $C_{1-4}$ alkyl, or $C_{6-10}$ aryl.

Preferred substituents included in group P defined above are halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —SO$_2$R, —CN, —NO$_2$, and 3- to 10-membered heterocyclyl; and more preferably halogen, $C_{1-4}$ haloalkyl, $C_{1-3}$ alkoxy, $C_{1-3}$ haloalkoxy, and 3- to 10-membered heterocyclyl. Specifically, this 3- to 10-membered heterocyclyl is particularly preferably a morpholinyl group.

Preferred substituents included in group Q defined above are halogen, $C_{1-4}$ alkyl, $C_{1-4}$ haloalkyl, —OH, $C_{1-3}$ alkoxy, $C_{1-6}$ monohydroxyalkyl, $C_{1-6}$ dihydroxyalkyl, $C_{1-6}$ trihydroxyalkyl, 3- to 10-membered heterocyclylamino, —SO$_2$R, —CN, —NO$_2$, $C_{3-7}$ cycloalkyl, —COR$_{19}$, and 3- to 10-membered heterocyclyl which is optionally substituted with $C_{1-4}$ alkyl; and more preferably halogen, $C_{1-4}$ alkyl, $C_{1-4}$ haloalkyl, —OH, $C_{1-3}$ alkoxy, $C_{1-6}$ monohydroxyalkyl, —SO$_2$R$_{16}$, $C_{3-7}$ cycloalkyl, —COR$_{19}$, and 3- to 10-membered heterocyclyl which is optionally substituted with $C_{1-4}$ alkyl. Specifically, this 3- to 10-membered heterocyclyl is more preferably a piperazinyl group, piperidinyl group, or morpholinyl group.

Specific examples of the compounds include:

(1) [5-amino-1-(2-methyl-1H-benzimidazol-5-yl)-1H-pyrazol-4-yl]-(1H-indol-2-yl)-methanone;

(2) [5-amino-1-(2-methyl-1H-benzimidazol-5-yl)-1H-pyrazol-4-yl]-(6-pyrrolidin-1-ylmethyl-1H-indol-2-yl)-methanone;

(3) [5-amino-1-(2-methyl-1H-benzimidazol-5-yl)-1H-pyrazol-4-yl]-[6-(4-hydroxy-piperidin-1-ylmethyl)-1H-indol-2-yl]-methanone;

(4) [5-amino-1-(2-methyl-1H-benzimidazol-5-yl)-1H-pyrazol-4-yl]-(1H-pyrrolo[3,2-c]pyridin-2-yl)-methanone;

(5) [5-amino-1-(2-methyl-1H-benzimidazol-5-yl)-1H-pyrazol-4-yl]-(6-piperazin-1-ylmethyl-1H-indol-2-yl)-methanone;

(6) [5-amino-1-(2-methyl-1H-benzimidazol-5-yl)-1H-pyrazol-4-yl]-[6-(2-morpholin-4-yl-ethoxy)-1H-indol-2-yl]-methanone;

(7) [5-amino-1-(2-methyl-1H-benzimidazol-5-yl)-1H-pyrazol-4-yl]-[6-(tetrahydro-pyran-4-yloxy)-1H-indol-2-yl]-methanone;

(8) [5-amino-1-(2-methyl-1H-benzimidazol-5-yl)-1H-pyrazol-4-yl]-(4-chloro-1H-indol-2-yl)-methanone;

(9) [5-amino-1-(2-methyl-1H-benzimidazol-5-yl)-1H-pyrazol-4-yl]-(5-bromo-1H-indol-2-yl)-methanone;

(10) [5-amino-1-(2-methyl-1H-benzimidazol-5-yl)-1H-pyrazol-4-yl]-(4-iodo-1H-indol-2-yl)-methanone;

(11) 2-[5-amino-1-(2-methyl-1H-benzimidazol-5-yl)-1H-pyrazole-4-carbonyl]-1H-indole-5-carbonitrile;

(12) [5-amino-1-(2-methyl-1H-benzimidazol-5-yl)-1H-pyrazol-4-yl]-(6-bromo-5-fluoro-1H-indol-2-yl)-methanone;

(13) [5-amino-1-(2-methyl-1H-benzimidazol-5-yl)-1H-pyrazol-4-yl]-(5-ethynyl-1H-indol-2-yl)-methanone;

(14) [5-amino-1-(2-methyl-1H-benzimidazol-5-yl)-1H-pyrazol-4-yl]-[6-(2-fluoro-phenyl)-1H-indol-2-yl]-methanone;

(15) [5-amino-1-(2-methyl-1H-benzimidazol-5-yl)-1H-pyrazol-4-yl]-[6-(3-fluoro-phenyl)-1H-indol-2-yl]-methanone;

(16) [5-amino-1-(2-methyl-1H-benzimidazol-5-yl)-1H-pyrazol-4-yl]-[6-(4-fluoro-phenyl)-1H-indol-2-yl]-methanone;

(17) [5-amino-1-(2-methyl-1H-benzimidazol-5-yl)-1H-pyrazol-4-yl]-[6-(2-chloro-phenyl)-1H-indol-2-yl]-methanone;

(18) [5-amino-1-(2-methyl-1H-benzimidazol-5-yl)-1H-pyrazol-4-yl]-[6-(3-chloro-phenyl)-1H-indol-2-yl]-methanone;

(19) [5-amino-1-(2-methyl-1H-benzimidazol-5-yl)-1H-pyrazol-4-yl]-[6-(4-chloro-phenyl)-1H-indol-2-yl]-methanone;

(20) [5-amino-1-(2-methyl-1H-benzimidazol-5-yl)-1H-pyrazol-4-yl]-[6-(2-trifluoromethyl-phenyl)-1H-indol-2-yl]-methanone;

(21) [5-amino-1-(2-methyl-1H-benzimidazol-5-yl)-1H-pyrazol-4-yl]-[6-(3-trifluoromethyl-phenyl)-1H-indol-2-yl]-methanone;

(22) [5-amino-1-(2-methyl-1H-benzimidazol-5-yl)-1H-pyrazol-4-yl]-[6-(4-trifluoromethyl-phenyl)-1H-indol-2-yl]-methanone;

(23) [5-amino-1-(2-methyl-1H-benzimidazol-5-yl)-1H-pyrazol-4-yl]-(4-bromo-1H-indol-2-yl)-methanone;
(24) [5-amino-1-(2-methyl-1H-benzimidazol-5-yl)-1H-pyrazol-4-yl]-[6-(3-fluoro-pyridin-2-yl)-1H-indol-2-yl]-methanone;
(25) [5-amino-1-(2-methyl-1H-benzimidazol-5-yl)-1H-pyrazol-4-yl]-(6-methyl-1H-indol-2-yl)-methanone;
(26) [5-amino-1-(2-methyl-1H-benzimidazol-5-yl)-1H-pyrazol-4-yl]-[5-(4,4-difluoro-piperidine-1-carbonyl)-1H-indol-2-yl]-methanone;
(27) [5-amino-1-(2-methyl-1H-benzimidazol-5-yl)-1H-pyrazol-4-yl]-[5-(3,3-difluoro-piperidine-1-carbonyl)-1H-indol-2-yl]-methanone;
(28) 2-[5-amino-1-(2-methyl-1H-benzimidazol-5-yl)-1H-pyrazole-4-carbonyl]-1H-indole-5-carboxylic acid (2,2,2-trifluoro-ethyl)-amide;
(29) [5-amino-1-(2-methyl-1H-benzimidazol-5-yl)-1H-pyrazol-4-yl]-[6-(5-trifluoromethyl-pyridin-2-yl)-1H-indol-2-yl]-methanone;
(30) [5-amino-1-(2-methyl-1H-benzimidazol-5-yl)-1H-pyrazol-4-yl]-[6-(6-trifluoromethyl-pyridin-2-yl)-1H-indol-2-yl]-methanone;
(31) [5-amino-1-(2-methyl-1H-benzimidazol-5-yl)-1H-pyrazol-4-yl]-[6-(5-chloro-pyridin-2-yl)-1H-indol-2-yl]-methanone;
(32) [5-amino-1-(2-methyl-1H-benzimidazol-5-yl)-1H-pyrazol-4-yl]-[6-(4-methyl-pyridin-2-yl)-1H-indol-2-yl]methanone;
(33) [5-amino-1-(2-methyl-1H-benzimidazol-5-yl)-1H-pyrazol-4-yl]-[6-(3-chloro-4-fluoro-phenyl)-1H-indol-2-yl]-methanone;
(34) [5-amino-1-(2-methyl-1H-benzimidazol-5-yl)-1H-pyrazol-4-yl]-[6-(3-trifluoromethyl-pyridin-2-yl)-1H-indol-2-yl]-methanone;
(35) [5-amino-1-(2-methyl-1H-benzimidazol-5-yl)-1H-pyrazol-4-yl]-[6-(4-trifluoromethyl-pyridin-2-yl)-1H-indol-2-yl]methanone;
(36) [5-amino-1-(6-fluoro-2-methyl-1H-benzimidazol-5-yl)-1H-pyrazol-4-yl]-(1H-indol-2-yl)-methanone;
(37) 2-[5-amino-1-(2-methyl-1H-benzimidazol-5-yl)-1H-pyrazole-4-carbonyl]-1H-indole-6-carboxylic acid;
(38) [5-amino-1-(2-methyl-1H-benzimidazol-5-yl)-1H-pyrazol-4-yl]-(6-hydroxymethyl-1H-indol-2-yl)-methanone;
(39) [5-amino-1-(2-methyl-1H-benzimidazol-5-yl)-1H-pyrazol-4-yl]-{6-[2-(4-methyl-piperazin-1-yl)-ethoxy]-1H-indol-2-yl}-methanone;
(40) [5-amino-1-(2-methyl-1H-benzimidazol-5-yl)-1H-pyrazol-4-yl]-[6-(3-methyl-oxetan-3-ylmethoxy)-1H-indol-2-yl]-methanone;
(41) [5-amino-1-(2-methyl-1H-benzimidazol-5-yl)-1H-pyrazol-4-yl]-[6-(3-fluoro-piperidin-1-ylmethyl)-1H-indol-2-yl]-methanone;
(42) [5-amino-1-(2-methyl-1H-benzimidazol-5-yl)-1H-pyrazol-4-yl]-(6-{[bis(2-methoxy-ethyl)-amino]-methyl}-1H-indol-2-yl)-methanone;
(43) [5-amino-1-(2-methyl-1H-benzimidazol-5-yl)-1H-pyrazol-4-yl]-{6-[(methyl-prop-2-ynyl-amino)-methyl]-1H-indol-2-yl}-methanone;
(44) [5-amino-1-(2-methyl-1H-benzimidazol-5-yl)-1H-pyrazol-4-yl]-[6-(3,3-difluoro-pyrrolidin-1-ylmethyl)-1H-indol-2-yl]-methanone;
(45) [5-amino-1-(2-methyl-1H-benzimidazol-5-yl)-1H-pyrazol-4-yl]-[6-(2,5-dimethyl-pyrrolidin-1-ylmethyl)-1H-indol-2-yl]-methanone;
(46) [5-amino-1-(2-methyl-1H-benzimidazol-5-yl)-1H-pyrazol-4-yl]-[6-(3,3-difluoro-piperidin-1-ylmethyl)-1H-indol-2-yl]-methanone;
(47) [5-amino-1-(2-methyl-1H-benzimidazol-5-yl)-1H-pyrazol-4-yl]-[6-((S)-3-methyl-morpholin-4-ylmethyl)-1H-indol-2-yl]-methanone;
(48) [5-amino-1-(2-methyl-1H-benzimidazol-5-yl)-1H-pyrazol-4-yl]-(6-bromo-1H-indol-2-yl)-methanone;
(49) [5-amino-1-(2-methyl-1H-benzimidazol-5-yl)-1H-pyrazol-4-yl]-(5-iodo-1H-indol-2-yl)-methanone;
(50) [5-amino-1-(2-methyl-1H-benzimidazol-5-yl)-1H-pyrazol-4-yl]-(1H-pyrrolo[3,2-b]pyridin-2-yl)-methanone;
(51) [5-amino-1-(2-methyl-1H-benzimidazol-5-yl)-1H-pyrazol-4-yl]-(5-bromo-6-trifluoromethyl-1H-indol-2-yl)-methanone;
(52) [5-amino-1-(2-methyl-1H-benzimidazol-5-yl)-1H-pyrazol-4-yl]-(6-iodo-1H-indol-2-yl)-methanone;
(53) [5-amino-1-(2-methyl-1H-benzimidazol-5-yl)-1H-pyrazol-4-yl]-(4-methyl-1H-indol-2-yl)-methanone;
(54) [5-amino-1-(2-methyl-1H-benzimidazol-5-yl)-1H-pyrazol-4-yl]-(4-isopropyl-1H-indol-2-yl)-methanone;
(55) [5-amino-1-(2-methyl-1H-benzimidazol-5-yl)-1H-pyrazol-4-yl]-[5-(2-fluoro-phenyl)-1H-indol-2-yl]-methanone;
(56) [5-amino-1-(2-methyl-1H-benzimidazol-5-yl)-1H-pyrazol-4-yl]-(5-benzyl-1H-indol-2-yl)-methanone;
(57) [5-amino-1-(2-methyl-1H-benzimidazol-5-yl)-1H-pyrazol-4-yl]-[5-(2-trifluoromethyl-phenyl)-1H-indol-2-yl]-methanone;
(58) [5-amino-1-(2-methyl-1H-benzimidazol-5-yl)-1H-pyrazol-4-yl]-[5-(3-fluorophenyl)-1H-indol-2-yl]-methanone;
(59) [5-amino-1-(2-methyl-1H-benzimidazol-5-yl)-1H-pyrazol-4-yl]-[5-(3-trifluoromethyl-phenyl)-1H-indol-2-yl]-methanone;
(60) [5-amino-1-(2-methyl-1H-benzimidazol-5-yl)-1H-pyrazol-4-yl]-(4-ethynyl-1H-indol-2-yl)-methanone;
(61) [5-amino-1-(2-methyl-1H-benzimidazol-5-yl)-1H-pyrazol-4-yl]-(5H-[1,3]dioxolo[4,5-f]indol-6-yl)-methanone;
(62) [5-amino-1-(7-fluoro-2-methyl-1H-benzimidazol-5-yl)-1H-pyrazol-4-yl]-(1H-indol-2-yl)-methanone;
(63) [5-amino-1-(2-methyl-1H-benzimidazol-5-yl)-1H-pyrazol-4-yl]-[5-(4-trifluoromethyl-phenyl)-1H-indol-2-yl]-methanone;
(64) [5-amino-1-(2-methyl-1H-benzimidazol-5-yl)-1H-pyrazol-4-yl]-(5-butoxy-1H-indol-2-yl)-methanone;
(65) [5-amino-1-(2-methyl-1H-benzimidazol-5-yl)-1H-pyrazol-4-yl]-[5-(1-methyl-piperidin-4-yl)-1H-indol-2-yl]methanone;
(66) N-{2-[5-amino-1-(2-methyl-1H-benzimidazol-5-yl)-1H-pyrazole-4-carbonyl]-1H-indol-6-yl}-methanesulfonamide;
(67) [5-amino-1-(2-methyl-1H-benzimidazol-5-yl)-1H-pyrazol-4-yl]-[6-(6-morpholin-4-yl-pyridin-3-yl)-1H-indol-2-yl]-methanone;
(68) [5-amino-1-(2-methyl-1H-benzimidazol-5-yl)-1H-pyrazol-4-yl]-(6-butyl-1H-indol-2-yl)-methanone;
(69) [5-amino-1-(2-methyl-1H-benzimidazol-5-yl)-1H-pyrazol-4-yl]-[6-(1-methyl-1H-pyrazol-4-yl)-1H-indol-2-yl]-methanone;
(70) [5-amino-1-(2-methyl-1H-benzimidazol-5-yl)-1H-pyrazol-4-yl]-[6-(5-methoxy-pyridin-3-yl)-1H-indol-2-yl]-methanone;

(71) [5-amino-1-(2-methyl-1H-benzimidazol-5-yl)-1H-pyrazol-4-yl]-[6-(2-methoxy-pyridin-3-yl)-1H-indol-2-yl]-methanone;
(72) [5-amino-1-(2-methyl-1H-benzimidazol-5-yl)-1H-pyrazol-4-yl]-(6-cyclopropyl-1H-indol-2-yl)-methanone;
(73) [5-amino-1-(2-methyl-1H-benzimidazol-5-yl)-1H-pyrazol-4-yl]-[6-(2-methoxy-phenyl)-1H-indol-2-yl]-methanone;
(74) [5-amino-1-(2-methyl-1H-benzimidazol-5-yl)-1H-pyrazol-4-yl]-(6-phenyl-1H-indol-2-yl)-methanone;
(75) [5-amino-1-(2-methyl-1H-benzimidazol-5-yl)-1H-pyrazol-4-yl]-[6-(5-methanesulfonyl-pyridin-3-yl)-1H-indol-2-yl]-methanone;
(76) [5-amino-1-(2-methyl-1H-benzimidazol-5-yl)-1H-pyrazol-4-yl]-(6-isopropyl-1H-indol-2-yl)-methanone;
(77) [5-amino-1-(2-methyl-1H-benzimidazol-5-yl)-1H-pyrazol-4-yl]-(6-pyridin-2-yl-1H-indol-2-yl)-methanone;
(78) [5-amino-1-(2-methyl-1H-benzimidazol-5-yl)-1H-pyrazol-4-yl]-(5-cyclopropyl-1H-indol-2-yl)-methanone;
(79) [5-amino-1-(2-methyl-1H-benzimidazol-5-yl)-1H-pyrazol-4-yl]-(6-pyridazin-3-yl-1H-indol-2-yl)-methanone;
(80) [5-amino-1-(2-methyl-1H-benzimidazol-5-yl)-1H-pyrazol-4-yl]-(5-isopropoxy-1H-indol-2-yl)-methanone;
(81) [5-amino-1-(2-methyl-1H-benzimidazol-5-yl)-1H-pyrazol-4-yl]-[5-(2-methoxy-ethoxy)-1H-indol-2-yl]-methanone;
(82) [5-amino-1-(2-methyl-1H-benzimidazol-5-yl)-1H-pyrazol-4-yl]-(5-cyclopropylmethoxy-1H-indol-2-yl)-methanone;
(83) [5-amino-1-(2-methyl-1H-benzimidazol-5-yl)-1H-pyrazol-4-yl]-(2,2-difluoro-5H-[1,3]dioxolo[4,5-f]indol-6-yl)-methanone;
(84) [5-amino-1-(2-methyl-1H-benzimidazol-5-yl)-1H-pyrazol-4-yl]-[6-(3-chloro-pyridin-2-yl)-1H-indol-2-yl]-methanone;
(85) [5-amino-1-(2-methyl-1H-benzimidazol-5-yl)-1H-pyrazol-4-yl]-[6-(5-fluoro-pyridin-2-yl)-1H-indol-2-yl]-methanone;
(86) [5-amino-1-(2-methyl-1H-benzimidazol-5-yl)-1H-pyrazol-4-yl]-[6-(6-morpholin-4-yl-pyridazin-3-yl)-1H-indol-2-yl]-methanone;
(87) [5-amino-1-(2-methyl-1H-benzimidazol-5-yl)-1H-pyrazol-4-yl]-(5-chloro-6-cyclopropylmethoxy-1H-indol-2-yl)-methanone;
(88) [5-amino-1-(2-methyl-1H-benzimidazol-5-yl)-1H-pyrazol-4-yl]-[6-(2,4-difluoro-phenyl)-1H-indol-2-yl]-methanone;
(89) [5-amino-1-(2-methyl-1H-benzimidazol-5-yl)-1H-pyrazol-4-yl]-(6-pyridazin-4-yl-1H-indol-2-yl)-methanone;
(90) [5-amino-1-(2-methyl-1H-benzimidazol-5-yl)-1H-pyrazol-4-yl]-(3-fluoro-1H-indol-2-yl)-methanone;
(91) [5-amino-1-(2-methyl-1H-benzimidazol-5-yl)-1H-pyrazol-4-yl]-[5-(1-isopropyl-piperidin-4-yl)-6-trifluoromethyl-1H-indol-2-yl]-methanone;
(92) 2-[5-amino-1-(2-methyl-1H-benzimidazol-5-yl)-1H-pyrazole-4-carbonyl]-1H-indole-6-carbonitrile;
(93) [5-amino-1-(2-methyl-1H-benzimidazol-5-yl)-1H-pyrazol-4-yl]-[5-(1,2,3,6-tetrahydro-pyridin-4-yl)-1H-indol-2-yl]-methanone;
(94) [5-amino-1-(2-methyl-1H-benzimidazol-5-yl)-1H-pyrazol-4-yl]-(5-piperidin-4-yl-1H-indol-2-yl)-methanone;
(95) [5-amino-1-(2-methyl-1H-benzimidazol-5-yl)-1H-pyrazol-4-yl]-[5-((R)-3-fluoro-pyrrolidin-1-ylmethyl)-1H-indol-2-yl]-methanone;
(96) [5-amino-1-(2-methyl-1H-benzimidazol-5-yl)-1H-pyrazol-4-yl]-(6-fluoro-5-piperidin-4-yl-1H-indol-2-yl)-methanone;
(97) [5-amino-1-(2-methyl-1H-benzimidazol-5-yl)-1H-pyrazol-4-yl]-[6-fluoro-5-(1-methyl-piperidin-4-yl)-1H-indol-2-yl]-methanone;
(98) [5-amino-1-(2-methyl-1H-benzimidazol-5-yl)-1H-pyrazol-4-yl]-[5-(1-isopropyl-piperidin-4-yl)-1H-indol-2-yl]-methanone;
(99) [5-amino-1-(2-methyl-1H-benzimidazol-5-yl)-1H-pyrazol-4-yl]-[6-fluoro-5-(1-isopropyl-piperidin-4-yl)-1H-indol-2-yl]-methanone;
(100) [5-amino-1-(2-methyl-1H-benzimidazol-5-yl)-1H-pyrazol-4-yl]-(6-pyridin-3-yl-1H-indol-2-yl)-methanone;
(101) [5-amino-1-(2-methyl-1H-benzimidazol-5-yl)-1H-pyrazol-4-yl]-[5-(6-morpholin-4-yl-pyridin-3-yl)-1H-indol-2-yl]-methanone;
(102) [5-amino-1-(2-methyl-1H-benzimidazol-5-yl)-1H-pyrazol-4-yl]-(5-pyridin-3-yl-1H-indol-2-yl)-methanone;
(103) [5-amino-1-(2-methyl-1H-benzimidazol-5-yl)-1H-pyrazol-4-yl]-[5-(6-piperazin-1-yl-pyridin-3-yl)-1H-indol-2-yl]-methanone;
(104) [5-amino-1-(2-methyl-1H-benzimidazol-5-yl)-1H-pyrazol-4-yl]-[5-(6-hydroxy-pyridin-3-yl)-1H-indol-2-yl]-methanone;
(105) [5-amino-1-(2-methyl-1H-benzimidazol-5-yl)-1H-pyrazol-4-yl]-[6-fluoro-5-(4-methyl-piperazin-1-ylmethyl)-1H-indol-2-yl]-methanone;
(106) [5-amino-1-(2-methyl-1H-benzimidazol-5-yl)-1H-pyrazol-4-yl]-(6-fluoro-5-pyrrolidin-1-ylmethyl-1H-indol-2-yl)-methanone;
(107) [5-amino-1-(2-methyl-1H-benzimidazol-5-yl)-1H-pyrazol-4-yl]-[6-(1-methyl-piperidin-4-yl)-1H-indol-2-yl]-methanone;
(108) [5-amino-1-(2-methyl-1H-benzimidazol-5-yl)-1H-pyrazol-4-yl]-[6-(4-morpholin-4-yl-phenyl)-1H-indol-2-yl]-methanone;
(109) [5-amino-1-(2-methyl-1H-benzimidazol-5-yl)-1H-pyrazol-4-yl]-[6-(3,4,5,6-tetrahydro-2H-[1,2']bipyridin-5'-yl)-1H-indol-2-yl]-methanone;
(110) [5-amino-1-(2-methyl-1H-benzimidazol-5-yl)-1H-pyrazol-4-yl]-[6-(6-piperazin-1-yl-pyridin-3-yl)-1H-indol-2-yl]-methanone;
(111) [5-amino-1-(2-methyl-1H-benzimidazol-5-yl)-1H-pyrazol-4-yl]-[5-(6-methoxy-pyridin-3-yl)-1H-indol-2-yl]-methanone;
(112) [5-amino-1-(2-methyl-1H-benzimidazol-5-yl)-1H-pyrazol-4-yl]-[5-((S)-3-methyl-morpholin-4-ylmethyl)-1H-indol-2-yl]-methanone;
(113) [5-amino-1-(2-methyl-1H-benzimidazol-5-yl)-1H-pyrazol-4-yl]-[6-((R)-3-fluoro-pyrrolidin-1-ylmethyl)-1H-indol-2-yl]-methanone;
(114) [5-amino-1-(2-methyl-1H-benzimidazol-5-yl)-1H-pyrazol-4-yl]-[5-(2,5-dimethyl-pyrrolidin-1-ylmethyl)-1H-indol-2-yl]-methanone;
(115) [5-amino-1-(2-methyl-1H-benzimidazol-5-yl)-1H-pyrazol-4-yl]-[5-(3-fluoro-piperidin-1-ylmethyl)-1H-indol-2-yl]-methanone;
(116) [5-amino-1-(2-methyl-1H-benzimidazol-5-yl)-1H-pyrazol-4-yl]-[5-(3,3-difluoro-piperidin-1-ylmethyl)-1H-indol-2-yl]-methanone;
(117) [5-amino-1-(2-methyl-1H-benzimidazol-5-yl)-1H-pyrazol-4-yl]-{6-[2-(4-methyl-piperazin-1-yl)pyridin-4-yl]-1H-indol-2-yl}-methanone;
(118) [5-amino-1-(2-methyl-1H-benzimidazol-5-yl)-1H-pyrazol-4-yl]-(6-pyridin-4-yl-1H-indol-2-yl)-methanone;

(119) [5-amino-1-(2-methyl-1H-benzimidazol-5-yl)-1H-pyrazol-4-yl]-[5-(4-fluoropiperidin-1-ylmethyl)-1H-indol-2-yl]-methanone;
(120) [5-amino-1-(2-methyl-1H-benzimidazol-5-yl)-1H-pyrazol-4-yl]-[5-(4,4-difluoro-piperidin-1-ylmethyl)-1H-indol-2-yl]-methanone;
(121) [5-amino-1-(2-difluoromethyl-1H-benzimidazol-5-yl)-1H-pyrazol-4-yl]-[5-(1-methyl-piperidin-4-yl)-1H-indol-2-yl]-methanone;
(122) [5-amino-1-(2-difluoromethyl-1H-benzimidazol-5-yl)-1H-pyrazol-4-yl]-(1H-indol-2-yl)-methanone;
(123) [5-amino-1-(2-methyl-1H-benzimidazol-5-yl)-1H-pyrazol-4-yl]-[5-(3,3-difluoro-pyrrolidin-1-ylmethyl)-1H-indol-2-yl]-methanone;
(124) [5-amino-1-(2-methyl-1H-benzimidazol-5-yl)-1H-pyrazol-4-yl]-[5-(1-cyclopentyl-piperidin-4-yl)-1H-indol-2-yl]-methanone;
(125) [5-amino-1-(2-methyl-1H-benzimidazol-5-yl)-1H-pyrazol-4-yl]-[5-(1-cyclohexyl-piperidin-4-yl)-1H-indol-2-yl]-methanone;
(126) [5-amino-1-(2-methyl-1H-benzimidazol-5-yl)-1H-pyrazol-4-yl]-(4-bromo-1H-pyrrol-2-yl)-methanone;
(127) [5-amino-1-(2-methyl-1H-benzimidazol-5-yl)-1H-pyrazol-4-yl]-(1H-pyrrol-2-yl)-methanone;
(128) [5-amino-1-(2-methyl-1H-benzimidazol-5-yl)-1H-pyrazol-4-yl]-(4-phenyl-1H-pyrrol-2-yl)-methanone;
(129) [5-amino-1-(2-methyl-1H-benzimidazol-5-yl)-1H-pyrazol-4-yl]-[4-(3-chloro-phenyl)-1H-pyrrol-2-yl]-methanone;
(130) [5-amino-1-(2-methyl-1H-benzimidazol-5-yl)-1H-pyrazol-4-yl]-[4-(4-fluoro-phenyl)-1H-pyrrol-2-yl]-methanone;
(131) [5-amino-1-(2-methyl-1H-benzimidazol-5-yl)-1H-pyrazol-4-yl]-[4-(3-fluoro-phenyl)-1H-pyrrol-2-yl]-methanone;
(132) [5-amino-1-(2-methyl-1H-benzimidazol-5-yl)-1H-pyrazol-4-yl]-(6-morpholin-4-ylmethyl-1H-indol-2-yl)-methanone;
(133) [5-amino-1-(2-methyl-1H-benzimidazol-5-yl)-1H-pyrazol-4-yl]-[4-(2-morpholin-4-yl-ethylamino)-1H-indol-2-yl]-methanone;
(134) [5-amino-1-(2-methyl-1H-benzimidazol-5-yl)-1H-pyrazol-4-yl]-[5-(4-methyl-piperazine-1-carbonyl)-1H-indol-2-yl]-methanone;
(135) [5-amino-1-(2-methyl-1H-benzimidazol-5-yl)-1H-pyrazol-4-yl]-[6-(2-morpholin-4-yl-ethylamino)-1H-indol-2-yl]-methanone;
(136) [5-amino-1-(2-methyl-1H-benzimidazol-5-yl)-1H-pyrazol-4-yl]-[5-(piperazine-1-carbonyl)-1H-indol-2-yl]-methanone;
(137) [5-amino-1-(2-methyl-1H-benzimidazol-5-yl)-1H-pyrazol-4-yl]-[4-(2-methoxy-ethylamino)-1H-indol-2-yl]-methanone;
(138) [5-amino-1-(2-methyl-1H-benzimidazol-5-yl)-1H-pyrazol-4-yl]-[4-(2-hydroxy-1-hydroxymethyl-ethylamino)-1H-indol-2-yl]-methanone;
(139) [5-amino-1-(2-methyl-1H-benzimidazol-5-yl)-1H-pyrazol-4-yl]-[4-(2-pyridin-4-yl-ethylamino)-1H-indol-2-yl]-methanone;
(140) [5-amino-1-(2-methyl-1H-benzimidazol-5-yl)-1H-pyrazol-4-yl]-[6-(2-methoxy-ethylamino)-1H-indol-2-yl]-methanone;
(141) [5-amino-1-(2-methyl-1H-benzimidazol-5-yl)-1H-pyrazol-4-yl]-(6-morpholin-4-yl-1H-indol-2-yl)-methanone;
(142) [5-amino-1-(2-methyl-1H-benzimidazol-5-yl)-1H-pyrazol-4-yl]-(4-morpholin-4-yl-1H-indol-2-yl)-methanone;
(143) [5-amino-1-(2-methyl-1H-benzimidazol-5-yl)-1H-pyrazol-4-yl]-(4-morpholin-4-ylmethyl-1H-indol-2-yl)-methanone;
(144) [5-amino-1-(2-methyl-1H-benzimidazol-5-yl)-1H-pyrazol-4-yl]-(5-morpholin-4-ylmethyl-1H-indol-2-yl)-methanone;
(145) [5-amino-1-(2-methyl-1H-benzimidazol-5-yl)-1H-pyrazol-4-yl]-[5-(morpholine-4-carbonyl)-1H-indol-2-yl]-methanone;
(146) [5-amino-1-(2-isopropyl-1H-benzimidazol-5-yl)-1H-pyrazol-4-yl]-(1H-indol-2-yl)-methanone;
(147) [5-amino-1-(2-propyl-1H-benzimidazol-5-yl)-1H-pyrazol-4-yl]-(1H-indol-2-yl)-methanone;
(148) [5-amino-1-(1H-benzimidazol-5-yl)-1H-pyrazol-4-yl]-(1H-indol-2-yl)-methanone;
(149) [5-amino-1-(2-trifluoromethyl-1H-benzimidazol-5-yl)-1H-pyrazol-4-yl]-(1H-indol-2-yl)-methanone;
(150) [5-amino-1-(2-ethyl-1H-benzimidazol-5-yl)-1H-pyrazol-4-yl]-(1H-indol-2-yl)-methanone;
(151) [5-amino-1-(2-benzyl-1H-benzimidazol-5-yl)-1H-pyrazol-4-yl]-(1H-indol-2-yl)methanone;
(152) 1-(4-{2-[5-amino-1-(2-methyl-1H-benzimidazol-5-yl)-1H-pyrazole-4-carbonyl]-1H-indol-5-ylmethyl}-piperazin-1-yl)-ethanone;
(153) [5-amino-1-(2-methyl-1H-benzimidazol-5-yl)-1H-pyrazol-4-yl]-[5-(4-methanesulfonyl-piperazin-1-ylmethyl)-1H-indol-2-yl]-methanone;
(154) [5-amino-1-(2-methyl-1H-benzimidazol-5-yl)-1H-pyrazol-4-yl]-(5-piperazin-1-ylmethyl-1H-indol-2-yl)-methanone;
(155) 1-(4-{2-[5-amino-1-(2-methyl-1H-benzimidazol-5-yl)-1H-pyrazole-4-carbonyl]-1H-indol-6-ylmethyl}-piperazin-1-yl)-ethanone;
(156) [5-amino-1-(2-methyl-1H-benzimidazol-5-yl)-1H-pyrazol-4-yl]-[6-(4-methyl-piperazin-1-ylmethyl)-1H-indol-2-yl]-methanone;
(157) [5-amino-1-(2-methyl-1H-benzimidazol-5-yl)-1H-pyrazol-4-yl]-[5-(4-methyl-piperazin-1-ylmethyl)-1H-indol-2-yl]-methanone;
(158) [5-amino-1-(2-methyl-1H-benzimidazol-5-yl)-1H-pyrazol-4-yl]-(5-pyrrolidin-1-ylmethyl-1H-indol-2-yl)-methanone;
(159) [5-amino-1-(2-methyl-1H-benzimidazol-5-yl)-1H-pyrazol-4-yl]-(4-fluoro-1H-indol-2-yl)-methanone;
(160) [5-amino-1-(2-methyl-1H-benzimidazol-5-yl)-1H-pyrazol-4-yl]-(5-fluoro-1H-indol-2-yl)-methanone;
(161) [5-amino-1-(2-methyl-1H-benzimidazol-5-yl)-1H-pyrazol-4-yl]-(6-fluoro-1H-indol-2-yl)-methanone;
(162) [5-amino-1-(2-methyl-1H-benzimidazol-5-yl)-1H-pyrazol-4-yl]-(1H-pyrrolo[2,3-b]pyridin-2-yl)-methanone;
(163) [5-amino-1-(2-methyl-1H-benzimidazol-5-yl)-1H-pyrazol-4-yl]-(5-fluoro-6-morpholin-4-ylmethyl-1H-indol-2-yl)-methanone;
(164) 2-[5-amino-1-(2-methyl-1H-benzimidazol-5-yl)-1H-pyrazole-4-carbonyl]-1H-indole-5-carboxylic acid;
(165) [5-amino-1-(2-methyl-1H-benzimidazol-5-yl)-1H-pyrazol-4-yl]-(5-methoxy-1H-indol-2-yl)-methanone;
(166) [5-amino-1-(2-methyl-1H-benzimidazol-5-yl)-1H-pyrazol-4-yl]-(4,6-dimethoxy-1H-indol-2-yl)-methanone;
(167) [5-amino-1-(2-methyl-1H-benzimidazol-5-yl)-1H-pyrazol-4-yl]-(4-methoxy-1H-indol-2-yl)-methanone;

(168) [5-amino-1-(2-methyl-1H-benzimidazol-5-yl)-1H-pyrazol-4-yl]-(6-methoxy-1H-indol-2-yl)-methanone;
(169) [5-amino-1-(2-methyl-1H-benzimidazol-5-yl)-1H-pyrazol-4-yl]-(4,6-dimethyl-1H-indol-2-yl)-methanone;
(170) [5-amino-1-(2-methyl-1H-benzimidazol-5-yl)-1H-pyrazol-4-yl]-(5-tert-butyl-1H-indol-2-yl)-methanone;
(171) [5-amino-1-(2-methyl-1H-benzimidazol-5-yl)-1H-pyrazol-4-yl]-(5-isopropyl-1H-indol-2-yl)-methanone;
(172) [5-amino-1-(2-methyl-1H-benzimidazol-5-yl)-1H-pyrazol-4-yl]-(5-benzyloxy-1H-indol-2-yl)-methanone;
(173) [5-amino-1-(2-methyl-1H-benzimidazol-5-yl)-1H-pyrazol-4-yl]-(4-benzyloxy-1H-indol-2-yl)-methanone;
(174) [5-amino-1-(2-methyl-1H-benzimidazol-5-yl)-1H-pyrazol-4-yl]-(5,6-dimethoxy-1H-indol-2-yl)-methanone;
(175) [5-amino-1-(2-methyl-1H-benzimidazol-5-yl)-1H-pyrazol-4-yl]-(6-tert-butyl-1H-indol-2-yl)-methanone;
(176) [5-amino-1-(2-methyl-1H-benzimidazol-5-yl)-1H-pyrazol-4-yl]-(5-fluoro-4-trifluoromethyl-1H-indol-2-yl)-methanone;
(177) [5-amino-1-(2-methyl-1H-benzimidazol-5-yl)-1H-pyrazol-4-yl]-(5-phenoxy-1H-indol-2-yl)-methanone;
(178) [5-amino-1-(2-methyl-1H-benzimidazol-5-yl)-1H-pyrazol-4-yl]-(6-methylsulfanyl-1H-indol-2-yl)-methanone;
(179) [5-amino-1-(2-methyl-1H-benzimidazol-5-yl)-1H-pyrazol-4-yl]-(4-tert-butyl-1H-indol-2-yl)-methanone;
(180) [5-amino-1-(2-methyl-1H-benzimidazol-5-yl)-1H-pyrazol-4-yl]-(5-methyl-1H-indol-2-yl)-methanone;
(181) [5-amino-1-(2-methyl-1H-benzimidazol-5-yl)-1H-pyrazol-4-yl]-(5-ethyl-1H-indol-2-yl)-methanone;
(182) [5-amino-1-(2-methyl-1H-benzimidazol-5-yl)-1H-pyrazol-4-yl]-(5-fluoro-6-trifluoromethyl-1H-indol-2-yl)-methanone;
(183) [5-amino-1-(2-methyl-1H-benzimidazol-5-yl)-1H-pyrazol-4-yl]-(6-fluoro-5-methoxy-1H-indol-2-yl)-methanone;
(184) [5-amino-1-(2-methyl-1H-benzimidazol-5-yl)-1H-pyrazol-4-yl]-(6-chloro-5-methoxy-1H-indol-2-yl)-methanone;
(185) [5-amino-1-(2-methyl-1H-benzimidazol-5-yl)-1H-pyrazol-4-yl]-(5-chloro-6-methoxy-1H-indol-2-yl)-methanone;
(186) [5-amino-1-(2-methyl-1H-benzimidazol-5-yl)-1H-pyrazol-4-yl]-(6-isopropoxy-1H-indol-2-yl)-methanone;
(187) [5-amino-1-(2-methyl-1H-benzimidazol-5-yl)-1H-pyrazol-4-yl]-(6-benzyloxy-1H-indol-2-yl)-methanone;
(188) [5-amino-1-(2-methyl-1H-benzimidazol-5-yl)-1H-pyrazol-4-yl]-(4-isopropoxy-1H-indol-2-yl)-methanone;
(189) [5-amino-1-(2-methyl-1H-benzimidazol-5-yl)-1H-pyrazol-4-yl]-(2,3-dihydro-6H-[1,4]dioxino[2,3-f]indol-7-yl)-methanone;
(190) [5-amino-1-(2-methyl-1H-benzimidazol-5-yl)-1H-pyrazol-4-yl]-(4,6-di-tert-butyl-1H-indol-2-yl)-methanone;
(191) 2-[5-amino-1-(2-methyl-1H-benzimidazol-5-yl)-1H-pyrazole-4-carbonyl]-1H-indole-4-carbonitrile;
(192) [5-amino-1-(2-methyl-1H-benzimidazol-5-yl)-1H-pyrazol-4-yl]-(5-imidazol-1-yl-1H-indol-2-yl)-methanone;
(193) [5-amino-1-(2-methyl-1H-benzimidazol-5-yl)-1H-pyrazol-4-yl]-(5-trifluoromethylsulfanyl-1H-indol-2-yl)-methanone;
(194) [5-amino-1-(2-methyl-1H-benzimidazol-5-yl)-1H-pyrazol-4-yl]-(5-methylsulfanyl-1H-indol-2-yl)-methanone;
(195) [5-amino-1-(2-methyl-1H-benzimidazol-5-yl)-1H-pyrazol-4-yl]-(5-methanesulfonyl-1H-indol-2-yl)-methanone;
(196) [5-amino-1-(2-methyl-1H-benzimidazol-5-yl)-1H-pyrazol-4-yl]-[6-(4,4-difluoro-piperidin-1-ylmethyl)-1H-indol-2-yl]-methanone;
(197) [5-amino-1-(2-methyl-1H-benzimidazol-5-yl)-1H-pyrazol-4-yl]-[6-(4-fluoro-piperidin-1-ylmethyl)-1H-indol-2-yl]-methanone;
(198) [5-amino-1-(2-methyl-1H-benzimidazol-5-yl)-1H-pyrazol-4-yl]-[6-(oxetan-3-yloxy)-1H-indol-2-yl]-methanone;
(199) [5-amino-1-(2-methyl-1H-benzimidazol-5-yl)-1H-pyrazol-4-yl]-(6-hydroxy-1H-indol-2-yl)-methanone;
(200) [5-amino-1-(2-methyl-1H-benzimidazol-5-yl)-1H-pyrazol-4-yl]-(6-methanesulfonyl-1H-indol-2-yl)-methanone;
(201) [5-amino-1-(2-methyl-1H-benzimidazol-5-yl)-1H-pyrazol-4-yl]-(4,5-dibromo-1H-pyrrol-2-yl)-methanone;
(202) [5-amino-1-(2-methyl-1H-benzimidazol-5-yl)-1H-pyrazol-4-yl]-(4,5-diphenyl-1H-pyrrol-2-yl)-methanone; and
(203) [5-amino-1-(2-methyl-1H-benzimidazol-5-yl)-1H-pyrazol-4-yl]-(4,5-dipyridin-3-yl-1H-pyrrol-2-yl)-methanone.
(204) [5-amino-1-(2-methyl-3H-benzimidazol-5-yl)-1H-pyrazol-4-yl]-(6-chloro-1H-indol-2-yl)-methanone;
(205) [5-amino-1-(2-methyl-1H-benzimidazol-5-yl)-1H-pyrazol-4-yl]-(5-chloro-1H-indol-2-yl)-methanone;
(206) [5-amino-1-(2-methyl-1H-benzimidazol-5-yl)-1H-pyrazol-4-yl]-(1H-indol-3-yl)-methanone;
(207) [5-amino-1-(2-methyl-1H-benzimidazol-5-yl)-1H-pyrazol-4-yl]-(1H-indol-6-yl)-methanone;
(208) [5-amino-1-(2-methyl-1H-benzimidazol-5-yl)-1H-pyrazol-4-yl]-(5-bromo-6-fluoro-1H-indol-2-yl)-methanone;
(209) [5-amino-1-(2-ethyl-1H-benzimidazol-5-yl)-1H-pyrazol-4-yl]-(5-bromo-6-fluoro-1H-indol-2-yl)-methanone;
(210) [5-amino-1-(2-methyl-1H-benzimidazol-5-yl)-1H-pyrazol-4-yl]-(5-trifluoromethyl-1H-indol-2-yl)-methanone;
(211) [5-amino-1-(2-methyl-1H-benzimidazol-5-yl)-1H-pyrazol-4-yl]-(5-trifluoromethoxy-1H-indol-2-yl)-methanone;
(212) [5-amino-1-(2-methyl-1H-benzimidazol-5-yl)-1H-pyrazol-4-yl]-(4,6-dichloro-1H-indol-2-yl)-methanone;
(213) [5-amino-1-(2-methyl-1H-benzimidazol-5-yl)-1H-pyrazol-4-yl]-(6-bromo-4-fluoro-1H-indol-2-yl)-methanone;
(214) [5-amino-1-(2-methyl-1H-benzimidazol-5-yl)-1H-pyrazol-4-yl]-(6-trifluoromethoxy-1H-indol-2-yl)-methanone;
(215) [5-amino-1-(2-ethyl-1H-benzimidazol-5-yl)-1H-pyrazol-4-yl]-(5-trifluoromethoxy-1H-indol-2-yl)-methanone;
(216) [5-amino-1-(2-ethyl-1H-benzimidazol-5-yl)-1H-pyrazol-4-yl]-(5-trifluoromethyl-1H-indol-2-yl)-methanone;
(217) [5-amino-1-(2-methyl-1H-benzimidazol-5-yl)-1H-pyrazol-4-yl]-(5,6-dichloro-1H-indol-2-yl)-methanone;
(218) [5-amino-1-(2-ethyl-1H-benzimidazol-5-yl)-1H-pyrazol-4-yl]-(6-bromo-5-fluoro-1H-indol-2-yl)-methanone;
(219) [5-amino-1-(2-methyl-1H-benzimidazol-5-yl)-1H-pyrazol-4-yl]-(4,5-dichloro-1H-indol-2-yl)-methanone;
(220) [5-amino-1-(2-methyl-1H-benzimidazol-5-yl)-1H-pyrazol-4-yl]-(4,6-difluoro-1H-indol-2-yl)-methanone;
(221) [5-amino-1-(2-methyl-1H-benzimidazol-5-yl)-1H-pyrazol-4-yl]-[6-(3-chloro-pyridin-4-yl)-1H-indol-2-yl]-methanone;

(222) [5-amino-1-(2-methyl-1H-benzimidazol-5-yl)-1H-pyrazol-4-yl]-[6-(6-methyl-pyridine-3-yl)-1H-indol-2-yl]-methanone;
(223) [5-amino-1-(2-methyl-1H-benzimidazol-5-yl)-1H-pyrazol-4-yl]-[6-(5-fluoro-pyridin-3-yl)-1H-indol-2-yl]-methanone;
(224) [5-amino-1-(2-methyl-1H-benzimidazol-5-yl)-1H-pyrazol-4-yl]-[6-(2-trifluoromethyl-pyridin-3-yl)-1H-indol-2-yl]-methanone;
(225) [5-amino-1-(2-methyl-1H-benzimidazol-5-yl)-1H-pyrazol-4-yl]-[6-(5-chloro-2-methoxy-pyridin-3-yl)-1H-indol-2-yl]-methanone;
(226) [5-amino-1-(2-methyl-1H-benzimidazol-5-yl)-1H-pyrazol-4-yl]-[6-(5-chloro-pyridin-3-yl)-1H-indol-2-yl]-methanone;
(227) [5-amino-1-(2-methyl-1H-benzimidazol-5-yl)-1H-pyrazol-4-yl]-(6-thiophen-3-yl-1H-indol-2-yl)-methanone;
(228) [5-amino-1-(2-methyl-1H-benzimidazol-5-yl)-1H-pyrazol-4-yl]-[6-(4-chloropyridin-3-yl)-1H-indol-2-yl]-methanone;
(229) [5-amino-1-(2-methyl-1H-benzimidazol-5-yl)-1H-pyrazol-4-yl]-(6-thiophen-2-yl-1H-indol-2-yl)-methanone;
(230) [5-amino-1-(2-methyl-1H-benzimidazol-5-yl)-1H-pyrazol-4-yl]-[6-(3-fluoro-pyridin-4-yl)-1H-indol-2-yl]-methanone;
(231) [5-amino-1-(2-methyl-1H-benzimidazol-5-yl)-1H-pyrazol-4-yl]-[6-(2-trifluoromethyl-pyridin-4-yl)-1H-indol-2-yl]-methanone;
(232) [5-amino-1-(2-methyl-1H-benzimidazol-5-yl)-1H-pyrazol-4-yl]-[5-(3,3-difluoro-pyrrolidine-1-carbonyl)-1H-indol-2-yl]-methanone;
(233) [5-amino-1-(2-methyl-1H-benzimidazol-5-yl)-1H-pyrazol-4-yl]-[5-(2,6-dimethyl-morpholine-4-carbonyl)-1H-indol-2-yl]-methanone;
(234) [5-amino-1-(2-methyl-1H-benzimidazol-5-yl)-1H-pyrazol-4-yl]-[5-([1,4']bipiperidinyl-1'-carbonyl)-1H-indol-2-yl]-methanone;
(235) [5-amino-1-(2-methyl-1H-benzimidazol-5-yl)-1H-pyrazol-4-yl]-{5-[4-(2,2,2-trifluoro-ethyl)-piperazine-1-carbonyl]-1H-indol-2-yl}-methanone;
(236) [5-amino-1-(2-methyl-1H-benzimidazol-5-yl)-1H-pyrazol-4-yl]-{5-[4-(2-hydroxy-ethyl)-piperazine-1-carbonyl]-1H-indol-2-yl}-methanone;
(237) [5-amino-1-(2-methyl-1H-benzimidazol-5-yl)-1H-pyrazol-4-yl]-[5-(3,3,4,4-tetrafluoro-pyrrolidine-1-carbonyl)-1H-indol-2-yl]-methanone;
(238) [5-amino-1-(2-methyl-1H-benzimidazol-5-yl)-1H-pyrazol-4-yl]-[5-((R)-3-fluoro-pyrrolidine-1-carbonyl)-1H-indol-2-yl]-methanone;
(239) [5-amino-1-(2-methyl-1H-benzimidazol-5-yl)-1H-pyrazol-4-yl]-[5-((S)-3-fluoro-pyrrolidine-1-carbonyl)-1H-indol-2-yl]-methanone;
(240) [5-amino-1-(2-methyl-1H-benzimidazol-5-yl)-1H-pyrazol-4-yl]-[4-(4-methoxy-phenyl)-1H-pyrrol-2-yl]-methanone;
(241) [5-amino-1-(2-methyl-1H-benzimidazol-5-yl)-1H-pyrazol-4-yl]-[4-(3-methoxy-phenyl)-1H-pyrrol-2-yl]-methanone;
(242) [5-amino-1-(2-methyl-1H-benzimidazol-5-yl)-1H-pyrazol-4-yl]-[4,5-bis-(3-fluoro-phenyl)-1H-pyrrol-2-yl]-methanone;
(243) [5-amino-1-(2-methyl-1H-benzimidazol-5-yl)-1H-pyrazol-4-yl]-[4,5-bis-(4-methoxy-phenyl)-1H-pyrrol-2-yl]-methanone;
(244) [5-amino-1-(2-methyl-1H-benzimidazol-5-yl)-1H-pyrazol-4-yl]-[4-(2,4-difluoro-phenyl)-1H-pyrrol-2-yl]-methanone;
(245) [5-amino-1-(2-methyl-1H-benzimidazol-5-yl)-1H-pyrazol-4-yl]-[4-(4-trifluoromethoxy-phenyl)-1H-pyrrol-2-yl]-methanone;
(246) [5-amino-1-(2-methyl-1H-benzimidazol-5-yl)-1H-pyrazol-4-yl]-[4,5-bis-(3-methoxy-phenyl)-1H-pyrrol-2-yl]-methanone;
(247) [5-amino-1-(2-methyl-1H-benzimidazol-5-yl)-1H-pyrazol-4-yl]-benzofuran-2-yl-methanone;
(248) [5-amino-1-(2-methyl-1H-benzimidazol-5-yl)-1H-pyrazol-4-yl]-benzo[b]thiophen-2-yl-methanone;
(249) [5-amino-1-(2-methyl-1H-benzimidazol-5-yl)-1H-pyrazol-4-yl]-benzothiazol-2-yl-methanone;
(250) [5-amino-1-(2-methyl-1H-benzimidazol-5-yl)-1H-pyrazol-4-yl]-(4-fluoro-phenyl)-methanone;
(251) [5-amino-1-(2-methyl-1H-benzimidazol-5-yl)-1H-pyrazol-4-yl]-(3-chloro-phenyl)-methanone;
(252) [5-amino-1-(2-methyl-1H-benzimidazol-5-yl)-1H-pyrazol-4-yl]-quinolin-3-yl-methanone;
(253) [5-amino-1-(2-methyl-1H-benzimidazol-5-yl)-1H-pyrazol-4-yl]-quinolin-7-yl-methanone; and
(254) [5-amino-1-(2-methyl-1H-benzimidazol-5-yl)-1H-pyrazol-4-yl]-quinolin-6-yl-methanone.

More specific examples include compounds in which A is indole and $R_3$ and $R_4$ are both hydrogen in formula (I) described above, and compounds shown in Tables 1 and 2 in the Examples described later can be included as examples.

The above-mentioned compounds can be produced according to the production method described in International Publication WO 2011/016528.

In the present invention, compounds having FGFR inhibitory activity as describe above include not only free forms but also pharmaceutically acceptable salts thereof.

Such "salts" include, for example, inorganic acid salts, organic salts, inorganic base salts, organic base salts, and acidic or basic amino acid salts.

Preferred inorganic acid salts include, for example, hydrochloride, hydrobromide, sulfate, nitrate, and phosphate. Preferred organic salts include, for example, acetate, succinate, fumarate, maleate, tartrate, citrate, lactate, malate, stearate, benzoate, methanesulfonate, and p-toluenesulfonate. A particularly preferred salt in the present invention is malate.

Preferred inorganic base salts include, for example, alkali metal salts such as sodium salts and potassium salts; alkali earth metal salts such as calcium salts and magnesium salts; aluminum salts; and ammonium salts. Preferred organic base salts include, for example, diethylamine salts, diethanolamine salts, meglumine salts, and N,N-dibenzylethylenediamine salts.

Preferred acidic amino acid salts include, for example, aspartate and glutamate.

Preferred basic amino acid salts include, for example, arginine salts, lysine salts, and ornithine salts.

In the present invention, compounds having FGFR inhibitory activity also include hydrates thereof. Furthermore, in the present invention, compounds having FGFR inhibitory activity may absorb some type of solvents to form solvates. Such solvates are also included.

In addition, compounds having FGFR inhibitory activity in the present invention include all possible structural isomers (geometric isomers, optical isomers, stereoisomers, tautomers, etc.), and mixtures of isomers.

Compounds having FGFR inhibitory activity in the present invention also include any crystalline polymorphism thereof.

In the present invention, compounds having FGFR inhibitory activity also include prodrugs thereof. "Prodrug" refers to derivatives of the compounds of the present invention which have a chemically or metabolically degradable group, and upon administration to the living body, revert to the original compounds and exhibit the original drug efficacy. The prodrugs include non-covalent complexes and salts.

In the present invention, compounds having FGFR inhibitory activity include those in which one or more atoms within the molecule have been replaced with isotopes. Herein, "isotope" refers to an atom which has the same atomic number (proton number) but different mass number (sum of protons and neutrons). The target atoms to be replaced with an isotope in the compounds of the present invention include, for example, hydrogen atom, carbon atom, nitrogen atom, oxygen atom, phosphorus atom, sulfur atom, fluorine atom, and chlorine atom. Their isotopes include $^{2}H$, $^{3}H$, $^{13}C$, $^{14}C$, $^{15}N$, $^{17}O$, $^{18}O$, $^{31}P$, $^{32}P$, $^{35}S$, $^{18}F$, and $^{36}Cl$. In particular, radioisotopes such as $^{3}H$ and $^{14}C$, which emit radiation and decay, are useful in in vivo tissue distribution studies or such of pharmaceuticals or compounds. Stable isotopes do not decay, and thus their quantity rarely changes; and since there is no emission of radiation, stable isotopes can be used safely. The compounds of the present invention can be converted into isotope-substituted compounds according to routine methods by replacing reagents used in synthesis with reagents containing corresponding isotopes.

Herein, "anticancer agent" or "pharmaceutical composition for treating cancer" which comprises an FGFR inhibitor are used interchangeably, and refers to a cancer therapeutic composition that comprises an above-described compound having FGFR inhibitory activity and pharmaceutically acceptable carriers.

The compounds having FGFR inhibitory activity of the present invention can be formulated into tablets, powders, fine granules, granules, coated tablets, capsules, syrups, troches, inhalants, suppositories, injections, ointments, eye ointments, eye drops, nasal drops, ear drops, cataplasms, lotions, and such by routine methods. For the formulation, conventional excipients, binders, lubricants, colorants, flavoring agents, and if needed, stabilizers, emulsifiers, absorbefacients, surfactants, pH adjusting agents, preservatives, antioxidants, and such can be used. The compounds of the present invention are formulated using routine methods, by combining ingredients that are generally used as materials for pharmaceutical preparations.

For example, to produce oral formulations, the compounds of the present invention or pharmacologically acceptable salts thereof are combined with excipients, and if needed, binders, disintegrating agents, lubricants, coloring agents, flavoring agents, and the like; and then formulated into powders, fine granules, granules, tablets, coated tablets, capsules, and such by routine methods.

The ingredients include, for example, animal and vegetable oils such as soybean oils, beef tallow, and synthetic glycerides; hydrocarbons such as liquid paraffin, squalane, and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid esters, sorbitan fatty acid esters, glycerin fatty acid esters, polyoxyethylene sorbitan fatty acid esters, polyoxyethylene hydrogenated castor oils, and polyoxyethylene/polyoxypropylene block copolymers; water-soluble polymers such as hydroxyethyl cellulose, polyacrylic acids, carboxyvinyl polymers, polyethylene glycol, polyvinylpyrrolidone, and methyl cellulose; lower alcohols such as ethanol and isopropanol; polyalcohols such as glycerin, propylene glycol, dipropylene glycol, and sorbitol; saccharides such as glucose and sucrose; inorganic powders such as silicic anhydride, magnesium aluminum silicate, and aluminum silicate; and purified water.

Excipients include, for example, lactose, cornstarch, sucrose, glucose, mannitol, sorbit, crystalline cellulose, and silicon dioxide.

Binders include, for example, polyvinyl alcohol, polyvinyl ether, methyl cellulose, ethyl cellulose, Arabic gum, tragacanth, gelatin, shellac, hydroxypropyl methyl cellulose, hydroxypropyl cellulose, polyvinylpyrrolidone, polypropylene glycol/polyoxyethylene block polymer, and meglumine.

Disintegrating agents include, for example, starch, agar, gelatin powder, crystalline cellulose, calcium carbonate, sodium bicarbonate, calcium citrate, dextran, pectin, and calcium carboxymethyl cellulose.

Lubricants include, for example, magnesium stearate, talc, polyethylene glycol, silica, and hardened vegetable oil.

Coloring agents approved for use as additives for pharmaceuticals are used. Flavoring agents used include, for example, cacao powder, menthol, aromatic powder, peppermint oil, borneol, and cinnamon powder.

Of course, these tablets and granules may be coated with sugar, or if needed, other appropriate coatings. Alternatively, when liquid preparations such as syrups and injections are produced, the compounds of the present invention or pharmacologically acceptable salts thereof are combined with pH adjusting agents, solubilizers, isotonizing agents, or such, and if needed, solubilizing agents, stabilizers, and such, and then formulated using routine methods.

Methods for producing external preparations are not limited, and they can be produced by conventional methods. Various conventional materials for pharmaceuticals, quasi-drugs, cosmetics, and such can be used as base materials in the production. Specifically, the base materials used include, for example, animal and vegetable oils, mineral oils, ester oils, waxes, higher alcohols, fatty acids, silicon oils, surfactants, phospholipids, alcohols, polyalcohols, water-soluble polymers, clay minerals, and purified water. Furthermore, as necessary, it is possible to add pH-adjusting agents, antioxidants, chelating agents, preservatives, colorants, flavoring agents, and such. However, the base materials for external preparations of the present invention are not limited thereto.

Furthermore, if needed, the preparations may be combined with components that have an activity of inducing differentiation, or components such as blood flow-enhancing agents, antimicrobial agents, antiphlogistic agents, cell-activating agents, vitamins, amino acids, humectants, and keratolytic agents. The amount of above-described base materials added is a quantity that provides a concentration typically selected in the production of external preparations.

The anticancer agents (granular pharmaceutical compositions for treating cancer) for administering a compound having FGFR inhibitory activity in the present invention are not particularly limited in their dosage form; and the agents may be administered orally or parenterally by commonly used methods. They can be formulated and administered as, for example, tablets, powders, granules, capsules, syrups, troches, inhalants, suppositories, injections, ointments, eye ointments, eye drops, nose drops, ear drops, cataplasms, lotions, etc.

In the present invention, the dosage of an FGFR inhibitor contained in an anticancer agent or a pharmaceutical composition for treating cancer can be appropriately selected according to the severity of symptoms, age, sex, weight, dosage form, salt type, specific type of disease, and such.

The dosage varies considerably depending on the patient's disease type, symptom severity, age, sex, sensitivity to the agent, and such. Typically, the agent is administered to an adult once or several times a day at a daily dose of about 0.03 to 1,000 mg, preferably 0.1 to 500 mg, and more preferably 0.1 to 100 mg. The agents or compositions of the present invention are administered once or several times a day. When an injection is used, the daily dose is generally about 1 µg/kg to 3,000 µg/kg, and preferably about 3 µg/kg to 1,000 µg/kg.

The present invention also relates to pharmaceutical compositions for treating cancer which comprise an above-described compound having FGFR inhibitory activity, and are characterized by their use of being administered to patients expressing a fusion polypeptide of the present invention or carrying a polynucleotide encoding the fusion polypeptide.

The present invention further relates to methods for treating or preventing cancer which comprise administering an effective amount of the above-mentioned compounds having FGFR inhibitory activity or pharmaceutically acceptable salts thereof to patients expressing the fusion polypeptides or carrying the polynucleotides; use of compounds having FGFR inhibitory activity or pharmaceutically acceptable salts thereof in the production of pharmaceutical compositions for cancer treatment for administration to patients expressing the fusion polypeptides or carrying the polynucleotides; compounds having FGFR inhibitory activity or pharmaceutically acceptable salts thereof for use in treatment or prevention for patients expressing the fusion polypeptides or carrying the polynucleotides; and such.

Specifically, use of the pharmaceutical compositions for treating cancer is characterized in that whether a patient expresses the fusion polypeptide or carries a polynucleotide encoding the fusion polypeptide is tested using a fusion polypeptide of the present invention as a biomarker before an above-described anticancer agent comprising an FGFR inhibitor is administered to the patient, and the anticancer agent containing an FGFR inhibitor is administered to the patient only if the patient expresses the fusion polypeptide or carries a polynucleotide encoding the fusion polypeptide. This enables one to avoid side effects in therapies using the agent and control the therapeutic condition to produce the best therapeutic effect, thus enabling personalized medicine.

In the present invention, specifically in the case of bladder cancer, the fusion genes of the present invention are found to be significantly expressed when bladder cancer progresses to stage 3 or later in stage classification.

Stage classification of bladder cancer is, specifically, classification by TNM classification. TNM classification is composed of a T factor (initial of tumor) showing the extent of tumor, an N factor (initial of lymph node) showing the presence or absence of lymph node metastasis of tumor, and an M factor (initial of metastasis) showing the presence or absence of distal metastasis other than lymph node metastasis. Among them, cancers in which the tumor has infiltrated into the subepithelial connective tissue are classified as stage 1, those in which the tumor has infiltrated into muscularis propria are classified as stage 2, those in which the tumor has infiltrated into the fatty tissue surrounding the bladder to those in which the tumor has infiltrated into any one of prostate interstitium, uterus, or vagina are classified as stage 3, and those in which the tumor has infiltrated into either the pelvic wall or the abdomen wall, or those that show lymph node metastasis or distal metastasis are classified as stage 4.

Whether a patient expresses a fusion polypeptide of the present invention or carries a polynucleotide encoding the fusion polypeptide can be tested by using methods of the present invention described above.

The present invention also relates to methods for identifying compounds having FGFR inhibitory activity.

Specifically, methods for identifying compounds having FGFR inhibitory activity in the present invention include methods comprising the steps of:

(a) culturing cells that express an above-described fusion polypeptide of the present invention in the presence or absence of a test compound and determining the level of cell proliferation;

(b) comparing the proliferation level of cultured cell between in the presence and absence of the test compound; and (c) judging that the test compound has FGFR inhibitory activity when the proliferation level of the cell cultured in the presence of the test compound is lower than that of the cell cultured in the absence of the test compound.

Cells used for the above method may be living cells, established cell lines, or recombinant cells, as long as they express a fusion polypeptide of the present invention. Such recombinant cells include those introduced with an above-described vector carrying a polynucleotide encoding a fusion polypeptide of the present invention.

Meanwhile, the living cells include cells collected from cancer patients. The established cell lines include cancer cell lines established from cancer cells collected from cancer patients.

In the present invention, cancer includes any cancer described above.

Methods for identifying compounds having FGFR inhibitory activity in the present invention also include those comprising the steps of:

(a) administering a test compound to a non-human mammal transplanted with cells that express an above-described fusion polypeptide of the present invention and determining the proliferation level of the cells;

(b) comparing the cell proliferation level determined in step (a) with that determined using a non-human mammal transplanted with the cells but not administered with the test compound; and (c) judging that the test compound has FGFR inhibitory activity when the cell proliferation level determined in step (a) is lower than that determined using a non-human mammal transplanted with the cells but not administered with the test compound.

Cells used for the above method may be living cells, established cell lines, or recombinant cells, as long as they express a fusion polypeptide of the present invention. Such recombinant cells include those introduced with an above-described vector carrying a polynucleotide encoding a fusion polypeptide of the present invention.

Meanwhile, the living cells include cells collected from cancer patients. The established cell lines include cancer cell lines established from cancer cells collected from cancer patients.

In the present invention, cancer includes any cancer described above.

In the methods of the present invention, the cell proliferation level can be tested according to routine methods, for example, by colorimetric methods that measure the enzyme activity of reducing a dye (MTT, XTT, MTS, WST, etc.) to formazan dye (purple).

When the above-described cells are cancer cells, the cell proliferation level can also be determined by measuring the volume or weight of tumor formed as a result of cell proliferation.

In the present invention, methods for identifying compounds having FGFR inhibitory activity also comprise embodiments that use reporter gene assays.

Reporter genes include commonly-used genes encoding arbitrary fluorescent proteins, for example, the green fluorescent protein (GFP) derived from *Aequorea coerulescens*, luciferase derived from *Renilla reniformis* or such, reef coral fluorescent proteins (RCFPs) derived from hermatypic coral, fruit fluorescent proteins, and variants thereof.

In the present invention, reporter gene assay can be carried out, for example, as follows.

Recombinant cells are prepared by transforming cells that are typically used for producing recombinant proteins with an expression vector inserted with a polynucleotide encoding the fusion polypeptide of the present invention and a gene encoding a reporter protein, so that the reporter protein-encoding gene is transcribed into mRNA dependently on the signal that transcribes the fusion polypeptide-encoding polynucleotide into mRNA. A test compound is contacted with the obtained transformed cells. Whether the compound affects the expression of the fusion polypeptide is indirectly analyzed by determining the expression level of the fusion polypeptide, which depends on the compound activity, by measuring the intensity of fluorescence emitted by the reporter protein simultaneously expressed with the fusion polypeptide (for example, U.S. Pat. Nos. 5,436,128; 5,401,629).

Identification of the compounds using the above-described assay can be achieved by manual operation; however, it can also be done readily and simply by so-called "high-throughput screening" using robots automatically (Soshiki Baiyou Kougaku (The Tissue Culture Engineering), Vol. 23, No. 13, p. 521-524; U.S. Pat. No. 5,670,113).

Hereinbelow, the present invention is specifically described using the Examples, but it is not to be construed as being limited thereto.

Unless otherwise specified, each assay step can be performed according to known methods.

Meanwhile, when using commercially available reagents, kits, or such, assays can be performed according to manuals included in the commercial products.

All prior art documents cited herein are incorporated by reference in their entirety.

Example 1

Expression of Fusion Polypeptides Between FGFR3 and Other Polypeptides in Various Cancer Cells (1) RNA analysis RNA was extracted with the miRNeasy Mini Kit (QIAGEN) from each of the four FGFR3-expressing human cell lines derived from bladder cancer, RT112/84 (available from European Collection of Cell Cultures (ECACC); catalog No. 85061106), RT4 (available from American Type Culture Collection (ATCC); catalog No. HTB-2), SW780 (available from ATCC; catalog No. CRL-2169), and BFTC-905 (available from Deutsche Sammlung von Mikroorganismen und Zellkulturen GmbH (DSMZ); catalog No. ACC 361). The sequences were determined using paired-end reads (Read Length: 2×75 bp) of the HiSeq™ Sequencing system (Illumina).

The determined nucleotide sequences were mapped to Refseq transcripts by referring to an existing method (Maher et al., PNAS, Jul. 28, 2009, 106(30): 12353-12358) to search for candidate fusion genes by looking for pairs of nucleotide sequences that are mapped to different genes. Furthermore, fusion sites were identified using nucleotide sequences that are not mapped to any Refseq transcript, in which one partner of the pair is mapped to one partner in a candidate fusion gene.

As a result, polynucleotides encoding a fusion polypeptide of FGFR3 and TACC3, a fusion polypeptide of FGFR3 and TACC3, and a fusion polypeptide of FGFR3 and BAIAP2L1 were identified from the three types of bladder cancer cell lines: RT112/84, RT4, and SW780. This suggests that the fusion polypeptides were expressed in these cell lines. Meanwhile, a polynucleotide encoding a wild-type FGFR3 polypeptide was confirmed in BFTC-905 cells.

(2) cDNA Analysis cDNAs were synthesized by reverse transcription using a reverse transcription kit, Transcriptor Universal cDNA Master (Roche), according to the instruction manual protocol attached to the kit. The RNAs used in Example 1(1), which were extracted from the three types of cells suggested to express a fusion polypeptide of FGFR3 and TACC3 or a fusion polypeptide of FGFR3 and BAIAP2L1, were each used as a template.

PCR was carried out (35 cycles of 15 seconds at 94° C., 30 seconds at 55° C., and one minute at 68° C.) using each of the prepared cDNAs as a template with DNA polymerase KOD-Plus-Ver. 2 (Toyobo), and a pair of oligonucleotide primers (set 1) having the nucleotide sequences of SEQ ID NO: 1 (F3fu-F3: gtgcacaacctcgactactacaag) and SEQ ID NO: 2 (RT112-R3: gtaatcctccacgcacttcttc), a pair of oligonucleotide primers (set 2) having the nucleotide sequences of SEQ ID NO: 1 (F3fu-F3: gtgcacaacctcgactactacaag) and SEQ ID NO: 5 (RT4-R3: gggtgtcactcttctgtctaagga), or a pair of oligonucleotide primers (set 3) having the nucleotide sequences of SEQ ID NO: 3 (F3fu-F2) tgtttgaccgagtctacact-cacc) and SEQ ID NO: 4 (SW780-R2: gacatgtcccagttcagt-tgac). Then, electrophoresis was performed.

The results showed that with primer set 1, a band of about 670 bp was observed only when the cDNA synthesized from RT112/84 RNA was used as a template. In the amplification with primer set 2, a band of about 610 bp was observed only when the cDNA synthesized from RT4 RNA was used as template. In the amplification with primer set 3, a band of about 450 bp was observed only when the cDNA synthesized from SW780 RNA was used as a template.

Sequencing was performed by Sanger's sequencing method with BigDye™ Terminator v3.1 Cycle Sequencing Kit (Life Technologies) using each PCR product as a template to determine the nucleotide sequence (SEQ ID NO: 14) of the fusion site in the fusion polynucleotide of FGFR3 and TACC3 (FGFR3-TACC3 polynucleotide v1) expressed in RT112/84, the nucleotide sequence (SEQ ID NO: 15) of the fusion site in the fusion polynucleotide of FGFR3 and TACC3 (FGFR3-TACC3 polynucleotide v2) expressed in RT4, and the nucleotide sequence (SEQ ID NO: 16) of the fusion site in the fusion polynucleotide of FGFR3 and BAIAP2L1 (FGFR3-BAIAP2L1 polynucleotide) expressed in SW780.

Based on the information obtained as described above, the nucleotide sequences of cDNAs encoding each fusion polypeptide (full-length) were determined by a common method.

The nucleotide sequence of the cDNA encoding the fusion polypeptide (full-length) of FGFR3 and TACC3 expressed in RT112/84 and its amino acid sequence are shown in SEQ ID NOs: 27 and 28, respectively.

The nucleotide sequence of the cDNA encoding the fusion polypeptide (full-length) of FGFR3 and TACC3 expressed in RT4 and its amino acid sequence are shown in SEQ ID NOs: 29 and 30, respectively.

Results of analyzing the nucleotide sequence of the cDNA showed that the nucleotide sequence at positions 2,281 to 2,379 of SEQ ID NO: 29 is an intron-derived nucleic acid sequence of a gene encoding FGFR3, and encodes the amino acid sequence at positions 761 to 793 of SEQ ID NO: 30.

The nucleotide sequence of the cDNA encoding the fusion polypeptide (full-length) of FGFR3 and BAIAP2L1 expressed in SW780 and its amino acid sequence are shown in SEQ ID NOs: 31 and 32, respectively.

As described above, while there are two types of wild-type polypeptides for human FGFR3 which comprise the amino acid sequences of SEQ ID NOs: 6 and 7, respectively, the N-terminal FGFR3-derived portions in these fusion polypeptides are those of wild-type FGFR3 that has the amino acid sequence of SEQ ID NO: 6.

Based on these test results, it is assumed that two types of fusion polypeptides of TACC3 and the other wild-type FGFR3 that has the amino acid sequence of SEQ ID NO: 7, and a fusion polypeptide of BAIAP2L1 and the other wild-type FGFR3 that has the amino acid sequence of SEQ ID NO: 7 are expressed in various types of human-derived cancer cells.

The nucleotide sequence of the cDNA encoding a fusion polypeptide (full-length) of TACC3 and wild-type FGFR3 that has the amino acid sequence of SEQ ID NO: 7, and its amino acid sequence are shown in SEQ ID NOs: 33 and 34, respectively.

The nucleotide sequence of the cDNA encoding another fusion polypeptide (full-length) of TACC3 and wild-type FGFR3 that has the amino acid sequence of SEQ ID NO: 7, and its amino acid sequence are shown in SEQ ID NOs: 35 and 36, respectively.

Here, the nucleotide sequence at positions 2,275 to 2,373 of the cDNA nucleotide sequence of SEQ ID NO: 35 is a nucleic acid sequence derived from an intron of a gene encoding FGFR3, and encodes the amino acid sequence at positions 759 to 791 of SEQ ID NO: 36.

The nucleotide sequence of the cDNA encoding another fusion polypeptide (full-length) of BAIAP2L1 and wild-type FGFR3 that has the amino acid sequence of SEQ ID NO: 7, and its amino acid sequence are shown in SEQ ID NOs: 37 and 38, respectively.

Furthermore, the presence of an FGFR3-TACC3 fusion polynucleotide was suspected in head and neck squamous cell carcinoma, lung adenocarcinoma, and lung squamous cell carcinoma, while the presence of an FGFR3-BAIAP2L1 fusion polynucleotide was suspected in head and neck squamous cell carcinoma, lung squamous cell carcinoma, and skin melanoma.

Example 2

Analysis of Various FGFR Inhibitors for their Activities of Inhibiting the Kinase Activity of FGFR1, FGFR2, and FGFR3, and Inhibiting the Cell Proliferation of Cell Lines Expressing the FGFR3-TACC3 Fusion Polypeptide 1. Analysis of Various FGFR Inhibitors for their Activity of Inhibiting the Kinase Activity of FGFR1, FGFR2, and FGFR3 (In Vitro)
(1) Inhibitory Activity Against the FGFR1 Enzyme The FGFR1 inhibitory activities of compounds listed in Tables 1-1 to 1-5 were measured based on their activity to inhibit phosphorylation of the biotinylated peptide (EGP-WLEEEEEAYGWMDF; SEQ ID NO: 39) by a human FGFR1 enzyme (Carna Biosciences, cat 08-133). Phosphorylated biotinylated peptide was detected by time-resolved fluorometry using a europium cryptate-linked anti-phosphotyrosine antibody, and streptavidin linked to an allophycocyanin derivative, XL665. The half maximal inhibitory concentration ($IC_{50}$) was calculated based on the inhibitory rate against the control group which does not contain the test substance.

The test result for each compound is shown in Tables 1-1 to 1-5.

(2) Inhibitory Activity Against the FGFR2 Enzyme

The FGFR2 inhibitory activities of compounds listed in Tables 1-1 to 1-5 were measured based on their activity to inhibit phosphorylation of the biotinylated peptide (EGP-WLEEEEEAYGWMDF; SEQ ID NO: 39) by human FGFR2 enzyme prepared using a baculovirus expression system. Phosphorylated biotinylated peptide was detected by time-resolved fluorometry using europium cryptate-linked anti-phosphotyrosine antibody, and streptavidin linked to an allophycocyanin derivative, XL665. The half maximal inhibitory concentration (IC50) was calculated based on the inhibitory rate against the control group which does not contain the test substance.

The test result for each compound is shown in Tables 1-1 to 1-5.

(3) Inhibitory Activity Against the FGFR3 Enzyme

The FGFR3 inhibitory activities of compounds listed in Tables 1-1 to 1-5 were measured based on their activity to inhibit phosphorylation of the biotinylated peptide (EGP-WLEEEEEAYGWMDF; SEQ ID NO: 39) by human FGFR3 enzyme (Carna Biosciences, cat 08-135). Phosphorylated biotinylated peptide was detected by time-resolved fluorometry using europium cryptate-linked anti-phosphotyrosine antibody, and streptavidin linked to an allophycocyanin derivative, XL665. The half maximal inhibitory concentration ($IC_{50}$) was calculated based on the inhibitory rate against the control group which does not contain the test substance.

The test result for each compound is shown in Tables 1-1 to 1-5.

(4) Inhibitory Activity of FGFR Inhibitors on the Cell Proliferation of Cell Lines (In Vitro)

Cells of a bladder cancer-derived cell line RT-4 which expresses an FGFR3-TACC3 fusion polypeptide, and cells of a colon cancer-derived cell line HCT116 which does not express an FGFR3 fusion polypeptide, were plated in 96-well plates, and cultured for four days in the presence of DMSO (used as a control) or each of the compounds listed in Tables 1-1 to 1-5 in 2-fold serial dilutions (18 steps) at a maximum concentration of 50 µM. Four days later, the cell proliferation level was determined using WST-8 (DOJINDO LABORATORIES).

The inhibitory activity of each compound on the cell proliferation of each cell line was calculated according to:

$$(1-T/C) \times 100 (\%)$$

where T represents absorbance at 450 nM in wells where cells were incubated in the presence of a compound at various concentrations, and C represents absorbance at 450 nM in wells where cells were incubated in the presence of DMSO. IC50 was calculated using the least-square method.

As shown in Tables 1-1 to 1-5, the result showed that the 50% cell proliferation inhibitory concentration (IC50) for cells expressing the fusion polypeptide was significantly lower than that for cells that do not express the fusion polypeptide.

TABLE 1-1

| COMPOUND | | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|---|
| 1 | [structure] | 0.0014 | 0.0034 | 0.0035 | 4.1 | 0.02 |
| 2 | [structure] | 0.0069 | 0.0084 | 0.018 | 2.7 | 0.016 |
| 3 | [structure] Chiral | 0.0027 | 0.0043 | 0.0054 | 2.9 | 0.018 |
| 4 | [structure] | 0.00067 | 0.0085 | 0.030 | 9.5 | 0.018 |
| 5 | [structure] | 0.00032 | 0.012 | 0.012 | 11 | 0.021 |
| 6 | [structure] | 0.00081 | 0.012 | 0.0037 | 12 | 0.024 |

TABLE 1-1-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 7 | 0.0029 | 0.0094 | 0.13 | 3.2 | 0.024 |
| 8 | 0.0096 | 0.023 | 0.034 | 11 | 0.029 |
| 9 | 0.010 | 0.015 | 0.046 | 6.3 | 0.030 |
| 10 | 0.009 | 0.0062 | 0.032 | >50 | 0.039 |
| 11 | 0.011 | 0.017 | 0.065 | 5.7 | 0.052 |
| 12 | 0.045 | 0.021 | 0.082 | 7.2 | 0.058 |

TABLE 1-1-continued
| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 13 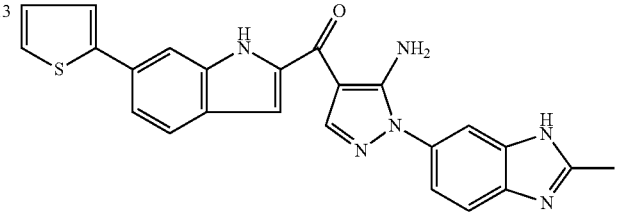 | 0.036 | 0.010 | 0.35 | 0.39 | 0.065 |
| 14 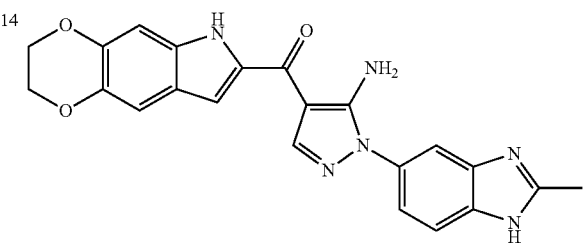 | 0.038 | 0.0076 | 0.10 | 3.1 | 0.075 |
| 15 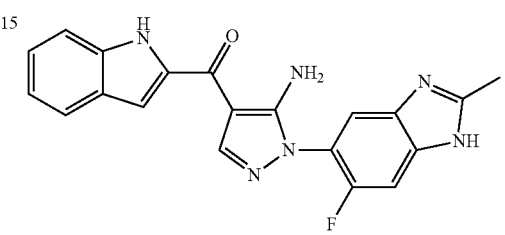 | 0.035 | 0.016 | 0.36 | 19 | 0.076 |
TABLE 1-2
| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 16 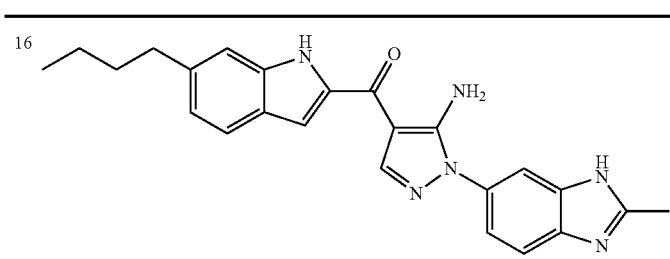 | 0.23 | 0.20 | 0.40 | 17 | 0.076 |

TABLE 1-2-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 17 | 0.011 | 0.012 | 0.041 | 3.8 | 0.077 |
| 18 | 0.048 | 0.021 | 0.079 | 11 | 0.082 |
| 19 | 0.017 | 0.017 | 0.070 | 2.5 | 0.084 |
| 20 | 0.029 | 0.025 | 0.082 | >50 | 0.088 |
| 21 | 0.021 | 0.020 | 0.090 | 21 | 0.088 |
| 22 | 0.016 | 0.0086 | 0.21 | 1.2 | 0.089 |

TABLE 1-2-continued
| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 23 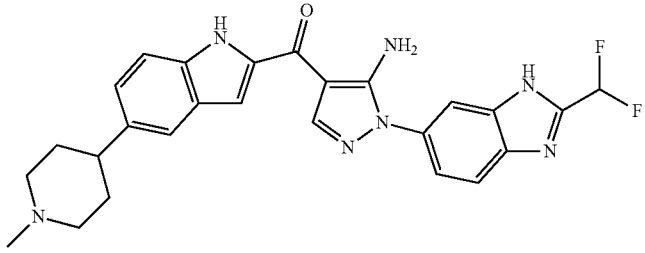 [SMILES: CN1CCC(c2ccc3[nH]c(C(=O)c4cnn(-c5ccc6nc(C(F)F)[nH]c6c5)c4N)cc3c2)CC1] | 0.087 | 0.11 | 0.13 | 10 | 0.09 |
| 24 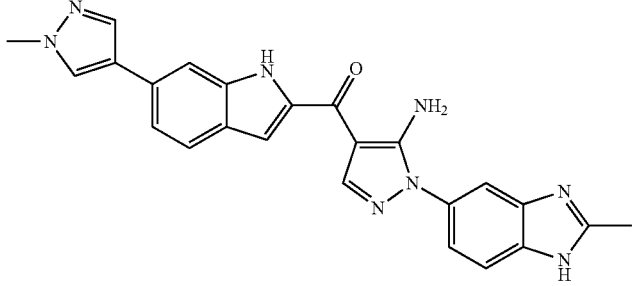 | 0.0023 | 0.016 | 0.060 | >50 | 0.092 |
| 25 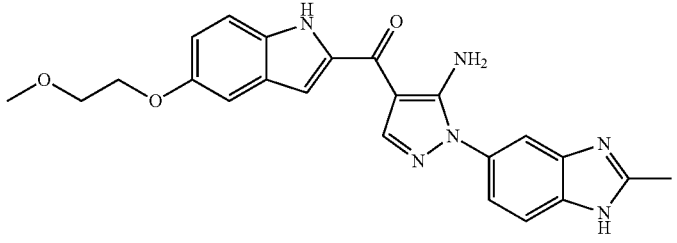 | 0.018 | 0.012 | 0.045 | >100 | 0.098 |
| 26 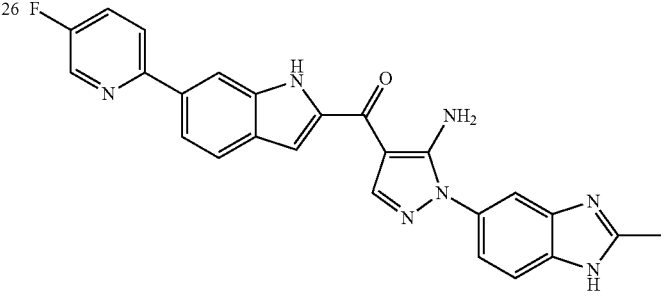 | 0.022 | 0.0055 | 0.094 | 11 | 0.13 |
| 27 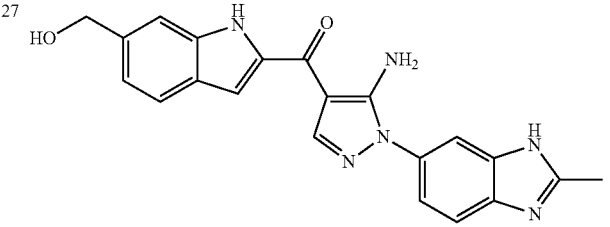 | 0.015 | 0.023 | 0.077 | 25 | 0.15 |

TABLE 1-2-continued
| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 28 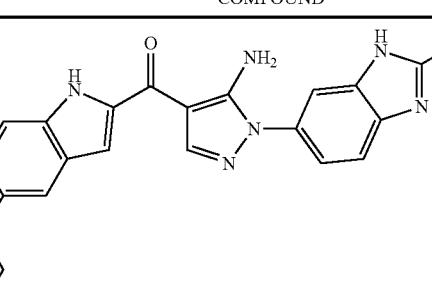 | 0.048 | 0.039 | 0.16 | 21 | 0.2 |
| 29 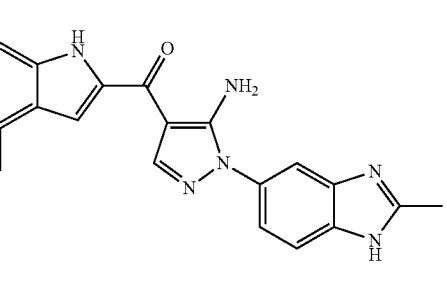 | 0.03 | 0.015 | 0.14 | 8.5 | 0.16 |
| 30 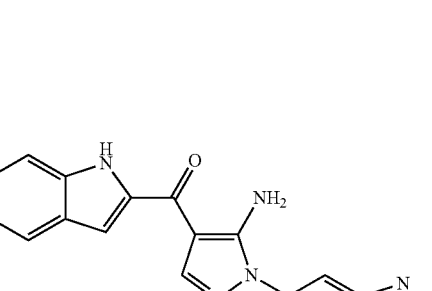 | 0.033 | 0.020 | 0.077 | 13 | 0.16 |
TABLE 1-3
| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 31 | 0.039 | 0.018 | 0.077 | 2 | 0.17 |

TABLE 1-3-continued

| COMPOUND | | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|---|
| 32 | | 0.043 | 0.039 | 0.015 | 8.7 | 0.18 |
| 33 | | 0.15 | 0.056 | 0.95 | 4.4 | 0.18 |
| 34 | | 0.050 | 0.026 | 0.23 | 3.8 | 0.19 |
| 35 | | 0.043 | 0.022 | 0.086 | 7.8 | 0.19 |
| 36 | | 0.075 | 0.040 | 0.38 | 4.8 | 0.19 |

TABLE 1-3-continued
| COMPOUND | | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|---|
| 37 | 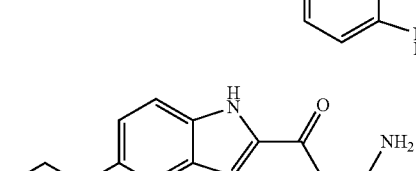 | 0.040 | 0.015 | 0.080 | 8.9 | 0.19 |
| 38 |  | 0.022 | 0.012 | 0.16 | 6.1 | 0.21 |
| 39 | 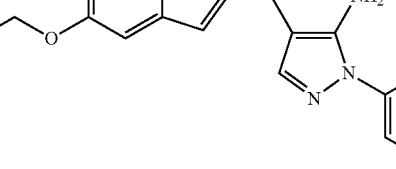 | 0.024 | 0.0083 | 0.37 | 11 | 0.21 |
| 40 |  | 0.042 | 0.026 | 0.15 | 19 | 0.22 |
| 41 | 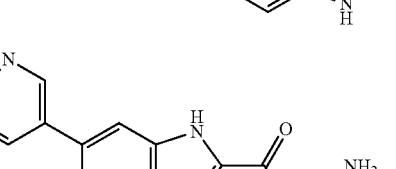 | 0.053 | 0.017 | 0.21 | >20 | 0.24 |
| 42 |  | 0.043 | 0.021 | 0.15 | 15 | 0.25 |

TABLE 1-3-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 43 | 0.060 | 0.027 | 0.13 | >50 | 0.25 |
| 44 | 0.030 | 0.0089 | 0.11 | 10 | 0.26 |
| 45 | 0.0027 | 0.0032 | 0.0054 | 9.4 | 0.29 |

TABLE 1-4

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 46 | 0.056 | 0.021 | 0.068 | 37 | 0.3 |

TABLE 1-4-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 47 | 0.0079 | 0.011 | 0.036 | 14 | 0.320 |
| 48 | 0.027 | 0.018 | 0.12 | 37 | 0.32 |
| 49 | 0.0050 | 0.023 | 0.018 | 13 | 0.350 |
| 50 | 0.091 | 0.057 | 0.37 | 34 | 0.39 |
| 51 | 0.076 | 0.036 | 0.80 | 5.1 | 0.41 |

TABLE 1-4-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 52 | 0.093 | 0.019 | 0.35 | 10 | 0.44 |
| 53 | 0.057 | 0.014 | 0.67 | >20 | 0.44 |
| 54 | 0.038 | 0.022 | 0.082 | >20 | 0.46 |
| 55 | 0.033 | 0.038 | 0.068 | 16 | 0.48 |
| 56 | 0.091 | 0.026 | 1.3 | 19 | 0.49 |

TABLE 1-4-continued

| COMPOUND | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|
| 57 | 0.095 | 0.040 | 0.32 | >20 | 0.51 |
| 58 | 0.0055 | 0.0040 | 0.029 | 12 | 0.56 |
| 59 | 0.046 | 0.016 | 0.25 | 3.3 | 0.58 |
| 60 | 0.030 | 0.0054 | 0.0031 | 17 | 0.6 |

TABLE 1-5

| COMPOUND | | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|---|
| 61 | | 0.14 | 0.078 | 0.037 | 9.1 | 0.62 |
| 62 | | 0.060 | 0.029 | 0.18 | 1.7 | 0.64 |
| 63 | | 0.077 | 0.022 | 0.32 | 13 | 0.67 |
| 64 | | 0.042 | 0.031 | 0.36 | 1.2 | 0.68 |
| 65 | | 0.031 | 0.020 | 0.11 | 23 | 0.68 |
| 66 | | 0.025 | 0.048 | 0.043 | >50 | 0.74 |

TABLE 1-5-continued

| COMPOUND | | FGFR1 IC$_{50}$ (μmol/L) | FGFR2 IC$_{50}$ (μmol/L) | FGFR3 IC$_{50}$ (μmol/L) | HCT116 (CRC) IC$_{50}$ (μmol/L) | RT-4 (Bladder) IC$_{50}$ (μmol/L) |
|---|---|---|---|---|---|---|
| 67 | | 0.0030 | 0.0043 | 0.0067 | 7.3 | 0.75 |
| 68 | | 0.092 | 0.037 | 0.33 | >2 | 0.91 |
| 69 | | 0.12 | 0.11 | 0.038 | 4.3 | 0.92 |
| 70 | | 0.031 | 0.0085 | 0.50 | 9 | 0.97 |
| 71 | | 0.051 | 0.034 | 0.18 | 3.8 | 0.99 |

Example 3

Analysis of FGFR Inhibitors on their Cell Proliferation Inhibitory Activity Against Various Cell Lines Expressing the FGFR3-TACC3 Fusion Polypeptide or FGFR3-BAIAP2L1 Fusion Polypeptide (1) Cell Proliferation Inhibitory Activity of FGFR Inhibitors Against Various Cell Lines (In Vitro)

Six compounds A to F (Tables 2-1 and 2-2), which are substances that suppress the kinase activity of FGFR, were assessed for their effect on cell proliferation in a total of six types of human bladder cancer-derived cell lines: three types of cell lines expressing an FGFR3-TACC3 or FGFR3-BAIAP2L1 fusion polypeptide: RT112/84 (available from ECACC; catalog No. 85061106), RT4 (available from ATCC; catalog No. HTB-2), and SW780 (available from ATCC; catalog No. CRL-2169); cell line BFTC-905 (available from DSMZ; catalog No. ACC 361) which expresses the wild-type FGFR polypeptide but does not express the fusion polypeptides; cell line UM-UC-14 (available from ECACC; catalog No. 08090509) which expresses the mutated type FGFR polypeptide but does not express the fusion polypeptides; and cell line HT-1376 (available from ATCC; catalog No. CRL-1472) which does not express FGFR3.

The cells plated in 96-well plates (RT112/84, BFTC-905, and UM-UC-14: 3.0E+03 cells/well; SW780, RT4, and HT-1376: 5.0E+03 cells/well) were cultured for four days in the presence of DMSO (used as a control) or each compound in three-fold serial dilutions (9 steps) at a maximum concentration of 20 μM. Four days later, the cell proliferation level was determined using WST-8 (DOJINDO LABORATORIES).

The cell proliferation inhibitory activity of each compound against each cell line was calculated according to:

$$(1 - T/C) \times 100(\%)$$

where T represents absorbance at 450 nM in wells where cells were incubated in the presence of a compound at various concentrations, and C represents absorbance at 450 nM in wells where cells were incubated in the presence of DMSO. IC50 was calculated using the least-square method.

As shown in Table 3, the result showed that the 50% cell proliferation inhibitory concentration (IC50) against cells expressing the fusion polypeptides was significantly lower than that against cells that do not express the fusion polypeptides.

TABLE 2-1

| CODE | STRUCTURAL FORMULA/CHEMICAL NAME |
|------|----------------------------------|
| A | [chemical structure] |
| B | COMPOUND REPRESENTED BY [COMPOUND 2] |
| | [chemical structure] |
| C | COMPOUND REPRESENTED BY [COMPOUND 3] |
| | [chemical structure] |

TABLE 2-2

| CODE | STRUCTURAL FORMULA/CHEMICAL NAME |
|---|---|
| D | COMPOUND REPRESENTED BY [COMPOUND 4] |
| E | COMPOUND REPRESENTED BY [COMPOUND 5] |
| F | COMPOUND REPRESENTED BY [COMPOUND 6] |

TABLE 3

| | IC50 (μmol/L) | | | | | |
|---|---|---|---|---|---|---|
| CELL NAME | COMPOUND A | COMPOUND B | COMPOUND C | COMPOUND D | COMPOUND E | COMPOUND F |
| UM-UC-14 | 0.11 | 0.010 | 0.016 | 0.017 | 0.066 | 0.075 |
| RT112/84 | 0.018 | 0.014 | 0.017 | 0.018 | 0.15 | 0.13 |
| SW780 | 0.12 | 0.069 | 0.16 | 1.1 | 0.53 | 0.57 |
| RT4 | 0.35 | 0.18 | 0.25 | 0.23 | 0.24 | 0.25 |
| BFTC-905 | >10 | 14 | 11 | >20 | 2.5 | 2.8 |
| HT-1376 | >10 | 11 | 6.7 | 10 | 1.1 | 0.62 |

(2) Cell Proliferation Inhibitory Activity of FGFR Inhibitors Against Cells Expressing the FGFR3-TACC3 Fusion Polypeptide (In Vivo)

Antitumor effect was assessed using cancer-bearing mice prepared by transplanting cells of the human bladder cancer cell line RT112/84 (ECACC) subcutaneously in the inguinal region of BALB/c nude mice (Charles River Japan, Inc.).

Nude mice were quarantined for about one week before use, and subjected to subcutaneous transplantation of about $1\times10^7$ RT112/84 cells in the inguinal region. When the tumor size reached about 200 mm$^3$, the mice were used in experiments.

Compound A was suspended in a solution containing 10% DMSO, 10% Cremophor EL, 15% PEG400, and 15% HPCD, and orally administered to the mice at a dose of 20 mL/kg once a day.

Antitumor effect was determined by comparing the tumor growth during 11 days after the first day of administration (Day 10 when the first day of administration is set at Day 0) with that of the control group.

Tumor growth inhibitory effect(TGI)=(1−[Average tumor growth level of treated group]/[Average tumor growth level of control group])×100(%)

The result is shown in Table 4.

FGFR inhibitors exhibited a markedly significant tumor growth inhibitory effect in mice bearing tumor cells expressing the FGFR3-TACC3 fusion polypeptide in a concentration-dependent manner.

TABLE 4

| | ANTITUMOR EFFECT | |
|---|---|---|
| | DOSE (mg/kg) | TGI AFTER 11 DAYS (%) |
| Vehicle | — | |
| COMPOUND A | 25 | 61 |
| | 50 | 86 |
| | 100 | 125 |

Example 4

Detection of Polynucleotides Encoding the FGFR3-TACC3 or FGFR3-BAIAP2L1 Fusion Polypeptide in Clinical Specimens (1) Detection of Polynucleotide v1 which Encodes the FGFR3-TACC3 Fusion Polypeptide In order to detect the cDNA of polynucleotide v1 encoding the FGFR3-TACC3 fusion polypeptide in clinical samples, PCR was carried out (42 cycles of 10 seconds at 98° C., 15 seconds at 60° C., and one minute at 68° C.) with Tks Gflex™ DNA Polymerase (Takara bio) using, as primers, oligonucleotides having the nucleotide sequences of SEQ ID NOs: 1 and 2, and as a substrate, cDNA (Origene) derived from bladder cancer samples collected from bladder cancer patients (20 patients) or cDNA synthesized from RT112/84 (ECACC) RNA. Each of the amplified samples was electrophoresed together with size marker DNAs (Invitrogen).

Figure 1:
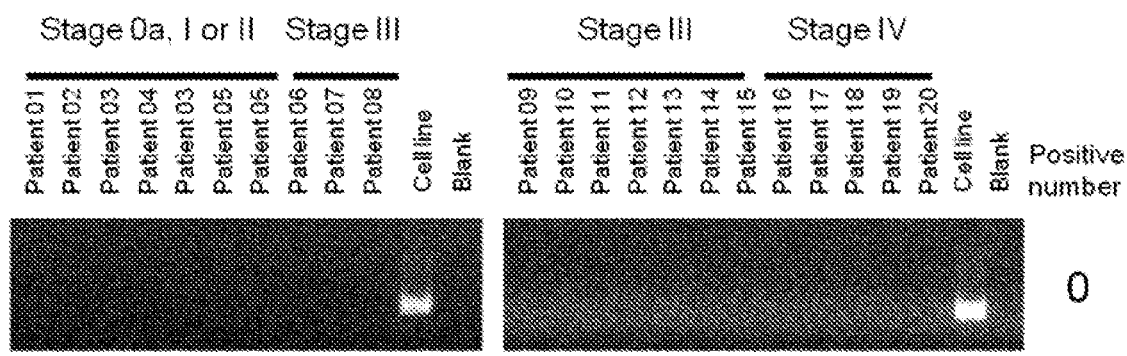
FIG. 1 is a photograph showing results on amplification of a polynucleotide v1 encoding the FGFR3-TACC3 fusion polypeptide, as tested by polymerase chain reaction (PCR) using cDNAs derived from bladder cancer samples collected from bladder cancer patients (20 patients) and cDNAs synthesized from RT112/84 RNA.

As shown in FIG. 1, the result showed that cDNA fragments of polynucleotide v1 encoding the FGFR3-TACC3 fusion polypeptide were not detected in the clinical samples.

(2) Detection of Polynucleotide v2 which Encodes the FGFR3-TACC3 Fusion Polypeptide In order to detect the cDNA of polynucleotide v2 encoding the FGFR3-TACC3 fusion polypeptide in clinical samples, PCR was carried out (42 cycles of 10 seconds at 98° C., 15 seconds at 60° C., and one minute at 68° C.) with Tks Gflex™ DNA Polymerase (Takara bio) using as primers, oligonucleotides having the nucleotide sequences of SEQ ID NOs: 1 and 5, and as a substrate, cDNA (Origene) derived from bladder cancer samples collected from bladder cancer patients (20 patients) or cDNA synthesized from RT4 (ATCC) RNA. Each of the amplified samples was electrophoresed together with size marker DNAs (Invitrogen).

Figure 2:
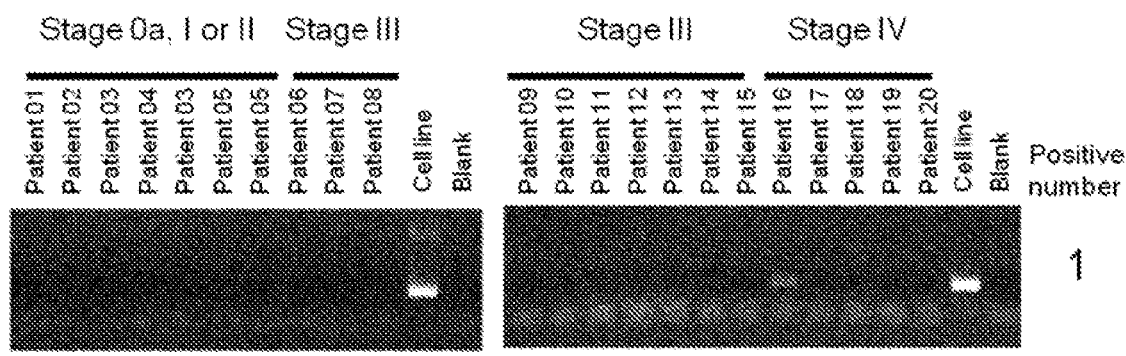
FIG. 2 is a photograph showing results on amplification of a polynucleotide v2 encoding the FGFR3-TACC3 fusion polypeptide, as tested by polymerase chain reaction (PCR)

As shown in FIG. 2, the result showed that a cDNA fragment of polynucleotide v2 encoding the FGFR3-TACC3 fusion polypeptide was detected in a single case.

The above finding shows that the method described above allows detection of polynucleotide v2 encoding the FGFR3-TACC3 fusion polypeptide in samples derived from clinical specimens of bladder cancer, and thus enables selection of patients who are positive for polynucleotide v2 encoding the FGFR3-TACC3 fusion polypeptide.

(3) Detection of a Polynucleotide Encoding the FGFR3-BAIAP2L1 Fusion Polypeptide In order to detect cDNA for an FGFR3-BAIAP2L1 polynucleotide in clinical samples, PCR was carried out (42 cycles of 10 seconds at 98° C., 15 seconds at 60° C., and one minute at 68° C.) with Tks Gflex™ DNA Polymerase (Takara bio) using, as primers, oligonucleotides having the nucleotide sequences of SEQ ID NOs: 3 and 4, and, as a substrate, cDNA (Origene) derived from bladder cancer samples collected from bladder cancer patients (20 patients) or cDNA synthesized from SW780 (ATCC) RNA. Each of the amplified samples was electrophoresed together with size marker DNAs (Invitrogen).

As shown in FIG. 3, the result showed that a cDNA fragment of the FGFR3-BAIAP2L1 fusion polynucleotide was detected in a total of two cases.

The above finding shows that the method described above allows detection of a polynucleotide encoding the FGFR3-BAIAP2L1 fusion polypeptide in samples derived from clinical specimens of bladder cancer, and thus enables selection of patients who are positive for a polynucleotide encoding the FGFR3-BAIAP2L1 fusion polypeptide.

Example 5

Detection of Polynucleotides Encoding the FGFR3-BAIAP2L1 Fusion Polypeptide and FGFR3-TACC3 Fusion Polypeptide in Clinical Specimens of Various Types of Cancers (1) Detection of a Polynucleotide Encoding the FGFR3-BAIAP2L1 Fusion Polypeptide in Clinical Specimens of Lung Cancer (Non-Bladder Cancer) (Test 1)

In order to detect cDNA for an FGFR3-BAIAP2L1 polynucleotide from clinical specimens of non-bladder cancer, PCR was carried out (42 cycles of 98° C. for 10 seconds, 60° C. for 15 seconds, and 68° C. for one minute) with Tks Gflex™ DNA Polymerase (TAKARA BIO INC.) using a pair of oligonucleotide primers having the nucleotide sequences of SEQ ID NO: 3 (F3fu-F2: tgtttgaccgagtctacactcacc) and SEQ ID NO: 4 (SW780-R2: gacatgtcccagttcagttgac), and, as a substrate, 40 samples of cDNAs derived from clinical specimens of lung cancer (OriGene) and cDNA synthesized from SW780 RNA. The amplified samples were electrophoresed together with a size marker DNA (Invitrogen).

As shown in FIG. 4A, the result showed that a cDNA fragment of a polynucleotide encoding the FGFR3-BAIAP2L1 fusion polypeptide was detected in a total of one case.

Furthermore, in order to confirm reproducibility, PCR was carried out (42 cycles of 98° C. for 10 seconds, 60° C. for 15 seconds, and 68° C. for one minute) with Tks Gflex™ DNA Polymerase (TAKARA BIO INC.) using a pair of oligonucleotide primers having the nucleotide sequences of SEQ ID NO: 17 (F3fu-F1: caactgcacacacgacctgta) and SEQ ID NO: 18 (SW780-R1: ccatcgtagtaggcttttcctg), and, as a substrate, cDNAs derived from the same clinical specimens of lung cancer and cDNA synthesized from SW780 RNA. The amplified samples were electrophoresed together with a size marker DNA (Invitrogen).

As shown FIG. 4B, the result showed that a cDNA fragment of a polynucleotide encoding the FGFR3-BAIAP2L1 fusion polypeptide was detected in a total of one case. The above finding shows that the method described above allows detection of a polynucleotide encoding the FGFR3-BAIAP2L1 fusion polypeptide in cDNAs derived from clinical specimens of non-bladder cancer with different types of primers, and thus enables selection of patients who are positive for a polynucleotide encoding the FGFR3-BAIAP2L1 fusion polypeptide.

(2) Detection of Polynucleotides Encoding the FGFR3-BAIAP2L1 Fusion Polypeptides in Clinical Specimens of Lung Cancer (Non-Bladder Cancer) (Test 2)

PCR was carried out (35 cycles of 98° C. for 10 seconds, 60° C. for 15 seconds, and 68° C. for one minute) with Tks Gflex™ DNA Polymerase (TAKARA BIO INC.) using a pair of oligonucleotide primers (Set 3) having the nucleotide sequences of SEQ ID NO: 3 (F3fu-F2: tgtttgaccgagtctacact-cacc) and SEQ ID NO: 4 (SW780-R2: gacatgtcccagttcagt-tgac), and, as a substrate, 83 samples of cDNAs derived from clinical specimens of lung cancer (OriGene). The presence or absence of DNA amplification was confirmed for each sample by agarose gel electrophoresis. DNA bands having the size of interest were detected in two specimens, and it was determined by DNA sequence analysis (Sanger method) that they are cDNA fragment sequences derived from FGFR3-BAIAP2L1 fusion polynucleotides. Accordingly, the FGFR3-BAIAP2L1 fusion polynucleotide was confirmed to exist in cDNAs derived from clinical cancer specimens.

(3) Detection of Polynucleotides Encoding the FGFR3-TACC3 Fusion Polypeptides in Clinical Specimens of Lung Cancer, Esophageal Cancer, Gastric Cancer, and Liver Cancer (all are Non-Bladder Cancers)

PCR was carried out (35 cycles of 98° C. for 10 seconds, 60° C. for 15 seconds, and 68° C. for one minute) with Tks Gflex™ DNA Polymerase (TAKARA BIO INC.) using a pair of oligonucleotide primers (Set 1) having the nucleotide sequences of SEQ ID NO: 1 (F3fu-F3: gtgcacaacctcgactac-tacaag) and SEQ ID NO: 2 (RT112-R3: gtaatcctccacgcact-tcttc), and, as a substrate, 83 samples of cDNAs derived from clinical specimens of lung cancer (OriGene), 18 samples of cDNAs derived from clinical specimens of esophageal cancer (OriGene), five samples of cDNAs derived from clinical specimens of gastric cancer (OriGene), and five samples of cDNAs derived from clinical specimens of liver cancer (OriGene). The presence or absence of DNA amplification was confirmed for each sample by agarose gel electrophoresis. DNA bands having the size of interest were detected in the specimens from two cases of lung cancer, two cases of esophageal cancer, one case of gastric cancer, and one case of liver cancer; and it was determined by DNA sequence analysis (Sanger method) that they are cDNA fragment sequences derived from FGFR3-TACC3 fusion polynucleotides. Accordingly, the FGFR3-TACC3 fusion polynucleotides were confirmed to exist in cDNAs derived from clinical specimens of various types of cancers.

(4) Detection of Polynucleotides Encoding the FGFR3-BAIAP2L1 Fusion Polypeptides in Bladder Cancer Cell Lines Using the FISH Method In order to detect the FGFR3-BAIAP2L1 fusion genes in bladder cancer cell lines using the fluorescence in situ hybridization (FISH) method, an experiment was performed using the following two probe sets and formalin-fixed paraffin-embedded (FFPE) samples of bladder cancer cell lines RT112/84 and SW780.

FISH analysis was performed by using FGFR3 Split Dual Color FISH Probe (Split signal probe set, GSP Lab., Inc.) to detect translocation of a part of the FGFR3 gene on human chromosome 4 to another chromosome, and by using FGFR3 and BAIAP2L1 FISH Probe (Fusion signal probe set, GSP Lab., Inc.) to detect integration of the FGFR3 gene on human chromosome 4 and the BAIAP2L1 gene on human chromosome 7 into the same chromosome.

As shown in FIG. 5, the results confirmed that, in FFPE samples prepared from SW780, signals of two colors were detected separately by FISH analysis with a Split signal probe (A2 of FIG. 5), and merged signal of two colors was detected by FISH analysis with a Fusion signal probe set (B2 of FIG. 5). Accordingly, the above-mentioned method showed that separation of the FGFR3 gene and fusion of the FGFR3 and BAIAP2L1 genes can be detected by the FISH method.

Example 6

Evaluation of Various Cell Lines that Express an FGFR3-TACC3 Fusion Polypeptide or an FGFR3-BAIAP2L1 Fusion Polypeptide (1) Evaluation of FGFR3-Dependency of Various Cell Lines siRNA against FGFR3 or BAIAP2L1 was added to a total of four types of cells: bladder cancer-derived human cell lines RT4 and SW780 which express an FGFR3-TACC3 fusion polypeptide or an FGFR3-BAIAP2L1 fusion polypeptide; the UM-UC-14 cell line which expresses a mutant FGFR3 polypeptide but does not express the fusion polypeptides; and the BFTC-905 cell line which express the wild-type FGFR3 polypeptide but does not express the fusion polypeptides, and effects of each type of siRNA on cell proliferation were examined.

The ON-TARGETplus siRNA Reagents (Thermo Fisher Scientific) were used for the siRNAs.

The cells plated in 96-well plates (UM-UC-14 and BFTC-905: 1.5E+03 cells/well; and SW780 and RT4: 2.5E+03 cells/well) were cultured for seven days in the presence of each siRNA or mock siRNA (used as a control) in ten-fold serial dilutions (3 steps) at a maximum concentration of 10 nM. Cell proliferation after seven days was measured by CellTiter-Glo™ Luminescent Cell Viability Assay (Promega).

As shown in FIG. 6, the result showed that the proliferation activity of cells which express a wild-type FGFR3 polypeptide but does not express the fusion polypeptides were not inhibited by siRNAs against each of FGFR3 and BAIAP2L1. On the other hand, the proliferation activity of the cell line which expresses a mutant FGFR3 polypeptide but does not express the fusion polypeptides, and the proliferation activity of cells which express an FGFR3-TACC3 fusion polypeptide were inhibited only by siRNA against FGFR3. On the other hand, proliferation of cells expressing an FGFR3-BAIAP2L1 fusion polypeptide was confirmed to be inhibited by either of the siRNAs against each of FGFR3 and BAIAP2L1.

(2) Evaluation of Apoptosis Induction by an FGFR Inhibitor Against Cancer Cells that Express an FGFR3-BAIAP2L1 Fusion Polypeptide Each of six compounds A to F (Tables 2-1 and 2-2), which are substances that suppress the kinase activity of FGFR, were added to a total of four types of cells: bladder cancer-derived human cell line SW780 which expresses an FGFR3-BAIAP2L1 fusion polypeptide; the BFTC-905 cell line which expresses the wild-type FGFR polypeptide but does not express the fusion polypeptides; the UM-UC-14 cell line which expresses the mutant FGFR3 polypeptide but does not express the fusion polypeptides; and the HT-1376 cell line which does not express FGFR3 to assess whether apoptosis was induced.

The cells plated in a PrimeSurface™ 96U plates (Sumitomo Bakelite Co. Ltd.) (UM-UC-14 and BFTC-905: 3.0E+03 cells/well; and SW780 and HT-1376: 5.0E+03 cells/well) were cultured for four days in the presence of DMSO (used as a control) or each compound in three-fold serial dilutions (4 steps) at a maximum concentration of 20 μM. Cell proliferation and caspase activity after four days was measured by CellTiter-Glo™ Luminescent Cell Viability Assay (Promega) Caspase-Glo™ 3/7 assay (Promega), respectively. The sum of caspase activity in a single well measured by Caspase-Glo™ 3/7 was divided by the relative viable cell count in a single well calculated from the CellTiter-Glo™ value to calculate the Apoptosis value. Apoptosis induction in each cell was evaluated by dividing the Apoptosis value by the Apoptosis value for each cell calculated under the DMSO-added conditions.

As shown in FIG. 7, the results confirmed that while apoptosis was not induced by the inhibitor in cells unresponsive to an FGFR inhibitor, apoptosis was induced by the FGFR inhibitor in cells responsive to an FGFR inhibitor.

(3) In Vivo Cell Proliferation Inhibitory Activity of FGFR Inhibitors Against Cells Expressing the FGFR3-BAIAP2L1 Fusion Polypeptide Antitumor effect was assessed using cancer-bearing mice prepared by transplanting cells of the human bladder cancer cell line SW780 (ATCC) subcutaneously in the inguinal region of BALB/c nude mice (Charles River Japan, Inc.). Nude mice were quarantined for about one week before use, and subjected to subcutaneous transplantation of $5 \times 10^6$ SW780 cells in the inguinal region. When the tumor size reached about 200 mm$^3$, the mice were used in experiments. Compound A was suspended in a solution containing 10% DMSO, 10% Cremophor EL, 15% PEG400, and 15% HPCD, and orally administered to the mice at 20 mL/kg once a day. Antitumor effect was determined by comparing the tumor growth during 11 days after the first day of administration (Day 10 when the first day of administration is set at Day 0) with that of the control group.

Tumor growth inhibitory effect(TGI)=(1−[Average tumor growth level of treated group]/[Average tumor growth level of control group])×100(%)

The result is shown in Table 5.

FGFR inhibitors exhibited a markedly significant tumor growth inhibitory effect in mice bearing tumor cells expressing the FGFR3-BAIAP2L1 fusion polypeptide in a concentration-dependent manner.

TABLE 5

| | ANTITUMOR EFFECT | |
|---|---|---|
| | DOSE (mg/kg) | TGI AFTER 11 DAYS (%) |
| Vehicle | — | |
| COMPOUND A | 25 | 47 |
| | 50 | 79 |
| | 100 | 111 |

Example 7

Examination of Transforming Ability and Tumorigenic Ability of FGFR3-BAIAP2L1 Fusion Polypeptides (1) Evaluation of Transforming Ability of an FGFR3-BAIAP2L1 Fusion Polypeptide A cDNA (SEQ ID NO: 10) encoding FGFR3 (SEQ ID NO: 6) and a cDNA (SEQ ID NO: 31) encoding FGFR3-BAIAP2L1 (SEQ ID NO: 32) were each subcloned into a lentiviral expression vector pReceiver-Lv156 (GeneCopoeia); and lentivirus for expression of each polypeptide was produced using the Lenti-Pac™ Lentiviral Packaging Systems (GeneCopoeia).

Rat fetus-derived RAT-2 cells were infected with each lentivirus, and the cells were cultured under a condition with a selection marker Puromycin to establish RAT-2 cells that stably express the FGFR3 polypeptide or the FGFR3-BAIAP2L1 fusion polypeptide. As shown in FIG. 8, morphological changes of the established cells stably expressing the FGFR3-BAIAP2L1 fusion polypeptide were observed in monolayer culture.

Untreated RAT-2 cells (parent cells), RAT-2 cells stably expressing the FGFR3 polypeptide, or RAT-2 cells stably expressing the FGFR3-BAIAP2L1 fusion polypeptide plated at $2.0 \times 10^3$ cells/well in a PrimeSurface™ 96U plate (Sumitomo Bakelite Co. Ltd.) were cultured for 14 days. As shown in FIG. 9, when the cells after 14 days were observed and photographed, scaffold-independent cell proliferation was found to be enhanced only in RAT-2 cells stably expressing the FGFR3-BAIAP2L1 fusion polypeptide.

From the result, the FGFR3-BAIAP2L1 fusion polypeptide was confirmed to have transforming ability in normal cells.

(2) Evaluation of the Transforming Ability of an FGFR3-BAIAP2L1 Fusion Polypeptide Lacking a Dimerization-Promoting Region A cDNA encoding FGFR3-BAIAP2L1 ΔBAR, which lacks the BAR domain which is a region promoting dimerization of the BAIAP2L1 polypeptide (amino acid sequence: SEQ ID NO: 8/nucleic acid sequence: SEQ ID NO: 12), was produced by a site-directed mutagenesis method using the PCR method. cDNAs encoding each of FGFR3 (same as the above), FGFR3-BAIAP2L1 (same as the above), and FGFR3-BAIAP2L1 ΔBAR were subcloned into the pCXND3 vector (KAKETSUKEN) to produce vectors for expressing each of the polypeptides.

The pCXND3 vector (vehicle) or a vector for expressing each polypeptide was introduced into human embryonic kidney 293 cells using the FuGENE™ HD Transfection Reagent (Promega). One day later, the cells were collected as cell lysates using Cell Lysis Buffer (Cell Signaling Technology). As shown in FIG. 10, when each cell lysate was analyzed by Western blotting using a Phospho-FGF Receptor (Tyr653/654) Antibody (Cell Signaling Technology) or an anti-FGFR3 antibody (Santa Cruz), FGFR phosphorylation which was enhanced on the FGFR3-BAIAP2L1 fusion polypeptide was confirmed to be attenuated in the FGFR3-BAIAP2L1 ΔBAR fusion polypeptide lacking the BAR domain which is a region promoting dimerization of the BAIAP2L1 polypeptide.

Furthermore, by a method similar to that of the aforementioned examination (1), RAT-2 cells that stably express the BAIAP2L1 polypeptide (the same as the above) or the FGFR3-BAIAP2L1 ΔBAR fusion polypeptide (the same as the above) were established using lentiviruses.

Untreated RAT-2 cells (parent cells), RAT-2 cells stably expressing the FGFR3 polypeptide, RAT-2 cells stably expressing the BAIAP2L1 polypeptide, RAT-2 cells stably expressing the FGFR3-BAIAP2L1 fusion polypeptide, or RAT-2 cells stably expressing the FGFR3-BAIAP2L1 ΔBAR fusion polypeptide were plated at $2.0 \times 10^3$ cells/well in a PrimeSurface™ 96U plate (Sumitomo Bakelite Co. Ltd.), and cultured for 14 days. The cell count after 14 days was determined by the CellTiter-Glo™ Luminescent Cell Viability Assay (Promega). As shown in FIG. 11, it was observed that RAT-2 cells stably expressing the BAIAP2L1 polypeptide did not have scaffold-independent cell proliferation ability, and scaffold-independent cell proliferation ability observed in RAT-2 cells stably expressing the FGFR3-BAIAP2L1 fusion polypeptide was lost in RAT-2 cells stably expressing the FGFR3-BAIAP2L1 ΔBAR fusion polypeptide.

Accordingly, the transforming ability of an FGFR3-BAIAP2L1 fusion polypeptide on normal cells was confirmed to be caused by enhanced trans-autophosphorylation of the FGFR3 polypeptide due to the dimerization-promoting domain in the BAIAP2L1 polypeptide.

(3) Evaluation of Tumorigenic Ability of an FGFR3-BAIAP2L1 Fusion Polypeptide, and Tumor Enlargement-Suppressing Activity of an FGFR Inhibitor RAT-2 cells that stably express the FGFR3 polypeptide, the BAIAP2L1 polypeptide, the FGFR3-BAIAP2L1 fusion polypeptide, or the FGFR3-BAIAP2L1 ΔBAR fusion polypeptide established in the above-mentioned experiments (1) and (2) were inoculated subcutaneously into the inguinal region of BALB/c nude mice (Charles River Laboratories Japan) at $4.8$-$5.4 \times 10^6$ cells, and the mice were observed for 15 days. As shown in FIG. 12, tumor enlargement was confirmed only in mice inoculated with RAT-2 cells stably expressing the FGFR3-BAIAP2L1 fusion polypeptide.

Furthermore, RAT-2 cells that stably express FGFR3-BAIAP2L1 were inoculated into nude mice at $5.04 \times 10^6$ cells. From seven days after planting the cells, an FGFR inhibitor compound A (same as the above) suspended in a solution containing 10% DMSO, 10% Cremophor EL, 15% PEG400, and 15% HPCD was orally administered once daily to mice at a concentration of 20 mL/kg. As shown in FIG. 13, tumor enlargement enhanced by the FGFR3-BAIAP2L1 fusion polypeptide was observed to be significantly suppressed by the FGFR inhibitor in a concentration-dependent manner.

The FGFR3-BAIAP2L1 fusion polypeptide was confirmed to have very strong tumorigenic ability, and this tumorigenic ability was suppressed by the FGFR inhibitor.

INDUSTRIAL APPLICABILITY

Fusion polypeptides comprising an FGFR3 polypeptide and another polypeptide of the present invention are expressed specifically in various types of cancer cells including bladder cancer cells. The proliferation of cells expressing such fusion polypeptides is significantly inhibited by compounds having FGFR inhibitory activity. Thus, the use of a fusion polypeptide of the present invention as a biomarker for FGFR inhibitor-based cancer therapy enables to assess each patient for the applicability or mode of use of the FGFR inhibitor, and enables to avoid side effects and control the mode of therapy to produce the best therapeutic effect in the FGFR inhibitor-based therapy. Thus, this allows personalized medicine.

In addition, the use of fusion polypeptides of the present invention as a target in developing cancer therapeutic agents that target FGFR, i.e., molecularly targeted therapeutic agents, enables to provide FGFR inhibitors with high level of specificity and antitumor activity to target cancer cells as well as cancer therapeutic agents comprising the inhibitors.

FGFR inhibitors obtained as described above have high specificity towards target cancer cells, and thus it becomes possible to provide cancer therapeutic agents with great antitumor activity but few side effects.

Furthermore, fusion polypeptides of the present invention have a close correlation to various types of cancers, and thus cancer susceptibility (sensitivity to cancer) of subjects, whether subjects are affected with cancer, or whether cancer has progressed in subjects can be tested by determining the presence or absence of the fusion polypeptide of the present invention or a polynucleotide encoding the fusion polypeptide in samples from subjects which include not only cancer patients but also healthy persons.

In addition, fusion polypeptides of the present invention have a close correlation to various types of cancers, and thus FGFR inhibitors with high specificity to FGFR can be provided by identifying a test compound that inhibits the proliferation of cells (such as cancer cells) expressing the fusion polypeptides of the present invention by comparing the cell proliferation level between in the presence and absence of the test compound.

SEQUENCE LISTING

```
<160> NUMBER OF SEQ ID NOS: 39

<210> SEQ ID NO 1
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 1
gtgcacaacc tcgactacta caag                                              24

<210> SEQ ID NO 2
<211> LENGTH: 22
<212> TYPE: DNA
<213> ORGANISM: Artificial Sequence
<220> FEATURE:
<223> OTHER INFORMATION: An artificially synthesized primer sequence

<400> SEQUENCE: 2
gtaatcctcc acgcacttct tc                                                22
```

<210> SEQ ID NO 3
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 3
tgtttgaccg agtctacact cacc                                          24

<210> SEQ ID NO 4
<211> LENGTH: 22
<212> TYPE: DNA
<213> ORGANISM: Artificial Sequence
<220> FEATURE:
<223> OTHER INFORMATION: An artificially synthesized primer sequence

<400> SEQUENCE: 4
gacatgtccc agttcagttg ac                                            22

<210> SEQ ID NO 5
<211> LENGTH: 24
<212> TYPE: DNA
<213> ORGANISM: Artificial Sequence
<220> FEATURE:
<223> OTHER INFORMATION: An artificially synthesized primer sequence

<400> SEQUENCE: 5
gggtgtcact cttctgtcta agga                                          24

<210> SEQ ID NO 6
<211> LENGTH: 808
<212> TYPE: PRT
<213> ORGANISM: Homo sapiens

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

```
Arg Glu Phe Arg Gly Glu His Arg Ile Gly Ile Lys Leu Arg His
            195                 200                 205

Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
        290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
        370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
        450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Lys Asp Leu Ser Asp Leu Val Ser Glu Met
        515                 520                 525

Glu Met Met Lys Met Ile Gly Lys His Lys Asn Ile Ile Asn Leu Leu
        530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605
```

```
Tyr Leu Ala Ser Gln Lys Cys Ile His Arg Asp Leu Ala Ala Arg Asn
    610             615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
                675                 680                 685
Ile Phe Thr Leu Gly Gly Ser Pro Tyr Pro Gly Ile Pro Val Glu Glu
690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
                740                 745                 750
Val Leu Thr Val Thr Ser Thr Asp Glu Tyr Leu Asp Leu Ser Ala Pro
                755                 760                 765
Phe Glu Gln Tyr Ser Pro Gly Gly Gln Asp Thr Pro Ser Ser Ser Ser
770                 775                 780
Ser Gly Asp Asp Ser Val Phe Ala His Asp Leu Leu Pro Pro Ala Pro
785                 790                 795                 800
Pro Ser Ser Gly Gly Ser Arg Thr
                805

<210> SEQ ID NO 7
<211> LENGTH: 806
<212> TYPE: PRT
<213> ORGANISM: Homo sapiens

<400> SEQUENCE: 7

Met Gly Ala Pro Ala Cys Ala Leu Ala Leu Cys Val Ala Val Ala Ile
1               5                   10                  15
Val Ala Gly Ala Ser Ser Glu Ser Leu Gly Thr Glu Gln Arg Val Val
                20                  25                  30
Gly Arg Ala Ala Glu Val Pro Gly Pro Glu Pro Gly Gln Gln Glu Gln
            35                  40                  45
Leu Val Phe Gly Ser Gly Asp Ala Val Glu Leu Ser Cys Pro Pro Pro
    50                  55                  60
Gly Gly Gly Pro Met Gly Pro Thr Val Trp Val Lys Asp Gly Thr Gly
65                  70                  75                  80
Leu Val Pro Ser Glu Arg Val Leu Val Gly Pro Gln Arg Leu Gln Val
                85                  90                  95
Leu Asn Ala Ser His Glu Asp Ser Gly Ala Tyr Ser Cys Arg Gln Arg
                100                 105                 110
Leu Thr Gln Arg Val Leu Cys His Phe Ser Val Arg Val Thr Asp Ala
            115                 120                 125
Pro Ser Ser Gly Asp Asp Glu Asp Gly Glu Asp Glu Ala Glu Asp Thr
    130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
```

```
Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
            290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
            325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
            370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
            405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
            450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
            485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

Met Lys Met Ile Gly Lys His Lys Asn Ile Ile Asn Leu Leu Gly Ala
            530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
            565                 570                 575

Tyr Ser Phe Asp Thr Cys Lys Pro Pro Glu Glu Gln Leu Thr Phe Lys
            580                 585                 590
```

```
Asp Leu Val Ser Cys Ala Tyr Gln Val Ala Arg Gly Met Glu Tyr Leu
            595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
    675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
    755                 760                 765

Gln Tyr Ser Pro Gly Gly Gln Asp Thr Pro Ser Ser Ser Ser Ser Gly
770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 8
<211> LENGTH: 511
<212> TYPE: PRT
<213> ORGANISM: Homo sapiens

<400> SEQUENCE: 8

Met Ser Arg Gly Pro Glu Glu Val Asn Arg Leu Thr Glu Ser Thr Tyr
1               5                   10                  15

Arg Asn Val Met Glu Gln Phe Asn Pro Gly Leu Arg Asn Leu Ile Asn
            20                  25                  30

Leu Gly Lys Asn Tyr Glu Lys Ala Val Asn Ala Met Ile Leu Ala Gly
        35                  40                  45

Lys Ala Tyr Tyr Asp Gly Val Ala Lys Ile Gly Glu Ile Ala Thr Gly
    50                  55                  60

Ser Pro Val Ser Thr Glu Leu Gly His Val Leu Ile Glu Ile Ser Ser
65                  70                  75                  80

Thr His Lys Lys Leu Asn Glu Ser Leu Asp Glu Asn Phe Lys Lys Phe
                85                  90                  95

His Lys Glu Ile Ile His Glu Leu Glu Lys Lys Ile Glu Leu Asp Val
            100                 105                 110

Lys Tyr Met Asn Ala Thr Leu Lys Arg Tyr Gln Thr Glu His Lys Asn
        115                 120                 125

Lys Leu Glu Ser Leu Glu Lys Ser Gln Ala Glu Leu Lys Lys Ile Arg
    130                 135                 140

Arg Lys Ser Gln Gly Ser Arg Asn Ala Leu Lys Tyr Glu His Lys Glu
145                 150                 155                 160
```

```
Ile Glu Tyr Val Glu Thr Val Thr Ser Arg Gln Ser Glu Ile Gln Lys
            165                 170                 175

Phe Ile Ala Asp Gly Cys Lys Glu Ala Leu Leu Glu Glu Lys Arg Arg
            180                 185                 190

Phe Cys Phe Leu Val Asp Lys His Cys Gly Phe Ala Asn His Ile His
            195                 200                 205

Tyr Tyr His Leu Gln Ser Ala Glu Leu Leu Asn Ser Lys Leu Pro Arg
            210                 215                 220

Trp Gln Glu Thr Cys Val Asp Ala Ile Lys Val Pro Glu Lys Ile Met
225                 230                 235                 240

Asn Met Ile Glu Glu Ile Lys Thr Pro Ala Ser Thr Pro Val Ser Gly
            245                 250                 255

Thr Pro Gln Ala Ser Pro Met Ile Glu Arg Ser Asn Val Val Arg Lys
            260                 265                 270

Asp Tyr Asp Thr Leu Ser Lys Cys Ser Pro Lys Met Pro Pro Ala Pro
            275                 280                 285

Ser Gly Arg Ala Tyr Thr Ser Pro Leu Ile Asp Met Phe Asn Asn Pro
            290                 295                 300

Ala Thr Ala Ala Pro Asn Ser Gln Arg Val Asn Asn Ser Thr Gly Thr
305                 310                 315                 320

Ser Glu Asp Pro Ser Leu Gln Arg Ser Val Ser Val Ala Thr Gly Leu
            325                 330                 335

Asn Met Met Lys Lys Gln Lys Val Lys Thr Ile Phe Pro His Thr Ala
            340                 345                 350

Gly Ser Asn Lys Thr Leu Leu Ser Phe Ala Gln Gly Asp Val Ile Thr
            355                 360                 365

Leu Leu Ile Pro Glu Glu Lys Asp Gly Trp Leu Tyr Gly Glu His Asp
            370                 375                 380

Val Ser Lys Ala Arg Gly Trp Phe Pro Ser Ser Tyr Thr Lys Leu Leu
385                 390                 395                 400

Glu Glu Asn Glu Thr Glu Ala Val Thr Val Pro Thr Pro Ser Pro Thr
            405                 410                 415

Pro Val Arg Ser Ile Ser Thr Val Asn Leu Ser Glu Asn Ser Ser Val
            420                 425                 430

Val Ile Pro Pro Pro Asp Tyr Leu Glu Cys Leu Ser Met Gly Ala Ala
            435                 440                 445

Ala Asp Arg Arg Ala Asp Ser Ala Arg Thr Thr Ser Thr Phe Lys Ala
450                 455                 460

Pro Ala Ser Lys Pro Glu Thr Ala Ala Pro Asn Asp Ala Asn Gly Thr
465                 470                 475                 480

Ala Lys Pro Pro Phe Leu Ser Gly Glu Asn Pro Phe Ala Thr Val Lys
            485                 490                 495

Leu Arg Pro Thr Val Thr Asn Asp Arg Ser Ala Pro Ile Ile Arg
            500                 505                 510

<210> SEQ ID NO 9
<211> LENGTH: 838
<212> TYPE: PRT
<213> ORGANISM: Homo sapiens

<400> SEQUENCE: 9

Met Ser Leu Gln Val Leu Asn Asp Lys Asn Val Ser Asn Glu Lys Asn
1               5                   10                  15

Thr Glu Asn Cys Asp Phe Leu Phe Ser Pro Pro Glu Val Thr Gly Arg
```

```
                20                  25                  30
Ser Ser Val Leu Arg Val Ser Gln Lys Glu Asn Val Pro Pro Lys Asn
            35                  40                  45

Leu Ala Lys Ala Met Lys Val Thr Phe Gln Thr Pro Leu Arg Asp Pro
        50                  55                  60

Gln Thr His Arg Ile Leu Ser Pro Ser Met Ala Ser Lys Leu Glu Ala
65                  70                  75                  80

Pro Phe Thr Gln Asp Asp Thr Leu Gly Leu Glu Asn Ser His Pro Val
                85                  90                  95

Trp Thr Gln Lys Glu Asn Gln Gln Leu Ile Lys Glu Val Asp Ala Lys
            100                 105                 110

Thr Thr His Gly Ile Leu Gln Lys Pro Val Glu Ala Asp Thr Asp Leu
        115                 120                 125

Leu Gly Asp Ala Ser Pro Ala Phe Gly Ser Gly Ser Ser Ser Glu Ser
    130                 135                 140

Gly Pro Gly Ala Leu Ala Asp Leu Asp Cys Ser Ser Ser Gln Ser
145                 150                 155                 160

Pro Gly Ser Ser Glu Asn Gln Met Val Ser Pro Gly Lys Val Ser Gly
                165                 170                 175

Ser Pro Glu Gln Ala Val Glu Glu Asn Leu Ser Ser Tyr Ser Leu Asp
            180                 185                 190

Arg Arg Val Thr Pro Ala Ser Glu Thr Leu Glu Asp Pro Cys Arg Thr
        195                 200                 205

Glu Ser Gln His Lys Ala Glu Thr Pro His Gly Ala Glu Glu Glu Cys
    210                 215                 220

Lys Ala Glu Thr Pro His Gly Ala Glu Glu Cys Arg His Gly Gly
225                 230                 235                 240

Val Cys Ala Pro Ala Ala Val Ala Thr Ser Pro Pro Gly Ala Ile Pro
                245                 250                 255

Lys Glu Ala Cys Gly Gly Ala Pro Leu Gln Gly Leu Pro Gly Glu Ala
            260                 265                 270

Leu Gly Cys Pro Ala Gly Val Gly Thr Pro Val Pro Ala Asp Gly Thr
        275                 280                 285

Gln Thr Leu Thr Cys Ala His Thr Ser Ala Pro Glu Ser Thr Ala Pro
    290                 295                 300

Thr Asn His Leu Val Ala Gly Arg Ala Met Thr Leu Ser Pro Gln Glu
305                 310                 315                 320

Glu Val Ala Ala Gly Gln Met Ala Ser Ser Arg Ser Gly Pro Val
                325                 330                 335

Lys Leu Glu Phe Asp Val Ser Asp Gly Ala Thr Ser Lys Arg Ala Pro
            340                 345                 350

Pro Pro Arg Arg Leu Gly Glu Ser Gly Leu Lys Pro Pro Leu Arg
        355                 360                 365

Lys Ala Ala Val Arg Gln Gln Lys Ala Pro Gln Glu Val Glu Glu Asp
    370                 375                 380

Asp Gly Arg Ser Gly Ala Gly Glu Asp Pro Pro Met Pro Ala Ser Arg
385                 390                 395                 400

Gly Ser Tyr His Leu Asp Trp Asp Lys Met Asp Asp Pro Asn Phe Ile
                405                 410                 415

Pro Phe Gly Gly Asp Thr Lys Ser Gly Cys Ser Glu Ala Gln Pro Pro
            420                 425                 430

Glu Ser Pro Glu Thr Arg Leu Gly Gln Pro Ala Ala Glu Gln Leu His
        435                 440                 445
```

```
Ala Gly Pro Ala Thr Glu Glu Pro Gly Pro Cys Leu Ser Gln Gln Leu
    450                 455                 460

His Ser Ala Ser Ala Glu Asp Thr Pro Val Val Gln Leu Ala Ala Glu
465                 470                 475                 480

Thr Pro Thr Ala Glu Ser Lys Glu Arg Ala Leu Asn Ser Ala Ser Thr
                485                 490                 495

Ser Leu Pro Thr Ser Cys Pro Gly Ser Glu Pro Val Pro Thr His Gln
            500                 505                 510

Gln Gly Gln Pro Ala Leu Glu Leu Lys Glu Glu Ser Phe Arg Asp Pro
        515                 520                 525

Ala Glu Val Leu Gly Thr Gly Ala Glu Val Asp Tyr Leu Glu Gln Phe
    530                 535                 540

Gly Thr Ser Ser Phe Lys Glu Ser Ala Leu Arg Lys Gln Ser Leu Tyr
545                 550                 555                 560

Leu Lys Phe Asp Pro Leu Leu Arg Asp Ser Pro Gly Arg Pro Val Pro
                565                 570                 575

Val Ala Thr Glu Thr Ser Ser Met His Gly Ala Asn Glu Thr Pro Ser
            580                 585                 590

Gly Arg Pro Arg Glu Ala Lys Leu Val Glu Phe Asp Phe Leu Gly Ala
        595                 600                 605

Leu Asp Ile Pro Val Pro Gly Pro Pro Gly Val Pro Ala Pro Gly
    610                 615                 620

Gly Pro Pro Leu Ser Thr Gly Pro Ile Val Asp Leu Leu Gln Tyr Ser
625                 630                 635                 640

Gln Lys Asp Leu Asp Ala Val Val Lys Ala Thr Gln Glu Glu Asn Arg
                645                 650                 655

Glu Leu Arg Ser Arg Cys Glu Glu Leu His Gly Lys Asn Leu Glu Leu
            660                 665                 670

Gly Lys Ile Met Asp Arg Phe Glu Glu Val Val Tyr Gln Ala Met Glu
        675                 680                 685

Glu Val Gln Lys Gln Lys Glu Leu Ser Lys Ala Glu Ile Gln Lys Val
    690                 695                 700

Leu Lys Glu Lys Asp Gln Leu Thr Thr Asp Leu Asn Ser Met Glu Lys
705                 710                 715                 720

Ser Phe Ser Asp Leu Phe Lys Arg Phe Glu Lys Gln Lys Glu Val Ile
                725                 730                 735

Glu Gly Tyr Arg Lys Asn Glu Glu Ser Leu Lys Lys Cys Val Glu Asp
            740                 745                 750

Tyr Leu Ala Arg Ile Thr Gln Glu Gly Gln Arg Tyr Gln Ala Leu Lys
        755                 760                 765

Ala His Ala Glu Glu Lys Leu Gln Leu Ala Asn Glu Glu Ile Ala Gln
    770                 775                 780

Val Arg Ser Lys Ala Gln Ala Glu Ala Leu Ala Leu Gln Ala Ser Leu
785                 790                 795                 800

Arg Lys Glu Gln Met Arg Ile Gln Ser Leu Glu Lys Thr Val Glu Gln
                805                 810                 815

Lys Thr Lys Glu Asn Glu Glu Leu Thr Arg Ile Cys Asp Asp Leu Ile
            820                 825                 830

Ser Lys Met Glu Lys Ile
        835
```

<210> SEQ ID NO 10
<211> LENGTH: 2427

<212> TYPE: DNA
<213> ORGANISM: Homo sapiens

<400> SEQUENCE: 10

```
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180
tgtcccccgc ccggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt tggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga atggcagcaa ggtgggcccg     900
gacggcacac cctacgttac cgtgctcaag tcctggatca gtgagagtgt ggaggccgac     960
gtgcgcctcc gcctggccaa tgtgtcggag cgggacgggg gcgagtacct ctgtcgagcc    1020
accaatttca taggcgtggc cgagaaggcc ttttggctga cgttcacgg gccccgagca    1080
gccgaggagg agctggtgga ggctgacgag gcgggcagtg tgtatgcagg catcctcagc    1140
tacggggtgg gcttcttcct gttcatcctg gtggtggcgg ctgtgacgct ctgccgcctg    1200
cgcagccccc ccaagaaagg cctgggctcc ccaccgtgc acaagatctc ccgcttcccg    1260
ctcaagcgac aggtgtccct ggagtccaac gcgtccatga gctccaacac accactggtg    1320
cgcatcgcaa ggctgtcctc aggggagggc cccacgctgg ccaatgtctc cgagctcgag    1380
ctgcctgccg accccaaatg ggagctgtct cgggcccggc tgaccctggg caagcccctt    1440
ggggagggct gcttcggcca ggtggtcatg gcggaggcca tcggcattga caaggaccgg    1500
gccgccaagc tgtcaccgt agccgtgaag atgctgaaag acgatgccac tgacaaggac    1560
ctgtcggacc tggtgtctga gatggagatg atgaagatga tcgggaaaca caaaacatc    1620
atcaacctgc tgggcgcctg cacgcagggc gggcccctgt acgtgctggt ggagtacgcg    1680
gccaagggta acctgcggga gtttctgcgc gcgcggcggc cccgggcct ggactactcc    1740
ttcgacacct gcaagccgcc cgaggagcag ctcaccttca ggacctggt gtcctgtgcc    1800
taccaggtgg cccggggcat ggagtacttg gcctcccaga agtgcatcca cagggacctg    1860
gctgcccgca atgtgctggt gaccgaggac aacgtgatga agatcgcaga cttcgggctg    1920
gcccgggaca tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg gctccccgta ccccggcatc    2100
cctgtggagg agtcttcaa gctgctgaag gagggccacc gcatggacaa gcccgccaac    2160
tgcacacacg acctgtacat gatcatgcgg gagtgctggc atgccgcgcc ctcccagagg    2220
```

```
cccaccttca agcagctggt ggaggacctg gaccgtgtcc ttaccgtgac gtccaccgac    2280
gagtacctgg acctgtcggc gcctttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                         2427

<210> SEQ ID NO 11
<211> LENGTH: 2421
<212> TYPE: DNA
<213> ORGANISM: Homo sapiens

<400> SEQUENCE: 11
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180
tgtcccccgc cgggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc tggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctcccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga tggcagcaa ggtgggcccg     900 gacggcacac cctacgttac cgtgctcaag acggcgggcg ctaacaccac cgacaaggag     960
ctagaggttc tctccttgca caacgtcacc tttgaggacg ccggggagta cacctgcctg    1020
gcgggcaatt ctattgggtt ttctcatcac tctgcgtggc tggtggtgct gccagccgag    1080
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt cccgctcaag    1260
cgacaggtgt ccctggagtc caacgcgtcc atgagctcca acacaccact ggtgcgcatc    1320
gcaaggctgt cctcagggga gggcccacg ctggccaatg tctccgagct cgagctgcct    1380
gccgacccca atgggagct gtctcgggcc cggctgaccc tgggcaagcc ccttgggag    1440 ggctgcttcg ccaggtggt catggcggag ccatcggca ttgacaagga ccgggccgcc    1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac    1620 ctgctgggcg cctgcacgca gggcgggccc ctgtacgtgc tggtgagta gcggccaag    1680 ggtaacctgc gggagtttct gcgggcgcgg cggccccgg gcctggacta ctccttcgac    1740
acctgcaagc cgcccgagga gcagctcacc ttcaaggacc tggtgtcctg tgcctaccag    1800
gtggcccggg gcatggagta cttggcctcc agaagtgca tccacaggga cctggctgcc    1860
cgcaatgtgc tggtgaccga ggacaacgtg atgaagatcg cagacttcgg gctggcccgg    1920
```

```
gacgtgcaca acctcgacta ctacaagaag acaaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtacccgg catccctgtg     2100 gaggagctct tcaagctgct gaaggagggc accgcatgg acaagcccgc caactgcaca    2160
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgcccccggc cccacccagc    2400
agtgggggct cgcggacgtg a                                              2421

<210> SEQ ID NO 12
<211> LENGTH: 1536
<212> TYPE: DNA
<213> ORGANISM: Homo sapiens

<400> SEQUENCE: 12
atgtcccggg ggcccgagga ggtgaaccgg ctcacggaga gcacctaccg gaatgttatg      60
gaacagttca atcctgggct gcgaaattta ataaacctgg ggaaaaatta tgagaaagct     120
gtaaacgcta tgatcctggc aggaaaagcc tactacgatg gagtggccaa gatcggtgag     180
attgccactg ggtcccccgt gtcaactgaa ctgggacatg tcctcataga gatttcaagt     240
acccacaaga aactcaacga gagtcttgat gaaaatttta aaaattcca caaagagatt      300 atccatgagc tggagaagaa gatagaactt gacgtgaaat atatgaacgc aactctaaaa     360
agataccaaa cagaacacaa gaataaatta gagtctttgg agaaatccca agctgagttg     420
aagaagatca gaaggaaaag ccaaggaagc cgaaacgcac tcaaatatga acacaaagaa     480
attgagtatg tggagaccgt tacttctcgt cagagtgaaa tccagaaatt cattgcagat     540
ggttgcaaag aggctctgct tgaagagaag aggcgcttct gctttctggt tgataagcac     600
tgtggctttg caaccacat acattattat cacttacagt ctgcagaact actgaattcc       660
aagctgcctc ggtggcagga gacctgtgtt gatgccatca aagtgccaga gaaaatcatg     720
aatatgatcg aagaaataaa gaccccagcc tctaccccg tgtctggaac tcctcaggct       780
tcacccatga tcgagagaag caatgtggtt aggaaagatt acgacaccct ttctaaatgc     840
tcaccaaaga tgcccccgc tccttcaggc agagcatata ccagtccctt gatcgatatg      900
tttaataacc cagccacggc tgccccgaat tcacaaaggg taaataattc aacaggtact     960
tccgaagatc ccagtttaca gcgatcagtt tcggttgcaa cgggactgaa catgatgaag    1020
aagcagaaag tgaagaccat cttcccgcac actgcgggct ccaacaagac cttactcagc    1080
tttgcacagg gagatgtcat cacgctgctc atccccgagg agaaggatgg ctggctctat    1140
ggagaacacg acgtgtccaa ggcgaggggt tggttcccgt cgtcgtacac gaagttgctg    1200
gaagaaaatg agacagaagc agtgaccgtg cccacgccaa gccccacacc agtgagaagc    1260
atcagcaccg tgaacttgtc tgagaatagc agtgttgtca tcccccccacc cgactacttg    1320 gaatgcttgt ccatgggggc agctgccgac aggagagcag attcggccag gacgacatcc    1380
acctttaagg ccccagcgtc caagcccgag accgcggctc ctaacgatgc caacgggact    1440
gcaaagccgc ctttctcag cggagaaaac ccctttgcca ctgtgaaact ccgcccgact    1500
gtgacgaatg atcgctcggc acccatcatt cgatga                             1536
```

<210> SEQ ID NO 13
<211> LENGTH: 2517
<212> TYPE: DNA
<213> ORGANISM: Homo sapiens

<400> SEQUENCE: 13

| | | | | | |
|---|---|---|---|---|---|
| atgagtctgc | aggtcttaaa | cgacaaaaat | gtcagcaatg | aaaaaaatac | agaaaattgc | 60 |
| gacttcctgt | tttcgccacc | agaagttacc | ggaagatcgt | ctgttcttcg | tgtgtcacag | 120 |
| aaagaaaatg | tgccacccaa | gaacctggcc | aaagctatga | aggtgacttt | tcagacacct | 180 |
| ctgcgggatc | cacagacgca | caggattcta | agtcctagca | tggccagcaa | acttgaggct | 240 |
| cctttcactc | aggatgacac | ccttggactg | gaaaactcac | acccggtctg | gacacagaaa | 300 |
| gagaaccaac | agctcatcaa | ggaagtggat | gccaaaacta | ctcatggaat | tctacagaaa | 360 |
| ccagtggagg | ctgacaccga | cctcctgggg | gatgcaagcc | cagcctttgg | gagtggcagc | 420 |
| tccagcgagt | ctggcccagg | tgccctggct | gacctggact | gctcaagctc | ttcccagagc | 480 |
| ccaggaagtt | ctgagaacca | aatggtgtct | ccaggaaaag | tgtctggcag | ccctgagcaa | 540 |
| gccgtggagg | aaaaccttag | ttcctattcc | ttagacagaa | gagtgacacc | cgcctctgag | 600 |
| accctagaag | acccttgcag | gacagagtcc | agcacaaaag | cggagactcc | gcacggagcc | 660 |
| gaggaagaat | gcaaagcgga | gactccgcac | ggagccgagg | aggaatgccg | gcacggtggg | 720 |
| gtctgtgctc | ccgcagcagt | ggccacttcg | cctcctggtg | caatccctaa | ggaagcctgc | 780 |
| ggaggagcac | ccctgcaggg | tctgcctggc | gaagccctgg | gctgccctgc | gggtgtgggc | 840 |
| acccccgtgc | cagcagatgg | cactcagacc | cttacctgtg | cacacacctc | tgctcctgag | 900 |
| agcacagccc | caaccaacca | cctggtggct | ggcagggcca | tgaccctgag | tcctcaggaa | 960 |
| gaagtggctc | aggccaaat | ggccagctcc | tcgaggagcg | gacctgtaaa | actagaattt | 1020 |
| gatgtatctg | atggcgccac | cagcaaaagg | gcacccccac | caaggagact | gggagagagg | 1080 |
| tccggcctca | gcctcccctt | gaggaaagca | gcagtgaggc | agcaaaaggc | cccgcaggag | 1140 |
| gtggaggagg | acgacggtag | gagcggagca | ggagaggacc | cccccatgcc | agcttctcgg | 1200 |
| ggctcttacc | acctcgactg | ggacaaaatg | gatgacccaa | acttcatccc | gttcggaggt | 1260 |
| gacaccaagt | ctggttgcag | tgaggcccag | cccccagaaa | gccctgagac | caggctgggc | 1320 |
| cagccagcgg | ctgaacagtt | gcatgctggg | cctgccacgg | aggagccagg | tccctgtctg | 1380 |
| agccagcagc | tgcattcagc | ctcagcggag | gacacgcctg | tggtgcagtt | ggcagccgag | 1440 |
| accccaacag | cagagagcaa | ggagagagcc | ttgaactctg | ccagcacctc | gcttcccaca | 1500 |
| agctgtccag | gcagtgagcc | agtgcccacc | catcagcagg | ggcagcctgc | cttggagctg | 1560 |
| aaagaggaga | gcttcagaga | ccccgctgag | gttctaggca | cgggcgcgga | ggtggattac | 1620 |
| ctggagcagt | ttggaacttc | ctcgtttaag | gagtcggcct | tgaggaagca | gtccttatac | 1680 |
| ctcaagttcg | accccctcct | gagggacagt | cctggtagac | cagtgcccgt | ggccaccgag | 1740 |
| accagcagca | tgcacggtgc | aaatgagact | ccctcaggac | gtccgcggga | agccaagctt | 1800 |
| gtggagttcg | atttcttggg | agcactggac | attcctgtgc | caggcccacc | cccaggtgtt | 1860 |
| cccgcgcctg | ggggcccacc | cctgtccacc | ggacctatag | tggacctgct | ccagtacagc | 1920 |
| cagaaggacc | tggatgcagt | ggtaaaggcg | acacaggagg | agaaccggga | gctgaggagc | 1980 |
| aggtgtgagg | agctccacgg | gaagaacctg | gaactgggga | agatcatgga | caggttcgaa | 2040 |
| gaggttgtgt | accaggccat | ggaggaagtt | cagaagcaga | aggaactttc | caaagctgaa | 2100 |
| atccagaaag | ttctaaaaga | aaaagaccaa | cttaccacag | atctgaactc | catggagaag | 2160 |

```
tccttctccg acctcttcaa gcgttttgag aaacagaaag aggtgatcga gggctaccgc      2220
aagaacgaag agtcactgaa gaagtgcgtg gaggattacc tggcaaggat cacccaggag      2280
ggccagaggt accaagccct gaaggcccac gcggaggaga agctgcagct ggcaaacgag      2340
gagatcgccc aggtccggag caaggcccag gcggaagcgt tggccctcca ggccagcctg      2400
aggaaggagc agatgcgcat ccagtcgctg gagaagacag tggagcagaa gactaaagag      2460
aacgaggagc tgaccaggat ctgcgacgac ctcatctcca gatggagaa gatctga         2517
```

<210> SEQ ID NO 14
<211> LENGTH: 383
<212> TYPE: DNA
<213> ORGANISM: Homo sapiens

<400> SEQUENCE: 14

```
aactgcacac acgacctgta catgatcatg cgggagtgct ggcatgccgc gccctcccag       60
aggcccacct tcaagcagct ggtggaggac ctggaccgtg tccttaccgt gacgtccacc      120
gacgtaaagg cgacacagga ggagaaccgg gagctgagga gcaggtgtga ggagctccac      180
gggaagaacc tggaactggg gaagatcatg gacaggttcg aagaggttgt gtaccaggcc      240
atggaggaag ttcagaagca gaaggaactt tccaaagctg aaatccagaa agttctaaaa      300
gaaaaagacc aacttaccac agatctgaac tccatggaga agtccttctc cgacctcttc      360
aagcgttttg agaaacagaa aga                                             383
```

<210> SEQ ID NO 15
<211> LENGTH: 448
<212> TYPE: DNA
<213> ORGANISM: Homo sapiens

<400> SEQUENCE: 15

```
gctccccgta ccccggcatc cctgtggagg agctcttcaa gctgctgaag gagggccacc       60
gcatggacaa gcccgccaac tgcacacacg acctgtacat gatcatgcgg gagtgctggc      120
atgccgcgcc ctcccagagg cccaccttca gcagctggt ggaggacctg gaccgtgtcc      180
ttaccgtgac gtccaccgac gtgagtgctg gctctgcct ggtgccaccc gcctatgccc      240
ctccccctgc cgtccccggc catcctgccc ccagagtgc tgaggtgtgg ggcgggcctt      300
ctggcccagg tgccctggct gacctggact gctcaagctc ttcccagagc ccaggaagtt      360
ctgagaacca atggtgtct ccaggaaaag tgtctggcag ccctgagcaa gccgtggagg      420
aaaaccttag ttcctattcc ttagacag                                        448
```

<210> SEQ ID NO 16
<211> LENGTH: 427
<212> TYPE: DNA
<213> ORGANISM: Homo sapiens

<400> SEQUENCE: 16

```
tctacactca ccagagtgac gtctggtcct ttggggtcct gctctgggag atcttcacgc       60 tgggggggctc cccgtacccc ggcatccctg tggaggagct cttcaagctg ctgaaggagg      120
gccaccgcat ggacaagccc gccaactgca cacacgacct gtacatgatc atgcgggagt      180
gctggcatgc cgcgccctcc cagaggccca ccttcaagca gctggtggag gacctggacc      240
gtgtccttac cgtgacgtcc accgacaatg ttatggaaca gttcaatcct gggctgcgaa      300
atttaataaa cctggggaaa aattatgaga aagctgtaaa cgctatgatc ctggcaggaa      360
```

```
aagcctacta cgatggagtg gccaagatcg gtgagattgc cactgggtcc cccgtgtcaa    420
ctgaact                                                              427
```

<210> SEQ ID NO 17
<211> LENGTH: 21
<212> TYPE: DNA
<213> ORGANISM: Artificial Sequence
<220> FEATURE:
<223> OTHER INFORMATION: An artificially synthesized primer sequence

<400> SEQUENCE: 17

```
caactgcaca cacgacctgt a                                              21
```

<210> SEQ ID NO 18
<211> LENGTH: 22
<212> TYPE: DNA
<213> ORGANISM: Artificial Sequence
<220> FEATURE:
<223> OTHER INFORMATION: An artificially synthesized primer sequence

<400> SEQUENCE: 18

```
ccatcgtagt aggcttttcc tg                                             22
```

<210> SEQ ID NO 19
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 19

Gly Gly Gly Ser
1

<210> SEQ ID NO 20
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 20

Ser Gly Gly Gly
1

<210> SEQ ID NO 21
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 21

Gly Gly Gly Gly Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Peptide linker sequence

<400> SEQUENCE: 22

Ser Gly Gly Gly Gly
1               5

```
<210> SEQ ID NO 23
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 23

Gly Gly Gly Gly Gly Ser
1               5

<210> SEQ ID NO 24
<211> LENGTH: 6
<212> TYPE: PRT
<213> ORGANISM: Artificial Sequence
<220> FEATURE:
<223> OTHER INFORMATION: Peptide linker sequence

<400> SEQUENCE: 24

Ser Gly Gly Gly Gly Gly
1               5

<210> SEQ ID NO 25
<211> LENGTH: 7
<212> TYPE: PRT
<213> ORGANISM: Artificial Sequence
<220> FEATURE:
<223> OTHER INFORMATION: Peptide linker sequence

<400> SEQUENCE: 25

Gly Gly Gly Gly Gly Gly Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Peptide linker sequence

<400> SEQUENCE: 26

Ser Gly Gly Gly Gly Gly Gly
1               5

<210> SEQ ID NO 27
<211> LENGTH: 2856
<212> TYPE: DNA
<213> ORGANISM: Homo sapiens
<220> FEATURE:
<221> NAME/KEY: CDS
<222> LOCATION: (1)..(2856)

<400> SEQUENCE: 27 atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag     144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc     192
Leu Val Phe Gly Ser Gly Asp Ala Val Glu Leu Ser Cys Pro Pro Pro
        50                  55                  60
```

| | | |
|---|---|---|
| ggg ggt ggt ccc atg ggg ccc act gtc tgg gtc aag gat ggc aca ggg<br>Gly Gly Gly Pro Met Gly Pro Thr Val Trp Val Lys Asp Gly Thr Gly<br>65                             70                     75                   80 | 240 |
| ctg gtg ccc tcg gag cgt gtc ctg gtg ggg ccc cag cgg ctg cag gtg<br>Leu Val Pro Ser Glu Arg Val Leu Val Gly Pro Gln Arg Leu Gln Val<br>               85                     90                     95 | 288 |
| ctg aat gcc tcc cac gag gac tcc ggg gcc tac agc tgc cgg cag cgg<br>Leu Asn Ala Ser His Glu Asp Ser Gly Ala Tyr Ser Cys Arg Gln Arg<br>             100                   105                 110 | 336 |
| ctc acg cag cgc gta ctg tgc cac ttc agt gtg cgg gtg aca gac gct<br>Leu Thr Gln Arg Val Leu Cys His Phe Ser Val Arg Val Thr Asp Ala<br>             115                   120                 125 | 384 |
| cca tcc tcg gga gat gac gaa gac ggg gag gac gag gct gag gac aca<br>Pro Ser Ser Gly Asp Asp Glu Asp Gly Glu Asp Glu Ala Glu Asp Thr<br>130                         135                   140 | 432 |
| ggt gtg gac aca ggg gcc cct tac tgg aca cgg ccc gag cgg atg gac<br>Gly Val Asp Thr Gly Ala Pro Tyr Trp Thr Arg Pro Glu Arg Met Asp<br>145                         150                   155                 160 | 480 |
| aag aag ctg ctg gcc gtg ccg gcc gcc aac acc gtc cgc ttc cgc tgc<br>Lys Lys Leu Leu Ala Val Pro Ala Ala Asn Thr Val Arg Phe Arg Cys<br>                 165                   170                 175 | 528 |
| cca gcc gct ggc aac ccc act ccc tcc atc tcc tgg ctg aag aac ggc<br>Pro Ala Ala Gly Asn Pro Thr Pro Ser Ile Ser Trp Leu Lys Asn Gly<br>                 180                   185                 190 | 576 |
| agg gag ttc cgc ggc gag cac cgc att gga ggc atc aag ctg cgg cat<br>Arg Glu Phe Arg Gly Glu His Arg Ile Gly Gly Ile Lys Leu Arg His<br>             195                   200                 205 | 624 |
| cag cag tgg agc ctg gtc atg gaa agc gtg gtg ccc tcg gac cgc ggc<br>Gln Gln Trp Ser Leu Val Met Glu Ser Val Val Pro Ser Asp Arg Gly<br>210                         215                   220 | 672 |
| aac tac acc tgc gtc gtg gag aac aag ttt ggc agc atc cgg cag acg<br>Asn Tyr Thr Cys Val Val Glu Asn Lys Phe Gly Ser Ile Arg Gln Thr<br>225                       230                   235                 240 | 720 |
| tac acg ctg gac gtg ctg gag cgc tcc ccg cac cgg ccc atc ctg cag<br>Tyr Thr Leu Asp Val Leu Glu Arg Ser Pro His Arg Pro Ile Leu Gln<br>                 245                   250                 255 | 768 |
| gcg ggg ctg ccg gcc aac cag acg gcg gtg ctg ggc agc gac gtg gag<br>Ala Gly Leu Pro Ala Asn Gln Thr Ala Val Leu Gly Ser Asp Val Glu<br>             260                   265                 270 | 816 |
| ttc cac tgc aag gtg tac agt gac gca cag ccc cac atc cag tgg ctc<br>Phe His Cys Lys Val Tyr Ser Asp Ala Gln Pro His Ile Gln Trp Leu<br>             275                   280                 285 | 864 |
| aag cac gtg gag gtg aat ggc agc aag gtg ggc ccg gac ggc aca ccc<br>Lys His Val Glu Val Asn Gly Ser Lys Val Gly Pro Asp Gly Thr Pro<br>290                         295                   300 | 912 |
| tac gtt acc gtg ctc aag tcc tgg atc agt gag agt gtg gag gcc gac<br>Tyr Val Thr Val Leu Lys Ser Trp Ile Ser Glu Ser Val Glu Ala Asp<br>305                         310                   315                 320 | 960 |
| gtg cgc ctc cgc ctg gcc aat gtg tcg gag cgg gac ggg ggc gag tac<br>Val Arg Leu Arg Leu Ala Asn Val Ser Glu Arg Asp Gly Gly Glu Tyr<br>             325                   330                 335 | 1008 |
| ctc tgt cga gcc acc aat ttc ata ggc gtg gcc gag aag gcc ttt tgg<br>Leu Cys Arg Ala Thr Asn Phe Ile Gly Val Ala Glu Lys Ala Phe Trp<br>             340                   345                 350 | 1056 |
| ctg agc gtt cac ggg ccc cga gca gcc gag gag gag ctg gtg gag gct<br>Leu Ser Val His Gly Pro Arg Ala Ala Glu Glu Glu Leu Val Glu Ala<br>             355                   360                 365 | 1104 |
| gac gag gcg ggc agt gtg tat gca ggc atc ctc agc tac ggg gtg ggc<br>Asp Glu Ala Gly Ser Val Tyr Ala Gly Ile Leu Ser Tyr Gly Val Gly | 1152 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     | 370 |     |     |     |     | 375 |     |     |     |     | 380 |     |     |     |     |
| ttc | ttc | ctg | ttc | atc | ctg | gtg | gtg | gcg | gct | gtg | acg | ctc | tgc | cgc | ctg | 1200 |
| Phe | Phe | Leu | Phe | Ile | Leu | Val | Val | Ala | Ala | Val | Thr | Leu | Cys | Arg | Leu |     |
| 385 |     |     |     |     | 390 |     |     |     |     | 395 |     |     |     |     | 400 |     |
| cgc | agc | ccc | ccc | aag | aaa | ggc | ctg | ggc | tcc | ccc | acc | gtg | cac | aag | atc | 1248 |
| Arg | Ser | Pro | Pro | Lys | Lys | Gly | Leu | Gly | Ser | Pro | Thr | Val | His | Lys | Ile |     |
|     |     |     |     | 405 |     |     |     |     | 410 |     |     |     |     | 415 |     |     |
| tcc | cgc | ttc | ccg | ctc | aag | cga | cag | gtg | tcc | ctg | gag | tcc | aac | gcg | tcc | 1296 |
| Ser | Arg | Phe | Pro | Leu | Lys | Arg | Gln | Val | Ser | Leu | Glu | Ser | Asn | Ala | Ser |     |
|     |     |     | 420 |     |     |     |     | 425 |     |     |     |     | 430 |     |     |     |
| atg | agc | tcc | aac | aca | cca | ctg | gtg | cgc | atc | gca | agg | ctg | tcc | tca | ggg | 1344 |
| Met | Ser | Ser | Asn | Thr | Pro | Leu | Val | Arg | Ile | Ala | Arg | Leu | Ser | Ser | Gly |     |
|     | 435 |     |     |     |     | 440 |     |     |     |     | 445 |     |     |     |     |     |
| gag | ggc | ccc | acg | ctg | gcc | aat | gtc | tcc | gag | ctc | gag | ctg | cct | gcc | gac | 1392 |
| Glu | Gly | Pro | Thr | Leu | Ala | Asn | Val | Ser | Glu | Leu | Glu | Leu | Pro | Ala | Asp |     |
| 450 |     |     |     |     | 455 |     |     |     |     | 460 |     |     |     |     |     |     |
| ccc | aaa | tgg | gag | ctg | tct | cgg | gcc | cgg | ctg | acc | ctg | ggc | aag | ccc | ctt | 1440 |
| Pro | Lys | Trp | Glu | Leu | Ser | Arg | Ala | Arg | Leu | Thr | Leu | Gly | Lys | Pro | Leu |     |
| 465 |     |     |     |     | 470 |     |     |     |     | 475 |     |     |     |     | 480 |     |
| ggg | gag | ggc | tgc | ttc | ggc | cag | gtg | gtc | atg | gcg | gag | gcc | atc | ggc | att | 1488 |
| Gly | Glu | Gly | Cys | Phe | Gly | Gln | Val | Val | Met | Ala | Glu | Ala | Ile | Gly | Ile |     |
|     |     |     |     | 485 |     |     |     |     | 490 |     |     |     |     | 495 |     |     |
| gac | aag | gac | cgg | gcc | gcc | aag | cct | gtc | acc | gta | gcc | gtg | aag | atg | ctg | 1536 |
| Asp | Lys | Asp | Arg | Ala | Ala | Lys | Pro | Val | Thr | Val | Ala | Val | Lys | Met | Leu |     |
|     |     |     | 500 |     |     |     |     | 505 |     |     |     |     | 510 |     |     |     |
| aaa | gac | gat | gcc | act | gac | aag | gac | ctg | tcg | gac | ctg | gtg | tct | gag | atg | 1584 |
| Lys | Asp | Asp | Ala | Thr | Asp | Lys | Asp | Leu | Ser | Asp | Leu | Val | Ser | Glu | Met |     |
|     |     | 515 |     |     |     |     | 520 |     |     |     |     | 525 |     |     |     |     |
| gag | atg | atg | aag | atg | atc | ggg | aaa | cac | aaa | aac | atc | atc | aac | ctg | ctg | 1632 |
| Glu | Met | Met | Lys | Met | Ile | Gly | Lys | His | Lys | Asn | Ile | Ile | Asn | Leu | Leu |     |
|     | 530 |     |     |     |     | 535 |     |     |     |     | 540 |     |     |     |     |     |
| ggc | gcc | tgc | acg | cag | ggc | ggg | ccc | ctg | tac | gtg | ctg | gtg | gag | tac | gcg | 1680 |
| Gly | Ala | Cys | Thr | Gln | Gly | Gly | Pro | Leu | Tyr | Val | Leu | Val | Glu | Tyr | Ala |     |
| 545 |     |     |     |     | 550 |     |     |     |     | 555 |     |     |     |     | 560 |     |
| gcc | aag | ggt | aac | ctg | cgg | gag | ttt | ctg | cgg | gcg | cgg | cgg | ccc | ccg | ggc | 1728 |
| Ala | Lys | Gly | Asn | Leu | Arg | Glu | Phe | Leu | Arg | Ala | Arg | Arg | Pro | Pro | Gly |     |
|     |     |     |     | 565 |     |     |     |     | 570 |     |     |     |     | 575 |     |     |
| ctg | gac | tac | tcc | ttc | gac | acc | tgc | aag | ccg | ccc | gag | gag | cag | ctc | acc | 1776 |
| Leu | Asp | Tyr | Ser | Phe | Asp | Thr | Cys | Lys | Pro | Pro | Glu | Glu | Gln | Leu | Thr |     |
|     |     |     | 580 |     |     |     |     | 585 |     |     |     |     | 590 |     |     |     |
| ttc | aag | gac | ctg | gtg | tcc | tgt | gcc | tac | cag | gtg | gcc | cgg | ggc | atg | gag | 1824 |
| Phe | Lys | Asp | Leu | Val | Ser | Cys | Ala | Tyr | Gln | Val | Ala | Arg | Gly | Met | Glu |     |
|     |     | 595 |     |     |     |     | 600 |     |     |     |     | 605 |     |     |     |     |
| tac | ttg | gcc | tcc | cag | aag | tgc | atc | cac | agg | gac | ctg | gct | gcc | cgc | aat | 1872 |
| Tyr | Leu | Ala | Ser | Gln | Lys | Cys | Ile | His | Arg | Asp | Leu | Ala | Ala | Arg | Asn |     |
|     | 610 |     |     |     |     | 615 |     |     |     |     | 620 |     |     |     |     |     |
| gtg | ctg | gtg | acc | gag | gac | aac | gtg | atg | aag | atc | gca | gac | ttc | ggg | ctg | 1920 |
| Val | Leu | Val | Thr | Glu | Asp | Asn | Val | Met | Lys | Ile | Ala | Asp | Phe | Gly | Leu |     |
| 625 |     |     |     |     | 630 |     |     |     |     | 635 |     |     |     |     | 640 |     |
| gcc | cgg | gac | gtg | cac | aac | ctc | gac | tac | tac | aag | aag | aca | acc | aac | ggc | 1968 |
| Ala | Arg | Asp | Val | His | Asn | Leu | Asp | Tyr | Tyr | Lys | Lys | Thr | Thr | Asn | Gly |     |
|     |     |     |     | 645 |     |     |     |     | 650 |     |     |     |     | 655 |     |     |
| cgg | ctg | ccc | gtg | aag | tgg | atg | gcg | cct | gag | gcc | ttg | ttt | gac | cga | gtc | 2016 |
| Arg | Leu | Pro | Val | Lys | Trp | Met | Ala | Pro | Glu | Ala | Leu | Phe | Asp | Arg | Val |     |
|     |     |     | 660 |     |     |     |     | 665 |     |     |     |     | 670 |     |     |     |
| tac | act | cac | cag | agt | gac | gtc | tgg | tcc | ttt | ggg | gtc | ctg | ctc | tgg | gag | 2064 |
| Tyr | Thr | His | Gln | Ser | Asp | Val | Trp | Ser | Phe | Gly | Val | Leu | Leu | Trp | Glu |     |
|     |     | 675 |     |     |     |     | 680 |     |     |     |     | 685 |     |     |     |     |
| atc | ttc | acg | ctg | ggg | ggc | tcc | ccg | tac | ccc | ggc | atc | cct | gtg | gag | gag | 2112 |

| | | | | | | | | | | | | | | | |
|---|---|---|---|---|---|---|---|---|---|---|---|---|---|---|---|
| Ile | Phe | Thr | Leu | Gly | Gly | Ser | Pro | Tyr | Pro | Gly | Ile | Pro | Val | Glu | Glu |
| | 690 | | | | 695 | | | | 700 | | | | | | |

```
ctc ttc aag ctg ctg aag gag ggc cac cgc atg gac aag ccc gcc aac      2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg      2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt      2256
Pro Ser Gln Arg Pro Thr Phe Lys Gln Leu Val Glu Asp Leu Asp Arg
        740                 745                 750 gtc ctt acc gtg acg tcc acc gac gta aag gcg aca cag gag gag aac      2304
Val Leu Thr Val Thr Ser Thr Asp Val Lys Ala Thr Gln Glu Glu Asn
755                 760                 765 cgg gag ctg agg agc agg tgt gag gag ctc cac ggg aag aac ctg gaa      2352
Arg Glu Leu Arg Ser Arg Cys Glu Glu Leu His Gly Lys Asn Leu Glu
770                 775                 780 ctg ggg aag atc atg gac agg ttc gaa gag gtt gtg tac cag gcc atg      2400
Leu Gly Lys Ile Met Asp Arg Phe Glu Glu Val Val Tyr Gln Ala Met
785                 790                 795                 800 gag gaa gtt cag aag cag aag gaa ctt tcc aaa gct gaa atc cag aaa      2448
Glu Glu Val Gln Lys Gln Lys Glu Leu Ser Lys Ala Glu Ile Gln Lys
                805                 810                 815 gtt cta aaa gaa aaa gac caa ctt acc aca gat ctg aac tcc atg gag      2496
Val Leu Lys Glu Lys Asp Gln Leu Thr Thr Asp Leu Asn Ser Met Glu
        820                 825                 830 aag tcc ttc tcc gac ctc ttc aag cgt ttt gag aaa cag aaa gag gtg      2544
Lys Ser Phe Ser Asp Leu Phe Lys Arg Phe Glu Lys Gln Lys Glu Val
835                 840                 845 atc gag ggc tac cgc aag aac gaa gag tca ctg aag aag tgc gtg gag      2592
Ile Glu Gly Tyr Arg Lys Asn Glu Glu Ser Leu Lys Lys Cys Val Glu
850                 855                 860 gat tac ctg gca agg atc acc cag gag ggc cag agg tac caa gcc ctg      2640
Asp Tyr Leu Ala Arg Ile Thr Gln Glu Gly Gln Arg Tyr Gln Ala Leu
865                 870                 875                 880 aag gcc cac gcg gag gag aag ctg cag ctg gca aac gag gag atc gcc      2688
Lys Ala His Ala Glu Glu Lys Leu Gln Leu Ala Asn Glu Glu Ile Ala
                885                 890                 895 cag gtc cgg agc aag gcc cag gcg gaa gcg ttg gcc ctc cag gcc agc      2736
Gln Val Arg Ser Lys Ala Gln Ala Glu Ala Leu Ala Leu Gln Ala Ser
        900                 905                 910 ctg agg aag gag cag atg cgc atc cag tcg ctg gag aag aca gtg gag      2784
Leu Arg Lys Glu Gln Met Arg Ile Gln Ser Leu Glu Lys Thr Val Glu
915                 920                 925 cag aag act aaa gag aac gag gag ctg acc agg atc tgc gac gac ctc      2832
Gln Lys Thr Lys Glu Asn Glu Glu Leu Thr Arg Ile Cys Asp Asp Leu
930                 935                 940 atc tcc aag atg gag aag atc tga                                       2856
Ile Ser Lys Met Glu Lys Ile
945                 950
```

<210> SEQ ID NO 28
<211> LENGTH: 951
<212> TYPE: PRT
<213> ORGANISM: Homo sapiens

<400> SEQUENCE: 28

| | | | | | | | | | | | | | | | |
|---|---|---|---|---|---|---|---|---|---|---|---|---|---|---|---|
| Met | Gly | Ala | Pro | Ala | Cys | Ala | Leu | Ala | Leu | Cys | Val | Ala | Val | Ala | Ile |
| 1 | | | | 5 | | | | | 10 | | | | | 15 | |
| Val | Ala | Gly | Ala | Ser | Ser | Glu | Ser | Leu | Gly | Thr | Glu | Gln | Arg | Val | Val |

```
             20                  25                  30
Gly Arg Ala Ala Glu Val Pro Gly Pro Glu Pro Gly Gln Gln Glu Gln
             35                  40                  45
Leu Val Phe Gly Ser Gly Asp Ala Val Glu Leu Ser Cys Pro Pro Pro
             50                  55                  60
Gly Gly Gly Pro Met Gly Pro Thr Val Trp Lys Asp Gly Thr Gly
 65                  70                  75                  80
Leu Val Pro Ser Glu Arg Val Leu Val Gly Pro Gln Arg Leu Gln Val
                     85                  90                  95
Leu Asn Ala Ser His Glu Asp Ser Gly Ala Tyr Ser Cys Arg Gln Arg
                    100                 105                 110
Leu Thr Gln Arg Val Leu Cys His Phe Ser Val Arg Val Thr Asp Ala
                    115                 120                 125
Pro Ser Ser Gly Asp Asp Glu Asp Gly Glu Asp Glu Ala Glu Asp Thr
                    130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                    165                 170                 175
Pro Ala Ala Gly Asn Pro Thr Pro Ser Ile Ser Trp Leu Lys Asn Gly
                    180                 185                 190
Arg Glu Phe Arg Gly Glu His Arg Ile Gly Gly Ile Lys Leu Arg His
                    195                 200                 205
Gln Gln Trp Ser Leu Val Met Glu Ser Val Val Pro Ser Asp Arg Gly
                    210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                    245                 250                 255
Ala Gly Leu Pro Ala Asn Gln Thr Ala Val Leu Gly Ser Asp Val Glu
                    260                 265                 270
Phe His Cys Lys Val Tyr Ser Asp Ala Gln Pro His Ile Gln Trp Leu
                    275                 280                 285
Lys His Val Glu Val Asn Gly Ser Lys Val Gly Pro Asp Gly Thr Pro
                    290                 295                 300
Tyr Val Thr Val Leu Lys Ser Trp Ile Ser Glu Ser Val Glu Ala Asp
305                 310                 315                 320
Val Arg Leu Arg Leu Ala Asn Val Ser Glu Arg Asp Gly Gly Glu Tyr
                    325                 330                 335
Leu Cys Arg Ala Thr Asn Phe Ile Gly Val Ala Glu Lys Ala Phe Trp
                    340                 345                 350
Leu Ser Val His Gly Pro Arg Ala Ala Glu Glu Glu Leu Val Glu Ala
                    355                 360                 365
Asp Glu Ala Gly Ser Val Tyr Ala Gly Ile Leu Ser Tyr Gly Val Gly
                    370                 375                 380
Phe Phe Leu Phe Ile Leu Val Val Ala Ala Val Thr Leu Cys Arg Leu
385                 390                 395                 400
Arg Ser Pro Pro Lys Lys Gly Leu Gly Ser Pro Thr Val His Lys Ile
                    405                 410                 415
Ser Arg Phe Pro Leu Lys Arg Gln Val Ser Leu Glu Ser Asn Ala Ser
                    420                 425                 430
Met Ser Ser Asn Thr Pro Leu Val Arg Ile Ala Arg Leu Ser Ser Gly
                    435                 440                 445
```

```
Glu Gly Pro Thr Leu Ala Asn Val Ser Glu Leu Glu Leu Pro Ala Asp
    450                 455                 460
Pro Lys Trp Glu Leu Ser Arg Ala Arg Leu Thr Leu Gly Lys Pro Leu
465                 470                 475                 480
Gly Glu Gly Cys Phe Gly Gln Val Val Met Ala Glu Ala Ile Gly Ile
                485                 490                 495
Asp Lys Asp Arg Ala Ala Lys Pro Val Thr Val Ala Val Lys Met Leu
            500                 505                 510
Lys Asp Asp Ala Thr Asp Lys Asp Leu Ser Asp Leu Val Ser Glu Met
        515                 520                 525
Glu Met Met Lys Met Ile Gly Lys His Lys Asn Ile Ile Asn Leu Leu
    530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
            580                 585                 590
Phe Lys Asp Leu Val Ser Cys Ala Tyr Gln Val Ala Arg Gly Met Glu
        595                 600                 605
Tyr Leu Ala Ser Gln Lys Cys Ile His Arg Asp Leu Ala Ala Arg Asn
    610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
            660                 665                 670
Tyr Thr His Gln Ser Asp Val Trp Ser Phe Gly Val Leu Leu Trp Glu
        675                 680                 685
Ile Phe Thr Leu Gly Gly Ser Pro Tyr Pro Gly Ile Pro Val Glu Glu
    690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
            740                 745                 750
Val Leu Thr Val Thr Ser Thr Asp Val Lys Ala Thr Gln Glu Glu Asn
        755                 760                 765
Arg Glu Leu Arg Ser Arg Cys Glu Glu Leu His Gly Lys Asn Leu Glu
    770                 775                 780
Leu Gly Lys Ile Met Asp Arg Phe Glu Glu Val Val Tyr Gln Ala Met
785                 790                 795                 800
Glu Glu Val Gln Lys Gln Lys Glu Leu Ser Lys Ala Glu Ile Gln Lys
                805                 810                 815
Val Leu Lys Glu Lys Asp Gln Leu Thr Thr Asp Leu Asn Ser Met Glu
            820                 825                 830
Lys Ser Phe Ser Asp Leu Phe Lys Arg Phe Glu Lys Gln Lys Glu Val
        835                 840                 845
Ile Glu Gly Tyr Arg Lys Asn Glu Glu Ser Leu Lys Lys Cys Val Glu
    850                 855                 860
```

```
Asp Tyr Leu Ala Arg Ile Thr Gln Glu Gly Gln Arg Tyr Gln Ala Leu
865                 870                 875                 880

Lys Ala His Ala Glu Glu Lys Leu Gln Leu Ala Asn Glu Glu Ile Ala
            885                 890                 895

Gln Val Arg Ser Lys Ala Gln Ala Glu Ala Leu Ala Leu Gln Ala Ser
                900                 905                 910

Leu Arg Lys Glu Gln Met Arg Ile Gln Ser Leu Glu Lys Thr Val Glu
            915                 920                 925

Gln Lys Thr Lys Glu Asn Glu Glu Leu Thr Arg Ile Cys Asp Asp Leu
        930                 935                 940

Ile Ser Lys Met Glu Lys Ile
945                 950

<210> SEQ ID NO 29
<211> LENGTH: 4467
<212> TYPE: DNA
<213> ORGANISM: Homo sapiens
<220> FEATURE:
<221> NAME/KEY: CDS
<222> LOCATION: (1)..(4467)

<400> SEQUENCE: 29
```

| | | | | | | | | | | | | | | | | |
|---|---|---|---|---|---|---|---|---|---|---|---|---|---|---|---|---|
| atg | ggc | gcc | cct | gcc | tgc | gcc | ctc | gcg | ctc | tgc | gtg | gcc | gtg | gcc | atc | 48 |
| Met | Gly | Ala | Pro | Ala | Cys | Ala | Leu | Ala | Leu | Cys | Val | Ala | Val | Ala | Ile | |
| 1 | | | 5 | | | | | 10 | | | | | 15 | | | |
| gtg | gcc | ggc | gcc | tcc | tcg | gag | tcc | ttg | ggg | acg | gag | cag | cgc | gtc | gtg | 96 |
| Val | Ala | Gly | Ala | Ser | Ser | Glu | Ser | Leu | Gly | Thr | Glu | Gln | Arg | Val | Val | |
| | | | 20 | | | | 25 | | | | | 30 | | | | |
| ggg | cga | gcg | gca | gaa | gtc | ccg | ggc | cca | gag | ccc | ggc | cag | cag | gag | cag | 144 |
| Gly | Arg | Ala | Ala | Glu | Val | Pro | Gly | Pro | Glu | Pro | Gly | Gln | Gln | Glu | Gln | |
| | | 35 | | | | | 40 | | | | | 45 | | | | |
| ttg | gtc | ttc | ggc | agc | ggg | gat | gct | gtg | gag | ctg | agc | tgt | ccc | ccg | ccc | 192 |
| Leu | Val | Phe | Gly | Ser | Gly | Asp | Ala | Val | Glu | Leu | Ser | Cys | Pro | Pro | Pro | |
| | 50 | | | | | 55 | | | | | 60 | | | | | |
| ggg | ggt | ggt | ccc | atg | ggg | ccc | act | gtc | tgg | gtc | aag | gat | ggc | aca | ggg | 240 |
| Gly | Gly | Gly | Pro | Met | Gly | Pro | Thr | Val | Trp | Val | Lys | Asp | Gly | Thr | Gly | |
| 65 | | | | | 70 | | | | | 75 | | | | | 80 | |
| ctg | gtg | ccc | tcg | gag | cgt | gtc | ctg | gtg | ggg | ccc | cag | cgg | ctg | cag | gtg | 288 |
| Leu | Val | Pro | Ser | Glu | Arg | Val | Leu | Val | Gly | Pro | Gln | Arg | Leu | Gln | Val | |
| | | | | 85 | | | | | 90 | | | | | 95 | | |
| ctg | aat | gcc | tcc | cac | gag | gac | tcc | ggg | gcc | tac | agc | tgc | cgg | cag | cgg | 336 |
| Leu | Asn | Ala | Ser | His | Glu | Asp | Ser | Gly | Ala | Tyr | Ser | Cys | Arg | Gln | Arg | |
| | | | 100 | | | | | 105 | | | | | 110 | | | |
| ctc | acg | cag | cgc | gta | ctg | tgc | cac | ttc | agt | gtg | cgg | gtg | aca | gac | gct | 384 |
| Leu | Thr | Gln | Arg | Val | Leu | Cys | His | Phe | Ser | Val | Arg | Val | Thr | Asp | Ala | |
| | | | 115 | | | | | 120 | | | | | 125 | | | |
| cca | tcc | tcg | gga | gat | gac | gaa | gac | ggg | gag | gac | gag | gct | gag | gac | aca | 432 |
| Pro | Ser | Ser | Gly | Asp | Asp | Glu | Asp | Gly | Glu | Asp | Glu | Ala | Glu | Asp | Thr | |
| | | 130 | | | | | 135 | | | | | 140 | | | | |
| ggt | gtg | gac | aca | ggg | gcc | cct | tac | tgg | aca | cgg | ccc | gag | cgg | atg | gac | 480 |
| Gly | Val | Asp | Thr | Gly | Ala | Pro | Tyr | Trp | Thr | Arg | Pro | Glu | Arg | Met | Asp | |
| 145 | | | | | 150 | | | | | 155 | | | | | 160 | |
| aag | aag | ctg | ctg | gcc | gtg | ccg | gcc | gcc | aac | acc | gtc | cgc | ttc | cgc | tgc | 528 |
| Lys | Lys | Leu | Leu | Ala | Val | Pro | Ala | Ala | Asn | Thr | Val | Arg | Phe | Arg | Cys | |
| | | | | 165 | | | | | 170 | | | | | 175 | | |
| cca | gcc | gct | ggc | aac | ccc | act | ccc | tcc | atc | tcc | tgg | ctg | aag | aac | ggc | 576 |
| Pro | Ala | Ala | Gly | Asn | Pro | Thr | Pro | Ser | Ile | Ser | Trp | Leu | Lys | Asn | Gly | |
| | | | 180 | | | | | 185 | | | | | 190 | | | |
| agg | gag | ttc | cgc | ggc | gag | cac | cgc | att | gga | ggc | atc | aag | ctg | cgg | cat | 624 |
| Arg | Glu | Phe | Arg | Gly | Glu | His | Arg | Ile | Gly | Gly | Ile | Lys | Leu | Arg | His | |

```
              195                 200                 205
cag cag tgg agc ctg gtc atg gaa agc gtg gtg ccc tcg gac cgc ggc      672
Gln Gln Trp Ser Leu Val Met Glu Ser Val Val Pro Ser Asp Arg Gly
    210                 215                 220 aac tac acc tgc gtc gtg gag aac aag ttt ggc agc atc cgg cag acg      720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag      768
Tyr Thr Leu Asp Val Leu Glu Arg Ser Pro His Arg Pro Ile Leu Gln
                245                 250                 255 gcg ggg ctg ccg gcc aac cag acg gcg gtg ctg ggc agc gac gtg gag      816
Ala Gly Leu Pro Ala Asn Gln Thr Ala Val Leu Gly Ser Asp Val Glu
            260                 265                 270 ttc cac tgc aag gtg tac agt gac gca cag ccc cac atc cag tgg ctc      864
Phe His Cys Lys Val Tyr Ser Asp Ala Gln Pro His Ile Gln Trp Leu
        275                 280                 285 aag cac gtg gag gtg aat ggc agc aag gtg ggc ccg gac ggc aca ccc      912
Lys His Val Glu Val Asn Gly Ser Lys Val Gly Pro Asp Gly Thr Pro
    290                 295                 300 tac gtt acc gtg ctc aag tcc tgg atc agt gag agt gtg gag gcc gac      960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac     1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg     1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct     1104
Leu Ser Val His Gly Pro Arg Ala Ala Glu Glu Glu Leu Val Glu Ala
        355                 360                 365 gac gag gcg ggc agt gtg tat gca ggc atc ctc agc tac ggg gtg ggc     1152
Asp Glu Ala Gly Ser Val Tyr Ala Gly Ile Leu Ser Tyr Gly Val Gly
    370                 375                 380 ttc ttc ctg ttc atc ctg gtg gtg gcg gct gtg acg ctc tgc cgc ctg     1200
Phe Phe Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc     1248
Arg Ser Pro Pro Lys Lys Gly Leu Gly Ser Pro Thr Val His Lys Ile
                405                 410                 415 tcc cgc ttc ccg ctc aag cga cag gtg tcc ctg gag tcc aac gcg tcc     1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg     1344
Met Ser Ser Asn Thr Pro Leu Val Arg Ile Ala Arg Leu Ser Ser Gly
        435                 440                 445 gag ggc ccc acg ctg gcc aat gtc tcc gag ctc gag ctg cct gcc gac     1392
Glu Gly Pro Thr Leu Ala Asn Val Ser Glu Leu Glu Leu Pro Ala Asp
    450                 455                 460 ccc aaa tgg gag ctg tct cgg gcc cgg ctg acc ctg ggc aag ccc ctt     1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att     1488
Gly Glu Gly Cys Phe Gly Gln Val Val Met Ala Glu Ala Ile Gly Ile
                485                 490                 495 gac aag gac cgg gcc gcc aag cct gtc acc gta gcc gtg aag atg ctg     1536
Asp Lys Asp Arg Ala Ala Lys Pro Val Thr Val Ala Val Lys Met Leu
            500                 505                 510 aaa gac gat gcc act gac aag gac ctg tcg gac ctg gtg tct gag atg     1584
Lys Asp Asp Ala Thr Asp Lys Asp Leu Ser Asp Leu Val Ser Glu Met
```

```
                        -continued

Lys Asp Asp Ala Thr Asp Lys Asp Leu Ser Asp Leu Val Ser Glu Met
            515                 520                 525 gag atg atg aag atg atc ggg aaa cac aaa aac atc atc aac ctg ctg     1632
Glu Met Met Lys Met Ile Gly Lys His Lys Asn Ile Ile Asn Leu Leu
            530                 535                 540 ggc gcc tgc acg cag ggc ggg ccc ctg tac gtg ctg gtg gag tac gcg     1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc     1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc     1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag     1824
Phe Lys Asp Leu Val Ser Cys Ala Tyr Gln Val Ala Arg Gly Met Glu
            595                 600                 605 tac ttg gcc tcc cag aag tgc atc cac agg gac ctg gct gcc cgc aat     1872
Tyr Leu Ala Ser Gln Lys Cys Ile His Arg Asp Leu Ala Ala Arg Asn
        610                 615                 620 gtg ctg gtg acc gag gac aac gtg atg aag atc gca gac ttc ggg ctg     1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc     1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc     2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag     2064
Tyr Thr His Gln Ser Asp Val Trp Ser Phe Gly Val Leu Leu Trp Glu
            675                 680                 685 atc ttc acg ctg ggg ggc tcc ccg tac ccc ggc atc cct gtg gag gag     2112
Ile Phe Thr Leu Gly Gly Ser Pro Tyr Pro Gly Ile Pro Val Glu Glu
690                 695                 700 ctc ttc aag ctg ctg aag gag ggc cac cgc atg gac aag ccc gcc aac     2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg     2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt     2256
Pro Ser Gln Arg Pro Thr Phe Lys Gln Leu Val Glu Asp Leu Asp Arg
            740                 745                 750 gtc ctt acc gtg acg tcc acc gac gtg agt gct ggc tct ggc ctg gtg     2304
Val Leu Thr Val Thr Ser Thr Asp Val Ser Ala Gly Ser Gly Leu Val
            755                 760                 765 cca ccc gcc tat gcc cct ccc cct gcc gtc ccc ggc cat cct gcc ccc     2352
Pro Pro Ala Tyr Ala Pro Pro Pro Ala Val Pro Gly His Pro Ala Pro
770                 775                 780 cag agt gct gag gtg tgg ggc ggg cct tct ggc cca ggt gcc ctg gct     2400
Gln Ser Ala Glu Val Trp Gly Gly Pro Ser Gly Pro Gly Ala Leu Ala
785                 790                 795                 800 gac ctg gac tgc tca agc tct tcc cag agc cca gga agt tct gag aac     2448
Asp Leu Asp Cys Ser Ser Ser Ser Gln Ser Pro Gly Ser Ser Glu Asn
                805                 810                 815 caa atg gtg tct cca gga aaa gtg tct ggc agc cct gag caa gcc gtg     2496
Gln Met Val Ser Pro Gly Lys Val Ser Gly Ser Pro Glu Gln Ala Val
            820                 825                 830
```

```
gag gaa aac ctt agt tcc tat tcc tta gac aga aga gtg aca ccc gcc    2544
Glu Glu Asn Leu Ser Ser Tyr Ser Leu Asp Arg Arg Val Thr Pro Ala
            835                 840                 845 tct gag acc cta gaa gac cct tgc agg aca gag tcc cag cac aaa gcg    2592
Ser Glu Thr Leu Glu Asp Pro Cys Arg Thr Glu Ser Gln His Lys Ala
850                 855                 860 gag act ccg cac gga gcc gag gaa gaa tgc aaa gcg gag act ccg cac    2640
Glu Thr Pro His Gly Ala Glu Glu Glu Cys Lys Ala Glu Thr Pro His
865                 870                 875                 880 gga gcc gag gag gaa tgc cgg cac ggt ggg gtc tgt gct ccc gca gca    2688
Gly Ala Glu Glu Glu Cys Arg His Gly Gly Val Cys Ala Pro Ala Ala
                885                 890                 895 gtg gcc act tcg cct cct ggt gca atc cct aag gaa gcc tgc gga gga    2736
Val Ala Thr Ser Pro Pro Gly Ala Ile Pro Lys Glu Ala Cys Gly Gly
            900                 905                 910 gca ccc ctg cag ggt ctg cct ggc gaa gcc ctg ggc tgc cct gcg ggt    2784
Ala Pro Leu Gln Gly Leu Pro Gly Glu Ala Leu Gly Cys Pro Ala Gly
                915                 920                 925 gtg ggc acc ccc gtg cca gca gat gga act cag acc ctt acc tgt gca    2832
Val Gly Thr Pro Val Pro Ala Asp Gly Thr Gln Thr Leu Thr Cys Ala
930                 935                 940 cac acc tct gct cct gag agc aca gcc cca acc aac cac ctg gtg gct    2880
His Thr Ser Ala Pro Glu Ser Thr Ala Pro Thr Asn His Leu Val Ala
945                 950                 955                 960 ggc agg gcc atg acc ctg agt cct cag gaa gaa gtg gct gca ggc caa    2928
Gly Arg Ala Met Thr Leu Ser Pro Gln Glu Glu Val Ala Ala Gly Gln
                965                 970                 975 atg gcc agc tcc tcg agg agc gga cct gta aaa cta gaa ttt gat gta    2976
Met Ala Ser Ser Ser Arg Ser Gly Pro Val Lys Leu Glu Phe Asp Val
            980                 985                 990 tct gat ggc gcc acc agc aaa agg gca ccc cca cca agg aga ctg gga    3024
Ser Asp Gly Ala Thr Ser Lys Arg Ala Pro Pro Pro Arg Arg Leu Gly
                995                 1000                1005 gag agg tcc ggc ctc aag cct ccc ttg agg aaa gca gca gtg agg        3069
Glu Arg Ser Gly Leu Lys Pro Pro Leu Arg Lys Ala Ala Val Arg
        1010                1015                1020 cag caa aag gcc ccg cag gag gtg gag gag gac gac ggt agg agc        3114
Gln Gln Lys Ala Pro Gln Glu Val Glu Glu Asp Asp Gly Arg Ser
    1025                1030                1035 gga gca gga gag gac ccc ccc atg cca gct tct cgg ggc tct tac        3159
Gly Ala Gly Glu Asp Pro Pro Met Pro Ala Ser Arg Gly Ser Tyr
    1040                1045                1050 cac ctc gac tgg gac aaa atg gat gac cca aac ttc atc ccg ttc        3204
His Leu Asp Trp Asp Lys Met Asp Asp Pro Asn Phe Ile Pro Phe
    1055                1060                1065 gga ggt gac acc aag tct ggt tgc agt gag gcc cag ccc cca gaa        3249
Gly Gly Asp Thr Lys Ser Gly Cys Ser Glu Ala Gln Pro Pro Glu
    1070                1075                1080 agc cct gag acc agg ctg ggc cag cca gcg gct gaa cag ttg cat        3294
Ser Pro Glu Thr Arg Leu Gly Gln Pro Ala Ala Glu Gln Leu His
    1085                1090                1095 gct ggg cct gcc acg gag gag cca ggt ccc tgt ctg agc cag cag        3339
Ala Gly Pro Ala Thr Glu Glu Pro Gly Pro Cys Leu Ser Gln Gln
    1100                1105                1110 ctg cat tca gcc tca gcg gag gac acg cct gtg gtg cag ttg gca        3384
Leu His Ser Ala Ser Ala Glu Asp Thr Pro Val Val Gln Leu Ala
    1115                1120                1125 gcc gag acc cca aca gca gag agc aag gag aga gcc ttg aac tct        3429
Ala Glu Thr Pro Thr Ala Glu Ser Lys Glu Arg Ala Leu Asn Ser
    1130                1135                1140
```

```
gcc agc acc tcg ctt ccc aca agc tgt cca ggc agt gag cca gtg      3474
Ala Ser Thr Ser Leu Pro Thr Ser Cys Pro Gly Ser Glu Pro Val
1145                1150                1155 ccc acc cat cag cag ggg cag cct gcc ttg gag ctg aaa gag gag      3519
Pro Thr His Gln Gln Gly Gln Pro Ala Leu Glu Leu Lys Glu Glu
    1160                1165                1170 agc ttc aga gac ccc gct gag gtt cta ggc acg ggc gcg gag gtg      3564
Ser Phe Arg Asp Pro Ala Glu Val Leu Gly Thr Gly Ala Glu Val
1175                1180                1185 gat tac ctg gag cag ttt gga act tcc tcg ttt aag gag tcg gcc      3609
Asp Tyr Leu Glu Gln Phe Gly Thr Ser Ser Phe Lys Glu Ser Ala
    1190                1195                1200 ttg agg aag cag tcc tta tac ctc aag ttc gac ccc ctc ctg agg      3654
Leu Arg Lys Gln Ser Leu Tyr Leu Lys Phe Asp Pro Leu Leu Arg
1205                1210                1215 gac agt cct ggt aga cca gtg ccc gtg gcc acc gag acc agc agc      3699
Asp Ser Pro Gly Arg Pro Val Pro Val Ala Thr Glu Thr Ser Ser
    1220                1225                1230 atg cac ggt gca aat gag act ccc tca gga cgt ccg cgg gaa gcc      3744
Met His Gly Ala Asn Glu Thr Pro Ser Gly Arg Pro Arg Glu Ala
1235                1240                1245 aag ctt gtg gag ttc gat ttc ttg gga gca ctg gac att cct gtg      3789
Lys Leu Val Glu Phe Asp Phe Leu Gly Ala Leu Asp Ile Pro Val
    1250                1255                1260 cca ggc cca ccc cca ggt gtt ccc gcg cct ggg ggc cca ccc ctg      3834
Pro Gly Pro Pro Pro Gly Val Pro Ala Pro Gly Gly Pro Pro Leu
1265                1270                1275 tcc acc gga cct ata gtg gac ctg ctc cag tac agc cag aag gac      3879
Ser Thr Gly Pro Ile Val Asp Leu Leu Gln Tyr Ser Gln Lys Asp
    1280                1285                1290 ctg gat gca gtg gta aag gcg aca cag gag gag aac cgg gag ctg      3924
Leu Asp Ala Val Val Lys Ala Thr Gln Glu Glu Asn Arg Glu Leu
1295                1300                1305 agg agc agg tgt gag gag ctc cac ggg aag aac ctg gaa ctg ggg      3969
Arg Ser Arg Cys Glu Glu Leu His Gly Lys Asn Leu Glu Leu Gly
    1310                1315                1320 aag atc atg gac agg ttc gaa gag gtt gtg tac cag gcc atg gag      4014
Lys Ile Met Asp Arg Phe Glu Glu Val Val Tyr Gln Ala Met Glu
1325                1330                1335 gaa gtt cag aag cag aag gaa ctt tcc aaa gct gaa atc cag aaa      4059
Glu Val Gln Lys Gln Lys Glu Leu Ser Lys Ala Glu Ile Gln Lys
    1340                1345                1350 gtt cta aaa gaa aaa gac caa ctt acc aca gat ctg aac tcc atg      4104
Val Leu Lys Glu Lys Asp Gln Leu Thr Thr Asp Leu Asn Ser Met
1355                1360                1365 gag aag tcc ttc tcc gac ctc ttc aag cgt ttt gag aaa cag aaa      4149
Glu Lys Ser Phe Ser Asp Leu Phe Lys Arg Phe Glu Lys Gln Lys
    1370                1375                1380 gag gtg atc gag ggc tac cgc aag aac gaa gag tca ctg aag aag      4194
Glu Val Ile Glu Gly Tyr Arg Lys Asn Glu Glu Ser Leu Lys Lys
1385                1390                1395 tgc gtg gag gat tac ctg gca agg atc acc cag gag ggc cag agg      4239
Cys Val Glu Asp Tyr Leu Ala Arg Ile Thr Gln Glu Gly Gln Arg
    1400                1405                1410 tac caa gcc ctg aag gcc cac gcg gag gag aag ctg cag ctg gca      4284
Tyr Gln Ala Leu Lys Ala His Ala Glu Glu Lys Leu Gln Leu Ala
1415                1420                1425 aac gag gag atc gcc cag gtc cgg agc aag gcc cag gcg gaa gcg      4329
Asn Glu Glu Ile Ala Gln Val Arg Ser Lys Ala Gln Ala Glu Ala
```

-continued

```
                1430                1435                1440
ttg gcc ctc cag gcc agc ctg agg aag gag cag atg cgc atc cag     4374
Leu Ala Leu Gln Ala Ser Leu Arg Lys Glu Gln Met Arg Ile Gln
1445                1450                1455 tcg ctg gag aag aca gtg gag cag aag act aaa gag aac gag gag     4419
Ser Leu Glu Lys Thr Val Glu Gln Lys Thr Lys Glu Asn Glu Glu
    1460                1465                1470 ctg acc agg atc tgc gac gac ctc atc tcc aag atg gag aag atc     4464
Leu Thr Arg Ile Cys Asp Asp Leu Ile Ser Lys Met Glu Lys Ile
1475                1480                1485 tga                                                              4467
```

<210> SEQ ID NO 30
<211> LENGTH: 1488
<212> TYPE: PRT
<213> ORGANISM: Homo sapiens

<400> SEQUENCE: 30

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
```

```
              290                 295                 300
Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Ala Glu Glu Leu Val Glu Ala
                355                 360                 365

Asp Glu Ala Gly Ser Val Tyr Ala Gly Ile Leu Ser Tyr Gly Val Gly
370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
                435                 440                 445

Glu Gly Pro Thr Leu Ala Asn Val Ser Glu Leu Glu Leu Pro Ala Asp
                450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
                515                 520                 525

Glu Met Met Lys Met Ile Gly Lys His Lys Asn Ile Ile Asn Leu Leu
530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
                580                 585                 590

Phe Lys Asp Leu Val Ser Cys Ala Tyr Gln Val Ala Arg Gly Met Glu
                595                 600                 605

Tyr Leu Ala Ser Gln Lys Cys Ile His Arg Asp Leu Ala Ala Arg Asn
                610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
                660                 665                 670

Tyr Thr His Gln Ser Asp Val Trp Ser Phe Gly Val Leu Leu Trp Glu
                675                 680                 685

Ile Phe Thr Leu Gly Gly Ser Pro Tyr Pro Gly Ile Pro Val Glu Glu
                690                 695                 700

Leu Phe Lys Leu Leu Lys Glu Gly His Arg Met Asp Lys Pro Ala Asn
705                 710                 715                 720
```

-continued

Cys Thr His Asp Leu Tyr Met Ile Met Arg Glu Cys Trp His Ala Ala
            725                 730                 735
Pro Ser Gln Arg Pro Thr Phe Lys Gln Leu Val Glu Asp Leu Asp Arg
            740                 745                 750
Val Leu Thr Val Thr Ser Thr Asp Val Ser Ala Gly Gly Leu Val
        755                 760                 765
Pro Pro Ala Tyr Ala Pro Pro Ala Val Pro Gly His Pro Ala Pro
770                 775                 780
Gln Ser Ala Glu Val Trp Gly Gly Pro Ser Gly Pro Gly Ala Leu Ala
785                 790                 795                 800
Asp Leu Asp Cys Ser Ser Ser Gln Ser Pro Gly Ser Ser Glu Asn
                805                 810                 815
Gln Met Val Ser Pro Gly Lys Val Ser Gly Ser Pro Glu Gln Ala Val
            820                 825                 830
Glu Glu Asn Leu Ser Ser Tyr Ser Leu Asp Arg Arg Val Thr Pro Ala
            835                 840                 845
Ser Glu Thr Leu Glu Asp Pro Cys Arg Thr Glu Ser Gln His Lys Ala
    850                 855                 860
Glu Thr Pro His Gly Ala Glu Glu Cys Lys Ala Gly Thr Pro His
865                 870                 875                 880
Gly Ala Glu Glu Cys Arg His Gly Gly Val Cys Ala Pro Ala Ala
                885                 890                 895
Val Ala Thr Ser Pro Pro Gly Ala Ile Pro Lys Glu Ala Cys Gly Gly
            900                 905                 910
Ala Pro Leu Gln Gly Leu Pro Gly Glu Ala Leu Gly Cys Pro Ala Gly
            915                 920                 925
Val Gly Thr Pro Val Pro Ala Asp Gly Thr Gln Thr Leu Thr Cys Ala
    930                 935                 940
His Thr Ser Ala Pro Glu Ser Thr Ala Pro Thr Asn His Leu Val Ala
945                 950                 955                 960
Gly Arg Ala Met Thr Leu Ser Pro Gln Glu Glu Val Ala Ala Gly Gln
                965                 970                 975
Met Ala Ser Ser Ser Arg Ser Gly Pro Val Lys Leu Glu Phe Asp Val
            980                 985                 990
Ser Asp Gly Ala Thr Ser Lys Arg Ala Pro Pro Pro Arg Arg Leu Gly
    995                 1000                1005
Glu Arg Ser Gly Leu Lys Pro Pro Leu Arg Lys Ala Ala Val Arg
    1010                1015                1020
Gln Gln Lys Ala Pro Gln Glu Val Glu Glu Asp Asp Gly Arg Ser
    1025                1030                1035
Gly Ala Gly Glu Asp Pro Pro Met Pro Ala Ser Arg Gly Ser Tyr
    1040                1045                1050
His Leu Asp Trp Asp Lys Met Asp Asp Pro Asn Phe Ile Pro Phe
    1055                1060                1065
Gly Gly Asp Thr Lys Ser Gly Cys Ser Glu Ala Gln Pro Pro Glu
    1070                1075                1080
Ser Pro Glu Thr Arg Leu Gly Gln Pro Ala Ala Glu Gln Leu His
    1085                1090                1095
Ala Gly Pro Ala Thr Glu Glu Pro Gly Pro Cys Leu Ser Gln Gln
    1100                1105                1110
Leu His Ser Ala Ser Ala Glu Asp Thr Pro Val Val Gln Leu Ala
    1115                1120                1125

-continued

| | | | | | | | | | | | |
|---|---|---|---|---|---|---|---|---|---|---|---|
| Ala | Glu | Thr | Pro | Thr | Ala | Glu | Ser | Lys | Glu | Arg | Ala | Leu | Asn | Ser |
| 1130 | | | | | 1135 | | | | | 1140 | | | | |

Ala Glu Thr Pro Thr Ala Glu Ser Lys Glu Arg Ala Leu Asn Ser
    1130                1135                1140

Ala Ser Thr Ser Leu Pro Thr Ser Cys Pro Gly Ser Glu Pro Val
    1145                1150                1155

Pro Thr His Gln Gln Gly Gln Pro Ala Leu Glu Leu Lys Glu Glu
    1160                1165                1170

Ser Phe Arg Asp Pro Ala Glu Val Leu Gly Thr Gly Ala Glu Val
    1175                1180                1185

Asp Tyr Leu Glu Gln Phe Gly Thr Ser Ser Phe Lys Glu Ser Ala
    1190                1195                1200

Leu Arg Lys Gln Ser Leu Tyr Leu Lys Phe Asp Pro Leu Leu Arg
    1205                1210                1215

Asp Ser Pro Gly Arg Pro Val Pro Val Ala Thr Glu Thr Ser Ser
    1220                1225                1230

Met His Gly Ala Asn Glu Thr Pro Ser Gly Arg Pro Arg Glu Ala
    1235                1240                1245

Lys Leu Val Glu Phe Asp Phe Leu Gly Ala Leu Asp Ile Pro Val
    1250                1255                1260

Pro Gly Pro Pro Pro Gly Val Pro Ala Pro Gly Pro Pro Leu
    1265                1270                1275

Ser Thr Gly Pro Ile Val Asp Leu Leu Gln Tyr Ser Gln Lys Asp
    1280                1285                1290

Leu Asp Ala Val Val Lys Ala Thr Gln Glu Glu Asn Arg Glu Leu
    1295                1300                1305

Arg Ser Arg Cys Glu Glu Leu His Gly Lys Asn Leu Glu Leu Gly
    1310                1315                1320

Lys Ile Met Asp Arg Phe Glu Glu Val Val Tyr Gln Ala Met Glu
    1325                1330                1335

Glu Val Gln Lys Gln Lys Glu Leu Ser Lys Ala Glu Ile Gln Lys
    1340                1345                1350

Val Leu Lys Glu Lys Asp Gln Leu Thr Thr Asp Leu Asn Ser Met
    1355                1360                1365

Glu Lys Ser Phe Ser Asp Leu Phe Lys Arg Phe Glu Lys Gln Lys
    1370                1375                1380

Glu Val Ile Glu Gly Tyr Arg Lys Asn Glu Glu Ser Leu Lys Lys
    1385                1390                1395

Cys Val Glu Asp Tyr Leu Ala Arg Ile Thr Gln Glu Gly Gln Arg
    1400                1405                1410

Tyr Gln Ala Leu Lys Ala His Ala Glu Glu Lys Leu Gln Leu Ala
    1415                1420                1425

Asn Glu Glu Ile Ala Gln Val Arg Ser Lys Ala Gln Ala Glu Ala
    1430                1435                1440

Leu Ala Leu Gln Ala Ser Leu Arg Lys Glu Gln Met Arg Ile Gln
    1445                1450                1455

Ser Leu Glu Lys Thr Val Glu Gln Lys Thr Lys Glu Asn Glu Glu
    1460                1465                1470

Leu Thr Arg Ile Cys Asp Asp Leu Ile Ser Lys Met Glu Lys Ile
    1475                1480                1485

<210> SEQ ID NO 31
<211> LENGTH: 3765
<212> TYPE: DNA
<213> ORGANISM: Homo sapiens
<220> FEATURE:
<221> NAME/KEY: CDS

<222> LOCATION: (1)..(3765)

<400> SEQUENCE: 31

| | | | | | | | | | | | | | | | | |
|---|---|---|---|---|---|---|---|---|---|---|---|---|---|---|---|---|
| atg | ggc | gcc | cct | gcc | tgc | gcc | ctc | gcg | ctc | tgc | gtg | gcc | gtg | gcc | atc | 48 |
| Met | Gly | Ala | Pro | Ala | Cys | Ala | Leu | Ala | Leu | Cys | Val | Ala | Val | Ala | Ile | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtg | gcc | ggc | gcc | tcc | tcg | gag | tcc | ttg | ggg | acg | gag | cag | cgc | gtc | gtg | 96 |
| Val | Ala | Gly | Ala | Ser | Ser | Glu | Ser | Leu | Gly | Thr | Glu | Gln | Arg | Val | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ggg | cga | gcg | gca | gaa | gtc | ccg | ggc | cca | gag | ccc | ggc | cag | cag | gag | cag | 144 |
| Gly | Arg | Ala | Ala | Glu | Val | Pro | Gly | Pro | Glu | Pro | Gly | Gln | Gln | Glu | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| ttg | gtc | ttc | ggc | agc | ggg | gat | gct | gtg | gag | ctg | agc | tgt | ccc | ccg | ccc | 192 |
| Leu | Val | Phe | Gly | Ser | Gly | Asp | Ala | Val | Glu | Leu | Ser | Cys | Pro | Pro | Pro | |
| | 50 | | | | | 55 | | | | | 60 | | | | | |

| | | | | | | | | | | | | | | | | |
|---|---|---|---|---|---|---|---|---|---|---|---|---|---|---|---|---|
| ggg | ggt | ggt | ccc | atg | ggg | ccc | act | gtc | tgg | gtc | aag | gat | ggc | aca | ggg | 240 |
| Gly | Gly | Gly | Pro | Met | Gly | Pro | Thr | Val | Trp | Val | Lys | Asp | Gly | Thr | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ctg | gtg | ccc | tcg | gag | cgt | gtc | ctg | gtg | ggg | ccc | cag | cgg | ctg | cag | gtg | 288 |
| Leu | Val | Pro | Ser | Glu | Arg | Val | Leu | Val | Gly | Pro | Gln | Arg | Leu | Gln | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | aat | gcc | tcc | cac | gag | gac | tcc | ggg | gcc | tac | agc | tgc | cgg | cag | cgg | 336 |
| Leu | Asn | Ala | Ser | His | Glu | Asp | Ser | Gly | Ala | Tyr | Ser | Cys | Arg | Gln | Arg | |
| | | | 100 | | | | | 105 | | | | | 110 | | | |

| | | | | | | | | | | | | | | | | |
|---|---|---|---|---|---|---|---|---|---|---|---|---|---|---|---|---|
| ctc | acg | cag | cgc | gta | ctg | tgc | cac | ttc | agt | gtg | cgg | gtg | aca | gac | gct | 384 |
| Leu | Thr | Gln | Arg | Val | Leu | Cys | His | Phe | Ser | Val | Arg | Val | Thr | Asp | Ala | |
| | | 115 | | | | | 120 | | | | | 125 | | | | |

| | | | | | | | | | | | | | | | | |
|---|---|---|---|---|---|---|---|---|---|---|---|---|---|---|---|---|
| cca | tcc | tcg | gga | gat | gac | gaa | gac | ggg | gag | gac | gag | gct | gag | gac | aca | 432 |
| Pro | Ser | Ser | Gly | Asp | Asp | Glu | Asp | Gly | Glu | Asp | Glu | Ala | Glu | Asp | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| ggt | gtg | gac | aca | ggg | gcc | cct | tac | tgg | aca | cgg | ccc | gag | cgg | atg | gac | 480 |
| Gly | Val | Asp | Thr | Gly | Ala | Pro | Tyr | Trp | Thr | Arg | Pro | Glu | Arg | Met | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aag | aag | ctg | ctg | gcc | gtg | ccg | gcc | gcc | aac | acc | gtc | cgc | ttc | cgc | tgc | 528 |
| Lys | Lys | Leu | Leu | Ala | Val | Pro | Ala | Ala | Asn | Thr | Val | Arg | Phe | Arg | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| cca | gcc | gct | ggc | aac | ccc | act | ccc | tcc | atc | tcc | tgg | ctg | aag | aac | ggc | 576 |
| Pro | Ala | Ala | Gly | Asn | Pro | Thr | Pro | Ser | Ile | Ser | Trp | Leu | Lys | Asn | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| agg | gag | ttc | cgc | ggc | gag | cac | cgc | att | gga | ggc | atc | aag | ctg | cgg | cat | 624 |
| Arg | Glu | Phe | Arg | Gly | Glu | His | Arg | Ile | Gly | Gly | Ile | Lys | Leu | Arg | His | |
| | | 195 | | | | | 200 | | | | | 205 | | | | |

| | | | | | | | | | | | | | | | | |
|---|---|---|---|---|---|---|---|---|---|---|---|---|---|---|---|---|
| cag | cag | tgg | agc | ctg | gtc | atg | gaa | agc | gtg | gtg | ccc | tcg | gac | cgc | ggc | 672 |
| Gln | Gln | Trp | Ser | Leu | Val | Met | Glu | Ser | Val | Val | Pro | Ser | Asp | Arg | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| aac | tac | acc | tgc | gtc | gtg | gag | aac | aag | ttt | ggc | agc | atc | cgg | cag | acg | 720 |
| Asn | Tyr | Thr | Cys | Val | Val | Glu | Asn | Lys | Phe | Gly | Ser | Ile | Arg | Gln | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | acg | ctg | gac | gtg | ctg | gag | cgc | tcc | ccg | cac | cgg | ccc | atc | ctg | cag | 768 |
| Tyr | Thr | Leu | Asp | Val | Leu | Glu | Arg | Ser | Pro | His | Arg | Pro | Ile | Leu | Gln | |
| | | | | 245 | | | | | 250 | | | | | 255 | | |

| | | | | | | | | | | | | | | | | |
|---|---|---|---|---|---|---|---|---|---|---|---|---|---|---|---|---|
| gcg | ggg | ctg | ccg | gcc | aac | cag | acg | gcg | gtg | ctg | ggc | agc | gac | gtg | gag | 816 |
| Ala | Gly | Leu | Pro | Ala | Asn | Gln | Thr | Ala | Val | Leu | Gly | Ser | Asp | Val | Glu | |
| | | | 260 | | | | | 265 | | | | | 270 | | | |

| | | | | | | | | | | | | | | | | |
|---|---|---|---|---|---|---|---|---|---|---|---|---|---|---|---|---|
| ttc | cac | tgc | aag | gtg | tac | agt | gac | gca | cag | ccc | cac | atc | cag | tgg | ctc | 864 |
| Phe | His | Cys | Lys | Val | Tyr | Ser | Asp | Ala | Gln | Pro | His | Ile | Gln | Trp | Leu | |
| | | 275 | | | | | 280 | | | | | 285 | | | | |

| | | | | | | | | | | | | | | | | |
|---|---|---|---|---|---|---|---|---|---|---|---|---|---|---|---|---|
| aag | cac | gtg | gag | gtg | aat | ggc | agc | aag | gtg | ggc | ccg | gac | ggc | aca | ccc | 912 |
| Lys | His | Val | Glu | Val | Asn | Gly | Ser | Lys | Val | Gly | Pro | Asp | Gly | Thr | Pro | |
| | 290 | | | | | 295 | | | | | 300 | | | | | |

```
tac gtt acc gtg ctc aag tcc tgg atc agt gag agt gtg gag gcc gac    960
Tyr Val Thr Val Leu Lys Ser Trp Ile Ser Glu Ser Val Glu Ala Asp
305                 310                 315                 320 gtg cgc ctc cgc ctg gcc aat gtg tcg gag cgg gac ggg ggc gag tac   1008
Val Arg Leu Arg Leu Ala Asn Val Ser Glu Arg Asp Gly Gly Glu Tyr
                325                 330                 335 ctc tgt cga gcc acc aat ttc ata ggc gtg gcc gag aag gcc ttt tgg   1056
Leu Cys Arg Ala Thr Asn Phe Ile Gly Val Ala Glu Lys Ala Phe Trp
            340                 345                 350 ctg agc gtt cac ggg ccc cga gca gcc gag gag gag ctg gtg gag gct   1104
Leu Ser Val His Gly Pro Arg Ala Ala Glu Glu Glu Leu Val Glu Ala
        355                 360                 365 gac gag gcg ggc agt gtg tat gca ggc atc ctc agc tac ggg gtg ggc   1152
Asp Glu Ala Gly Ser Val Tyr Ala Gly Ile Leu Ser Tyr Gly Val Gly
    370                 375                 380 ttc ttc ctg ttc atc ctg gtg gtg gcg gct gtg acg ctc tgc cgc ctg   1200
Phe Phe Leu Phe Ile Leu Val Val Ala Ala Val Thr Leu Cys Arg Leu
385                 390                 395                 400 cgc agc ccc ccc aag aaa ggc ctg ggc tcc ccc acc gtg cac aag atc   1248
Arg Ser Pro Pro Lys Lys Gly Leu Gly Ser Pro Thr Val His Lys Ile
                405                 410                 415 tcc cgc ttc ccg ctc aag cga cag gtg tcc ctg gag tcc aac gcg tcc   1296
Ser Arg Phe Pro Leu Lys Arg Gln Val Ser Leu Glu Ser Asn Ala Ser
            420                 425                 430 atg agc tcc aac aca cca ctg gtg cgc atc gca agg ctg tcc tca ggg   1344
Met Ser Ser Asn Thr Pro Leu Val Arg Ile Ala Arg Leu Ser Ser Gly
        435                 440                 445 gag ggc ccc acg ctg gcc aat gtc tcc gag ctc gag ctg cct gcc gac   1392
Glu Gly Pro Thr Leu Ala Asn Val Ser Glu Leu Glu Leu Pro Ala Asp
    450                 455                 460 ccc aaa tgg gag ctg tct cgg gcc cgg ctg acc ctg ggc aag ccc ctt   1440
Pro Lys Trp Glu Leu Ser Arg Ala Arg Leu Thr Leu Gly Lys Pro Leu
465                 470                 475                 480 ggg gag ggc tgc ttc ggc cag gtg gtc atg gcg gag gcc atc ggc att   1488
Gly Glu Gly Cys Phe Gly Gln Val Val Met Ala Glu Ala Ile Gly Ile
                485                 490                 495 gac aag gac cgg gcc gcc aag cct gtc acc gta gcc gtg aag atg ctg   1536
Asp Lys Asp Arg Ala Ala Lys Pro Val Thr Val Ala Val Lys Met Leu
            500                 505                 510 aaa gac gat gcc act gac aag gac ctg tcg gac ctg gtg tct gag atg   1584
Lys Asp Asp Ala Thr Asp Lys Asp Leu Ser Asp Leu Val Ser Glu Met
        515                 520                 525 gag atg atg aag atg atc ggg aaa cac aaa aac atc atc aac ctg ctg   1632
Glu Met Met Lys Met Ile Gly Lys His Lys Asn Ile Ile Asn Leu Leu
    530                 535                 540 ggc gcc tgc acg cag ggc ggg ccc ctg tac gtg ctg gtg gag tac gcg   1680
Gly Ala Cys Thr Gln Gly Gly Pro Leu Tyr Val Leu Val Glu Tyr Ala
545                 550                 555                 560 gcc aag ggt aac ctg cgg gag ttt ctg cgg gcg cgg cgg ccc ccg ggc   1728
Ala Lys Gly Asn Leu Arg Glu Phe Leu Arg Ala Arg Arg Pro Pro Gly
                565                 570                 575 ctg gac tac tcc ttc gac acc tgc aag ccg ccc gag gag cag ctc acc   1776
Leu Asp Tyr Ser Phe Asp Thr Cys Lys Pro Pro Glu Glu Gln Leu Thr
            580                 585                 590 ttc aag gac ctg gtg tcc tgt gcc tac cag gtg gcc cgg ggc atg gag   1824
Phe Lys Asp Leu Val Ser Cys Ala Tyr Gln Val Ala Arg Gly Met Glu
        595                 600                 605 tac ttg gcc tcc cag aag tgc atc cac agg gac ctg gct gcc cgc aat   1872
Tyr Leu Ala Ser Gln Lys Cys Ile His Arg Asp Leu Ala Ala Arg Asn
```

-continued

|     |     |     |     |     |     |     |     |     |     |     |     |     |     |     |     |     |
|---|---|---|---|---|---|---|---|---|---|---|---|---|---|---|---|---|
|   | 610 |   |   |   |   | 615 |   |   |   |   | 620 |   |   |   |   |   |

```
gtg ctg gtg acc gag gac aac gtg atg aag atc gca gac ttc ggg ctg       1920
Val Leu Val Thr Glu Asp Asn Val Met Lys Ile Ala Asp Phe Gly Leu
625                 630                 635                 640 gcc cgg gac gtg cac aac ctc gac tac tac aag aag aca acc aac ggc       1968
Ala Arg Asp Val His Asn Leu Asp Tyr Tyr Lys Lys Thr Thr Asn Gly
                645                 650                 655 cgg ctg ccc gtg aag tgg atg gcg cct gag gcc ttg ttt gac cga gtc       2016
Arg Leu Pro Val Lys Trp Met Ala Pro Glu Ala Leu Phe Asp Arg Val
            660                 665                 670 tac act cac cag agt gac gtc tgg tcc ttt ggg gtc ctg ctc tgg gag       2064
Tyr Thr His Gln Ser Asp Val Trp Ser Phe Gly Val Leu Leu Trp Glu
        675                 680                 685 atc ttc acg ctg ggg ggc tcc ccg tac ccc ggc atc cct gtg gag gag       2112
Ile Phe Thr Leu Gly Gly Ser Pro Tyr Pro Gly Ile Pro Val Glu Glu
690                 695                 700 ctc ttc aag ctg ctg aag gag ggc cac cgc atg gac aag ccc gcc aac       2160
Leu Phe Lys Leu Leu Lys Glu Gly His Arg Met Asp Lys Pro Ala Asn
705                 710                 715                 720 tgc aca cac gac ctg tac atg atc atg cgg gag tgc tgg cat gcc gcg       2208
Cys Thr His Asp Leu Tyr Met Ile Met Arg Glu Cys Trp His Ala Ala
                725                 730                 735 ccc tcc cag agg ccc acc ttc aag cag ctg gtg gag gac ctg gac cgt       2256
Pro Ser Gln Arg Pro Thr Phe Lys Gln Leu Val Glu Asp Leu Asp Arg
            740                 745                 750 gtc ctt acc gtg acg tcc acc gac aat gtt atg gaa cag ttc aat cct       2304
Val Leu Thr Val Thr Ser Thr Asp Asn Val Met Glu Gln Phe Asn Pro
        755                 760                 765 ggg ctg cga aat tta ata aac ctg ggg aaa aat tat gag aaa gct gta       2352
Gly Leu Arg Asn Leu Ile Asn Leu Gly Lys Asn Tyr Glu Lys Ala Val
770                 775                 780 aac gct atg atc ctg gca gga aaa gcc tac tac gat gga gtg gcc aag       2400
Asn Ala Met Ile Leu Ala Gly Lys Ala Tyr Tyr Asp Gly Val Ala Lys
785                 790                 795                 800 atc ggt gag att gcc act ggg tcc ccc gtg tca act gaa ctg gga cat       2448
Ile Gly Glu Ile Ala Thr Gly Ser Pro Val Ser Thr Glu Leu Gly His
                805                 810                 815 gtc ctc ata gag att tca agt acc cac aag aaa ctc aac gag agt ctt       2496
Val Leu Ile Glu Ile Ser Ser Thr His Lys Lys Leu Asn Glu Ser Leu
            820                 825                 830 gat gaa aat ttt aaa aaa ttc cac aaa gag att atc cat gag ctg gag       2544
Asp Glu Asn Phe Lys Lys Phe His Lys Glu Ile Ile His Glu Leu Glu
        835                 840                 845 aag aag ata gaa ctt gac gtg aaa tat atg aac gca act cta aaa aga       2592
Lys Lys Ile Glu Leu Asp Val Lys Tyr Met Asn Ala Thr Leu Lys Arg
850                 855                 860 tac caa aca gaa cac aag aat aaa tta gag tct ttg gag aaa tcc caa       2640
Tyr Gln Thr Glu His Lys Asn Lys Leu Glu Ser Leu Glu Lys Ser Gln
865                 870                 875                 880 gct gag ttg aag aag atc aga agg aaa agc caa gga agc cga aac gca       2688
Ala Glu Leu Lys Lys Ile Arg Arg Lys Ser Gln Gly Ser Arg Asn Ala
                885                 890                 895 ctc aaa tat gaa cac aaa gaa att gag tat gtg gag acc gtt act tct       2736
Leu Lys Tyr Glu His Lys Glu Ile Glu Tyr Val Glu Thr Val Thr Ser
            900                 905                 910 cgt cag agt gaa atc cag aaa ttc att gca gat ggt tgc aaa gag gct       2784
Arg Gln Ser Glu Ile Gln Lys Phe Ile Ala Asp Gly Cys Lys Glu Ala
        915                 920                 925 ctg ctt gaa gag aag agg cgc ttc tgc ttt ctg gtt gat aag cac tgt       2832
```

```
                Leu Leu Glu Glu Lys Arg Arg Phe Cys Phe Leu Val Asp Lys His Cys
                    930                 935                 940 ggc ttt gca aac cac ata cat tat tat cac tta cag tct gca gaa cta              2880
Gly Phe Ala Asn His Ile His Tyr Tyr His Leu Gln Ser Ala Glu Leu
945                 950                 955                 960 ctg aat tcc aag ctg cct cgg tgg cag gag acc tgt gtt gat gcc atc              2928
Leu Asn Ser Lys Leu Pro Arg Trp Gln Glu Thr Cys Val Asp Ala Ile
                965                 970                 975 aaa gtg cca gag aaa atc atg aat atg atc gaa gaa ata aag acc cca              2976
Lys Val Pro Glu Lys Ile Met Asn Met Ile Glu Glu Ile Lys Thr Pro
                    980                 985                 990 gcc tct acc ccc gtg tct gga act cct cag gct tca ccc atg atc gag              3024
Ala Ser Thr Pro Val Ser Gly Thr Pro Gln Ala Ser Pro Met Ile Glu
                995                 1000                1005 aga agc aat gtg gtt agg aaa gat tac gac acc ctt tct aaa tgc                  3069
Arg Ser Asn Val Val Arg Lys Asp Tyr Asp Thr Leu Ser Lys Cys
        1010                1015                1020 tca cca aag atg ccc ccc gct cct tca ggc aga gca tat acc agt                  3114
Ser Pro Lys Met Pro Pro Ala Pro Ser Gly Arg Ala Tyr Thr Ser
    1025                1030                1035 ccc ttg atc gat atg ttt aat aac cca gcc acg gct gcc ccg aat                  3159
Pro Leu Ile Asp Met Phe Asn Asn Pro Ala Thr Ala Ala Pro Asn
    1040                1045                1050 tca caa agg gta aat aat tca aca ggt act tcc gaa gat ccc agt                  3204
Ser Gln Arg Val Asn Asn Ser Thr Gly Thr Ser Glu Asp Pro Ser
    1055                1060                1065 tta cag cga tca gtt tcg gtt gca acg gga ctg aac atg atg aag                  3249
Leu Gln Arg Ser Val Ser Val Ala Thr Gly Leu Asn Met Met Lys
    1070                1075                1080 aag cag aaa gtg aag acc atc ttc ccg cac act gcg ggc tcc aac                  3294
Lys Gln Lys Val Lys Thr Ile Phe Pro His Thr Ala Gly Ser Asn
    1085                1090                1095 aag acc tta ctc agc ttt gca cag gga gat gtc atc acg ctg ctc                  3339
Lys Thr Leu Leu Ser Phe Ala Gln Gly Asp Val Ile Thr Leu Leu
    1100                1105                1110 atc ccc gag gag aag gat ggc tgg ctc tat gga gaa cac gac gtg                  3384
Ile Pro Glu Glu Lys Asp Gly Trp Leu Tyr Gly Glu His Asp Val
    1115                1120                1125 tcc aag gcg agg ggt tgg ttc ccg tcg tcg tac acg aag ttg ctg                  3429
Ser Lys Ala Arg Gly Trp Phe Pro Ser Ser Tyr Thr Lys Leu Leu
    1130                1135                1140 gaa gaa aat gag aca gaa gca gtg acc gtg ccc acg cca agc ccc                  3474
Glu Glu Asn Glu Thr Glu Ala Val Thr Val Pro Thr Pro Ser Pro
    1145                1150                1155 aca cca gtg aga agc atc agc acc gtg aac ttg tct gag aat agc                  3519
Thr Pro Val Arg Ser Ile Ser Thr Val Asn Leu Ser Glu Asn Ser
    1160                1165                1170 agt gtt gtc atc ccc cca ccc gac tac ttg gaa tgc ttg tcc atg                  3564
Ser Val Val Ile Pro Pro Pro Asp Tyr Leu Glu Cys Leu Ser Met
    1175                1180                1185 ggg gca gct gcc gac agg aga gca gat tcg gcc agg acg aca tcc                  3609
Gly Ala Ala Ala Asp Arg Arg Ala Asp Ser Ala Arg Thr Thr Ser
    1190                1195                1200 acc ttt aag gcc cca gcg tcc aag ccc gag acc gcg gct cct aac                  3654
Thr Phe Lys Ala Pro Ala Ser Lys Pro Glu Thr Ala Ala Pro Asn
    1205                1210                1215 gat gcc aac ggg act gca aag ccg cct ttt ctc agc gga gaa aac                  3699
Asp Ala Asn Gly Thr Ala Lys Pro Pro Phe Leu Ser Gly Glu Asn
    1220                1225                1230
```

```
ccc  ttt  gcc  act  gtg  aaa  ctc  cgc  ccg  act  gtg  acg  aat  gat  cgc        3744
Pro  Phe  Ala  Thr  Val  Lys  Leu  Arg  Pro  Thr  Val  Thr  Asn  Asp  Arg
     1235                1240                               1245 tcg  gca  ccc  atc  att  cga  tga                                                3765
Ser  Ala  Pro  Ile  Ile  Arg
     1250
```

<210> SEQ ID NO 32
<211> LENGTH: 1254
<212> TYPE: PRT
<213> ORGANISM: Homo sapiens

<400> SEQUENCE: 32

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335
```

-continued

```
Leu Cys Arg Ala Thr Asn Phe Ile Gly Val Ala Glu Lys Ala Phe Trp
                340                 345                 350
Leu Ser Val His Gly Pro Arg Ala Ala Glu Glu Leu Val Glu Ala
            355                 360                 365
Asp Glu Ala Gly Ser Val Tyr Ala Gly Ile Leu Ser Tyr Gly Val Gly
        370                 375                 380
Phe Phe Leu Phe Ile Leu Val Val Ala Ala Val Thr Leu Cys Arg Leu
385                 390                 395                 400
Arg Ser Pro Pro Lys Lys Gly Leu Gly Ser Pro Thr Val His Lys Ile
                405                 410                 415
Ser Arg Phe Pro Leu Lys Arg Gln Val Ser Leu Glu Ser Asn Ala Ser
                420                 425                 430
Met Ser Ser Asn Thr Pro Leu Val Arg Ile Ala Arg Leu Ser Ser Gly
            435                 440                 445
Glu Gly Pro Thr Leu Ala Asn Val Ser Glu Leu Glu Leu Pro Ala Asp
        450                 455                 460
Pro Lys Trp Glu Leu Ser Arg Ala Arg Leu Thr Leu Gly Lys Pro Leu
465                 470                 475                 480
Gly Glu Gly Cys Phe Gly Gln Val Val Met Ala Glu Ala Ile Gly Ile
                485                 490                 495
Asp Lys Asp Arg Ala Ala Lys Pro Val Thr Val Ala Val Lys Met Leu
                500                 505                 510
Lys Asp Asp Ala Thr Asp Lys Asp Leu Ser Asp Leu Val Ser Glu Met
            515                 520                 525
Glu Met Met Lys Met Ile Gly Lys His Lys Asn Ile Ile Asn Leu Leu
        530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
            580                 585                 590
Phe Lys Asp Leu Val Ser Cys Ala Tyr Gln Val Ala Arg Gly Met Glu
        595                 600                 605
Tyr Leu Ala Ser Gln Lys Cys Ile His Arg Asp Leu Ala Ala Arg Asn
        610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
            660                 665                 670
Tyr Thr His Gln Ser Asp Val Trp Ser Phe Gly Val Leu Leu Trp Glu
        675                 680                 685
Ile Phe Thr Leu Gly Gly Ser Pro Tyr Pro Gly Ile Pro Val Glu Glu
        690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
            740                 745                 750
Val Leu Thr Val Thr Ser Thr Asp Asn Val Met Glu Gln Phe Asn Pro
```

-continued

```
            755                 760                 765
Gly Leu Arg Asn Leu Ile Asn Leu Gly Lys Asn Tyr Glu Lys Ala Val
            770                 775                 780
Asn Ala Met Ile Leu Ala Gly Lys Ala Tyr Tyr Asp Gly Val Ala Lys
785                 790                 795                 800
Ile Gly Glu Ile Ala Thr Gly Ser Pro Val Ser Thr Glu Leu Gly His
                    805                 810                 815
Val Leu Ile Glu Ile Ser Ser Thr His Lys Lys Leu Asn Glu Ser Leu
                    820                 825                 830
Asp Glu Asn Phe Lys Lys Phe His Lys Glu Ile Ile His Glu Leu Glu
                    835                 840                 845
Lys Lys Ile Glu Leu Asp Val Lys Tyr Met Asn Ala Thr Leu Lys Arg
            850                 855                 860
Tyr Gln Thr Glu His Lys Asn Lys Leu Glu Ser Leu Glu Lys Ser Gln
865                 870                 875                 880
Ala Glu Leu Lys Lys Ile Arg Arg Lys Ser Gln Gly Ser Arg Asn Ala
                    885                 890                 895
Leu Lys Tyr Glu His Lys Glu Ile Glu Tyr Val Glu Thr Val Thr Ser
                    900                 905                 910
Arg Gln Ser Glu Ile Gln Lys Phe Ile Ala Asp Gly Cys Lys Glu Ala
            915                 920                 925
Leu Leu Glu Glu Lys Arg Arg Phe Cys Phe Leu Val Asp Lys His Cys
930                 935                 940
Gly Phe Ala Asn His Ile His Tyr Tyr His Leu Gln Ser Ala Glu Leu
945                 950                 955                 960
Leu Asn Ser Lys Leu Pro Arg Trp Gln Glu Thr Cys Val Asp Ala Ile
                    965                 970                 975
Lys Val Pro Glu Lys Ile Met Asn Met Ile Glu Glu Ile Lys Thr Pro
                    980                 985                 990
Ala Ser Thr Pro Val Ser Gly Thr Pro Gln Ala Ser Pro Met Ile Glu
                    995                 1000                1005
Arg Ser Asn Val Val Arg Lys Asp Tyr Asp Thr Leu Ser Lys Cys
            1010                1015                1020
Ser Pro Lys Met Pro Pro Ala Pro Ser Gly Arg Ala Tyr Thr Ser
            1025                1030                1035
Pro Leu Ile Asp Met Phe Asn Asn Pro Ala Thr Ala Ala Pro Asn
            1040                1045                1050
Ser Gln Arg Val Asn Asn Ser Thr Gly Thr Ser Glu Asp Pro Ser
            1055                1060                1065
Leu Gln Arg Ser Val Ser Val Ala Thr Gly Leu Asn Met Met Lys
            1070                1075                1080
Lys Gln Lys Val Lys Thr Ile Phe Pro His Thr Ala Gly Ser Asn
            1085                1090                1095
Lys Thr Leu Leu Ser Phe Ala Gln Gly Asp Val Ile Thr Leu Leu
            1100                1105                1110
Ile Pro Glu Glu Lys Asp Gly Trp Leu Tyr Gly Glu His Asp Val
            1115                1120                1125
Ser Lys Ala Arg Gly Trp Phe Pro Ser Ser Tyr Thr Lys Leu Leu
            1130                1135                1140
Glu Glu Asn Glu Thr Glu Ala Val Thr Val Pro Thr Pro Ser Pro
            1145                1150                1155
Thr Pro Val Arg Ser Ile Ser Thr Val Asn Leu Ser Glu Asn Ser
            1160                1165                1170
```

```
Ser Val Val Ile Pro Pro Pro Asp Tyr Leu Glu Cys Leu Ser Met
    1175            1180                1185

Gly Ala Ala Ala Asp Arg Arg Ala Asp Ser Ala Arg Thr Thr Ser
    1190            1195                1200

Thr Phe Lys Ala Pro Ala Ser Lys Pro Glu Thr Ala Ala Pro Asn
    1205            1210                1215

Asp Ala Asn Gly Thr Ala Lys Pro Pro Phe Leu Ser Gly Glu Asn
    1220            1225                1230

Pro Phe Ala Thr Val Lys Leu Arg Pro Thr Val Thr Asn Asp Arg
    1235            1240                1245

Ser Ala Pro Ile Ile Arg
    1250

<210> SEQ ID NO 33
<211> LENGTH: 2850
<212> TYPE: DNA
<213> ORGANISM: Homo sapiens
<220> FEATURE:
<221> NAME/KEY: CDS
<222> LOCATION: (1)..(2850)

<400> SEQUENCE: 33
```

| | | | | | | | | | | | | | | | |
|---|---|---|---|---|---|---|---|---|---|---|---|---|---|---|---|
| atg | ggc | gcc | cct | gcc | tgc | gcc | ctc | gcg | ctc | tgc | gtg | gcc | gtg | gcc | atc | 48 |
| Met | Gly | Ala | Pro | Ala | Cys | Ala | Leu | Ala | Leu | Cys | Val | Ala | Val | Ala | Ile |
| 1 | | | 5 | | | | | 10 | | | | | 15 | | |
| gtg | gcc | ggc | gcc | tcc | tcg | gag | tcc | ttg | ggg | acg | gag | cag | cgc | gtc | gtg | 96 |
| Val | Ala | Gly | Ala | Ser | Ser | Glu | Ser | Leu | Gly | Thr | Glu | Gln | Arg | Val | Val |
| | | | 20 | | | | | 25 | | | | | 30 | | |
| ggg | cga | gcg | gca | gaa | gtc | ccg | ggc | cca | gag | ccc | ggc | cag | cag | gag | cag | 144 |
| Gly | Arg | Ala | Ala | Glu | Val | Pro | Gly | Pro | Glu | Pro | Gly | Gln | Gln | Glu | Gln |
| | | 35 | | | | | 40 | | | | | 45 | | | |
| ttg | gtc | ttc | ggc | agc | ggg | gat | gct | gtg | gag | ctg | agc | tgt | ccc | ccg | ccc | 192 |
| Leu | Val | Phe | Gly | Ser | Gly | Asp | Ala | Val | Glu | Leu | Ser | Cys | Pro | Pro | Pro |
| | 50 | | | | | 55 | | | | | 60 | | | | |
| ggg | ggt | ggt | ccc | atg | ggg | ccc | act | gtc | tgg | gtc | aag | gat | ggc | aca | ggg | 240 |
| Gly | Gly | Gly | Pro | Met | Gly | Pro | Thr | Val | Trp | Val | Lys | Asp | Gly | Thr | Gly |
| 65 | | | | | 70 | | | | | 75 | | | | | 80 |
| ctg | gtg | ccc | tcg | gag | cgt | gtc | ctg | gtg | ggg | ccc | cag | cgg | ctg | cag | gtg | 288 |
| Leu | Val | Pro | Ser | Glu | Arg | Val | Leu | Val | Gly | Pro | Gln | Arg | Leu | Gln | Val |
| | | | | 85 | | | | | 90 | | | | | 95 | |
| ctg | aat | gcc | tcc | cac | gag | gac | tcc | ggg | gcc | tac | agc | tgc | cgg | cag | cgg | 336 |
| Leu | Asn | Ala | Ser | His | Glu | Asp | Ser | Gly | Ala | Tyr | Ser | Cys | Arg | Gln | Arg |
| | | | 100 | | | | | 105 | | | | | 110 | | |
| ctc | acg | cag | cgc | gta | ctg | tgc | cac | ttc | agt | gtg | cgg | gtg | aca | gac | gct | 384 |
| Leu | Thr | Gln | Arg | Val | Leu | Cys | His | Phe | Ser | Val | Arg | Val | Thr | Asp | Ala |
| | | 115 | | | | | 120 | | | | | 125 | | | |
| cca | tcc | tcg | gga | gat | gac | gaa | gac | ggg | gag | gac | gag | gct | gag | gac | aca | 432 |
| Pro | Ser | Ser | Gly | Asp | Asp | Glu | Asp | Gly | Glu | Asp | Glu | Ala | Glu | Asp | Thr |
| | 130 | | | | | 135 | | | | | 140 | | | | |
| ggt | gtg | gac | aca | ggg | gcc | cct | tac | tgg | aca | cgg | ccc | gag | cgg | atg | gac | 480 |
| Gly | Val | Asp | Thr | Gly | Ala | Pro | Tyr | Trp | Thr | Arg | Pro | Glu | Arg | Met | Asp |
| 145 | | | | | 150 | | | | | 155 | | | | | 160 |
| aag | aag | ctg | ctg | gcc | gtg | ccg | gcc | gcc | aac | acc | gtc | cgc | ttc | cgc | tgc | 528 |
| Lys | Lys | Leu | Leu | Ala | Val | Pro | Ala | Ala | Asn | Thr | Val | Arg | Phe | Arg | Cys |
| | | | | 165 | | | | | 170 | | | | | 175 | |
| cca | gcc | gct | ggc | aac | ccc | act | ccc | tcc | atc | tcc | tgg | ctg | aag | aac | ggc | 576 |
| Pro | Ala | Ala | Gly | Asn | Pro | Thr | Pro | Ser | Ile | Ser | Trp | Leu | Lys | Asn | Gly |
| | | | 180 | | | | | 185 | | | | | 190 | | |
| agg | gag | ttc | cgc | ggc | gag | cac | cgc | att | gga | ggc | atc | aag | ctg | cgg | cat | 624 |

```
                          -continued

Arg Glu Phe Arg Gly Glu His Arg Ile Gly Gly Ile Lys Leu Arg His
        195                 200                 205 cag cag tgg agc ctg gtc atg gaa agc gtg gtg ccc tcg gac cgc ggc      672
Gln Gln Trp Ser Leu Val Met Glu Ser Val Val Pro Ser Asp Arg Gly
210                 215                 220 aac tac acc tgc gtc gtg gag aac aag ttt ggc agc atc cgg cag acg      720
Asn Tyr Thr Cys Val Val Glu Asn Lys Phe Gly Ser Ile Arg Gln Thr
225                 230                 235                 240 tac acg ctg gac gtg ctg gag cgc tcc ccg cac cgg ccc atc ctg cag      768
Tyr Thr Leu Asp Val Leu Glu Arg Ser Pro His Arg Pro Ile Leu Gln
                    245                 250                 255 gcg ggg ctg ccg gcc aac cag acg gcg gtg ctg ggc agc gac gtg gag      816
Ala Gly Leu Pro Ala Asn Gln Thr Ala Val Leu Gly Ser Asp Val Glu
                260                 265                 270 ttc cac tgc aag gtg tac agt gac gca cag ccc cac atc cag tgg ctc      864
Phe His Cys Lys Val Tyr Ser Asp Ala Gln Pro His Ile Gln Trp Leu
            275                 280                 285 aag cac gtg gag gtg aat ggc agc aag gtg ggc ccg gac ggc aca ccc      912
Lys His Val Glu Val Asn Gly Ser Lys Val Gly Pro Asp Gly Thr Pro
        290                 295                 300 tac gtt acc gtg ctc aag acg gcg ggc gct aac acc acc gac aag gag      960
Tyr Val Thr Val Leu Lys Thr Ala Gly Ala Asn Thr Thr Asp Lys Glu
305                 310                 315                 320 cta gag gtt ctc tcc ttg cac aac gtc acc ttt gag gac gcc ggg gag     1008
Leu Glu Val Leu Ser Leu His Asn Val Thr Phe Glu Asp Ala Gly Glu
                    325                 330                 335 tac acc tgc ctg gcg ggc aat tct att ggg ttt tct cat cac tct gcg     1056
Tyr Thr Cys Leu Ala Gly Asn Ser Ile Gly Phe Ser His His Ser Ala
                340                 345                 350 tgg ctg gtg gtg ctg cca gcc gag gag gag ctg gtg gag gct gac gag     1104
Trp Leu Val Val Leu Pro Ala Glu Glu Glu Leu Val Glu Ala Asp Glu
            355                 360                 365 gcg ggc agt gtg tat gca ggc atc ctc agc tac ggg gtg ggc ttc ttc     1152
Ala Gly Ser Val Tyr Ala Gly Ile Leu Ser Tyr Gly Val Gly Phe Phe
        370                 375                 380 ctg ttc atc ctg gtg gtg gcg gct gtg acg ctc tgc cgc ctg cgc agc     1200
Leu Phe Ile Leu Val Val Ala Ala Val Thr Leu Cys Arg Leu Arg Ser
385                 390                 395                 400 ccc ccc aag aaa ggc ctg ggc tcc ccc acc gtg cac aag atc tcc cgc     1248
Pro Pro Lys Lys Gly Leu Gly Ser Pro Thr Val His Lys Ile Ser Arg
                    405                 410                 415 ttc ccg ctc aag cga cag gtg tcc ctg gag tcc aac gcg tcc atg agc     1296
Phe Pro Leu Lys Arg Gln Val Ser Leu Glu Ser Asn Ala Ser Met Ser
                420                 425                 430 tcc aac aca cca ctg gtg cgc atc gca agg ctg tcc tca ggg gag ggc     1344
Ser Asn Thr Pro Leu Val Arg Ile Ala Arg Leu Ser Ser Gly Glu Gly
            435                 440                 445 ccc acg ctg gcc aat gtc tcc gag ctc gag ctg cct gcc gac ccc aaa     1392
Pro Thr Leu Ala Asn Val Ser Glu Leu Glu Leu Pro Ala Asp Pro Lys
        450                 455                 460 tgg gag ctg tct cgg gcc cgg ctg acc ctg ggc aag ccc ctt ggg gag     1440
Trp Glu Leu Ser Arg Ala Arg Leu Thr Leu Gly Lys Pro Leu Gly Glu
465                 470                 475                 480 ggc tgc ttc ggc cag gtg gtc atg gcg gag gcc atc ggc att gac aag     1488
Gly Cys Phe Gly Gln Val Val Met Ala Glu Ala Ile Gly Ile Asp Lys
                    485                 490                 495 gac cgg gcc gcc aag cct gtc acc gta gcc gtg aag atg ctg aaa gac     1536
Asp Arg Ala Ala Lys Pro Val Thr Val Ala Val Lys Met Leu Lys Asp
                500                 505                 510
```

```
gat gcc act gac aag gac ctg tcg gac ctg gtg tct gag atg gag atg    1584
Asp Ala Thr Asp Lys Asp Leu Ser Asp Leu Val Ser Glu Met Glu Met
            515                 520                 525 atg aag atg atc ggg aaa cac aaa aac atc atc aac ctg ctg ggc gcc    1632
Met Lys Met Ile Gly Lys His Lys Asn Ile Ile Asn Leu Leu Gly Ala
530                 535                 540 tgc acg cag ggc ggg ccc ctg tac gtg ctg gtg gag tac gcg gcc aag    1680
Cys Thr Gln Gly Gly Pro Leu Tyr Val Leu Val Glu Tyr Ala Ala Lys
545                 550                 555                 560 ggt aac ctg cgg gag ttt ctg cgg gcg cgg cgg ccc ccg ggc ctg gac    1728
Gly Asn Leu Arg Glu Phe Leu Arg Ala Arg Arg Pro Pro Gly Leu Asp
                565                 570                 575 tac tcc ttc gac acc tgc aag ccg ccc gag gag cag ctc acc ttc aag    1776
Tyr Ser Phe Asp Thr Cys Lys Pro Pro Glu Glu Gln Leu Thr Phe Lys
            580                 585                 590 gac ctg gtg tcc tgt gcc tac cag gtg gcc cgg ggc atg gag tac ttg    1824
Asp Leu Val Ser Cys Ala Tyr Gln Val Ala Arg Gly Met Glu Tyr Leu
            595                 600                 605 gcc tcc cag aag tgc atc cac agg gac ctg gct gcc cgc aat gtg ctg    1872
Ala Ser Gln Lys Cys Ile His Arg Asp Leu Ala Ala Arg Asn Val Leu
610                 615                 620 gtg acc gag gac aac gtg atg aag atc gca gac ttc ggg ctg gcc cgg    1920
Val Thr Glu Asp Asn Val Met Lys Ile Ala Asp Phe Gly Leu Ala Arg
625                 630                 635                 640 gac gtg cac aac ctc gac tac tac aag aag aca acc aac ggc cgg ctg    1968
Asp Val His Asn Leu Asp Tyr Tyr Lys Lys Thr Thr Asn Gly Arg Leu
                645                 650                 655 ccc gtg aag tgg atg gcg cct gag gcc ttg ttt gac cga gtc tac act    2016
Pro Val Lys Trp Met Ala Pro Glu Ala Leu Phe Asp Arg Val Tyr Thr
            660                 665                 670 cac cag agt gac gtc tgg tcc ttt ggg gtc ctg ctc tgg gag atc ttc    2064
His Gln Ser Asp Val Trp Ser Phe Gly Val Leu Leu Trp Glu Ile Phe
            675                 680                 685 acg ctg ggg ggc tcc ccg tac ccc ggc atc cct gtg gag gag ctc ttc    2112
Thr Leu Gly Gly Ser Pro Tyr Pro Gly Ile Pro Val Glu Glu Leu Phe
            690                 695                 700 aag ctg ctg aag gag ggc cac cgc atg gac aag ccc gcc aac tgc aca    2160
Lys Leu Leu Lys Glu Gly His Arg Met Asp Lys Pro Ala Asn Cys Thr
705                 710                 715                 720 cac gac ctg tac atg atc atg cgg gag tgc tgg cat gcc gcg ccc tcc    2208
His Asp Leu Tyr Met Ile Met Arg Glu Cys Trp His Ala Ala Pro Ser
                725                 730                 735 cag agg ccc acc ttc aag cag ctg gtg gag gac ctg gac cgt gtc ctt    2256
Gln Arg Pro Thr Phe Lys Gln Leu Val Glu Asp Leu Asp Arg Val Leu
            740                 745                 750 acc gtg acg tcc acc gac gta aag gcg aca cag gag gag aac cgg gag    2304
Thr Val Thr Ser Thr Asp Val Lys Ala Thr Gln Glu Glu Asn Arg Glu
            755                 760                 765 ctg agg agc agg tgt gag gag ctc cac ggg aag aac ctg gaa ctg ggg    2352
Leu Arg Ser Arg Cys Glu Glu Leu His Gly Lys Asn Leu Glu Leu Gly
770                 775                 780 aag atc atg gac agg ttc gaa gag gtt gtg tac cag gcc atg gag gaa    2400
Lys Ile Met Asp Arg Phe Glu Glu Val Val Tyr Gln Ala Met Glu Glu
785                 790                 795                 800 gtt cag aag cag aag gaa ctt tcc aaa gct gaa atc cag aaa gtt cta    2448
Val Gln Lys Gln Lys Glu Leu Ser Lys Ala Glu Ile Gln Lys Val Leu
                805                 810                 815 aaa gaa aaa gac caa ctt acc aca gat ctg aac tcc atg gag aag tcc    2496
Lys Glu Lys Asp Gln Leu Thr Thr Asp Leu Asn Ser Met Glu Lys Ser
            820                 825                 830
```

| | | | | | | | | | | | | | | | | |
|---|---|---|---|---|---|---|---|---|---|---|---|---|---|---|---|---|
| ttc | tcc | gac | ctc | ttc | aag | cgt | ttt | gag | aaa | cag | aaa | gag | gtg | atc | gag | 2544 |
| Phe | Ser | Asp | Leu | Phe | Lys | Arg | Phe | Glu | Lys | Gln | Lys | Glu | Val | Ile | Glu | |
| | | 835 | | | | 840 | | | | 845 | | | | | | |
| ggc | tac | cgc | aag | aac | gaa | gag | tca | ctg | aag | aag | tgc | gtg | gag | gat | tac | 2592 |
| Gly | Tyr | Arg | Lys | Asn | Glu | Glu | Ser | Leu | Lys | Lys | Cys | Val | Glu | Asp | Tyr | |
| 850 | | | | | 855 | | | | | 860 | | | | | | |
| ctg | gca | agg | atc | acc | cag | gag | ggc | cag | agg | tac | caa | gcc | ctg | aag | gcc | 2640 |
| Leu | Ala | Arg | Ile | Thr | Gln | Glu | Gly | Gln | Arg | Tyr | Gln | Ala | Leu | Lys | Ala | |
| 865 | | | | | 870 | | | | | 875 | | | | | 880 | |
| cac | gcg | gag | gag | aag | ctg | cag | ctg | gca | aac | gag | gag | atc | gcc | cag | gtc | 2688 |
| His | Ala | Glu | Glu | Lys | Leu | Gln | Leu | Ala | Asn | Glu | Glu | Ile | Ala | Gln | Val | |
| | | | | 885 | | | | | 890 | | | | | 895 | | |
| cgg | agc | aag | gcc | cag | gcg | gaa | gcg | ttg | gcc | ctc | cag | gcc | agc | ctg | agg | 2736 |
| Arg | Ser | Lys | Ala | Gln | Ala | Glu | Ala | Leu | Ala | Leu | Gln | Ala | Ser | Leu | Arg | |
| | | 900 | | | | 905 | | | | 910 | | | | | | |
| aag | gag | cag | atg | cgc | atc | cag | tcg | ctg | gag | aag | aca | gtg | gag | cag | aag | 2784 |
| Lys | Glu | Gln | Met | Arg | Ile | Gln | Ser | Leu | Glu | Lys | Thr | Val | Glu | Gln | Lys | |
| | | | | 915 | | | | | 920 | | | | | 925 | | |
| act | aaa | gag | aac | gag | gag | ctg | acc | agg | atc | tgc | gac | gac | ctc | atc | tcc | 2832 |
| Thr | Lys | Glu | Asn | Glu | Glu | Leu | Thr | Arg | Ile | Cys | Asp | Asp | Leu | Ile | Ser | |
| 930 | | | | | 935 | | | | | 940 | | | | | | |
| aag | atg | gag | aag | atc | tga | | | | | | | | | | | 2850 |
| Lys | Met | Glu | Lys | Ile | | | | | | | | | | | | |
| 945 | | | | | | | | | | | | | | | | |

<210> SEQ ID NO 34
<211> LENGTH: 949
<212> TYPE: PRT
<213> ORGANISM: Homo sapiens

<400> SEQUENCE: 34

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

```
Gln Gln Trp Ser Leu Val Met Glu Ser Val Val Pro Ser Asp Arg Gly
        210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
            245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
        290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
        370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620
```

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
            645                 650                 655

Pro Val Lys Trp Met Ala Pro Glu Ala Leu Phe Asp Arg Val Tyr Thr
        660                 665                 670

His Gln Ser Asp Val Trp Ser Phe Gly Val Leu Leu Trp Glu Ile Phe
    675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
            725                 730                 735

Gln Arg Pro Thr Phe Lys Gln Leu Val Glu Asp Leu Asp Arg Val Leu
        740                 745                 750

Thr Val Thr Ser Thr Asp Val Lys Ala Thr Gln Glu Glu Asn Arg Glu
    755                 760                 765

Leu Arg Ser Arg Cys Glu Glu Leu His Gly Lys Asn Leu Glu Leu Gly
770                 775                 780

Lys Ile Met Asp Arg Phe Glu Val Val Tyr Gln Ala Met Glu Glu
785                 790                 795                 800

Val Gln Lys Gln Lys Glu Leu Ser Lys Ala Glu Ile Gln Lys Val Leu
            805                 810                 815

Lys Glu Lys Asp Gln Leu Thr Thr Asp Leu Asn Ser Met Glu Lys Ser
        820                 825                 830

Phe Ser Asp Leu Phe Lys Arg Phe Glu Lys Gln Lys Glu Val Ile Glu
    835                 840                 845

Gly Tyr Arg Lys Asn Glu Glu Ser Leu Lys Lys Cys Val Glu Asp Tyr
850                 855                 860

Leu Ala Arg Ile Thr Gln Glu Gly Gln Arg Tyr Gln Ala Leu Lys Ala
865                 870                 875                 880

His Ala Glu Glu Lys Leu Gln Leu Ala Asn Glu Glu Ile Ala Gln Val
            885                 890                 895

Arg Ser Lys Ala Gln Ala Glu Ala Leu Ala Leu Gln Ala Ser Leu Arg
        900                 905                 910

Lys Glu Gln Met Arg Ile Gln Ser Leu Glu Lys Thr Val Glu Gln Lys
    915                 920                 925

Thr Lys Glu Asn Glu Glu Leu Thr Arg Ile Cys Asp Asp Leu Ile Ser
930                 935                 940

Lys Met Glu Lys Ile
945

<210> SEQ ID NO 35
<211> LENGTH: 4461
<212> TYPE: DNA
<213> ORGANISM: Homo sapiens
<220> FEATURE:
<221> NAME/KEY: CDS
<222> LOCATION: (1)..(4461)

<400> SEQUENCE: 35 atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96

-continued

| | | |
|---|---|---|
| Val Ala Gly Ala Ser Ser Glu Ser Leu Gly Thr Glu Gln Val Val<br>20 25 30 | | |
| ggg cga gcg gca gaa gtc ccg ggc cca gag ccc ggc cag cag gag cag<br>Gly Arg Ala Ala Glu Val Pro Gly Pro Glu Pro Gly Gln Gln Glu Gln<br>35 40 45 | 144 | |
| ttg gtc ttc ggc agc ggg gat gct gtg gag ctg agc tgt ccc ccg ccc<br>Leu Val Phe Gly Ser Gly Asp Ala Val Glu Leu Ser Cys Pro Pro Pro<br>50 55 60 | 192 | |
| ggg ggt ggt ccc atg ggg ccc act gtc tgg gtc aag gat ggc aca ggg<br>Gly Gly Gly Pro Met Gly Pro Thr Val Trp Val Lys Asp Gly Thr Gly<br>65 70 75 80 | 240 | |
| ctg gtg ccc tcg gag cgt gtc ctg gtg ggg ccc cag cgg ctg cag gtg<br>Leu Val Pro Ser Glu Arg Val Leu Val Gly Pro Gln Arg Leu Gln Val<br>85 90 95 | 288 | |
| ctg aat gcc tcc cac gag gac tcc ggg gcc tac agc tgc cgg cag cgg<br>Leu Asn Ala Ser His Glu Asp Ser Gly Ala Tyr Ser Cys Arg Gln Arg<br>100 105 110 | 336 | |
| ctc acg cag cgc gta ctg tgc cac ttc agt gtg cgg gtg aca gac gct<br>Leu Thr Gln Arg Val Leu Cys His Phe Ser Val Arg Val Thr Asp Ala<br>115 120 125 | 384 | |
| cca tcc tcg gga gat gac gaa gac ggg gag gac gag gct gag gac aca<br>Pro Ser Ser Gly Asp Asp Glu Asp Gly Glu Asp Glu Ala Glu Asp Thr<br>130 135 140 | 432 | |
| ggt gtg gac aca ggg gcc cct tac tgg aca cgg ccc gag cgg atg gac<br>Gly Val Asp Thr Gly Ala Pro Tyr Trp Thr Arg Pro Glu Arg Met Asp<br>145 150 155 160 | 480 | |
| aag aag ctg ctg gcc gtg ccg gcc gcc aac acc gtc cgc ttc cgc tgc<br>Lys Lys Leu Leu Ala Val Pro Ala Ala Asn Thr Val Arg Phe Arg Cys<br>165 170 175 | 528 | |
| cca gcc gct ggc aac ccc act ccc tcc atc tcc tgg ctg aag aac ggc<br>Pro Ala Ala Gly Asn Pro Thr Pro Ser Ile Ser Trp Leu Lys Asn Gly<br>180 185 190 | 576 | |
| agg gag ttc cgc ggc gag cac cgc att gga ggc atc aag ctg cgg cat<br>Arg Glu Phe Arg Gly Glu His Arg Ile Gly Gly Ile Lys Leu Arg His<br>195 200 205 | 624 | |
| cag cag tgg agc ctg gtc atg gaa agc gtg gtg ccc tcg gac cgc ggc<br>Gln Gln Trp Ser Leu Val Met Glu Ser Val Val Pro Ser Asp Arg Gly<br>210 215 220 | 672 | |
| aac tac acc tgc gtc gtg gag aac aag ttt ggc agc atc cgg cag acg<br>Asn Tyr Thr Cys Val Val Glu Asn Lys Phe Gly Ser Ile Arg Gln Thr<br>225 230 235 240 | 720 | |
| tac acg ctg gac gtg ctg gag cgc tcc ccg cac cgg ccc atc ctg cag<br>Tyr Thr Leu Asp Val Leu Glu Arg Ser Pro His Arg Pro Ile Leu Gln<br>245 250 255 | 768 | |
| gcg ggg ctg ccg gcc aac cag acg gcg gtg ctg ggc agc gac gtg gag<br>Ala Gly Leu Pro Ala Asn Gln Thr Ala Val Leu Gly Ser Asp Val Glu<br>260 265 270 | 816 | |
| ttc cac tgc aag gtg tac agt gac gca cag ccc cac atc cag tgg ctc<br>Phe His Cys Lys Val Tyr Ser Asp Ala Gln Pro His Ile Gln Trp Leu<br>275 280 285 | 864 | |
| aag cac gtg gag gtg aat ggc agc aag gtg ggc ccg gac ggc aca ccc<br>Lys His Val Glu Val Asn Gly Ser Lys Val Gly Pro Asp Gly Thr Pro<br>290 295 300 | 912 | |
| tac gtt acc gtg ctc aag acg gcg ggc gct aac acc acc gac aag gag<br>Tyr Val Thr Val Leu Lys Thr Ala Gly Ala Asn Thr Thr Asp Lys Glu<br>305 310 315 320 | 960 | |
| cta gag gtt ctc tcc ttg cac aac gtc acc ttt gag gac gcc ggg gag<br>Leu Glu Val Leu Ser Leu His Asn Val Thr Phe Glu Asp Ala Gly Glu<br>325 330 335 | 1008 | |

```
tac acc tgc ctg gcg ggc aat tct att ggg ttt tct cat cac tct gcg    1056
Tyr Thr Cys Leu Ala Gly Asn Ser Ile Gly Phe Ser His His Ser Ala
                340                 345                 350 tgg ctg gtg gtg ctg cca gcc gag gag gag ctg gtg gag gct gac gag    1104
Trp Leu Val Val Leu Pro Ala Glu Glu Glu Leu Val Glu Ala Asp Glu
        355                 360                 365 gcg ggc agt gtg tat gca ggc atc ctc agc tac ggg gtg ggc ttc ttc    1152
Ala Gly Ser Val Tyr Ala Gly Ile Leu Ser Tyr Gly Val Gly Phe Phe
    370                 375                 380 ctg ttc atc ctg gtg gtg gcg gct gtg acg ctc tgc cgc ctg cgc agc    1200
Leu Phe Ile Leu Val Val Ala Ala Val Thr Leu Cys Arg Leu Arg Ser
385                 390                 395                 400 ccc ccc aag aaa ggc ctg ggc tcc ccc acc gtg cac aag atc tcc cgc    1248
Pro Pro Lys Lys Gly Leu Gly Ser Pro Thr Val His Lys Ile Ser Arg
                405                 410                 415 ttc ccg ctc aag cga cag gtg tcc ctg gag tcc aac gcg tcc atg agc    1296
Phe Pro Leu Lys Arg Gln Val Ser Leu Glu Ser Asn Ala Ser Met Ser
        420                 425                 430 tcc aac aca cca ctg gtg cgc atc gca agg ctg tcc tca ggg gag ggc    1344
Ser Asn Thr Pro Leu Val Arg Ile Ala Arg Leu Ser Ser Gly Glu Gly
    435                 440                 445 ccc acg ctg gcc aat gtc tcc gag ctc gag ctg cct gcc gac ccc aaa    1392
Pro Thr Leu Ala Asn Val Ser Glu Leu Glu Leu Pro Ala Asp Pro Lys
450                 455                 460 tgg gag ctg tct cgg gcc cgg ctg acc ctg ggc aag ccc ctt ggg gag    1440
Trp Glu Leu Ser Arg Ala Arg Leu Thr Leu Gly Lys Pro Leu Gly Glu
465                 470                 475                 480 ggc tgc ttc ggc cag gtg gtc atg gcg gag gcc atc ggc att gac aag    1488
Gly Cys Phe Gly Gln Val Val Met Ala Glu Ala Ile Gly Ile Asp Lys
                485                 490                 495 gac cgg gcc gcc aag cct gtc acc gta gcc gtg aag atg ctg aaa gac    1536
Asp Arg Ala Ala Lys Pro Val Thr Val Ala Val Lys Met Leu Lys Asp
        500                 505                 510 gat gcc act gac aag gac ctg tcg gac ctg gtg tct gag atg gag atg    1584
Asp Ala Thr Asp Lys Asp Leu Ser Asp Leu Val Ser Glu Met Glu Met
    515                 520                 525 atg aag atg atc ggg aaa cac aaa aac atc atc aac ctg ctg ggc gcc    1632
Met Lys Met Ile Gly Lys His Lys Asn Ile Ile Asn Leu Leu Gly Ala
530                 535                 540 tgc acg cag ggc ggg ccc ctg tac gtg ctg gtg gag tac gcg gcc aag    1680
Cys Thr Gln Gly Gly Pro Leu Tyr Val Leu Val Glu Tyr Ala Ala Lys
545                 550                 555                 560 ggt aac ctg cgg gag ttt ctg cgg gcg cgg cgg ccc ccg ggc ctg gac    1728
Gly Asn Leu Arg Glu Phe Leu Arg Ala Arg Arg Pro Pro Gly Leu Asp
                565                 570                 575 tac tcc ttc gac acc tgc aag ccg ccc gag gag cag ctc acc ttc aag    1776
Tyr Ser Phe Asp Thr Cys Lys Pro Pro Glu Glu Gln Leu Thr Phe Lys
        580                 585                 590 gac ctg gtg tcc tgt gcc tac cag gtg gcc cgg ggc atg gag tac ttg    1824
Asp Leu Val Ser Cys Ala Tyr Gln Val Ala Arg Gly Met Glu Tyr Leu
    595                 600                 605 gcc tcc cag aag tgc atc cac agg gac ctg gct gcc cgc aat gtg ctg    1872
Ala Ser Gln Lys Cys Ile His Arg Asp Leu Ala Ala Arg Asn Val Leu
610                 615                 620 gtg acc gag gac aac gtg atg aag atc gca gac ttc ggg ctg gcc cgg    1920
Val Thr Glu Asp Asn Val Met Lys Ile Ala Asp Phe Gly Leu Ala Arg
625                 630                 635                 640 gac gtg cac aac ctc gac tac tac aag aag aca acc aac ggc cgg ctg    1968
Asp Val His Asn Leu Asp Tyr Tyr Lys Lys Thr Thr Asn Gly Arg Leu
                645                 650                 655
```

-continued

```
ccc gtg aag tgg atg gcg cct gag gcc ttg ttt gac cga gtc tac act       2016
Pro Val Lys Trp Met Ala Pro Glu Ala Leu Phe Asp Arg Val Tyr Thr
            660                 665                 670 cac cag agt gac gtc tgg tcc ttt ggg gtc ctg ctc tgg gag atc ttc       2064
His Gln Ser Asp Val Trp Ser Phe Gly Val Leu Leu Trp Glu Ile Phe
        675                 680                 685 acg ctg ggg ggc tcc ccg tac ccc ggc atc cct gtg gag gag ctc ttc       2112
Thr Leu Gly Gly Ser Pro Tyr Pro Gly Ile Pro Val Glu Glu Leu Phe
    690                 695                 700 aag ctg ctg aag gag ggc cac cgc atg gac aag ccc gcc aac tgc aca       2160
Lys Leu Leu Lys Glu Gly His Arg Met Asp Lys Pro Ala Asn Cys Thr
705                 710                 715                 720 cac gac ctg tac atg atc atg cgg gag tgc tgg cat gcc gcg ccc tcc       2208
His Asp Leu Tyr Met Ile Met Arg Glu Cys Trp His Ala Ala Pro Ser
                725                 730                 735 cag agg ccc acc ttc aag cag ctg gtg gag gac ctg gac cgt gtc ctt       2256
Gln Arg Pro Thr Phe Lys Gln Leu Val Glu Asp Leu Asp Arg Val Leu
            740                 745                 750 acc gtg acg tcc acc gac gtg agt gct ggc tct ggc ctg gtg cca ccc       2304
Thr Val Thr Ser Thr Asp Val Ser Ala Gly Ser Gly Leu Val Pro Pro
        755                 760                 765 gcc tat gcc cct ccc cct gcc gtc ccc ggc cat cct gcc ccc cag agt       2352
Ala Tyr Ala Pro Pro Pro Ala Val Pro Gly His Pro Ala Pro Gln Ser
    770                 775                 780 gct gag gtg tgg ggc ggg cct tct ggc cca ggt gcc ctg gct gac ctg       2400
Ala Glu Val Trp Gly Gly Pro Ser Gly Pro Gly Ala Leu Ala Asp Leu
785                 790                 795                 800 gac tgc tca agc tct tcc cag agc cca gga agt tct gag aac caa atg       2448
Asp Cys Ser Ser Ser Ser Gln Ser Pro Gly Ser Ser Glu Asn Gln Met
                805                 810                 815 gtg tct cca gga aaa gtg tct ggc agc cct gag caa gcc gtg gag gaa       2496
Val Ser Pro Gly Lys Val Ser Gly Ser Pro Glu Gln Ala Val Glu Glu
            820                 825                 830 aac ctt agt tcc tat tcc tta gac aga aga gtg aca ccc gcc tct gag       2544
Asn Leu Ser Ser Tyr Ser Leu Asp Arg Arg Val Thr Pro Ala Ser Glu
        835                 840                 845 acc cta gaa gac cct tgc agg aca gag tcc cag cac aaa gcg gag act       2592
Thr Leu Glu Asp Pro Cys Arg Thr Glu Ser Gln His Lys Ala Glu Thr
    850                 855                 860 ccg cac gga gcc gag gaa gaa tgc aaa gcg gag act ccg cac gga gcc       2640
Pro His Gly Ala Glu Glu Glu Cys Lys Ala Glu Thr Pro His Gly Ala
865                 870                 875                 880 gag gag gaa tgc cgg cac ggt ggg gtc tgt gct ccc gca gca gtg gcc       2688
Glu Glu Glu Cys Arg His Gly Gly Val Cys Ala Pro Ala Ala Val Ala
                885                 890                 895 act tcg cct cct ggt gca atc cct aag gaa gcc tgc gga gga gca ccc       2736
Thr Ser Pro Pro Gly Ala Ile Pro Lys Glu Ala Cys Gly Gly Ala Pro
            900                 905                 910 ctg cag ggt ctg cct ggc gaa gcc ctg ggc tgc cct gcg ggt gtg ggc       2784
Leu Gln Gly Leu Pro Gly Glu Ala Leu Gly Cys Pro Ala Gly Val Gly
        915                 920                 925 acc ccc gtg cca gca gat ggc act cag acc ctt acc tgt gca cac acc       2832
Thr Pro Val Pro Ala Asp Gly Thr Gln Thr Leu Thr Cys Ala His Thr
    930                 935                 940 tct gct cct gag agc aca gcc cca acc aac cac ctg gtg gct ggc agg       2880
Ser Ala Pro Glu Ser Thr Ala Pro Thr Asn His Leu Val Ala Gly Arg
945                 950                 955                 960 gcc atg acc ctg agt cct cag gaa gaa gtg gct gca ggc caa atg gcc       2928
Ala Met Thr Leu Ser Pro Gln Glu Glu Val Ala Ala Gly Gln Met Ala
```

-continued

|     |     |     |     | 965 |     |     |     | 970 |     |     |     | 975 |     |     |      |
|---|---|---|---|---|---|---|---|---|---|---|---|---|---|---|---|
| agc | tcc | tcg | agg | agc | gga | cct | gta | aaa | cta | gaa | ttt | gat | gta | tct | gat | 2976 |
| Ser | Ser | Ser | Arg | Ser | Gly | Pro | Val | Lys | Leu | Glu | Phe | Asp | Val | Ser | Asp |      |
|     |     |     | 980 |     |     |     |     | 985 |     |     |     |     | 990 |     |     |      |

```
agc tcc tcg agg agc gga cct gta aaa cta gaa ttt gat gta tct gat    2976
Ser Ser Ser Arg Ser Gly Pro Val Lys Leu Glu Phe Asp Val Ser Asp
            980                 985                 990 ggc gcc acc agc aaa agg gca ccc cca cca agg aga ctg gga gag agg    3024
Gly Ala Thr Ser Lys Arg Ala Pro Pro Pro Arg Arg Leu Gly Glu Arg
            995                1000                1005 tcc ggc ctc aag cct ccc ttg agg aaa gca gca gtg agg cag caa        3069
Ser Gly Leu Lys Pro Pro Leu Arg Lys Ala Ala Val Arg Gln Gln
        1010                1015                1020 aag gcc ccg cag gag gtg gag gag gac gac ggt agg agc gga gca        3114
Lys Ala Pro Gln Glu Val Glu Glu Asp Asp Gly Arg Ser Gly Ala
        1025                1030                1035 gga gag gac ccc ccc atg cca gct tct cgg ggc tct tac cac ctc        3159
Gly Glu Asp Pro Pro Met Pro Ala Ser Arg Gly Ser Tyr His Leu
        1040                1045                1050 gac tgg gac aaa atg gat gac cca aac ttc atc ccg ttc gga ggt        3204
Asp Trp Asp Lys Met Asp Asp Pro Asn Phe Ile Pro Phe Gly Gly
        1055                1060                1065 gac acc aag tct ggt tgc agt gag gcc cag ccc cca gaa agc cct        3249
Asp Thr Lys Ser Gly Cys Ser Glu Ala Gln Pro Pro Glu Ser Pro
        1070                1075                1080 gag acc agg ctg ggc cag cca gcg gct gaa cag ttg cat gct ggg        3294
Glu Thr Arg Leu Gly Gln Pro Ala Ala Glu Gln Leu His Ala Gly
        1085                1090                1095 cct gcc acg gag gag cca ggt ccc tgt ctg agc cag cag ctg cat        3339
Pro Ala Thr Glu Glu Pro Gly Pro Cys Leu Ser Gln Gln Leu His
        1100                1105                1110 tca gcc tca gcg gag gac acg cct gtg gtg cag ttg gca gcc gag        3384
Ser Ala Ser Ala Glu Asp Thr Pro Val Val Gln Leu Ala Ala Glu
        1115                1120                1125 acc cca aca gca gag agc aag gag aga gcc ttg aac tct gcc agc        3429
Thr Pro Thr Ala Glu Ser Lys Glu Arg Ala Leu Asn Ser Ala Ser
        1130                1135                1140 acc tcg ctt ccc aca agc tgt cca ggc agt gag cca gtg ccc acc        3474
Thr Ser Leu Pro Thr Ser Cys Pro Gly Ser Glu Pro Val Pro Thr
        1145                1150                1155 cat cag cag ggg cag cct gcc ttg gag ctg aaa gag gag agc ttc        3519
His Gln Gln Gly Gln Pro Ala Leu Glu Leu Lys Glu Glu Ser Phe
        1160                1165                1170 aga gac ccc gct gag gtt cta ggc acg ggc gcg gag gtg gat tac        3564
Arg Asp Pro Ala Glu Val Leu Gly Thr Gly Ala Glu Val Asp Tyr
        1175                1180                1185 ctg gag cag ttt gga act tcc tcg ttt aag gag tcg gcc ttg agg        3609
Leu Glu Gln Phe Gly Thr Ser Ser Phe Lys Glu Ser Ala Leu Arg
        1190                1195                1200 aag cag tcc tta tac ctc aag ttc gac ccc ctc ctg agg gac agt        3654
Lys Gln Ser Leu Tyr Leu Lys Phe Asp Pro Leu Leu Arg Asp Ser
        1205                1210                1215 cct ggt aga cca gtg ccc gtg gcc acc gag acc agc agc atg cac        3699
Pro Gly Arg Pro Val Pro Val Ala Thr Glu Thr Ser Ser Met His
        1220                1225                1230 ggt gca aat gag act ccc tca gga cgt ccg cgg gaa gcc aag ctt        3744
Gly Ala Asn Glu Thr Pro Ser Gly Arg Pro Arg Glu Ala Lys Leu
        1235                1240                1245 gtg gag ttc gat ttc ttg gga gca ctg gac att cct gtg cca ggc        3789
Val Glu Phe Asp Phe Leu Gly Ala Leu Asp Ile Pro Val Pro Gly
        1250                1255                1260 cca ccc cca ggt gtt ccc gcg cct ggg ggc cca ccc ctg tcc acc        3834
```

```
            Pro Pro Pro Gly Val Pro Ala Pro Gly Gly Pro Pro Leu Ser Thr
                1265            1270            1275 gga cct ata gtg gac ctg ctc cag tac agc cag aag gac ctg gat         3879
Gly Pro Ile Val Asp Leu Leu Gln Tyr Ser Gln Lys Asp Leu Asp
    1280            1285            1290 gca gtg gta aag gcg aca cag gag gag aac cgg gag ctg agg agc         3924
Ala Val Val Lys Ala Thr Gln Glu Glu Asn Arg Glu Leu Arg Ser
1295            1300            1305 agg tgt gag gag ctc cac ggg aag aac ctg gaa ctg ggg aag atc         3969
Arg Cys Glu Glu Leu His Gly Lys Asn Leu Glu Leu Gly Lys Ile
    1310            1315            1320 atg gac agg ttc gaa gag gtt gtg tac cag gcc atg gag gaa gtt         4014
Met Asp Arg Phe Glu Glu Val Val Tyr Gln Ala Met Glu Glu Val
1325            1330            1335 cag aag cag aag gaa ctt tcc aaa gct gaa atc cag aaa gtt cta         4059
Gln Lys Gln Lys Glu Leu Ser Lys Ala Glu Ile Gln Lys Val Leu
    1340            1345            1350 aaa gaa aaa gac caa ctt acc aca gat ctg aac tcc atg gag aag         4104
Lys Glu Lys Asp Gln Leu Thr Thr Asp Leu Asn Ser Met Glu Lys
1355            1360            1365 tcc ttc tcc gac ctc ttc aag cgt ttt gag aaa cag aaa gag gtg         4149
Ser Phe Ser Asp Leu Phe Lys Arg Phe Glu Lys Gln Lys Glu Val
    1370            1375            1380 atc gag ggc tac cgc aag aac gaa gag tca ctg aag aag tgc gtg         4194
Ile Glu Gly Tyr Arg Lys Asn Glu Glu Ser Leu Lys Lys Cys Val
1385            1390            1395 gag gat tac ctg gca agg atc acc cag gag ggc cag agg tac caa         4239
Glu Asp Tyr Leu Ala Arg Ile Thr Gln Glu Gly Gln Arg Tyr Gln
    1400            1405            1410 gcc ctg aag gcc cac gcg gag gag aag ctg cag ctg gca aac gag         4284
Ala Leu Lys Ala His Ala Glu Glu Lys Leu Gln Leu Ala Asn Glu
1415            1420            1425 gag atc gcc cag gtc cgg agc aag gcc cag gcg gaa gcg ttg gcc         4329
Glu Ile Ala Gln Val Arg Ser Lys Ala Gln Ala Glu Ala Leu Ala
    1430            1435            1440 ctc cag gcc agc ctg agg aag gag cag atg cgc atc cag tcg ctg         4374
Leu Gln Ala Ser Leu Arg Lys Glu Gln Met Arg Ile Gln Ser Leu
1445            1450            1455 gag aag aca gtg gag cag aag act aaa gag aac gag gag ctg acc         4419
Glu Lys Thr Val Glu Gln Lys Thr Lys Glu Asn Glu Glu Leu Thr
    1460            1465            1470 agg atc tgc gac gac ctc atc tcc aag atg gag aag atc tga             4461
Arg Ile Cys Asp Asp Leu Ile Ser Lys Met Glu Lys Ile
1475            1480            1485

<210> SEQ ID NO 36
<211> LENGTH: 1486
<212> TYPE: PRT
<213> ORGANISM: Homo sapiens

<400> SEQUENCE: 36

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60
```

```
Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Gly Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
```

```
                485                 490                 495
Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
                515                 520                 525

Met Lys Met Ile Gly Lys His Lys Asn Ile Ile Asn Leu Leu Gly Ala
                530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
                610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
                690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
                740                 745                 750

Thr Val Thr Ser Thr Asp Val Ser Ala Gly Ser Gly Leu Val Pro Pro
                755                 760                 765

Ala Tyr Ala Pro Pro Pro Ala Val Pro Gly His Pro Ala Pro Gln Ser
                770                 775                 780

Ala Glu Val Trp Gly Gly Pro Ser Gly Pro Gly Ala Leu Ala Asp Leu
785                 790                 795                 800

Asp Cys Ser Ser Ser Gln Ser Pro Gly Ser Ser Glu Asn Gln Met
                805                 810                 815

Val Ser Pro Gly Lys Val Ser Gly Ser Pro Glu Gln Ala Val Glu Glu
                820                 825                 830

Asn Leu Ser Ser Tyr Ser Leu Asp Arg Arg Val Thr Pro Ala Ser Glu
                835                 840                 845

Thr Leu Glu Asp Pro Cys Arg Thr Glu Ser Gln His Lys Ala Glu Thr
850                 855                 860

Pro His Gly Ala Glu Glu Cys Lys Ala Glu Thr Pro His Gly Ala
865                 870                 875                 880

Glu Glu Glu Cys Arg His Gly Gly Val Cys Ala Pro Ala Ala Val Ala
                885                 890                 895

Thr Ser Pro Pro Gly Ala Ile Pro Lys Glu Ala Cys Gly Gly Ala Pro
                900                 905                 910
```

-continued

Leu Gln Gly Leu Pro Gly Glu Ala Leu Gly Cys Pro Ala Gly Val Gly
       915                 920                 925

Thr Pro Val Pro Ala Asp Gly Thr Gln Thr Leu Thr Cys Ala His Thr
930                 935                 940

Ser Ala Pro Glu Ser Thr Ala Pro Thr Asn His Leu Val Ala Gly Arg
945                 950                 955                 960

Ala Met Thr Leu Ser Pro Gln Glu Val Ala Ala Gly Gln Met Ala
            965                 970                 975

Ser Ser Ser Arg Ser Gly Pro Val Lys Leu Glu Phe Asp Val Ser Asp
            980                 985                 990

Gly Ala Thr Ser Lys Arg Ala Pro Pro Arg Arg Leu Gly Glu Arg
            995                 1000                1005

Ser Gly Leu Lys Pro Pro Leu Arg Lys Ala Ala Val Arg Gln Gln
    1010                1015                1020

Lys Ala Pro Gln Glu Val Glu Glu Asp Asp Gly Arg Ser Gly Ala
    1025                1030                1035

Gly Glu Asp Pro Pro Met Pro Ala Ser Arg Gly Ser Tyr His Leu
    1040                1045                1050

Asp Trp Asp Lys Met Asp Asp Pro Asn Phe Ile Pro Phe Gly Gly
    1055                1060                1065

Asp Thr Lys Ser Gly Cys Ser Glu Ala Gln Pro Pro Glu Ser Pro
    1070                1075                1080

Glu Thr Arg Leu Gly Gln Pro Ala Ala Glu Gln Leu His Ala Gly
    1085                1090                1095

Pro Ala Thr Glu Glu Pro Gly Pro Cys Leu Ser Gln Gln Leu His
    1100                1105                1110

Ser Ala Ser Ala Glu Asp Thr Pro Val Val Gln Leu Ala Ala Glu
    1115                1120                1125

Thr Pro Thr Ala Glu Ser Lys Glu Arg Ala Leu Asn Ser Ala Ser
    1130                1135                1140

Thr Ser Leu Pro Thr Ser Cys Pro Gly Ser Glu Pro Val Pro Thr
    1145                1150                1155

His Gln Gln Gly Gln Pro Ala Leu Glu Leu Lys Glu Glu Ser Phe
    1160                1165                1170

Arg Asp Pro Ala Glu Val Leu Gly Thr Gly Ala Glu Val Asp Tyr
    1175                1180                1185

Leu Glu Gln Phe Gly Thr Ser Ser Phe Lys Glu Ser Ala Leu Arg
    1190                1195                1200

Lys Gln Ser Leu Tyr Leu Lys Phe Asp Pro Leu Leu Arg Asp Ser
    1205                1210                1215

Pro Gly Arg Pro Val Pro Val Ala Thr Glu Thr Ser Ser Met His
    1220                1225                1230

Gly Ala Asn Glu Thr Pro Ser Gly Arg Pro Arg Glu Ala Lys Leu
    1235                1240                1245

Val Glu Phe Asp Phe Leu Gly Ala Leu Asp Ile Pro Val Pro Gly
    1250                1255                1260

Pro Pro Pro Gly Val Pro Ala Pro Gly Gly Pro Pro Leu Ser Thr
    1265                1270                1275

Gly Pro Ile Val Asp Leu Leu Gln Tyr Ser Gln Lys Asp Leu Asp
    1280                1285                1290

Ala Val Val Lys Ala Thr Gln Glu Glu Asn Arg Glu Leu Arg Ser
    1295                1300                1305

```
Arg Cys Glu Glu Leu His Gly Lys Asn Leu Glu Leu Gly Lys Ile
    1310                1315                1320

Met Asp Arg Phe Glu Glu Val Val Tyr Gln Ala Met Glu Glu Val
    1325                1330                1335

Gln Lys Gln Lys Glu Leu Ser Lys Ala Glu Ile Gln Lys Val Leu
    1340                1345                1350

Lys Glu Lys Asp Gln Leu Thr Thr Asp Leu Asn Ser Met Glu Lys
    1355                1360                1365

Ser Phe Ser Asp Leu Phe Lys Arg Phe Glu Lys Gln Lys Glu Val
    1370                1375                1380

Ile Glu Gly Tyr Arg Lys Asn Glu Glu Ser Leu Lys Lys Cys Val
    1385                1390                1395

Glu Asp Tyr Leu Ala Arg Ile Thr Gln Glu Gly Gln Arg Tyr Gln
    1400                1405                1410

Ala Leu Lys Ala His Ala Glu Glu Lys Leu Gln Leu Ala Asn Glu
    1415                1420                1425

Glu Ile Ala Gln Val Arg Ser Lys Ala Gln Ala Glu Ala Leu Ala
    1430                1435                1440

Leu Gln Ala Ser Leu Arg Lys Glu Gln Met Arg Ile Gln Ser Leu
    1445                1450                1455

Glu Lys Thr Val Glu Gln Lys Thr Lys Glu Asn Glu Glu Leu Thr
    1460                1465                1470

Arg Ile Cys Asp Asp Leu Ile Ser Lys Met Glu Lys Ile
    1475                1480                1485

<210> SEQ ID NO 37
<211> LENGTH: 3759
<212> TYPE: DNA
<213> ORGANISM: Homo sapiens
<220> FEATURE:
<221> NAME/KEY: CDS
<222> LOCATION: (1)..(3759)

<400> SEQUENCE: 37 atg ggc gcc cct gcc tgc gcc ctc gcg ctc tgc gtg gcc gtg gcc atc      48
Met Gly Ala Pro Ala Cys Ala Leu Ala Leu Cys Val Ala Val Ala Ile
1               5                   10                  15 gtg gcc ggc gcc tcc tcg gag tcc ttg ggg acg gag cag cgc gtc gtg      96
Val Ala Gly Ala Ser Ser Glu Ser Leu Gly Thr Glu Gln Arg Val Val
                20                  25                  30 ggg cga gcg gca gaa gtc ccg ggc cca gag ccc ggc cag cag gag cag     144
Gly Arg Ala Ala Glu Val Pro Gly Pro Glu Pro Gly Gln Gln Glu Gln
            35                  40                  45 ttg gtc ttc ggc agc ggg gat gct gtg gag ctg agc tgt ccc ccg ccc     192
Leu Val Phe Gly Ser Gly Asp Ala Val Glu Leu Ser Cys Pro Pro Pro
        50                  55                  60 ggg ggt ggt ccc atg ggg ccc act gtc tgg gtc aag gat ggc aca ggg     240
Gly Gly Gly Pro Met Gly Pro Thr Val Trp Val Lys Asp Gly Thr Gly
65                  70                  75                  80 ctg gtg ccc tcg gag cgt gtc ctg gtg ggg ccc cag cgg ctg cag gtg     288
Leu Val Pro Ser Glu Arg Val Leu Val Gly Pro Gln Arg Leu Gln Val
                85                  90                  95 ctg aat gcc tcc cac gag gac tcc ggg gcc tac agc tgc cgg cag cgg     336
Leu Asn Ala Ser His Glu Asp Ser Gly Ala Tyr Ser Cys Arg Gln Arg
                100                 105                 110 ctc acg cag cgc gta ctg tgc cac ttc agt gtg cgg gtg aca gac gct     384
Leu Thr Gln Arg Val Leu Cys His Phe Ser Val Arg Val Thr Asp Ala
            115                 120                 125
```

|     |     |     |     |     |     |     |     |     |     |     |     |     |     |     |     |     |
|---|---|---|---|---|---|---|---|---|---|---|---|---|---|---|---|---|
| cca | tcc | tcg | gga | gat | gac | gaa | gac | ggg | gag | gac | gag | gct | gag | gac | aca | 432 |
| Pro | Ser | Ser | Gly | Asp | Asp | Glu | Asp | Gly | Glu | Asp | Glu | Ala | Glu | Asp | Thr | |
| | | 130 | | | | 135 | | | | 140 | | | | | | |
| ggt | gtg | gac | aca | ggg | gcc | cct | tac | tgg | aca | cgg | ccc | gag | cgg | atg | gac | 480 |
| Gly | Val | Asp | Thr | Gly | Ala | Pro | Tyr | Trp | Thr | Arg | Pro | Glu | Arg | Met | Asp | |
| 145 | | | | 150 | | | | | 155 | | | | | 160 | | |
| aag | aag | ctg | ctg | gcc | gtg | ccg | gcc | gcc | aac | acc | gtc | cgc | ttc | cgc | tgc | 528 |
| Lys | Lys | Leu | Leu | Ala | Val | Pro | Ala | Ala | Asn | Thr | Val | Arg | Phe | Arg | Cys | |
| | | | | 165 | | | | | 170 | | | | | 175 | | |
| cca | gcc | gct | ggc | aac | ccc | act | ccc | tcc | atc | tcc | tgg | ctg | aag | aac | ggc | 576 |
| Pro | Ala | Ala | Gly | Asn | Pro | Thr | Pro | Ser | Ile | Ser | Trp | Leu | Lys | Asn | Gly | |
| | | | 180 | | | | | 185 | | | | | 190 | | | |
| agg | gag | ttc | cgc | ggc | gag | cac | cgc | att | gga | ggc | atc | aag | ctg | cgg | cat | 624 |
| Arg | Glu | Phe | Arg | Gly | Glu | His | Arg | Ile | Gly | Gly | Ile | Lys | Leu | Arg | His | |
| | | 195 | | | | 200 | | | | 205 | | | | | | |
| cag | cag | tgg | agc | ctg | gtc | atg | gaa | agc | gtg | gtg | ccc | tcg | gac | cgc | ggc | 672 |
| Gln | Gln | Trp | Ser | Leu | Val | Met | Glu | Ser | Val | Val | Pro | Ser | Asp | Arg | Gly | |
| 210 | | | | | 215 | | | | | 220 | | | | | | |
| aac | tac | acc | tgc | gtc | gtg | gag | aac | aag | ttt | ggc | agc | atc | cgg | cag | acg | 720 |
| Asn | Tyr | Thr | Cys | Val | Val | Glu | Asn | Lys | Phe | Gly | Ser | Ile | Arg | Gln | Thr | |
| 225 | | | | 230 | | | | | 235 | | | | | 240 | | |
| tac | acg | ctg | gac | gtg | ctg | gag | cgc | tcc | ccg | cac | cgg | ccc | atc | ctg | cag | 768 |
| Tyr | Thr | Leu | Asp | Val | Leu | Glu | Arg | Ser | Pro | His | Arg | Pro | Ile | Leu | Gln | |
| | | | | 245 | | | | | 250 | | | | | 255 | | |
| gcg | ggg | ctg | ccg | gcc | aac | cag | acg | gcg | gtg | ctg | ggc | agc | gac | gtg | gag | 816 |
| Ala | Gly | Leu | Pro | Ala | Asn | Gln | Thr | Ala | Val | Leu | Gly | Ser | Asp | Val | Glu | |
| | | | 260 | | | | | 265 | | | | | 270 | | | |
| ttc | cac | tgc | aag | gtg | tac | agt | gac | gca | cag | ccc | cac | atc | cag | tgg | ctc | 864 |
| Phe | His | Cys | Lys | Val | Tyr | Ser | Asp | Ala | Gln | Pro | His | Ile | Gln | Trp | Leu | |
| | | 275 | | | | 280 | | | | 285 | | | | | | |
| aag | cac | gtg | gag | gtg | aat | ggc | agc | aag | gtg | ggc | ccg | gac | ggc | aca | ccc | 912 |
| Lys | His | Val | Glu | Val | Asn | Gly | Ser | Lys | Val | Gly | Pro | Asp | Gly | Thr | Pro | |
| | | 290 | | | | | 295 | | | | | 300 | | | | |
| tac | gtt | acc | gtg | ctc | aag | acg | gcg | ggc | gct | aac | acc | acc | gac | aag | gag | 960 |
| Tyr | Val | Thr | Val | Leu | Lys | Thr | Ala | Gly | Ala | Asn | Thr | Thr | Asp | Lys | Glu | |
| 305 | | | | | 310 | | | | | 315 | | | | | 320 | |
| cta | gag | gtt | ctc | tcc | ttg | cac | aac | gtc | acc | ttt | gag | gac | gcc | ggg | gag | 1008 |
| Leu | Glu | Val | Leu | Ser | Leu | His | Asn | Val | Thr | Phe | Glu | Asp | Ala | Gly | Glu | |
| | | | | 325 | | | | | 330 | | | | | 335 | | |
| tac | acc | tgc | ctg | gcg | ggc | aat | tct | att | ggg | ttt | tct | cat | cac | tct | gcg | 1056 |
| Tyr | Thr | Cys | Leu | Ala | Gly | Asn | Ser | Ile | Gly | Phe | Ser | His | His | Ser | Ala | |
| | | | 340 | | | | | 345 | | | | | 350 | | | |
| tgg | ctg | gtg | gtg | ctg | cca | gcc | gag | gag | gag | ctg | gtg | gag | gct | gac | gag | 1104 |
| Trp | Leu | Val | Val | Leu | Pro | Ala | Glu | Glu | Glu | Leu | Val | Glu | Ala | Asp | Glu | |
| | | 355 | | | | | 360 | | | | | 365 | | | | |
| gcg | ggc | agt | gtg | tat | gca | ggc | atc | ctc | agc | tac | ggg | gtg | ggc | ttc | ttc | 1152 |
| Ala | Gly | Ser | Val | Tyr | Ala | Gly | Ile | Leu | Ser | Tyr | Gly | Val | Gly | Phe | Phe | |
| | 370 | | | | | 375 | | | | | 380 | | | | | |
| ctg | ttc | atc | ctg | gtg | gtg | gcg | gct | gtg | acg | ctc | tgc | cgc | ctg | cgc | agc | 1200 |
| Leu | Phe | Ile | Leu | Val | Val | Ala | Ala | Val | Thr | Leu | Cys | Arg | Leu | Arg | Ser | |
| 385 | | | | | 390 | | | | | 395 | | | | | 400 | |
| ccc | ccc | aag | aaa | ggc | ctg | ggc | tcc | ccc | acc | gtg | cac | aag | atc | tcc | cgc | 1248 |
| Pro | Pro | Lys | Lys | Gly | Leu | Gly | Ser | Pro | Thr | Val | His | Lys | Ile | Ser | Arg | |
| | | | | 405 | | | | | 410 | | | | | 415 | | |
| ttc | ccg | ctc | aag | cga | cag | gtg | tcc | ctg | gag | tcc | aac | gcg | tcc | atg | agc | 1296 |
| Phe | Pro | Leu | Lys | Arg | Gln | Val | Ser | Leu | Glu | Ser | Asn | Ala | Ser | Met | Ser | |
| | | | 420 | | | | | 425 | | | | | 430 | | | |
| tcc | aac | aca | cca | ctg | gtg | cgc | atc | gca | agg | ctg | tcc | tca | ggg | gag | ggc | 1344 |
| Ser | Asn | Thr | Pro | Leu | Val | Arg | Ile | Ala | Arg | Leu | Ser | Ser | Gly | Glu | Gly | |
| | | 435 | | | | | 440 | | | | | 445 | | | | |

| | | |
|---|---|---|
| ccc acg ctg gcc aat gtc tcc gag ctc gag ctg cct gcc gac ccc aaa<br>Pro Thr Leu Ala Asn Val Ser Glu Leu Glu Leu Pro Ala Asp Pro Lys<br>450                           455                    460 | | 1392 |
| tgg gag ctg tct cgg gcc cgg ctg acc ctg ggc aag ccc ctt ggg gag<br>Trp Glu Leu Ser Arg Ala Arg Leu Thr Leu Gly Lys Pro Leu Gly Glu<br>465                    470                    475                  480 | | 1440 |
| ggc tgc ttc ggc cag gtg gtc atg gcg gag gcc atc ggc att gac aag<br>Gly Cys Phe Gly Gln Val Val Met Ala Glu Ala Ile Gly Ile Asp Lys<br>                     485                    490                    495 | | 1488 |
| gac cgg gcc gcc aag cct gtc acc gta gcc gtg aag atg ctg aaa gac<br>Asp Arg Ala Ala Lys Pro Val Thr Val Ala Val Lys Met Leu Lys Asp<br>        500                    505                    510 | | 1536 |
| gat gcc act gac aag gac ctg tcg gac ctg gtg tct gag atg gag atg<br>Asp Ala Thr Asp Lys Asp Leu Ser Asp Leu Val Ser Glu Met Glu Met<br>515                         520                    525 | | 1584 |
| atg aag atg atc ggg aaa cac aaa aac atc atc aac ctg ctg ggc gcc<br>Met Lys Met Ile Gly Lys His Lys Asn Ile Ile Asn Leu Leu Gly Ala<br>530                    535                    540 | | 1632 |
| tgc acg cag ggc ggg ccc ctg tac gtg ctg gtg gag tac gcg gcc aag<br>Cys Thr Gln Gly Gly Pro Leu Tyr Val Leu Val Glu Tyr Ala Ala Lys<br>545                         550                    555                  560 | | 1680 |
| ggt aac ctg cgg gag ttt ctg cgg gcg cgg cgg ccc ccg ggc ctg gac<br>Gly Asn Leu Arg Glu Phe Leu Arg Ala Arg Arg Pro Pro Gly Leu Asp<br>                     565                    570                    575 | | 1728 |
| tac tcc ttc gac acc tgc aag ccg ccc gag gag cag ctc acc ttc aag<br>Tyr Ser Phe Asp Thr Cys Lys Pro Pro Glu Glu Gln Leu Thr Phe Lys<br>        580                    585                    590 | | 1776 |
| gac ctg gtg tcc tgt gcc tac cag gtg gcc cgg ggc atg gag tac ttg<br>Asp Leu Val Ser Cys Ala Tyr Gln Val Ala Arg Gly Met Glu Tyr Leu<br>            595                    600                    605 | | 1824 |
| gcc tcc cag aag tgc atc cac agg gac ctg gct gcc cgc aat gtg ctg<br>Ala Ser Gln Lys Cys Ile His Arg Asp Leu Ala Ala Arg Asn Val Leu<br>                610                    615                    620 | | 1872 |
| gtg acc gag gac aac gtg atg aag atc gca gac ttc ggg ctg gcc cgg<br>Val Thr Glu Asp Asn Val Met Lys Ile Ala Asp Phe Gly Leu Ala Arg<br>625                         630                    635                  640 | | 1920 |
| gac gtg cac aac ctc gac tac tac aag aag aca acc aac ggc cgg ctg<br>Asp Val His Asn Leu Asp Tyr Tyr Lys Lys Thr Thr Asn Gly Arg Leu<br>                     645                    650                    655 | | 1968 |
| ccc gtg aag tgg atg gcg cct gag gcc ttg ttt gac cga gtc tac act<br>Pro Val Lys Trp Met Ala Pro Glu Ala Leu Phe Asp Arg Val Tyr Thr<br>        660                    665                    670 | | 2016 |
| cac cag agt gac gtc tgg tcc ttt ggg gtc ctc ctc tgg gag atc ttc<br>His Gln Ser Asp Val Trp Ser Phe Gly Val Leu Leu Trp Glu Ile Phe<br>            675                    680                    685 | | 2064 |
| acg ctg ggg ggc tcc ccg tac ccc ggc atc cct gtg gag gag ctc ttc<br>Thr Leu Gly Gly Ser Pro Tyr Pro Gly Ile Pro Val Glu Glu Leu Phe<br>                690                    695                    700 | | 2112 |
| aag ctg ctg aag gag ggc cac cgc atg gac aag ccc gcc aac tgc aca<br>Lys Leu Leu Lys Glu Gly His Arg Met Asp Lys Pro Ala Asn Cys Thr<br>705                         710                    715                  720 | | 2160 |
| cac gac ctg tac atg atc atg cgg gag tgc tgg cat gcc gcg ccc tcc<br>His Asp Leu Tyr Met Ile Met Arg Glu Cys Trp His Ala Ala Pro Ser<br>                        725                    730                    735 | | 2208 |
| cag agg ccc acc ttc aag cag ctg gtg gag gac ctg gac cgt gtc ctt<br>Gln Arg Pro Thr Phe Lys Gln Leu Val Glu Asp Leu Asp Arg Val Leu<br>        740                    745                    750 | | 2256 |
| acc gtg acg tcc acc gac aat gtt atg gaa cag ttc aat cct ggg ctg<br>Thr Val Thr Ser Thr Asp Asn Val Met Glu Gln Phe Asn Pro Gly Leu | | 2304 |

```
                755                 760                 765
cga aat tta ata aac ctg ggg aaa aat tat gag aaa gct gta aac gct       2352
Arg Asn Leu Ile Asn Leu Gly Lys Asn Tyr Glu Lys Ala Val Asn Ala
    770                 775                 780 atg atc ctg gca gga aaa gcc tac tac gat gga gtg gcc aag atc ggt       2400
Met Ile Leu Ala Gly Lys Ala Tyr Tyr Asp Gly Val Ala Lys Ile Gly
785                 790                 795                 800 gag att gcc act ggg tcc ccc gtg tca act gaa ctg gga cat gtc ctc       2448
Glu Ile Ala Thr Gly Ser Pro Val Ser Thr Glu Leu Gly His Val Leu
                805                 810                 815 ata gag att tca agt acc cac aag aaa ctc aac gag agt ctt gat gaa       2496
Ile Glu Ile Ser Ser Thr His Lys Lys Leu Asn Glu Ser Leu Asp Glu
            820                 825                 830 aat ttt aaa aaa ttc cac aaa gag att atc cat gag ctg gag aag aag       2544
Asn Phe Lys Lys Phe His Lys Glu Ile Ile His Glu Leu Glu Lys Lys
        835                 840                 845 ata gaa ctt gac gtg aaa tat atg aac gca act cta aaa aga tac caa       2592
Ile Glu Leu Asp Val Lys Tyr Met Asn Ala Thr Leu Lys Arg Tyr Gln
    850                 855                 860 aca gaa cac aag aat aaa tta gag tct ttg gag aaa tcc caa gct gag       2640
Thr Glu His Lys Asn Lys Leu Glu Ser Leu Glu Lys Ser Gln Ala Glu
865                 870                 875                 880 ttg aag aag atc aga agg aaa agc caa gga agc cga aac gca ctc aaa       2688
Leu Lys Lys Ile Arg Arg Lys Ser Gln Gly Ser Arg Asn Ala Leu Lys
                885                 890                 895 tat gaa cac aaa gaa att gag tat gtg gag acc gtt act tct cgt cag       2736
Tyr Glu His Lys Glu Ile Glu Tyr Val Glu Thr Val Thr Ser Arg Gln
            900                 905                 910 agt gaa atc cag aaa ttc att gca gat ggt tgc aaa gag gct ctg ctt       2784
Ser Glu Ile Gln Lys Phe Ile Ala Asp Gly Cys Lys Glu Ala Leu Leu
        915                 920                 925 gaa gag aag agg cgc ttc tgc ttt ctg gtt gat aag cac tgt ggc ttt       2832
Glu Glu Lys Arg Arg Phe Cys Phe Leu Val Asp Lys His Cys Gly Phe
    930                 935                 940 gca aac cac ata cat tat tat cac tta cag tct gca gaa cta ctg aat       2880
Ala Asn His Ile His Tyr Tyr His Leu Gln Ser Ala Glu Leu Leu Asn
945                 950                 955                 960 tcc aag ctg cct cgg tgg cag gag acc tgt gtt gat gcc atc aaa gtg       2928
Ser Lys Leu Pro Arg Trp Gln Glu Thr Cys Val Asp Ala Ile Lys Val
                965                 970                 975 cca gag aaa atc atg aat atg atc gaa gaa ata aag acc cca gcc tct       2976
Pro Glu Lys Ile Met Asn Met Ile Glu Glu Ile Lys Thr Pro Ala Ser
            980                 985                 990 acc ccc gtg tct gga act cct cag gct tca ccc atg atc gag aga agc       3024
Thr Pro Val Ser Gly Thr Pro Gln Ala Ser Pro Met Ile Glu Arg Ser
        995                 1000                1005 aat gtg gtt agg aaa gat tac gac acc ctt tct aaa tgc tca cca           3069
Asn Val Val Arg Lys Asp Tyr Asp Thr Leu Ser Lys Cys Ser Pro
    1010                1015                1020 aag atg ccc ccc gct cct tca ggc aga gca tat acc agt ccc ttg           3114
Lys Met Pro Pro Ala Pro Ser Gly Arg Ala Tyr Thr Ser Pro Leu
    1025                1030                1035 atc gat atg ttt aat aac cca gcc acg gct gcc ccg aat tca caa           3159
Ile Asp Met Phe Asn Asn Pro Ala Thr Ala Ala Pro Asn Ser Gln
    1040                1045                1050 agg gta aat aat tca aca ggt act tcc gaa gat ccc agt tta cag           3204
Arg Val Asn Asn Ser Thr Gly Thr Ser Glu Asp Pro Ser Leu Gln
    1055                1060                1065 cga tca gtt tcg gtt gca acg gga ctg aac atg atg aag aag cag           3249
```

```
Arg Ser Val Ser Val Ala Thr Gly Leu Asn Met Met Lys Lys Gln
    1070                1075                1080 aaa gtg aag acc atc ttc ccg cac act gcg ggc tcc aac aag acc        3294
Lys Val Lys Thr Ile Phe Pro His Thr Ala Gly Ser Asn Lys Thr
1085                1090                1095 tta ctc agc ttt gca cag gga gat gtc atc acg ctg ctc atc ccc        3339
Leu Leu Ser Phe Ala Gln Gly Asp Val Ile Thr Leu Leu Ile Pro
    1100                1105                1110 gag gag aag gat ggc tgg ctc tat gga gaa cac gac gtg tcc aag        3384
Glu Glu Lys Asp Gly Trp Leu Tyr Gly Glu His Asp Val Ser Lys
    1115                1120                1125 gcg agg ggt tgg ttc ccg tcg tcg tac acg aag ttg ctg gaa gaa        3429
Ala Arg Gly Trp Phe Pro Ser Ser Tyr Thr Lys Leu Leu Glu Glu
    1130                1135                1140 aat gag aca gaa gca gtg acc gtg ccc acg cca agc ccc aca cca        3474
Asn Glu Thr Glu Ala Val Thr Val Pro Thr Pro Ser Pro Thr Pro
    1145                1150                1155 gtg aga agc atc agc acc gtg aac ttg tct gag aat agc agt gtt        3519
Val Arg Ser Ile Ser Thr Val Asn Leu Ser Glu Asn Ser Ser Val
    1160                1165                1170 gtc atc ccc cca ccc gac tac ttg gaa tgc ttg tcc atg ggg gca        3564
Val Ile Pro Pro Pro Asp Tyr Leu Glu Cys Leu Ser Met Gly Ala
    1175                1180                1185 gct gcc gac agg aga gca gat tcg gcc agg acg aca tcc acc ttt        3609
Ala Ala Asp Arg Arg Ala Asp Ser Ala Arg Thr Thr Ser Thr Phe
    1190                1195                1200 aag gcc cca gcg tcc aag ccc gag acc gcg gct cct aac gat gcc        3654
Lys Ala Pro Ala Ser Lys Pro Glu Thr Ala Ala Pro Asn Asp Ala
    1205                1210                1215 aac ggg act gca aag ccg cct ttt ctc agc gga gaa aac ccc ttt        3699
Asn Gly Thr Ala Lys Pro Pro Phe Leu Ser Gly Glu Asn Pro Phe
    1220                1225                1230 gcc act gtg aaa ctc cgc ccg act gtg acg aat gat cgc tcg gca        3744
Ala Thr Val Lys Leu Arg Pro Thr Val Thr Asn Asp Arg Ser Ala
    1235                1240                1245 ccc atc att cga tga                                                3759
Pro Ile Ile Arg
    1250

<210> SEQ ID NO 38
<211> LENGTH: 1252
<212> TYPE: PRT
<213> ORGANISM: Homo sapiens

<400> SEQUENCE: 38

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110
```

-continued

Leu Thr Gln Arg Val Leu Cys His Phe Ser Val Arg Val Thr Asp Ala
            115                 120                 125

Pro Ser Ser Gly Asp Asp Glu Asp Gly Glu Asp Ala Glu Asp Thr
130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Ile Lys Leu Arg His
            195                 200                 205

Gln Gln Trp Ser Leu Val Met Glu Ser Val Val Pro Ser Asp Arg Gly
210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
            275                 280                 285

Lys His Val Glu Val Asn Gly Ser Lys Val Gly Pro Asp Gly Thr Pro
290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
                340                 345                 350

Trp Leu Val Val Leu Pro Ala Glu Glu Leu Val Glu Ala Asp Glu
            355                 360                 365

Ala Gly Ser Val Tyr Ala Gly Ile Leu Ser Tyr Gly Val Gly Phe Phe
                370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
                420                 425                 430

Ser Asn Thr Pro Leu Val Arg Ile Ala Arg Leu Ser Ser Gly Glu Gly
            435                 440                 445

Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
            515                 520                 525

-continued

```
Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Asn Val Met Glu Gln Phe Asn Pro Gly Leu
        755                 760                 765

Arg Asn Leu Ile Asn Leu Gly Lys Asn Tyr Glu Lys Ala Val Asn Ala
    770                 775                 780

Met Ile Leu Ala Gly Lys Ala Tyr Tyr Asp Gly Val Ala Lys Ile Gly
785                 790                 795                 800

Glu Ile Ala Thr Gly Ser Pro Val Ser Thr Glu Leu Gly His Val Leu
                805                 810                 815

Ile Glu Ile Ser Ser Thr His Lys Lys Leu Asn Glu Ser Leu Asp Glu
            820                 825                 830

Asn Phe Lys Lys Phe His Lys Glu Ile Ile His Glu Leu Glu Lys Lys
        835                 840                 845

Ile Glu Leu Asp Val Lys Tyr Met Asn Ala Thr Leu Lys Arg Tyr Gln
    850                 855                 860

Thr Glu His Lys Asn Lys Leu Glu Ser Leu Glu Lys Ser Gln Ala Glu
865                 870                 875                 880

Leu Lys Lys Ile Arg Arg Lys Ser Gln Gly Ser Arg Asn Ala Leu Lys
                885                 890                 895

Tyr Glu His Lys Glu Ile Glu Tyr Val Glu Thr Val Thr Ser Arg Gln
            900                 905                 910

Ser Glu Ile Gln Lys Phe Ile Ala Asp Gly Cys Lys Glu Ala Leu Leu
        915                 920                 925

Glu Glu Lys Arg Arg Phe Cys Phe Leu Val Asp Lys His Cys Gly Phe
    930                 935                 940

Ala Asn His Ile His Tyr Tyr His Leu Gln Ser Ala Glu Leu Leu Asn
```

```
              945                 950                 955                 960
Ser Lys Leu Pro Arg Trp Gln Glu Thr Cys Val Asp Ala Ile Lys Val
                    965                 970                 975

Pro Glu Lys Ile Met Asn Met Ile Glu Glu Ile Lys Thr Pro Ala Ser
                980                 985                 990

Thr Pro Val Ser Gly Thr Pro Gln Ala Ser Pro Met Ile Glu Arg Ser
            995                 1000                1005

Asn Val Val Arg Lys Asp Tyr Asp Thr Leu Ser Lys Cys Ser Pro
        1010                1015                1020

Lys Met Pro Pro Ala Pro Ser Gly Arg Ala Tyr Thr Ser Pro Leu
        1025                1030                1035

Ile Asp Met Phe Asn Asn Pro Ala Thr Ala Ala Pro Asn Ser Gln
        1040                1045                1050

Arg Val Asn Asn Ser Thr Gly Thr Ser Glu Asp Pro Ser Leu Gln
        1055                1060                1065

Arg Ser Val Ser Val Ala Thr Gly Leu Asn Met Met Lys Lys Gln
        1070                1075                1080

Lys Val Lys Thr Ile Phe Pro His Thr Ala Gly Ser Asn Lys Thr
        1085                1090                1095

Leu Leu Ser Phe Ala Gln Gly Asp Val Ile Thr Leu Leu Ile Pro
        1100                1105                1110

Glu Glu Lys Asp Gly Trp Leu Tyr Gly Glu His Asp Val Ser Lys
        1115                1120                1125

Ala Arg Gly Trp Phe Pro Ser Ser Tyr Thr Lys Leu Leu Glu Glu
        1130                1135                1140

Asn Glu Thr Glu Ala Val Thr Val Pro Thr Pro Ser Pro Thr Pro
        1145                1150                1155

Val Arg Ser Ile Ser Thr Val Asn Leu Ser Glu Asn Ser Ser Val
        1160                1165                1170

Val Ile Pro Pro Pro Asp Tyr Leu Glu Cys Leu Ser Met Gly Ala
        1175                1180                1185

Ala Ala Asp Arg Arg Ala Asp Ser Ala Arg Thr Thr Ser Thr Phe
        1190                1195                1200

Lys Ala Pro Ala Ser Lys Pro Glu Thr Ala Ala Pro Asn Asp Ala
        1205                1210                1215

Asn Gly Thr Ala Lys Pro Pro Phe Leu Ser Gly Glu Asn Pro Phe
        1220                1225                1230

Ala Thr Val Lys Leu Arg Pro Thr Val Thr Asn Asp Arg Ser Ala
        1235                1240                1245

Pro Ile Ile Arg
        1250

<210> SEQ ID NO 39
<211> LENGTH: 17
<212> TYPE: PRT
<213> ORGANISM: Artificial Sequence
<220> FEATURE:
<223> OTHER INFORMATION: Biotinylated peptide sequence

<400> SEQUENCE: 39

Glu Gly Pro Trp Leu Glu Glu Glu Glu Ala Tyr Gly Trp Met Asp
1               5                   10                  15

Phe
```

32. The method of claim 16, wherein the FGFR3 inhibitor is a 2-hydroxypropionic acid salt of a compound having the formula:
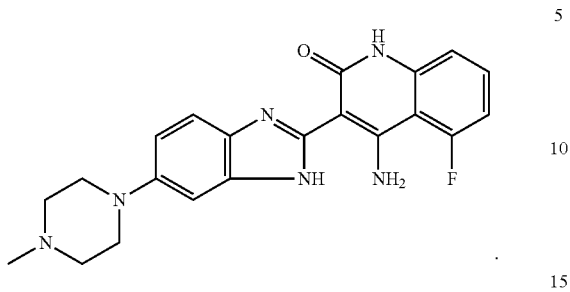

The invention claimed is:

1. A method of treating a subject who has cancer, the method comprising
   (a) determining that a sample comprising tumor cells from the subject comprises:
      (i) a fusion polypeptide, wherein the amino acid sequence of the fusion polypeptide consists of the amino acid sequence of SEQ ID NO: 32; or
      (ii) a polynucleotide encoding the fusion polypeptide, and
   (b) administering to the subject an FGFR3 inhibitor in an amount effective to inhibit tumor growth in the subject.

2. The method of claim 1, wherein the cancer is bladder cancer.

3. The method of claim 2, wherein the bladder cancer is classified as stage 3 or later according to TNM (Tumor-lymph Node-Metastasis) classification.

4. The method of claim 1, wherein the FGFR3 inhibitor is a tyrosine kinase inhibitor that inhibits phosphorylation by FGFR3.

5. The method of claim 1, wherein the cancer is selected from the group consisting of bladder cancer, brain tumor, head and neck squamous cell carcinoma, lung cancer, lung adenocarcinoma, lung squamous cell carcinoma, skin melanoma, esophageal cancer, gastric cancer, and liver cancer.

6. The method of claim 1, wherein the cancer is lung cancer.

7. The method of claim 1, wherein the FGFR3 inhibitor is a compound of formula I or a pharmaceutically acceptable salt thereof:

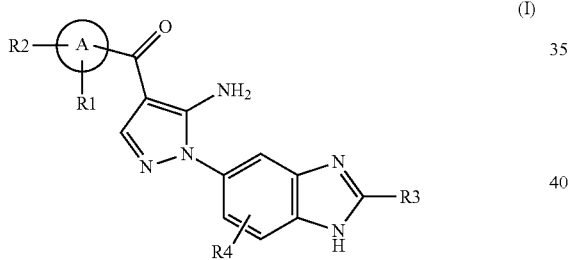

(I)

wherein $R_1$, $R_2$, $R_3$, and $R_4$ each independently represents the group listed below:

$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{11}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-5}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); or alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

$R_{23}$ represents hydrogen, $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{24}$ represents hydrogen, $C_{1-4}$ alkyl, or $C_{1-4}$ haloalkyl;

$R_{25}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{26}$ and $R_{27}$, which can be the same or different, each represents hydrogen, $C_{1-4}$ alkyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{26}$ and $R_{27}$, together with a nitrogen atom linked thereto, form 3- to 10-membered heterocyclyl or 5- to 10-membered heteroaryl;

$R_{28}$ and $R_{29}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxyl $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, or 3- to 10-membered cycloaliphatic ring; or alternatively $R_{28}$ and $R_{29}$, together with a nitrogen atom linked thereto, form 3- to 10-membered heterocyclyl or 5- to 10-membered heteroaryl;

$R_{30}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{31}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{32}$ represents $C_{1-4}$ alkyl or $C_{6-10}$ aryl;

<group P> halogen, $C_{1-4}$ alkyl, $C_{1-4}$ haloalkyl, —OH, $C_{1-3}$ alkoxy, $C_{1-3}$ haloalkoxy, 3- to 10-membered heterocyclylamino, —$SO_2R_{16}$, —CN, —$NO_2$, and 3- to 10-membered heterocyclyl;

<group Q> halogen, $C_{1-4}$ alkyl, $C_{1-4}$ haloalkyl, —OH, $C_{1-3}$ alkoxy, $C_{1-6}$ monohydroxy alkyl, $C_{1-6}$ dihydroxy alkyl, $C_{1-6}$ trihydroxy alkyl, 3- to 10-membered heterocyclyl amine, —$SO_2R_{16}$, —CN, —$NO_2$, $C_{3-7}$ cycloalkyl, —$COR_{19}$, and 3- to 10-membered heterocyclyl which is optionally substituted by $C_{1-4}$ alkyl.

8. The method of claim 7, wherein A is indole, and R3 and R4 are both hydrogen.

9. The method of claim 7, wherein A is a 5- to 10-membered heteroaryl ring or $C_{6-10}$ aryl ring, $R_4$ is hydrogen, and $R_3$ represents hydrogen, $C_{1-4}$ alkyl, $C_{6-10}$ aryl $C_{1-4}$ alkyl, or $C_{1-3}$ perfluoroalkyl.

10. The method of claim 1, wherein the FGFR3 inhibitor is a compound having the formula:

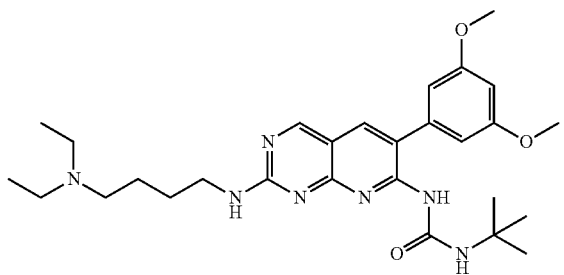 [SMILES: CCN(CC)CCCCNc1ncc2cc(-c3cc(OC)cc(OC)c3)c(NC(=O)NC(C)(C)C)nc2n1]

or a pharmaceutically acceptable salt thereof.

11. The method of claim 1, wherein the FGFR3 inhibitor is a compound having the formula:

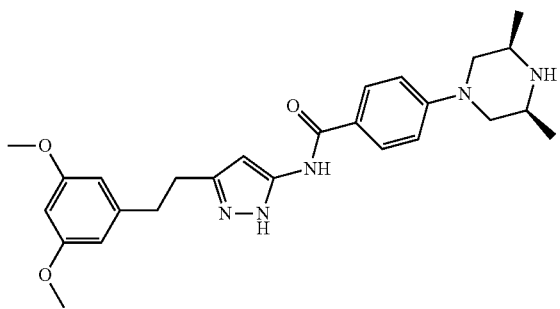

or a pharmaceutically acceptable salt thereof.

12. The method of claim 1, wherein the FGFR3 inhibitor is a compound having the formula:

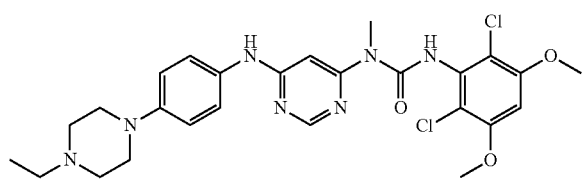 [SMILES: CCN1CCN(c2ccc(Nc3cc(N(C)C(=O)Nc4c(Cl)c(OC)cc(OC)c4Cl)ncn3)cc2)CC1]

or a pharmaceutically acceptable salt thereof.

13. The method of claim 1, wherein the FGFR3 inhibitor is a compound having the formula:

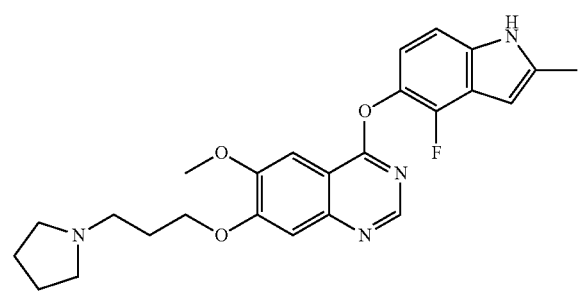 [SMILES: COc1cc2c(Oc3ccc4[nH]c(C)cc4c3F)ncnc2cc1OCCCN1CCCC1]

or a pharmaceutically acceptable salt thereof.

14. The method of claim 1, wherein the FGFR3 inhibitor is a 2-hydroxypropionic acid salt of a compound having the formula:

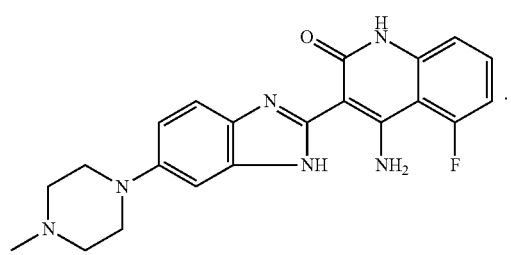 [SMILES: CN1CCN(c2ccc3nc(-c4c(N)c5c(F)cccc5[nH]c4=O)[nH]c3c2)CC1]

15. The method of claim 1, wherein the FGFR3 inhibitor is a compound having the formula:

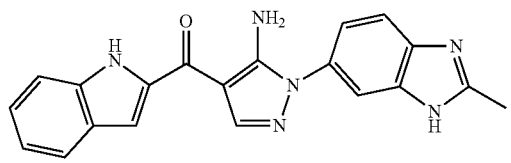 [SMILES: Cc1nc2ccc(-n3ncc(C(=O)c4cc5ccccc5[nH]4)c3N)cc2[nH]1]

or a pharmaceutically acceptable salt thereof.

16. A method of treating a subject who has cancer, the method comprising
   (a) determining that a sample comprising tumor cells from the subject comprises:
      (i) a fusion polypeptide, wherein the amino acid sequence of the fusion polypeptide comprises the amino acid sequence of SEQ ID NO: 32; or
      (ii) a polynucleotide encoding the fusion polypeptide, and
   (b) administering to the subject an FGFR3 inhibitor in an amount effective to inhibit tumor growth in the subject.

17. The method of claim 16, wherein the cancer is bladder cancer.

18. The method of claim 17, wherein the bladder cancer is classified as stage 3 or later according to TNM (Tumor-lymph Node-Metastasis) classification.

19. The method of claim 1, wherein the FGFR3 inhibitor is an antibody.

20. The method of claim 16, wherein the FGFR3 inhibitor is a tyrosine kinase inhibitor that inhibits phosphorylation by FGFR3.

21. The method of claim 16, wherein the FGFR3 inhibitor is an antibody.

22. The method of claim 16, wherein the cancer is selected from the group consisting of bladder cancer, brain tumor, head and neck squamous cell carcinoma, lung cancer, lung adenocarcinoma, lung squamous cell carcinoma, skin melanoma, esophageal cancer, gastric cancer, and liver cancer.

23. The method of claim 16, wherein the cancer is lung cancer.

24. The method of claim 16, wherein the FGFR3 inhibitor is a compound of formula I or a pharmaceutically acceptable salt thereof:

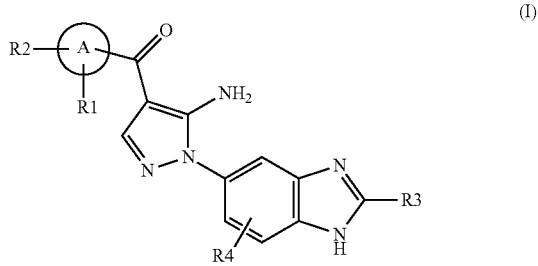

wherein $R_1$, $R_2$, $R_3$, and $R_4$ each independently represents the group listed below:
$R_1$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, $-OR_5$, $-NR_6R_7$, $-(CR_8R_9)_nZ_1$, $-C(O)NR_{12}R_{13}$, $-SR_{14}$, $-SOR_{15}$, $-SO_2R_{16}$, $-NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{21}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$;

$R_2$ represents hydrogen, hydroxy, halogen, cyano, nitro, $C_{1-4}$ haloalkyl, $C_{1-6}$ alkyl, $C_{2-6}$ alkenyl, $C_{2-6}$ alkynyl, $C_{3-7}$ cycloalkyl, $C_{6-10}$ aryl $C_{1-4}$ alkyl, —$OR_5$, —$NR_6R_7$, —$(CR_8R_9)_nZ_1$, —$C(O)NR_{12}R_{13}$, —$SR_{14}$, —$SOR_{15}$, —$SO_2R_{16}$, —$NR_{17}SO_2R_{18}$, COOH, $C_{6-10}$ aryl which is optionally substituted by one or more groups independently selected from group P, 5- to 10-membered heteroaryl or 3- to 10-membered heterocyclyl which is optionally substituted by one or more groups independently selected from group Q, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_{28}R_{29}$, —$OSO_2R_{30}$, —$SO_3R_{31}$, or —$Si(R_{32})_3$; or $R_1$ and $R_2$, together with an atom linked thereto, form 3- to 10-membered heterocyclyl or 5- to 10-membered heteroaryl, wherein the heterocyclyl or heteroaryl is optionally substituted by halogen;

$R_3$ represents hydrogen, $C_{1-5}$ alkyl, $C_{6-10}$ aryl $C_{1-6}$ alkyl, or $C_{1-4}$ haloalkyl;

$R_4$ represents hydrogen, halogen, $C_{1-3}$ alkyl, $C_{1-4}$ haloalkyl, hydroxy, cyano, nitro, $C_{1-4}$ alkoxy, —$(CH_2)_nZ_1$, —$NR_6R_7$, —$OR_5$, —$C(O)NR_{12}R_{13}$, —$SR_{14}$, —$SOR_{15}$, —$SO_2R_{16}$, $NR_{17}SO_2R_{18}$, COOH, —$COR_{19}$, —$COOR_{20}$, —$OC(O)R_{21}$, —$NR_{22}C(O)R_{23}$, —$NR_{24}C(S)R_{25}$, —$C(S)NR_{26}R_{27}$, —$SO_2NR_2R_{29}$, —$OSO_2R_{30}$, —$SO_3R_{31}$, or —$Si(R_{32})_3$;

A represents a 5- to 10-membered heteroaryl ring or $C_{6-10}$ aryl ring;

$R_5$ represents $C_{1-8}$ alkyl, $C_{3-7}$ cycloalkyl, $C_{3-7}$ cycloalkyl $C_{1-3}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{1-3}$ alkoxy $C_{1-4}$ alkoxy $C_{1-4}$ alkyl, $C_{1-4}$ aminoalkyl, $C_{1-4}$ alkylamino $C_{1-4}$ alkyl, di($C_{1-4}$ alkyl)amino $C_{1-4}$ alkyl, $C_{6-10}$ aryl, $C_{6-10}$ aryl $C_{1-3}$ alkyl, or 3- to 10-membered heterocyclyl $C_{1-3}$ alkyl, 3- to 10-membered heterocyclyl, 5- to 10-membered heteroaryl, 5- to 10-membered heteroaryl $C_{1-3}$ alkyl, $C_{1-6}$ monohydroxy alkyl, $C_{1-6}$ dihydroxy alkyl, or $C_{1-6}$ trihydroxy alkyl which is optionally substituted by one or more groups independently selected from group Q;

$R_6$ and $R_7$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl $C_{1-3}$ alkyl, 3- to 10-membered heterocyclyl $C_{1-3}$ alkyl, 5- to 10-membered heteroaryl $C_{1-3}$ alkyl, $C_{1-6}$ monohydroxy alkyl, $C_{1-6}$ dihydroxy alkyl, $C_{1-6}$ trihydroxy alkyl, 3- to 10-membered heterocyclyl, $C_{1-4}$ aminoalkyl, $C_{1-4}$ alkylamino $C_{1-4}$ alkyl, di($C_{1-4}$ alkyl)amino $C_{1-4}$ alkyl, or cyano($C_{1-3}$ alkyl); alternatively $R_6$ and $R_7$, together with a nitrogen atom linked thereto, form 3- to 10-membered heterocyclyl or 5- to 10-membered heteroaryl;

n represents 1 to 3;

$R_8$ and $R_9$, which can be the same or different, each represents hydrogen, $C_{1-4}$ alkyl, or halogen; or alternatively $R_8$ and $R_9$, together with a carbon atom linked thereto, form a cycloaliphatic ring;

$Z_1$ represents hydrogen, $NR_{10}R_{11}$, —OH, or 3- to 10-membered heterocyclyl or 5- to 10-membered heteroaryl which is optionally substituted by one or more groups independently selected from group Q;

$R_{10}$ and $R_{11}$, which can be the same or different, each represents $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, cyano($C_{1-3}$ alkyl), or $C_{1-3}$ alkylsulfonyl $C_{1-4}$ alkyl; or alternatively $R_{10}$ and $R_{11}$, together with a nitrogen atom linked thereto, form 3- to 10-membered heterocyclyl or 5- to 10-membered heteroaryl;

$R_{12}$ and $R_{13}$, which can be the same or different, each represents hydrogen, $C_{1-4}$ alkyl, $C_{2-6}$ alkenyl, $C_{2-6}$ alkynyl, $C_{1-4}$ haloalkyl, $C_{1-3}$ alkoxy $C_{1-4}$ alkyl, $C_{6-10}$ aryl, 5- to 10-membered heteroaryl, 3- to 10-membered heterocyclyl, $C_{6-10}$ aryl $C_{1-4}$ alkyl, 3- to 10-membered heterocyclyl $C_{1-3}$ alkyl, 5- to 10-membered heteroaryl $C_{1-3}$ alkyl, cyano($C_{1-3}$ alkyl), $C_{1-3}$ alkylsulfonyl $C_{1-4}$ alkyl, 3- to 10-membered cycloaliphatic ring, 5- to 10-membered heteroaryl, or 3- to 10-membered heterocyclyl; or alternatively $R_{12}$ and $R_{13}$, together with a nitrogen atom linked thereto, form 3- to 10-membered heterocyclyl or 5- to 10-membered heteroaryl which is optionally substituted by one or more groups independently selected from group Q;

$R_{14}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{15}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{16}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{17}$ represents hydrogen or $C_{1-4}$ alkyl;

$R_{18}$ represents $C_{1-4}$ alkyl, $C_{2-6}$ alkenyl, $C_{2-6}$ alkynyl, $C_{1-4}$ haloalkyl, $C_{6-10}$ aryl which is optionally substituted by one or more groups independently selected from group P, or 5- to 10-membered heteroaryl or 3- to 10-membered heterocyclyl which is optionally substituted by one or more groups independently selected from group Q;

$R_{19}$ represents hydrogen, $C_{1-4}$ alkyl, $C_{3-7}$ cycloalkyl, $C_{1-4}$ haloalkyl, $C_{6-10}$ aryl, or 5- to 10-membered heteroaryl or 3- to 10-membered heterocyclyl which is optionally substituted by one or more groups independently selected from group Q;

$R_{20}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{21}$ represents $C_{1-4}$ alkyl, $C_{3-7}$ cycloalkyl, $C_{1-4}$ haloalkyl, $C_{6-10}$ aryl, 5- to 10-membered heteroaryl, or 3- to 10-membered heterocyclyl;

$R_{22}$ represents hydrogen, $C_{1-4}$ alkyl, or $C_{1-4}$ haloalkyl;

R$_{23}$ represents hydrogen, C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{24}$ represents hydrogen, C$_{1-4}$ alkyl, or C$_{1-4}$ haloalkyl;

R$_{25}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{26}$ and R$_{27}$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxyl C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered cycloaliphatic ring; or alternatively R$_{26}$ and R$_{27}$, together with a nitrogen atom linked thereto, form 3- to 10-membered heterocyclyl or 5- to 10-membered heteroaryl;

R$_{28}$ and R$_{29}$, which can be the same or different, each represents hydrogen, C$_{1-4}$ alkyl, C$_{2-6}$ alkenyl, C$_{2-6}$ alkynyl, C$_{1-4}$ haloalkyl, C$_{1-3}$ alkoxyl C$_{1-4}$ alkyl, C$_{6-10}$ aryl, 5- to 10-membered heteroaryl, 3- to 10-membered heterocyclyl, C$_{6-10}$ aryl C$_{1-4}$ alkyl, 3- to 10-membered heterocyclyl C$_{1-3}$ alkyl, 5- to 10-membered heteroaryl C$_{1-3}$ alkyl, cyano(C$_{1-3}$ alkyl), C$_{1-3}$ alkylsulfonyl C$_{1-4}$ alkyl, or 3- to 10-membered cycloaliphatic ring; or alternatively R$_{28}$ and R$_{29}$, together with a nitrogen atom linked thereto, form 3- to 10-membered heterocyclyl or 5- to 10-membered heteroaryl;

R$_{30}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{31}$ represents C$_{1-4}$ alkyl, C$_{3-7}$ cycloalkyl, C$_{1-4}$ haloalkyl, C$_{6-10}$ aryl, 5- to 10-membered heteroaryl, or 3- to 10-membered heterocyclyl;

R$_{32}$ represents C$_{1-4}$ alkyl or C$_{6-10}$ aryl;

<group P>
halogen, C$_{1-4}$ alkyl, C$_{1-4}$ haloalkyl, —OH, C$_{1-3}$ alkoxy, C$_{1-3}$ haloalkoxy, 3- to 10-membered heterocyclylamino, —SO$_2$R$_{16}$, —CN, —NO$_2$, and 3- to 10-membered heterocyclyl;

<group Q>
halogen, C$_{1-4}$ alkyl, C$_{1-4}$ haloalkyl, —OH, C$_{1-3}$ alkoxy, C$_{1-6}$ monohydroxy alkyl, C$_{1-6}$ dihydroxy alkyl, C$_{1-6}$ trihydroxy alkyl, 3- to 10-membered heterocyclyl amine, —SO$_2$R$_{16}$, —CN, —NO$_2$, C$_{3-7}$ cycloalkyl, —COR$_{19}$, and 3- to 10-membered heterocyclyl which is optionally substituted by C$_{1-4}$ alkyl.

25. The method of claim 24, wherein A is indole, and R3 and R4 are both hydrogen.

26. The method of claim 24, wherein A is a 5- to 10-membered heteroaryl ring or C6-10 aryl ring, R$_4$ is hydrogen, and R$_3$ represents hydrogen, C$_{1-4}$ alkyl, C$_{6-10}$ aryl C$_{1-4}$ alkyl, or C$_{1-3}$ perfluoroalkyl.

27. The method of claim 16, wherein the FGFR3 inhibitor is a compound having the formula:

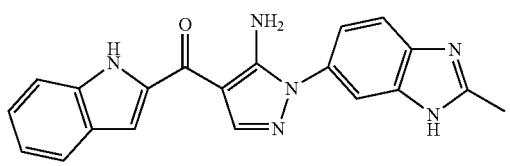 [SMILES: Cc1nc2ccc(-n3ncc(C(=O)c4cc5ccccc5[nH]4)c3N)cc2[nH]1]

or a pharmaceutically acceptable salt thereof.

28. The method of claim 16, wherein the FGFR3 inhibitor is a compound having the formula:

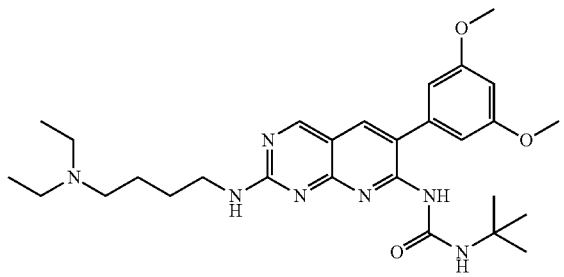 [SMILES: CCN(CC)CCCCNc1ncc2cc(-c3cc(OC)cc(OC)c3)c(NC(=O)NC(C)(C)C)nc2n1]

or a pharmaceutically acceptable salt thereof.

29. The method of claim 16, wherein the FGFR3 inhibitor is a compound having the formula:

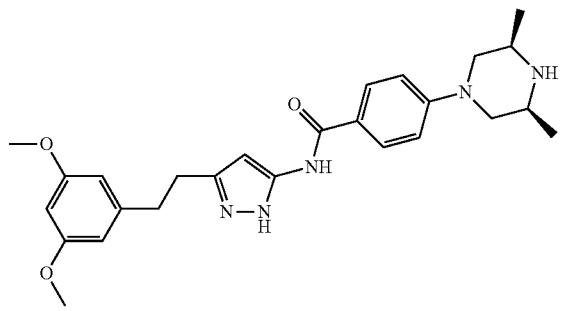

or a pharmaceutically acceptable salt thereof.

30. The method of claim 16, wherein the FGFR3 inhibitor is a compound having the formula:

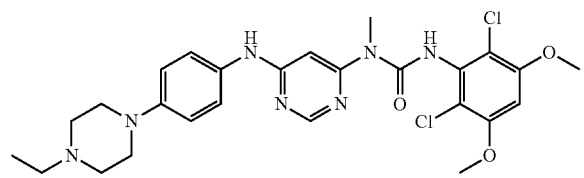 [SMILES: CCN1CCN(c2ccc(Nc3cc(N(C)C(=O)Nc4c(Cl)c(OC)cc(OC)c4Cl)ncn3)cc2)CC1]

or a pharmaceutically acceptable salt thereof.

31. The method of claim 16, wherein the FGFR3 inhibitor is a compound having the formula:

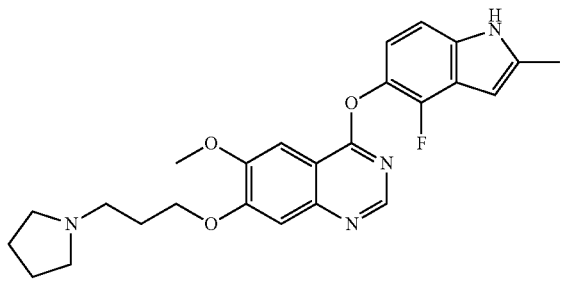 [SMILES: COc1cc2c(Oc3ccc4[nH]c(C)cc4c3F)ncnc2cc1OCCCN1CCCC1]

or a pharmaceutically acceptable salt thereof.

UNITED STATES PATENT AND TRADEMARK OFFICE
CERTIFICATE OF CORRECTION

PATENT NO. : 10,689,705 B2  
APPLICATION NO. : 14/380399  
DATED : June 23, 2020  
INVENTOR(S) : Yoshito Nakanishi, Nukinori Akiyama and Yukari Nishito Page 1 of 1

It is certified that error appears in the above-identified patent and that said Letters Patent is hereby corrected as shown below:

In the Specification

Column 27, Line 37: After "compound" and before "a" insert -- or --.

Columns 95-96 (TABLE 1-2-continued), the line for Compound 24: Delete "0.0023" and insert -- 0.023 -- therefor.

Columns 111-112 (TABLE 1-5), the line for Compound 61: Delete "0.037" and insert -- 0.37 -- therefor.

Columns 113-114 (TABLE 1-5-continued), the line for Compound 69: Delete "0.038" and insert -- 0.38 -- therefor.

In the Claims

Column 243, Line 50: In Claim 7, delete "-C(O)NR$_{12}$R$_3$," and insert -- -C(O)NR$_{12}$R$_{13}$, -- therefor.

Column 243, Line 64: In Claim 7, delete "-C(O)NR$_{12}$R$_3$," and insert -- -C(O)NR$_{12}$R$_{13}$, -- therefor.

Column 244, Line 4: In Claim 7, delete "-COR$_{11}$," and insert -- -COR$_{19}$, -- therefor.

Column 249, Line 3: In Claim 24, delete "-COR$_{21}$," and insert -- -COR$_{19}$, -- therefor.

Column 249, Line 33: In Claim 24, delete "-SO$_2$NR$_2$R$_{29}$," and insert -- -SO$_2$NR$_{28}$R$_{29}$, -- therefor.

Column 249, Line 37: In Claim 24, delete "C$_{1-S}$ alkyl" and insert -- C$_{1-5}$ alkyl -- therefor.

Signed and Sealed this  
Eighth Day of December, 2020

Andrei Iancu  
*Director of the United States Patent and Trademark Office*